US011806392B2

(12) United States Patent
Briles et al.

(10) Patent No.: US 11,806,392 B2
(45) Date of Patent: Nov. 7, 2023

(54) PNEUMOCOCCAL VACCINE COMBINING SELECTED ALPHA HELICAL DOMAINS AND PROLINE RICH DOMAINS OF PNEUMOCOCCAL SURFACE PROTEIN A

(71) Applicants: The UAB Research Foundation, Birmingham, AL (US); The University of Tokyo, Tokyo (JP)

(72) Inventors: David E. Briles, Birmingham, AL (US); Hiroshi Kiyono, Tokyo (JP); Robert Kneller, Tokyo (JP); Reshmi Mukerji, Birmingham, AL (US); Kristopher Genschmer, Irondale, AL (US); Yoshikazu Yuki, Tokyo (JP)

(73) Assignees: The UAB Research Foundation, Birmingham, AL (US); The University of Tokyo, Tokyo (JP)

( * ) Notice: Subject to any disclaimer, the term of this patent is extended or adjusted under 35 U.S.C. 154(b) by 382 days.

(21) Appl. No.: 16/463,364

(22) PCT Filed: Dec. 1, 2017

(86) PCT No.: PCT/US2017/064347
§ 371 (c)(1),
(2) Date: May 22, 2019

(87) PCT Pub. No.: WO2018/102774
PCT Pub. Date: Jun. 7, 2018

(65) Prior Publication Data
US 2019/0351043 A1 Nov. 21, 2019

Related U.S. Application Data

(60) Provisional application No. 62/429,782, filed on Dec. 3, 2016.

(51) Int. Cl.
| | | |
|---|---|---|
| *A61K 39/09* | (2006.01) | |
| *A61P 31/04* | (2006.01) | |
| *C07K 14/315* | (2006.01) | |
| *A61K 39/00* | (2006.01) | |

(52) U.S. Cl.
CPC ............ *A61K 39/092* (2013.01); *A61P 31/04* (2018.01); *C07K 14/3156* (2013.01); *A61K 2039/54* (2013.01); *A61K 2039/543* (2013.01); *A61K 2039/55505* (2013.01); *A61K 2039/55583* (2013.01)

(58) Field of Classification Search
None
See application file for complete search history.

(56) References Cited

U.S. PATENT DOCUMENTS

| | | |
|---|---|---|
| 5,728,387 A | 3/1998 | Briles et al. |
| 5,753,463 A | 5/1998 | Briles et al. |
| 6,500,613 B1 * | 12/2002 | Briles ............... C07K 14/3156 435/6.15 |
| 6,592,876 B1 | 7/2003 | Briles et al. |
| 9,938,326 B2 | 4/2018 | Akeda et al. |
| 2015/0032085 A1 | 1/2015 | Azamian et al. |
| 2015/0320851 A1 | 11/2015 | Akeda et al. |
| 2016/0324947 A1 * | 11/2016 | Ghasparian .......... A61K 39/092 |

FOREIGN PATENT DOCUMENTS

| | | |
|---|---|---|
| AU | 2017366726 A1 | 5/2019 |
| CA | 3044112 A1 | 6/2018 |
| CN | 103834667 A | 6/2014 |
| CN | 104812405 A | 7/2015 |
| CN | 104844712 A | 8/2015 |
| CN | 110381992 A | 10/2019 |
| EP | 0 622 081 A2 | 11/1994 |
| EP | 2 910 251 A1 | 8/2015 |
| EP | 2910251 A1 | 8/2015 |
| EP | 3548076 A2 | 10/2019 |
| KR | 10-2019-0110090 A | 9/2019 |
| RU | 2510281 C2 | 3/2014 |

(Continued)

OTHER PUBLICATIONS

Brile et al. Vaccine, vol. 14, No. 9, Jun. 1, 1996 pp. 858-867 (Year: 1996).*
Fukuyama et al. Mucosal Immunology, vol. 8, No. 5, pp. 1144-1153 Feb. 11, 2015 (Year: 2015).*
Beall, et al. "Pneumococcal pspA Sequence Types of Prevalent Multiresistant Pneumococcal Strains in the United States and of Internationally Disseminated Clones", Journal of Clinical Microbiology, vol. 38, No. 10, Oct. 2000, pp. 3663-3669.
Darrieux, et al. "Recognition of Pneumococcal Isolates by Antisera Raised Against PspA Fragments from Different Clades", Journal of Medical Microbiology, vol. 57, 2008, pp. 273-278.

(Continued)

*Primary Examiner* — Jana A Hines
*Assistant Examiner* — Khatol S Shahnan Shah
(74) *Attorney, Agent, or Firm* — Wiley Rein

(57) ABSTRACT

The present embodiments provide compositions and methods related to novel recombinant protein immunogens, comprising specific portions of alpha helical domains (aHD) and proline rich regions (PRD) of pneumococcal surface protein A (PspA), which portions are linked to provide aHD-PRD constructs. The aHD and PRD proteins constituting the aHD-PRD constructs are selected to maximize cross-reactivity and provide protection against a broad spectrum of pneumococcal serotypes. Immunogenic compositions, including vaccines, comprising at least one aHD PRD construct may also include a non-linked aHD portion. Also provided are recombinant nucleic acid molecules that encode aHD-PRD constructs, vectors and recombinant host cells containing such molecules, aHD-PRD expression products, use of such nucleic acid molecules to express aHD-PRD constructs by recombinant techniques, and use of the expression products to elicit an immune or protective response against pneumococcal disease in a suitable host.

7 Claims, 13 Drawing Sheets

Specification includes a Sequence Listing.

(56) References Cited

FOREIGN PATENT DOCUMENTS

| RU | 2019118969 A | 1/2021 | | |
|---|---|---|---|---|
| WO | 2007/089866 A2 | 8/2007 | | |
| WO | WO-2007089866 A2 * | 8/2007 | ............ | A61P 11/00 |
| WO | 2014/045621 A1 | 3/2014 | | |
| WO | 2018/102774 A2 | 6/2018 | | |

OTHER PUBLICATIONS

Office Action received for Russian Patent Application No. 2019118969, dated Jul. 13, 2021, 9 pages (3 pages of English Translation and 6 pages of Official Copy).
Office Action received for Australian Patent Application No. 2017366726, dated Jun. 28, 2021, 3 pages (Official Copy Only).
Office Action received for Canadian Patent Application No. 3044112, dated Oct. 19, 2021, 4 pages.
Office Action received for Japanese Patent Application No. 2019-528878, dated Nov. 1, 2021, 6 pages (3 pages of English Translation and 3 pages of Official Copy).
International Search issued in WO 2018/102774 A3, filed Jun. 7, 2018, which claims priority from PCT/US2017/064347, filed Dec. 1, 2017.
Briles, D.E. et al., "PspA, a protection-eliciting pneumococcal protein: immunogenicity of isolated native PspA in mice", Vaccine, Elsevier, Amsterdam, NL, vol. 14, No. 9, Jun. 1, 1996, pp. 858-867, XP004069573, ISSN: 0264-410X, DOI: 10.1016/0264-410X(96) 82948-3, abstract p. 863, left-hand column, table 5.
Y. Fukuyama et al: "Nanogel-based pneumococcal surface protein A nasal vaccine induces microRNA-associated Th17 cell responses with neutralizing antibodies against *Streptococcus pneumoniae* in macaques", Mucosal Immunology, vol. 8, No. 5, Feb. 11, 2015 (Feb. 11, 2015), pp. 1144-1153, XP055459610, US, ISSN: 1933-0219, DOI: 10.1038/mi.2015.5 cited in the application abstract, p. 1147-p. 1148, p. 1151, right-hand column paragraph 2.
C.C. Daniels, et al.: "The Proline-Rich Region of Pneumococcal Surface Proteins A and C Contains Surface-Accessible Epitopes Common to All Pneumococci and Elicits Antibody-Mediated Protection against Sepsis", Infection and Immunity, vol. 78, No. 5, May 1, 2010 (May 1, 2010), pp. 2163-2172, XP055115771, ISSN: 0019-9567, DOI: 10.1128/IAI.01199-09 p. 2167-p. 2168.
Piao Zhenyu et al.: "Protective properties of a fusion pneumococcal surface protein A (PspA) vaccine against pneumococcal challenge by five different PspA clades in mice", Vaccine , Elsevier, Amsterdam, NL, vol. 32, No. 43, Aug. 12, 2014) (Aug. 12, 2014), pp. 5607-5613. XPO29062562, ISSN: 0264-410X, DOI: 10.1016/J. VACCINE.2014.07.108, the whole document.

Breles D E et al: "Immunization of humans with recombinant pneumococcai surface protein A (rPspA) elicits antibodies that passiveiy protect mice from fatal infection with *Streptococcus pneumoniae* bearingheterologous PspA", Journal of Infectious Diseases, JID, UNIVERSITY of CHicago Press, Chicago, IL, vol. 182, No. 6, Dec. 1, 2000 (Dec. 1, 2000), pp. 1694-1701, XP002756434, ISSN: 0022-1899, DOI: 10.1086/317602 [retrieved on Nov. 8, 2000] the whole document.
Hollingshead et al., Diversity of PspA: Mosaic Genes and Evidence for Past Recombination in *Streptococcus pneumoniae*, Infection and Immunity, vol. 68, No. 10, Oct. 2000, pp. 5889-5900.
Pakula et al., Genetic Analysis of Protein Stability and Function, Annual Review of Genetics, vol. 23, 1989, pp. 289-310.
Proteomes—*Streptococcus pneumoniae* GA47439, Available online at: <https://www.uniprot.org/proteomes/UP000004128>, 2011.
Office Action Received for Australian Patent Application No. 2017366726, dated Nov. 25, 2020, 6 pages.
Office Action Received for Russian Patent Application No. 2019118969, dated Dec. 14, 2020, 10 Pages (3 pages of English Translation and 7 pages of Official Copy).
Office Action Received for Russian Patent Application No. 2019118969, dated Jul. 15, 2020, 10 Pages (3 pages of English Translation and 7 pages of Official Copy).
Office Action received for Japanese Patent Application No. 2019-528878, dated Jun. 21, 2022, 4 pages (official copy only).
Darrieux, et al. "Fusion Proteins Containing Family 1 and Family 2 PspA Fragments Elicit Protection against *Streptococcus pneumoniae* That Correlates with Antibody-Mediated Enhancement of Complement Debosition",Journal of Infection and Immunity, vol. 75, No. 12, 2007, pp. 5930-5938.
Xin, et al. "PspA Family Fusion Proteins Delivered by Attenuated Salmonella enterica Serovar Typhimurium Extend and Enhance Protection against *Streptococcus pneumoniae*",Journal of Infection and Immunity, vol. 77, No. 10, 2009, pp. 4518-4528.
International Preliminary Report on Patentability Chapter I received for International PCT Application Serial No. PCT/US17/64347 dated Jun. 13, 2019, 11 pages.
"Choline-Binding Protein, Partial [*Streptococcus pneumoniae*]", NCBI, GenBank, Accession KYA26723, Version KYA26723.1, Mar. 10, 2016, 2 Pages.
Nabors et al., "Immunization of Healthy Adults with a Single Recombinant Pneumococcal Surface Protein A (PspA) Variant Stimulates Broadly Cross-Reactive Antibodies to Heterologous PspA Molecules", Vaccine, vol. 18, 2000, pp. 1743-1754.
Office Action received for Chinese Patent Application Serial No. 201780086110.6, dated Sep. 21, 2022, 16 Pages (Official Copy Only).

* cited by examiner

PNEUMOCOCCAL VACCINE COMBINING SELECTED ALPHA HELICAL DOMAINS AND PROLINE RICH DOMAINS OF PNEUMOCOCCAL SURFACE PROTEIN A

RELATED APPLICATION

This Application is a National Phase entry of PCT/US2017/064347, filed Dec. 1, 2017, which claims priority benefit of U.S. Provisional Patent Application No. 62/429,782, filed Dec. 3, 2016, both of which are incorporated fully herein by reference for all purposes.

GOVERNMENT LICENSE RIGHTS

This invention was made with government support under Grants No. R01AI118805 and No. 2R56AI021548, awarded by NIH/NIAID. The government has certain rights in the invention.

SEQUENCE LISTING

The instant application contains a Sequence Listing, which has been submitted concurrently in ASCII format, and is incorporated in its entirety as part of this specification.

FIELD

The present embodiments relate to recombinant pneumococcal proteins, recombinant genetic constructs expressing these, and antigens, immunogens, and vaccines comprising these proteins.

BACKGROUND

*Streptococcus pneumoniae*, also known as pneumococcus, is the leading cause of bacterial pneumonia deaths worldwide. It is also a leading cause of meningitis and bacterial blood infection (sepsis), conditions that are classified as invasive pneumococcal disease (IPD). Its victims are primarily young children and elderly adults. Even today with the widespread use of vaccines, about 50,000 cases of pneumococcal bacteremia and 5000 cases of meningitis occur annually in the United States. Over 25% of these patients die, and survivors of meningitis are usually permanently impaired; and over 120,000 Americans are hospitalized each year for pneumococcal pneumonia for which sepsis is not confirmed. In addition, pneumococcus is a major cause of childhood otitis media.

Currently approved vaccines comprise several pneumococcal surface polysaccharides (also known as capsular antigens) either conjugated to a protein carrier (pneumococcal conjugate vaccines: PCV) or unconjugated (pneumococcal polysaccharide vaccines: PPSV). There are over eighty pneumococcal serotypes, each characterized by capsular antigen; so although the present PVCs are efficacious against several serotypes, they generally do not offer broad protection against disease because the vast majority of capsular antigens are simply not included in the vaccines. Data from several countries indicate that following introduction of PCVs, incidence rates of IPD declined dramatically to less than 10% of the pre-PCV-era level; but IPD rates have recently surpassed half the pre-PCV-era levels in infants, and have exceeded pre-PCV-era levels in elderly adults. This increase is due almost entirely to non-PCV-covered pneumococcal serotypes. Thus, there is great and increasing need for a vaccine that has broader coverage against pneumococcal disease than those offered currently. Finally, regarding PPSVs, these vaccines do not induce protective immune responses in children, and induce only weak to moderate responses in elderly adults against the 23 capsular antigens included in this vaccine.

SUMMARY

The present embodiments provide a novel protein immunogen that maximizes cross-reactivity and provides protection against a broad spectrum of pneumococcal serotypes. More specifically, the recombinant constructs described herein provide selected, linked portions of pneumococcal surface protein A (PspA) that can provide broad immunity against pneumococcal disease, including pneumonia, meningitis, and sepsis caused by *S. pneumoniae*. In particular, these embodiments provide novel recombinant antigenic and immunogenic proteins comprising an alpha helical domain (aHD), or a portion thereof, and a proline rich domain (PRD), or a portion thereof, each domain derived from the PspA protein of a different pneumococcal strain; the recombinant protein referred to herein as an aHD-PRD construct. The present embodiments also provide vaccines comprising at least one aHD-PRD construct, such as one, two, three, or four aHD-PRD constructs. The vaccine may further comprise a recombinant aHD protein that is not linked to a PRD polypeptide. In a vaccine comprising more than one aHD-PRD construct, the respective PRD portions of each construct can be selected from one, two, or three different PRD Groups, which Groups have not been characterized previously. Additionally, the present embodiments provide nucleic acid molecules (e.g., DNA) that encode the amino acids constituting aHD-PRD constructs; vectors comprising such nucleic acid molecules; recombinant host cells comprising such nucleic acid molecules or vectors; expression products of such nucleic acid molecules; use of such nucleic acid molecules to express aHD-PRD constructs by recombinant techniques; and use of the expression products to elicit an immune or protective response against pneumococcal disease in a suitable host.

One aspect of the present embodiments provides an artificial, chimeric protein consisting of a combination of an antigenic aHD protein and an antigenic PRD polypeptide: an aHD-PRD construct. In other words, particular embodiments provide alpha-helical domains of PspA or portions thereof (aHDs) linked with proline rich domains of PspA or portions thereof (PRDs) (i.e., fusion or chimeric proteins) capable of inducing an immune response against pneumococcal disease (hereinafter, aHD-PRD constructs). In some embodiments, an aHD is linked to a PRD by a direct, end-to-end peptide bond; i.e., the C-terminus of an aHD is linked by a peptide bond directly to the N-terminus of a PRD. In some embodiments, the aHD and PRD are linked through a peptide "linker." In other embodiments, the aHD and PRD are linked or conjugated via a chemical moiety. In some embodiments, an immunogenic aHD-PRD construct or a combination of aHD-PRD constructs, when used as a component of a vaccine, provides protective immunity against pneumococcal disease. In other embodiments, a combination of aHD-PRD constructs and unlinked aHDs, when used as components of a vaccine, provide protective immunity against pneumococcal disease.

Another aspect provides a process for selecting aHDs and PRDs for inclusion in a plurality of aHD-PRD constructs, which selection process maximizes the likelihood of protective cross-reactivity against pathogenic pneumococci. In particular, aHD-PRD constructs comprising one of three different PRD Groups may be selected based upon patterns of amino acid sequences that characterize these PRDs into Groups. In one embodiment, the process comprises (a) selecting a first aHD from a first clade within a first family of pneumococcal serotypes for inclusion in a first aHD-PRD construct, and selecting a first PRD from a first Group of PRD serotypes for inclusion in the first aHD-PRD construct; and (b) selecting a second aHD from a second clade within the first or a second family of pneumococcal serotypes for inclusion in a second aHD-PRD construct, and selecting a second PRD from a second Group of PRD serotypes for inclusion in the second aHD-PRD construct. This process may be repeated to select additional, different pairings of aHD and PRD to design a plurality of aHD-PRD constructs.

A further embodiment provides a process for selecting at least one additional aHD for supplementing a composition comprising at least one aHD-PRD construct, wherein the aHD is not linked to a PRD, and wherein the unlinked aHD is selected in a manner to increase immunogenic cross-reactivity for expanded coverage of pneumococcal strains. For example, the supplemental aHD may be selected from a clade or family not represented in the aHD-PRD construct.

A specific embodiment provides an antigenic composition, an immunogenic composition, or a vaccine, comprising a plurality of aHD-PRD constructs, wherein the aHD and PRD are selected according to a process described herein. A further specific embodiment provides an immunogenic composition or vaccine comprising three aHD-PRD constructs, wherein the aHD and PRD are selected according to a process described herein.

At least one embodiment provides an immunogenic composition or vaccine comprising at least one of the proteins or constructs described herein, e.g., at least one aHD-PRD construct, and at least one adjuvant. The vaccine may further comprise at least one supplemental, unlinked aHD.

Another aspect of the present embodiments provides formulations and delivery processes for a vaccine as described herein, for example, formulations suitable for administration and methods of administering such vaccine formulations. One embodiment provides a vaccine as described herein, i.e., comprising at least one aHD-PRD construct, formulated for intramuscular (IM) injection. Another embodiment provides a vaccine as described herein formulated for mucosal administration; and a specific embodiment provides formulations that may be administered intranasally (IN), orally (e.g., sublingual [SL]), or by spray into the lung bronchi. A specific embodiment provides a vaccine comprising at least one aHD-PRD construct entrapped in a nanogel for mucosal surface administration. For example, the nanogel can comprise a cationic cholesteryl-group-bearing pullulan (cCHP).

A further aspect of the present embodiments relates to antigenic or immunogenic combinations comprising other antigens. At least one embodiment provides vaccines or immunogenic compositions comprising at least one aHD-PRD construct and at least one other antigen, wherein the other antigen enhances an immune response against S. pneumonia. A specific embodiment provides a vaccine against S. pneumonia comprising at least one aHD-PRD construct and at least one other S. pneumoniae antigen, such as pneumolysin or neuraminidase.

Another aspect of the present embodiments provides a process of expressing aHD-PRD constructs using genetically modified cells, including genetically modified microorganisms. Accordingly, an embodiment provides recombinant nucleic acids (polynucleotides) (such as DNA molecules) that encode antigenic or immunogenic aHD-PRD constructs. An embodiment provides isolated synthetic DNA molecules or recombinant DNA molecules (including cDNA and semi-synthetic cDNA) that encode the aHD-PRD constructs described herein.

The recombinant aHD-PRD constructs described herein provide selected portions of PspA that can provide broad immunity against pneumococcal disease, including pneumonia, meningitis, and sepsis caused by S. pneumoniae. In particular, these embodiments provide antigens and immunogens comprising the alpha helical domains (aHDs) and the proline rich domains (PRDs) of PspA; genes or portions of genes encoding the amino acid sequences that constitute aHD-PRD constructs, the use of these to express aHD-PRD constructs by recombinant techniques, and their use in vaccines. The present embodiments also relate to vaccines comprising one or more of these aHD-PRD immunogenic constructs.

BRIEF DESCRIPTION OF THE DRAWINGS

FIG. 3A evidences how diversity among PRDs can be grouped; and this information may be used to design vaccine components that cover each group and provide cross-reactivity at least within that group. Because of the large number of repeat motifs within each of the PRD Groups as well as variation in PRD lengths, the summed length of the branch lines connecting strains/Groups does not reliably estimate the likelihood of site-specific single-pair amino acid substitutions between species/Groups, as was possible for CDRs in FIG. 2.

FIG. 7B: 50° C.). y-axis: reciprocal $\log_2$ ELISA titer; bars indicate standard deviations; according to immunizing antigen. These data illustrate the ability of each of the nasally administered nanogel-formulated antigens to elicit a strong systemic, antigen-specific IgG response.

Figure 1:
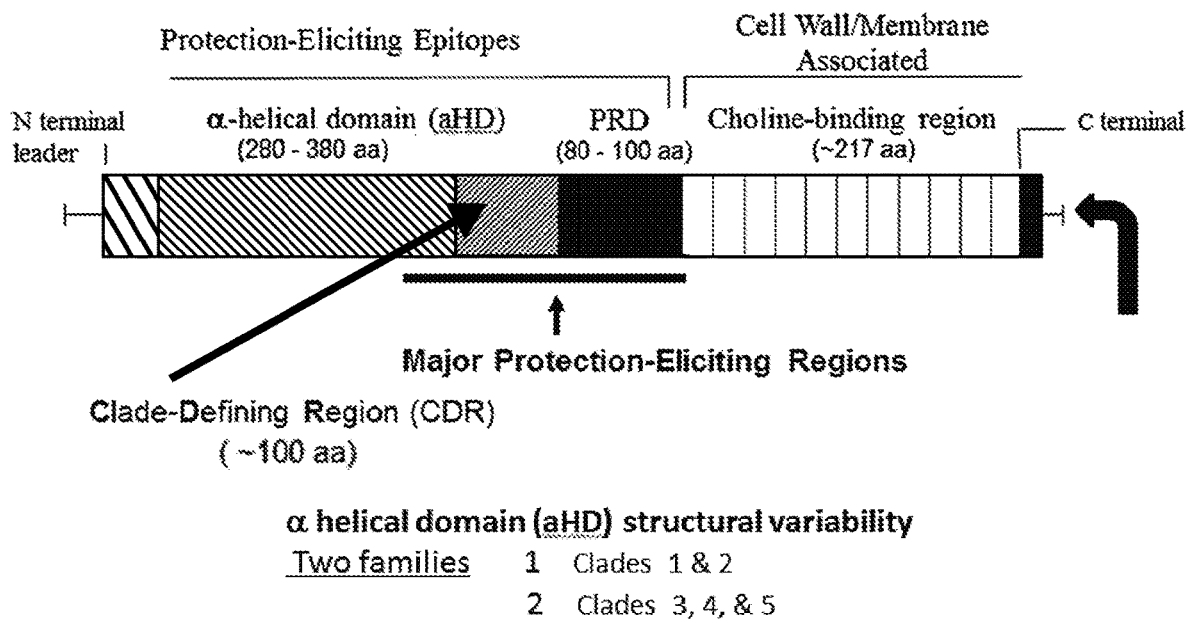
FIG. 1 illustrates the structure of PspA domains and a schematic relationship of PspA to the pneumococcal bacterial surface; showing positions and relative sizes of aHD, PRD, and choline-binding regions, and the relationship of PspA to the surface structure of S. pneumoniae.
Figure 1:
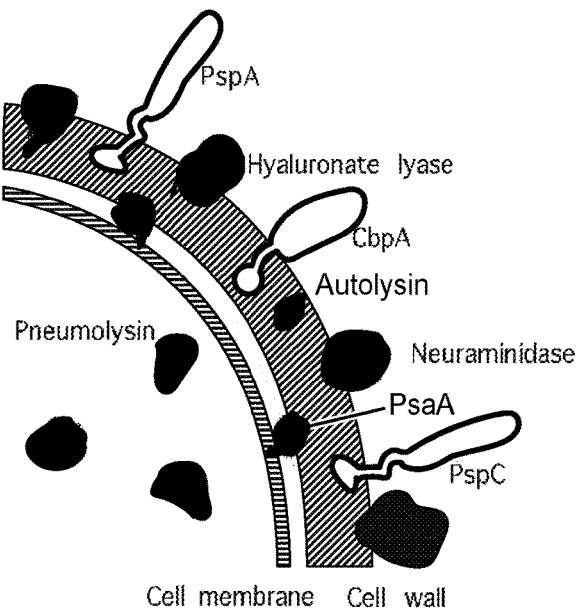

ATCC6303 1×10⁷ CFU. ○ control; ▲ IN; ■ IM; *poorly covered by PCV13 and PPSV23; **not covered by PPSV23. These data suggest that IM or IN-nanogel immunization with three aHD-PRD constructs protects against pneumococcal disease. Protection extends even against strains with PspA aHD clades not represented in the vaccine antigens, and against capsular types not covered by current vaccines.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list.

All values are approximate as there is some fluctuation in the ratio of carrier molecules (e.g., nanogel) or adjuvant (e.g., alum) to antigen, the precise compositions of these carrier molecules, adjuvants and antigens, and in the formulation processes. Accordingly, other than in the operating examples, or where otherwise indicated, all numbers expressing quantities or reaction conditions used herein should be understood as modified in all instances by the term "about" unless stated to the contrary; "about" refers generally to ±1% of the designated value, but may allow for ±5% or ±10% of the designated value as accepted in the relevant context by one of skill in the art.

Recombinant DNA techniques can be carried out according to standard protocols as known in the art. See e.g., Sambrook et al., MOLECULAR CLONING: LAB. MANUAL (2nd Ed., Cold Spring Harbor Lab. Press, NY, 1989); Ausubel et al., CURRENT PROTOCOLS MOLEC. BIOL. (1994 and updates); DNA CLONING: PRACTICAL APPROACH, Vols. 1-4 (Glover & Hames, Eds., IRL Press 1995, 1996), Croy, PLANT MOLEC. BIOL. LABFAX (BIOS Sci. Pub. Ltd. & Blackwell Sci. Pub., UK, 1993); WO 2015089587.

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. In order that the present disclosure can be more readily understood, certain terms are defined; additional definitions are set forth throughout the detailed description.

An antigen is a substance that is recognized by a product of the immune response. Under appropriate conditions, an antigen is capable of acting as an immunogen: inducing a specific immune response in the body; and, accordingly, the antigen is capable of reacting with product(s) of that response. Generally speaking, the specific immune response products may be antibodies that bind specifically to the antigen, or T-lymphocytes that are sensitized to react to the antigen. Antigens include foreign substances, such as proteins or portions thereof (polypeptides or peptides), nucleic acids or polysaccharides of a bacterium, virus, fungus, or other microbe.

Cross reactivity generally means the degree to which an immune response to a particular antigen also covers other antigens. Antigens or pathogens that elicit the most protective responses often tend to be variable in structure. In the case of a vaccine intended to produce a protective response against an infectious microorganism, cross-reactivity typically refers to the degree to which the immune response to the particular antigens in the vaccine produce antibodies that react not only with the immunizing antigens, but also with a wider array of variants of the same antigen in different strains of the pathogenic organism. Because it is often impractical to commercially produce a vaccine that contains all the variations of such an antigen, careful selection of a number of variants of the antigen that are highly cross-reactive from a limited number of strains can induce antibodies that react against strains with many different variants of the antigen. In the case of the pneumococcus, capsular polysaccharide antigens (i.e., the antigens in current vaccines) have low cross-reactivity. Some protein antigens, particularly PspA, have high cross reactivity.

An immune response (immunogenic response) is a host response to an antigen, effected by elements of the immune system. Among the elements of the immune system most commonly involved in immune responses are leukocytes (white cells), consisting of neutrophils, basophils, eosinophils, monocytes and their progeny, and lymphocytes. Lymphocytes, in turn, can be classified into natural killer cells; B-cells which produce antibodies; and T-cells, of which there are various types that regulate or enhance various aspects of an immune response. Most vaccines are designed to elicit an adaptive immune response that involves identification of the vaccine antigen as "foreign" followed by production of antibody molecules or T-cells that react with these antigens. Effective antibody and T-cell reactions can lead to the destruction of the pathogens displaying such antigens. Effective antibody responses can also interfere with the function of virulence molecules that are on the pathogen's surface, or are released by the pathogen.

An immunogen is a substance capable of generating an immune response, typically an antigen. More specifically, an immunogen refers to a molecule that is capable of eliciting an immune response by an organism's immune system, whereas an antigen refers to a molecule (a hapten) that is capable of binding to the product of that immune response. Hence, an immunogen is typically an antigen, but an antigen may not necessarily be an immunogen. Accordingly, immunogenicity is the ability to induce humoral or cell-mediated immune responses. For example, when a B-cell is activated by an immunogen, it differentiates into a plasma B-cell that produces antibodies that bind with an antigen. In the context of pneumococcal vaccines, capsular polysaccharides are antigens, but do not act as immunogens in infants unless conjugated to a protein carrier.

A vaccine is a composition used to induce an immune response, usually to provide specific and protective immunity against a particular disease without causing a severe form of that disease. In the case of vaccines against infectious diseases, a vaccine typically contains an agent that resembles antigen(s) of the disease-causing pathogen. Often, this agent is a weakened (attenuated) or killed form of the pathogen, its toxoids (non-toxic versions of toxins), or one of its surface proteins or surface polysaccharides. The agent mimics a pathogenic immunogen and stimulates the body's immune system to recognize the pathogen as foreign (i.e., an antigen) and destroy it, or to destroy cells containing the pathogen. Ideally, a vaccine also causes the immune system to "remember" the immunogen and the pathogen from which the immunogen was derived, so that the immune system will more easily recognize and neutralize the pathogen's antigens in the future. Vaccine compositions can be formulated in any appropriate form, and may include pharmaceutically acceptable excipients, such as diluents or carriers or further ingredients. Excipients typically do not contribute to the effects elicited by the immunogens of the present embodiments upon administration; but ingredients or compounds that contribute or modulate the effect of the present immunogenic constructs are envisioned: particularly adjuvants. A person skilled in the art can determine such suitable excipients, which are well-known and, in the case of human and animal vaccines, FDA approved. Vaccines can be administered in the appropriate dosage form via injection, ingestion, application to the skin, or application to mucosal surfaces.

As noted above, the present embodiments provide novel antigens, immunogens, and vaccines against S. pneumoniae, the leading cause of bacterial pneumonia deaths worldwide, a leading cause of IPD, and a major cause of childhood otitis media.

Almost 100 pneumococcal serotypes have been identified on the basis of the antigenic capsular polysaccharides covering the bacterial cell wall. Current pneumococcal vaccines contain a mixture of several capsular polysaccharides. The earliest-approved pneumococcal polysaccharide vaccine (known as PPSV14 or Pneumovax® vaccine, FDA-approved in 1977), contained capsular polysaccharides from fourteen commonly found pneumococcal serotypes. These antigens were unconjugated, meaning the polysaccharides were not attached (conjugated) to proteins that serve as immune system co-stimulants. Later, PPSV23 vaccine (Pneumovax®23 vaccine, FDA-approved in 1983), containing an additional nine unconjugated polysaccharide capsular antigens, was introduced. Children under age 2, however, generally do not respond to the unconjugated capsular antigens in these vaccines. Wald, 40 Clin. Pediatr. 601 (2001). Additionally, protection is low in older children with existing medical conditions. In adults aged over 65, PPSV23 reduces the risk of developing pneumonia associated with sepsis by about 45%; but does not reduce the overall risk for pneumonia, and probably does not reduce the overall risk of death within three years of vaccination. Jackson et al., 348 N. Engl. J. Med. (2003); Ladhani et al., 58 Clin. Infect. Dis. 517 (2014).

More recent vaccines contain capsular polysaccharides conjugated to a protein molecule that co-stimulates the immune system. These pneumococcal conjugate vaccines (PCVs) activate both a T-cell immune response and an antibody producing B-cell (humoral) response. PCVs have been shown to reduce risk of IPD due to covered serotypes by over 95% in infants. A large study in adults aged over 66 indicated that PCV immunization reduced by 75% the risk of sepsis-associated-pneumonia caused by the vaccine-covered serotypes, while reducing by about 45% the risk of pneumonia without sepsis due to covered serotypes. Bonten et al., 372 N. Engl. J. Med. 1114 (2015).

Although the seven serotypes in the first PCV vaccine (PCV7 or Prevnar® vaccine, FDA-approved in 2000) were selected to cover what were then the most common and virulent serotypes, incidence of disease due to non-covered serotypes soon began to increase in vaccine-enhanced population immunity, a phenomenon called serotype replacement. In response, six more serotypes were added to make PCV13 (Prevnar13® vaccine, FDA-approved in 2010), which has replaced PCV7 as the standard of care in most developed countries. Despite declines in disease due to the newly-covered six serotypes, serotype replacement continues unabated and disease rates may rise because of serotypes other than the thirteen covered by PCV13. More specifically, data from several countries indicate that although incidence rates of IPD declined dramatically following introduction of PCV7—to less than 10% of incidence rates of the pre-PCV era—those rates have recently surpassed half the pre-PCV-vaccine-era levels in infants, and have exceeded pre-PCV-era levels in elderly adults. This increase is due, almost entirely, to non-PCV-13-covered serotypes. CDC, PINK BOOK 13TH ED. (2015); Leputre et al., 33 Vaccine 359 (2015); Public Health England (Mar. 4, 2016).

Thus, there is great and increasing need for a pneumococcal vaccine that has broader coverage than PCV13. Simply adding many additional capsular polysaccharide antigens to PCV13 may fail in the long run because: (1) the process of conjugating polysaccharide antigens is technically complex; and (2) it is likely that as more antigens are added, the immune responses against each of the existing thirteen capsular antigens will diminish, a phenomenon known as antigen competition. Paton & Bosiego, PROTEIN VACCINES 421 (Siber, ed., ASM Press, 2008); Andrews et al., 14 Lancet Infect. Dis. 839 (2014).

Pneumococcal proteins may provide an immunogenic alternative to conventional PPSV and PCV vaccines. Several antigenic proteins near the pneumococcal surface have been identified (see FIG. 1). Pneumococcal surface protein A (PspA) is among the most promising of these in terms of antigenicity, surface exposure, immunogenicity, cross-reactivity among its various strains, and extent to which some development as a vaccine has already occurred. See U.S. Pat. No. 6,592,876 (Briles et al., 2003) and U.S. Pat. No. 5,997,882 (Briles et al., 1999); Ginsberg et al., 11 Expert Rev. Vaccines 279 (2012); Moreno et al., 17 Clin. Vaccine Immunol. 439 (2010); Daniels et al., 40 Microbial Path. 228 (2006). In its native state, PspA functions to reduce pneumococci-induced complement activation, and thus is a major factor in pneumococcal survival and virulence in the infected host. The most distal extension of PspA from the pneumococcal surface (i.e., the N-terminal region of PspA) consists of 280 to 380 amino acids known as the alpha helical domain (aHD) (see FIG. 1). Of all the regions of PspA, the aHD has been most-studied in terms of terms of safety and efficacy as a vaccine antigen. U.S. Pat. Nos. 6,592,876, 6,638,516 (Briles et al., 2003); Briles et al., 18 Vaccine 1707 (2000a); Hollingshead et al., 68 Infect. Immun 5889 (2000); Nabors et al., 18 Vaccine 1743 (2000).

More recently, the proline rich domain (PRD) of PspA, which extends from the proximal C-terminus of the aHD to the bacterial membrane, has also been shown to be immunogenic. U.S. Pat. No. 8,808,704 (Hollingshead & Briles, 2014); Daniels et al., 78 Infect. Immun 2163 (2010). Previous studies, however, did not fully recognize or characterize the diversity of PRDs, examine PRD cross-reactivity, nor attempt to incorporate PRDs into immunogenic aHD-PRD construct-based vaccines as described herein.

A challenge with respect to developing effective PspA vaccines is to induce strong cross-reactivity against most forms of PspA found on pathogenic pneumococci; while using antigenic regions of a relatively small number of different PspA proteins to avoid antigenic competition and provide a vaccine that is easy to manufacture. These design challenges are not unique to PspA-based vaccines, but remain challenging for design and manufacture of most vaccines.

It has been reported that the proximal (C terminal) 30% of the aHD is its most immunogenic region. Hollingshead et al., 2000. This portion of the aHD is known as the clade defining region (CDR) of PspA. On the basis of the amino acid sequences of their clade defining regions (CDRs), aHDs can be grouped into two main families that together account for about 98% of known pathogenic subtypes. These families can, in turn, be grouped into five clades (clade 1 and clade 2 constitute family 1; clades 3, 4 and 5 constitute family 2), depending upon their amino acid sequences. A third family consists only of clade 6 and accounts for only about 2.2% of *S. pneumoniae* isolated from patients (Hollingshead et al., 2000; Vela Coral et al., 7 Emerging Infect. Dis. 823 (2001); Hotomi et al., PloS one 8:e58124 (2013), and only 3 of the 136 unique *S. pneumoniae* strains whose PspA gene sequences are characterized herein (see Example 2). The aHDs from the same clade share similar amino acid sequences, while aHDs from clades in different families share the least homology. Hollingshead & Briles, 2000. FIG. 2 is a tree diagram of the 136 pneumococcal strains whose PspA gene sequences we analyzed. It shows these strained mapped according to homology among the amino acids that constitute their CDRs. This confirms earlier research on the clustering of CDRs into three families (two of which are clinically significant) and six clades (five of which are clinically significant).

Unexpectedly, the study also indicated that the CDRs of many strains in the same clade are identical, and an even larger number are similar. This suggests that aHDs containing CDRs that are shared across a number of clinically important strains are likely to be prime candidates for vaccine antigens. In addition, FIG. 2 enables approximate quantification of the degree of homology between the CDRs of any pneumococcal family, clade, or characterized strain (see Example 2). Thus, the tree diagram in FIG. 2A-FIG. 2D, and the details views therein, provides a novel and advantageous guide for the strategic selection of a limited number of aHDs (and their highly antigenic CDRs) to include as vaccine antigens so as to maximize cross-reactivity between the selected aHDs and the aHDs of pneumococcal strains not included in the vaccine.

Unlike polysaccharide capsular antigens which have low immuno-cross-reactivity, antibodies triggered by exposure to a particular aHD usually exhibit cross-reactivity; not only against pneumococci from the same PspA clade, but also against pneumococci from different clades in the same family (U.S. Pat. No. 6,638,516; McDaniel et al., 59 Infect. Immun 222 (1991); Nabors et al., 2000; Vela Coral et al., 2001, Darrieux et al., 75 Infect. Immun 5930 (2007); and even, in the case of some immunizing aHDs, against pneumococci from a different PspA family (Roche et al., 71 Infect. Immun 1033 (2003), Darrieux et al., 57 J. Med. Micro. 273 (2008), Moreno et al., 2010, Fukuyama et al., 2015). This cross-reactivity against pneumococci with different aHDs supports the present strategy of selecting, with novel guidance from FIG. 2, a relatively small number of aHDs as components of a vaccine that can protect against a wide range of pathogenic pneumococci.

Importantly and quite unexpectedly, analysis of the amino acid sequences of PRDs across many pneumococcal strains revealed that PRDs can be characterized into one of three distinct Groups based on sequences of the amino acids comprising the PRDs (FIG. 3A-FIG. 3D). Within each of these Groups, not only are sequence homologies high, but characteristic motifs of repeated amino acid sequences appear frequently (Table 1-Table 4). Unexpectedly, many PRDs from different pneumococcal strains within each group are identical, which helps narrow the range of possible PRD antigens to include in a vaccine. At least some of these PRDs (or portions thereof) are antigenic (Examples 4-6, below) (see also U.S. Pat. No. 8,808,704; Daniels et al., 2010). Because of the high similarity in repeated motifs within PRD groups, cross-reactivity within PRD groups may likely prove high. Thus, a vaccine that contains at least one PRD from each of the three groups has a higher probability of inducing an immune response that covers many strains of pathogenic pneumococci. FIG. 3A-FIG. 3D provides a novel tree diagram, and details thereof, for the 136 pneumococcal strains whose PRDs we analyzed. Thus, the tree diagram in FIG. 3A-FIG. 3D provides a novel and advantageous guide for the strategic selection of a limited number of PRDs to include as vaccine antigens, thus maximizing cross-reactivity between the selected PRDs and the PRDs of pneumococcal strains not included in the vaccine.

The present embodiments also enable confirmation of whether certain PRD features enhance or diminish immunogenicity. For example, the long PKPAPA (SEQ ID NO:7) repeats characteristic of PRD Group 2 polypeptides may be less immunogenic than the more varied motifs found in Groups 1 and 3, particularly the non-proline blocks (NPBs) that characterizes Group 3. Daniels, 2010. As noted, the selection of PRDs may also be guided by FIG. 3, which provides a novel approach that suggests how, within a particular PRD group, to select as a vaccine candidate a particular PRD that is relatively close in homology to the other PRDs in the same group. Other factors (such as length) being equal, this may maximize the likelihood of extensive cross-reactivity with at least other same-Group PRDs.

By combining selection of PRDs (or portions of PRDs) from each of the three PRD Groups with selection of highly immunogenic and cross-reactive aHDs (or portions thereof) from each of the aHD families to provide a single vaccine, we may generate strong, redundant, cross-reactive immunity that protects against nearly all pathogenic pneumococcal strains.

Figure 6A:
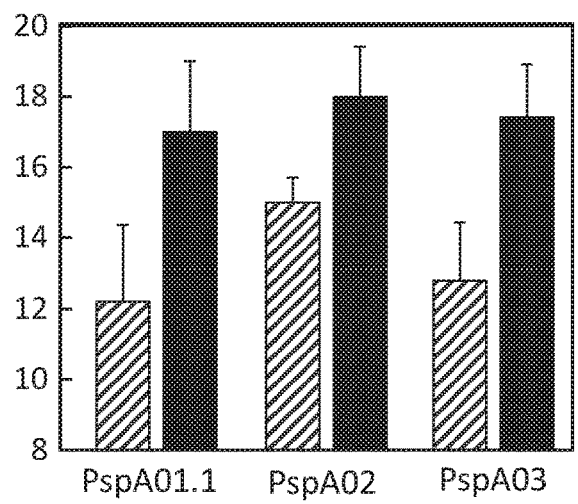
FIG. 6A and FIG. 6B show antigen-specific serum IgG responses in mice (n=5 per group) following primary (white) and boost (black) IM immunization with individual exemplative aHD-PRD constructs (n=5 per group, bars indicate standard deviations, two dose levels [FIG. 6A: 3 µg/dose, FIG. 6B: 10 µg/dose] for each of three constructs). y-axis: reciprocal $\log_2$ ELISA titer; bars indicate standard deviations. These data illustrate the ability of IM immunization to elicit a strong antigen-specific, systemic IgG response.
Figure 6B:
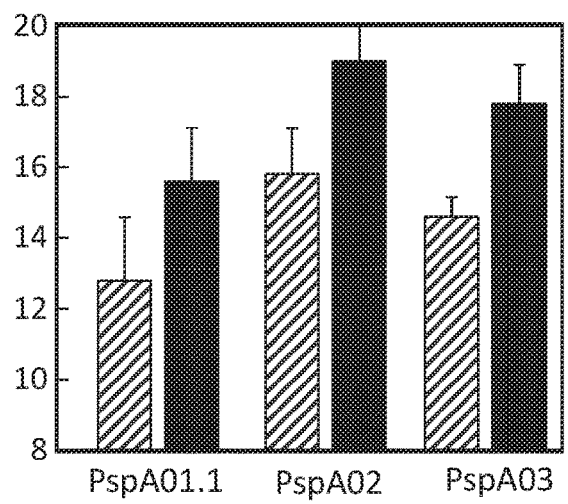
Figure 7A:
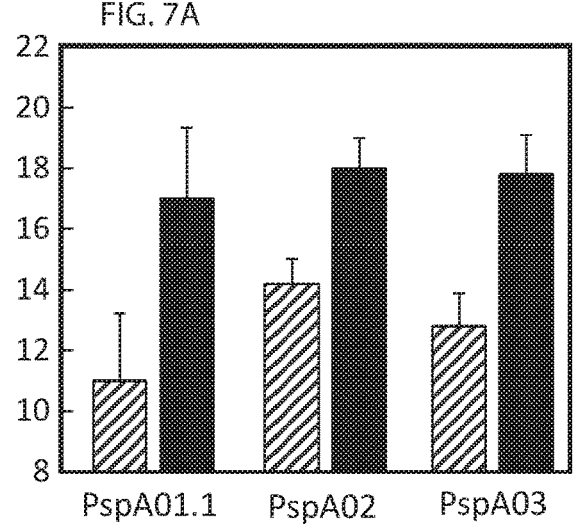
FIG. 7A and FIG. 7B show antigen-specific serum IgG responses in mice (n=5 per group) following primary (white) and boost (black) IN immunization (nasally administered nanogel formulation) with individual exemplative cCHP-aHD-PRD constructs. Nanogel complexes (i.e., cCHP-aHD-PRD) were formulated by heat treatment at two different temperatures (FIG. 7A: 40° C.
Figure 7B:
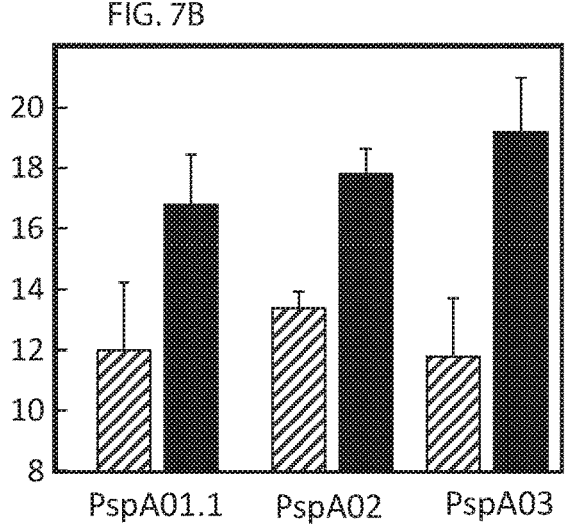

Following this reasoning, at least one embodiment provides recombinant protein constructs that combine a single aHD and a single PRD (or portions thereof), that are individually highly immunogenic and cross-reactive (Examples 4 and 5, FIG. 6-FIG. 7). Additionally, at least one embodiment provides a combination of multiple aHD-PRD constructs in one vaccine procedure: in laboratory animals, a relatively small number of aHD-PRD constructs, for example three aHD-PDR constructs, protected test subjects against a wide range of challenge strains, whether administered systemically (e.g., IM), or intranasally (IN) using a nanogel formulation described herein. The strains used in the protective challenge represent not only different PspA clades and PRD groups, but also represent different capsular polysaccharide strains. In particular, for example, the present embodiments provide a vaccine that protects against strains not covered well by PCV13, or PPCV23 (Example 6). Thus, immunization with a mixture of approximately three diverse aHD-PRD constructs may protect against most pathogenic pneumococci.

Further, the aHD and PRD sub-segments in each vaccine construct need not be from the same pneumococcus strain, but can be selected more widely for optimal cross-protection. For example, some of the most antigenic aHD-PRD constructs combine aHDs and PRDs from strains of different PspA clades or sometimes from different PspA families.

Although it has been suggested that a pneumococcal vaccine might include an aHD together with its naturally occurring PRD, as in the PspA protein (Patent Pub. US20150320851; Piao et al., 32 Vaccine 5607 (2014); Darrieux et al., 2007), these publications do not refer to the concept of characterizing distinct PRD Groups or the advisably of choosing PRDs from as many of the three distinct PRD Groups as possible. In fact, to our knowledge, PDR homologies have not been previously characterized or mapped as provided in FIG. 3A. Nor do these publications teach or suggest the chimeric fusion proteins of the present aHD-PDR constructs. Nor do these publications refer to a vaccine that is relatively simple and easy to manufacture: a composition comprising a relatively small number of chimeric antigenic proteins that also minimizes the risk of antigen competition. In short, these publications do not teach or suggest creating an effective (and universal) pneumococcal vaccine from as few as three easy-to-manufacture recombinant aHD-PRD constructs, each of which is no more than 60 kilo Daltons (kDa) in size.

The vaccine embodiments described herein induce protection not only when injected systemically (i.e., intramuscularly (IM), as is the case with most vaccines) but also when applied to nasal and oral mucosal surfaces. Previous research has showed that humans administered aHDs IM produced antibodies that protected mice against otherwise fatal pneumococcal challenge. Briles et al., 182 J. Infect. Dis. 1694 (2000b). IM formulations of aHD antigens using $Al(OH)_3$ as an adjuvant have also been shown to be safe in humans Briles et al., 2000a; Nabors et al., 2000.

Regarding IN immunization, the IN mucosal formulation of the present embodiments includes, as a delivery molecule, a hydrophilic polysaccharide to which hydrophobic cholesterol side chains have been added. An embodiment of such a delivery molecule also includes positively charged functional groups, such as cationic amino groups, on or near its surface. This enables the antigen-delivery molecule complex to be retained longer on the negatively charged nasal mucosa surface. A further embodiment of this delivery molecule comprises the hydrophilic polysaccharide pullulan, a polymer of maltotriose units. Pullulan has been used as an antioxidant in cosmetics and pharmaceutical coatings, as a food additive and preservative, and in mouth washes such as LISTERINE® mouthwash or LISTERINE POCKETPAKS® breath strips. Thus, a specific embodiment of a nasal-delivery molecule is a cationic cholesteryl-group-bearing pullulan (cCHP or nanogel). See U.S. Pat. No. 8,961,983 (Akiyoshi et al., 2015); WO 2015/122518 (Kiyono et al., 2015). Manufacture of a cCHP embodiment is described in Example 5.

Previous reports indicate that nasal formulations comprising a single aHD antigen entrapped in a cCHP molecule elicited strong protective immune responses in mice and non-human primates. Kong et al., 81 Infect. Immun 1625 (2013); Fukuyama et al., 8 Mucosal Immun 1144 (2015). In addition to protection against lethal challenge, the IN immunizations elicited T-cell immune responses that contributed to overall, long-term immunity and also prevented bacterial colonization in the nasal passages of mice. The success of cCHP-based IN immunization may be because the nanogel apparently both protects the protein immunogen and prolongs its presence on the nasal mucosal surface, hence enabling its gradual absorption into the mucosa and uptake by dendritic cells at the mucosal basement membrane. Nochi et al., 9 Nat. Mats. 572 (2010); Kong et al., 2013; Fukuyama et al., 2015. This feature applies whether the antigen sequestered in the cCHP is an aHD-PRD construct or an unlinked aHD. The administration of this IN formulation to non-human primates was not associated with any adverse effects. In particular, no penetration of the nanogel or antigen into the olfactory bulb or other portions of the central nervous system was observed. Fukuyama et al, 2015.

Figure 4:
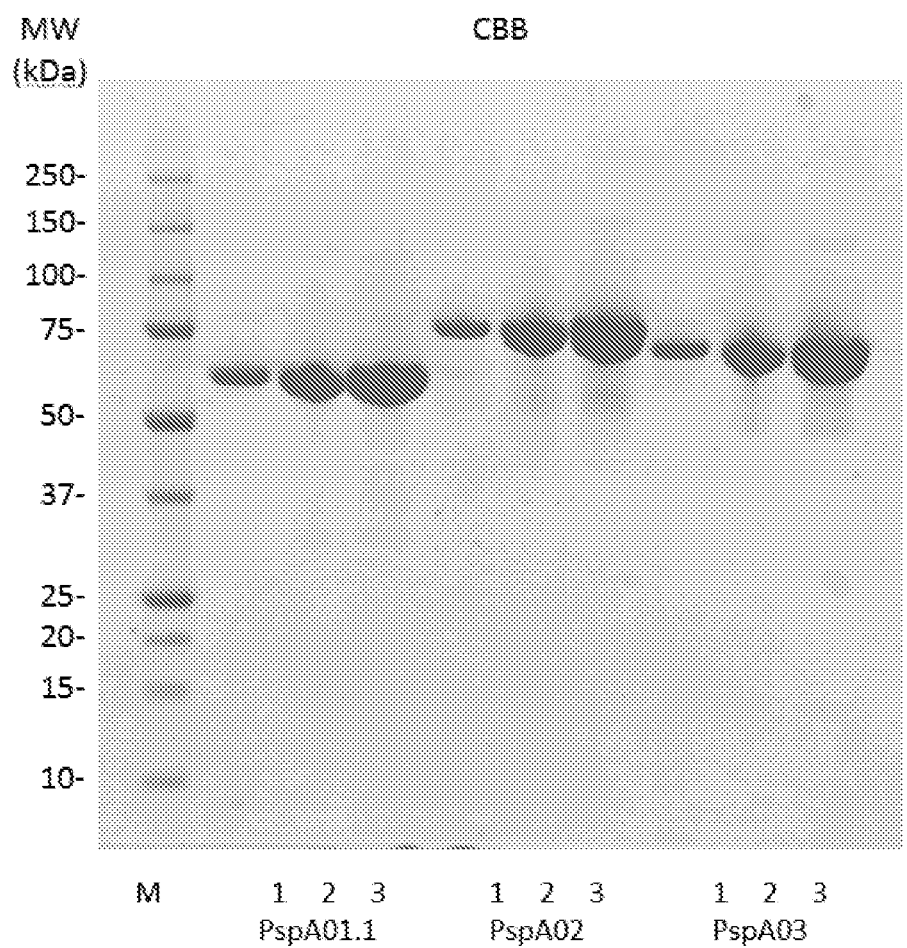
FIG. 4 illustrates the high purity analysis ((LDS-PAGE) of three expression products from host bacteria genetically engineered to produce example embodiments of recombinant aHD-PRD fusion proteins. Lane M: Protein Standard; lane 1: 1 µg/lane; lane 2: 5 µg/lane; lane 3: 10 µg/lane.

The aHD-PRD constructs described herein are stable when produced in recombinant host cells. The aHD-PRD constructs can be expressed in cell free expression system or recombinant host cells, such as bacteria (for example, *Escherichia coli* B strain, *E. coli* K12 strain, *Corynebacterium ammoniagenes, C. glutamicum, Serratia liquefaciens, Streptomyces lividans*, and *Pseudomonas putida*); *Baculovirus*; fungi such as *Penicillium camembertii, Acremonium chrysogenum*, or yeast (for example, *Saccharomyces cerevisiae* and *Pichia pastoris*); Chinese hamster ovary cells (CHO) or other mammalian expression systems; plant expression systems; and other recombinant expression systems known in the art. The process of genetic engineering required for such expression is known to persons skilled in the art. In the case of bacterial expression systems, bacteria are genetically engineered to contain vectors (plasmids) encoding the desired aHD-PRD constructs (see Example 3). Disclosed herein are four embodiments of particular aHD-PRD constructs expressed in recombinant bacteria obtained in high purity and yields (see, e.g., FIG. 4). In addition to production in recombinant expression systems, the immunogens of the present embodiments may be produced by entirely synthetic means, or by a combination of recombinant and chemical synthesis techniques.

For construct production via expression in recombinant hosts, based on reference to FIG. 2A-FIG. 3E, the amino acid sequences provided herein, and knowledge of the genetic code, one skilled in the art can design a nucleic acid molecule (e.g., a DNA) that encodes such fusion proteins; optionally optimized for expression in a desired host cell system. For example, a gene coding for PspA01.1 can be obtained by de novo synthesis: by referring to the amino acid sequence of SEQ ID NO.1, one of skill can reverse-translate the selected sequence into a nucleic acid sequence and have the molecule synthesized accordingly. The skilled artisan can also introduce one or more mutations, including insertions, substitutions and deletions to the amino acid sequence chosen or the corresponding nucleic acid sequence. For reverse translation, the skilled person can typically use nucleic acid codons that reflect codon frequency of the host system intended for expression. "Codon-optimized" is well understood in the art: a codon optimized nucleic acid (polynucleotide) is modified in comparison with the nucleic acid sequence in the organism from which the sequence originated, in that it is adapted to the codon usage in one or more host species. Typically, the polynucleotide, in particular the coding region, is adapted for expression in a given organism (such as a bacterial strain) by replacing at least one codon with at least one codon that is more frequently used in the genes of the planned host organism.

Reference to nucleic acid molecules or polynucleotides also encompasses variants or derivatives of the specific polynucleotides discussed herein, including orthologs, paralogs or other homologs of the polynucleotides, or variants, or derivatives thereof. Nucleic acid variants or derivatives differ from a given reference polynucleotide by at least one nucleotide substitution, addition, or deletion. Such variants are obtainable, for example by PCR-based techniques such as mixed oligonucleotide primer based amplification of DNA, i.e., using degenerate primers against conserved domains of aHD proteins or PRD polypeptides. When the reference polynucleotide encodes an antigenic or immunogenic protein, particularly a chimeric aHD-PDR construct or a portion thereof, the antigenic nature of the encoded polypeptide should be conserved in the variant or derivative polynucleotide, such that a variant nucleic acid encodes a polypeptide having antigenic or immunogenic characteristics as discussed herein. Conserved domains of the polypeptides of the present embodiments are discussed in detail herein, and may be identified by a sequence comparison of their nucleic acid or amino acid sequences, particularly using FIG. 2 and FIG. 3 as references for selection of cross-reactive immunogenic domains.

Variants or derivatives also encompass complements and other polynucleotides that include nucleic acid molecules capable of hybridizing to the specific nucleic acid molecules described herein, typically under stringent hybridization conditions. Stringent conditions are well-known, and the skilled worker knows how to determine hybridization conditions by referring to standard texts such as those referenced above.

Further, variants include polynucleotides comprising sequences that are at least 50%, at least 55%, at least 60%, at least 65%, at least 70%, at least 75%, at least 80%, at least 85%, at least 90%, at least 95%, at least 98%, at least 99%, or any % there between, identical to the nucleic acids shown in the Sequence Listings, or are obtainable from the amino acid sequences provided in the Sequence Listings; with the caveat that acceptable antigenicity or immunogenicity is retained. Similarly, a functional homolog of a polypeptide or protein as described herein may be at least 50%, at least 55%, at least 60%, at least 65%, at least 70%, at least 75%, at least 80%, at least 85%, at least 90%, at least 95%, at least 98%, at least 99%, or any % there between, identical to the peptides polypeptides, or proteins described herein. These percent identity values are typically calculated over the entire protein or nucleic acid molecule. Many computer programs, employing a variety of algorithms, are available to one of skill in the art for comparing sequences of different nucleic acids or polypeptides.

Additionally, substituting amino acids of a protein, e.g., one selected from SEQ ID NO:1 to SEQ ID NO:4, without regard to the occurrence of amino acids in the sequences of other polypeptides, the following applies, in which letters indicate L-amino acids using their common abbreviation (replacements listed generally in order of preference): A may be replaced by S, or C, G, T, or V; C may be replaced by A; D may be replaced by E, or N, Q, or S; E may be replaced by D or Q, or by K, H, N, R, or S; F may be replaced by Y, or by W, I, L, or M; G may be replaced by A, N, or S; H may be replaced by Y, or by N, E, Q, or R; I may be replaced by V or L, or by M or F; K may be replaced by R, or by E, Q, N, or S; L may be replaced by I or M, or by V or F; M may be replaced by L, or by I, V, F, or Q; N may be replaced by D, H, S, E, G, K, Q, R, or T; Q may be replaced by E, or by K, R, D, H, M, N, or S; R may be replaced by K, or by Q, E, H, or N; S may be replaced by A, N, T, D, E, G, K, or Q; T may be replaced by S, A, N, or V; V may be replaced by I, or by L, M, A, or T; W may be replaced by Y or F; and Y may be replaced by F, H, or W. It must be understood, however, that the antigenic or immunogenic features of the protein constructs described herein remain crucial to any polypeptide or protein into which such substitutions are introduced. Indeed, such substitution strategies would likely benefit by reference to the common motifs or patterns presented herein, such as shown in FIG. 2A-FIG. 3D. Accordingly, the proteins of the present embodiments may include amino acid substitutions, deletions or additions that enhance immunogenicity.

For expression in a recombinant host, an expression cassette comprising a nucleic acid molecule encoding a particular protein of interest, e.g., an aHD-PDR construct and appropriate regulatory control regions (e.g., promoters, terminators), are included in a vector, which may be a phage, plasmid, or viral vector, or an artificial chromosome, such as bacterial or yeast artificial chromosome. In other words, a vector of the present embodiments may be an expression vector, which comprises the polynucleotide of interest operatively linked to expression control sequences (an expression cassette), that enables expression in host cells or isolated fractions thereof. A vector is also typically suitable as a cloning vector, i.e., replicable in microbial systems; even if the cloning vector is designed for replication in one host while the expression cassette is designed for expression in a different host. A vector comprising the polypeptides and proteins of the present embodiments may further comprise a selectable marker for propagation or selection in a host cell. Vectors can be introduced into prokaryotic or eukaryotic cells via conventional transformation or transfection techniques.

Several embodiments of aHD-PDR constructs have been tested in animals (FIG. 6 to FIG. 10) and are immunogenic candidates for inclusion in human vaccines. In the following discussion of particular constructs, their designators, aHD clade and PRD Group origins, and amino acid sequences are as follows (PRD Groups in bold. For each construct, the aHD sequence stops where the PRD starts):

PspA01.1 (aHD from clade 2 [family 1], PRD from Group 2), length: 384 amino acids, weight: 41 kDa:

```
                                          (SEQ ID NO: 1)
EESPVASQSKAEKDYDAAKKDAKNAKKAVEDAQKALDDAKAAQKKYDEDQ

KKTEEKAALEKAASEEMDKAVAAVQQAYLAYQQATDKAAKDAADKMIDEA

KKREEEAKTKFNTVRAMVVPEPEQLAETKKKSEEAKQKAPELTKKLEEAK

AKLEEAEKKATEAKQKVDAEEVAPQAKIAELENQVHRLEQELKEIDESES

EDYAKEGFRAPLQSKLDAKKAKLSKLEELSDKIDELDAEIAKLEDQLKAA

EENNNVEDYFKEGLEKTIAAKKAELEKTEADLKKAVNEPETPAPAPAPAP

APAPAPAPKPAPAPKPAPAPKPAPAPKPAPAPKPAPAPAPAPAPKPAPAP

KPAPAPAPAPAPAPKPEKPAEKPAPAPKPETPKT
```

(In the sequence, "PETPAPAPAPAP" at the end of line 6 and all of lines 7–8 are printed in bold.)

PspA01.2 (aHD from clade 2 (family 1), PRD from Group 2), length: 356 aa, weight: 39 kDa:

(SEQ ID NO: 2)
EESPVASQSKAEKDYDAAKKDAKNAKKAVEDAQKALDDAKAAQKKYDEDQ

KKTEEKAALEKAASEEMDKAVAAVQQAYLAYQQATDKAAKDAADKMIDEA

KKREEEAKTKFNTVRAMVVPEPEQLAETKKKSEEAKQKAPELTKKLEEAK

AKLEEAEKKATEAKQKVDAEEVAPQAKIAELENQVHRLEQELKEIDESES

EDYAKEGFRAPLQSKLDAKKAKLSKLEELSDKIDELDAEIAKLEDQLKAA

EENNNVEDYFKEGLEKTIAAKKAELEKTEADLKKAVNEPETPAPAPAPAP

APAPAPAPAPKPAPAPKPAPAPKPAPAPAPAPAPKPEKPAEKPAPAPK

PETPKT

PspA01.3 (aHD from clade 2 (family 1), PRD from Group 3 (partial)), length: 302 aa, weight: 33 kDa:

(SEQ ID NO: 158)
EESPVASQSKAEKDYDAAKKDAKNAKKAVEDAQKALDDAKAAQKKYDEDQ

KKTEEKAALEKAASEEMDKAVAAVQQAYLAYQQATDKAAKDAADKMIDEA

KKREEEAKTKFNTVRAMVVPEPEQLAETKKKSEEAKQKAPELTKKLEEAK

AKLEEAEKKATEAKQKVDAEEVAPQAKIAELENQVHRLEQELKEIDESES

EDYAKEGFRAPLQSKLDAKKAKLSKLEELSDKIDELDAEIAKLEDQLKAA

EENNNVEDYFKEGLEKTIAAKKAELEKTEADLKKAVNEPEKPAPAPETPA

PE

PspA02 (aHD from clade 3 (family 2), PRD from Group 1) length: 495 aa, weight: 55 kDa:

(SEQ ID NO: 3)
EESPQVVEKSSLEKKYEEAKAKADTAKKDYETAKKKAEDAQKKYEDDQKR

TEEKARKEAEASQKLNDVALVVQNAYKEYREVQNQRSKYKSDAEYQKKLT

EVDSKIEKARKEQQDLQNKFNEVRAVVVPEPNALAETKKKAEEAKAEEKV

AKRKYDYATLKVALAKKEVEAKELEIEKLQYEISTLEQEVATAQHQVDNL

KKLLAGADPDDGTEVIEAKLKKGEAELNAKQAELAKKQTELEKLLDSLDP

EGKTQDELDKEAEEAELDKKADELQNKVADLEKEISNLEILLGGADPEDD

TAALQNKLAAKKAELAKKQTELEKLLDSLDPEGKTQDELDKEAEEAELDK

KADELQNKVADLEKEISNLEILLGGADSEDDTAALQNKLATKKAELEKTQ

KELDAALNELGPDGDEEETPAPAPQPEQPAPAPKPEQPAPAPKPEQPAPA

PKPEQPAPAPKPEQPAPAPKPEQPAKPEKPAEEPTQPEKPATPKT

PspA03 (aHD from clade 4 (family 2), PRD from Group 3) length: 430 aa, weight: 48 kDa:

(SEQ ID NO: 4)
EEAPVANQSKAEKDYDAAVKKSEAAKKDYETAKKKAEDAQKKYDEDQKKT

EAKAEKERKASEKIAEATKEVQQAYLAYLQASNESQRKEADKKIKEATQR

KDEAEAAFATIRTTIVVPEPSELAETKKKAEEATKEAEVAKKKSEEAAKE

VEVEKNKILEQDAENEKKIDVLQNKVADLEKGIAPYQNEVAELNKEIARL

QSDLKDAEENNVEDYIKEGLEQAITNKKAELATTQQNIDKTQKDLEDAEL

ELEKVLATLDPEGKTQDELDKEAAEAELNEKVEALQNQVAELEEELSKLE

DNLKDAETNNVEDYIKEGLEEAIATKKAELEKTQKELDAALNELGPEKPA

EETPAPAPKPEQPAEQPKPAPAPQPAPAPKPEKTDDQQAEEDYARRSEEE

YNRLPQQQPPKAEKPAPAPKPEQPVPAPKT

Details regarding the expression procedure and the antigen yields are discussed in Example 3. Additional aHD-PRD constructs comprising other aHDs (including aHDs from clade 1 (family 1) and clade 5 (family 2)) and other PRDs are suitable for inclusion in aHD-PDR constructs.

Figure 5:
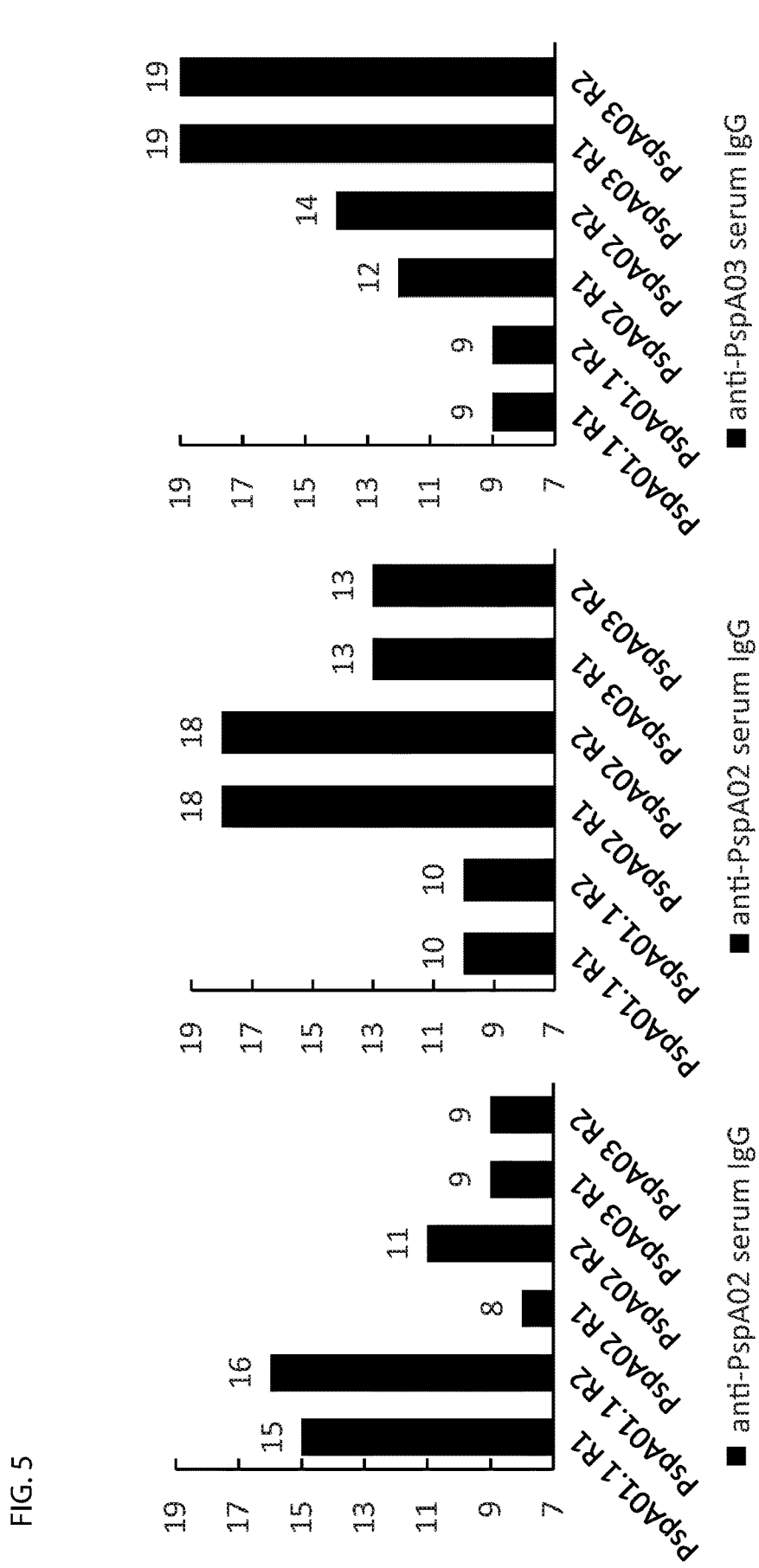
FIG. 5 shows cross reactivity characterized by concentration of antigen-specific serum per construct. Serum antigen-specific IgG ELISA titers (reciprocal $\log_2$) were determined against each of three aHD-PRD constructs (PspA 01.1, PspA 02, or pspA 03) by immunizing rabbits IM with single aHD-PRD constructs (two rabbits per construct, each designated by construct and suffix "R1" or "R2"). Titers generated against the non-immunizing constructs indicate the degree of cross-reactivity against dissimilar PspA antigens. See Example 4.

Immunizing rabbits with three individual embodiments of aHD-PRD constructs induced strong immunogenicity, as shown by antigen-specific serum IgG responses. Additionally, two constructs with family 2 aHDs elicited antibodies that cross-reacted well with each other, even though the constructs were from different aHD clades (FIG. 5).

Using procedures known to persons skilled in the art, we prepared formulations for IM administration using aluminum compounds as adjuvants. More specifically, such preparations typically involve absorption of aHD-PRD constructs on an aluminum gel such as aluminum hydroxide ($Al(OH)_3$) or aluminum phosphate ($AlPO_4$), or precipitation of aHD-PRD constructs on aluminum potassium sulfate ($AlK(SO_4)_2$). See, e.g., Lindblad, 2004. Individual aHD-PRD constructs described herein and formulated with $AlK(SO_4)_2$ or $Al(OH)_3$ elicited strong antigen-specific serum IgG responses in mice, including sustained strong memory responses following administration of a booster dose (FIG. 6; Example 4; Example 6).

Example aHD-PRD constructs described herein were further formulated for intranasal delivery using procedures described elsewhere (Nochi et al., 2010; Kong et al., 2013; Fukuyama et al., 2015) and outlined in Example 5. Each formulation included an embodiment of an aHD-PRD construct entrapped in the cross-linked structure of a cationic cholesteryl-group-bearing pullulan (cCHP or nanogel) molecule. The formulations were used as vaccines administered by dripping the formulation into the nose of a mouse or other laboratory animal. This IN delivery formulation elicited strong antigen-specific serum IgG responses in mice, including sustained memory responses following a vaccination with a booster dose (FIG. 7; Examples 5 and 6).

To date, none of the studies with laboratory animals have indicated significant adverse reactions to cCHP nanogel formulations. In particular, PET studies of radiolabeled cCHP-aHD administered to non-human primates IN showed no uptake into the olfactory bulb or other CNS structures. Fukuyama et al., 2015. This provides assurance that IN administration does not risk the types of CNS inflammation that were noted in the past: when vaccines containing adjuvants such heat labile enterotoxin were administered IN to humans (Mutsch et al., 350 N. Engl. J. Med. 896 (2004)), or antigens with cholera toxin adjuvant were administered IN to mice (van Ginkel et al., 165 J. Immunol. 4778 (2000)).

The immune responses induced by the aHD-PRD constructs described herein are protective in both IM and IN formulations, not only against strains of *S. pneumoniae* that have aHDs or PRDs that are identical with those of the immunizing aHD-PRD constructs, but also against challenge strains that have different aHDs or PRDs. In other words, we have shown that the aHD-PRD constructs produce cross-reactive protective immunity (Example 6). More-over, this immunity extends to pneumococcal strains that are not covered by current vaccines.

EXAMPLES

The following ingredients, formulations, processes and procedures for practicing the methods disclosed herein correspond to that described above. Other embodiments and uses will be apparent to one skilled in the art in light of the present disclosures. The following examples are provided merely as illustrative of various embodiments and shall not be construed to limit the invention in any way.

Example 1: Characterization of Three PRD Groups, and PRD Antigen Selection

The PRD is a relatively short polypeptide, usually between 60 and 100 amino acids in length. The PRD is considered to start at the end of the aHD, at the first proline of a succession of prolines interspersed with other amino acids that form several motifs that repeat within and among the PRDs, and the PRD typically (but not exclusively) ends with the amino acid residues PKT. See FIG. 1. We identified and analyzed 124 unique PspA sequences out of 208 complete PspA sequences posted on the BLAST server provided on-line by the U.S. National Library of Medicine. These PspA sequences account for most unique PspA genome sequences available on public data bases. To these 124 polypeptide sequences, we added twelve PspA polypeptide sequences that had been analyzed previously (Hollingshead et al., 2000), but had not been included in those obtained from the National Library of Medicine on-line BLAST server. We extracted the PRD sequences from these 136 total PspA amino acid sequences and aligned them in Geneious v7.1.7 using the Blosum30 amino acid matrix. Following this, we constructed dendrograms using the Neighbor Joining (NJ) method.

Unexpectedly, this method identified three distinct PRD "Groups" as shown in FIG. 3A-FIG. 3D, and Table 1-Table 3. We also identified short repeat motifs, each about 6-8 amino acids in length that, along with a 22-amino acid non-proline block (NPB), characterize most of each PRD polypeptide. The five short repeat motifs are PKPEQP (SEQ ID NO:5), QPAPAP (SEQ ID NO:6), PKPAPA (SEQ ID NO:7), EKPAPAP (SEQ ID NO:8), and PEKPAE (SEQ ID NO:9), and these motifs are indicated in Table 1-Table 4. The NPBs are usually QQAEEDYARRSEEEYNRLPQQQ (SEQ ID NO:10) or QQAEEDYARRSEEEYNRLTQQQ (SEQ ID NO:11). NPBs also have highly conserved flanking regions, usually consisting of four amino acids on either side within the PRD.

Each of the three PRD Groups has distinct patterns of these motifs. This can be seen from Table 1, Table 2, and Table 3, which provide the amino acid sequence and motifs for the PRDs of Group 1, Group 2, and Group 3, respectively. The vast majority of these sequences have not been identified previously; known amino acid sequences are encompassed by the embodiments herein only to the extent they are included in novel recombinant aHD-PRD constructs or provide novel immunogenic peptides. Table 1 presents the amino acid sequences of many Group 1 PRD polypeptides, in which different repeating motifs are indicated by different typeface:

TABLE 1

Example Group 1 PRDs

| Strain | Amino acid sequence |
|---|---|
| SP9-BS68 | PDGDEEELPARALQPEqpapaPKPEQPTPAPKPEQPTPAPKPEQPapaPKPEQPapaPKPEQPapaP KPEQPTPAPKT* (SEQ ID NO: 105) |
| GA08780 | PDGDEEETPAPAPQPEqpapaPKPEQPTPAPKPEQPTPAPKPEQPapaPKPEQPapaPKPEQPapaP KPEQPTPAPKT (SEQ ID NO: 106) |
| GA17570 | PDGDEEETPAPAPQPEqpapaPKPEQPTPAPKPEQPTPAPKPEQPapaPKPEQPapaPKPEQPapaP KPEQPTPAPKT (SEQ ID NO: 106) |
| GA17301 | PDGDEEETPAPAPQPEqpapaPKPEQPTPAPKPEQPTPAPKPEQPapaPKPEQPapaPKPEQPapaP KPEQPTPAPKT (SEQ ID NO: 106) |
| AC122 | PDGDEEETPAPAPQPEqpapaPKPEQPTPAPKPEQPTPAPKPEQPapaPKPEQPapaPKPEQPapaP KPEQPTPGPKI (SEQ ID NO: 107) |
| GA54644 | PDGDEEETPAPAPQPEqpapaPKPEQPTPAPKPEQPTPAPKPEQPapaPKPEQPapaPKPEQPapaP KPEQPTPAPKT (SEQ ID NO: 106) |
| 2070531 | PDGDEEETPAPAPQPEqpapaPKPEQPTPAPKPEQPTPAPKPEQPapaPKPEQPapaPKPEQPapaP KPEQPTPAPKT (SEQ ID NO: 106) |
| SPAR55 | PDGDEEETPAPAPQPEqpapapQPEqpapaPKPEQPapaPKPEQPTPAPKPEQPTPAPKPEQPTPAP KPEQPTPAPKT (SEQ ID NO: 108) |
| CDC1087-00 | PDGDEEETPAPAPQPEqpapapQPEqpapaPKPEQPapaPKPEQPTPAPKPEQPTPAPKPEQPTPAP KPEQPTPAPKT (SEQ ID NO 108:) |
| NP141 | PDGDEEETPAPAPQPEqpapapQPEqpapaPKPEQPapaPKPEQPTPAPKPEQPTPAPKPEQPTPAP KPEQPTPAPKT (SEQ ID NO: 108) |
| CDC1873-00 | PDGDEEETPAPAPQPEqpapapQPEqpapaPKPEQPapaPKPEQPTPAPKPEQPTPAPKPEQPTPAP KPEQPTPAPKT (SEQ ID NO: 108) |
| GA02270 | PDGDEEETPAPAPQPEqpapapQPEqpapaPKPEQPapaPKPEQPTPAPKPEQPTPAPKPEQPTPAP KPEQPTPAPKT (SEQ ID NO: 108) |

TABLE 1-continued

Example Group 1 PRDs

| Strain | Amino acid sequence |
|---|---|
| GA41410 | PDGDEEETPAPAPQPEqpapapQPEqpapaPKPEQPapaPKPEQPTPAPKPEQPTPAPKPEQPTPAPKPEQPTPAPKT (SEQ ID NO: 108) |
| GA47751 | PDGDEEETPAPAPQPEqpapapQPEqpapaPKPEQPapaPKPEQPTPAPKPEQPTPAPKPEQPTPAPKT (SEQ ID NO: 109) |
| GA40028 | PDGDEEETPAPAPQPEqpapapQPEqpapaPKPEQPapaPKPEQPTPAPKPEQPTPAPKPEQPTPAPKT (SEQ ID NO: 109) |
| GA47283 | PDGDEEETPAPAPQPEqpapapQPEqpapaPKPEQPapaPKPEQPTPAPKPEQPTPAPKPEQPTPAPKT (SEQ ID NO: 109) |
| GA16531 | PDGDEEETPAPAPQPEqpapapQPEqpapaPKPEQPapaPKPEQPapaPKPEQPTPAPKPEQPTPAPKT (SEQ ID NO: 128) |
| GA13637 | PDGDEEETPAPAPQPEqpapapQPEqpapaPKPEQPapaPKPEQPTPAPKPEQPTPAPKT (SEQ ID NO: 110) |
| GA02714 | PDGDEEETPAPAPQPEqpapapQPEqpapaPKPEQPapaPKPEQPTPAPKPEQPTPAPKT (SEQ ID NO: 110) |
| GA02506 | PDGDEEETPAPAPQP*EKPAPA*PKPEQPapaPKPEQPTPAPKPEQPTPAPKPEQPTPAPKP (SEQ ID NO: 111) |
| GA04216 | PDGDEEETPAPAPQP*EKPAPA*PKPEQPapaPKPEQPTPAPKPEQPTPAPKPEQPTPAPKP (SEQ ID NO: 111) |
| GA07914 | PDGDEEETPAPAPAPKPEQPapapAPKPEQPapapAPKPEQPapapAPKPEQPapapAPKPEQPapapAPKPEQPTPAPKT (SEQ ID NO: 112) |
| GA47794 | PDGDEEETPAPAPAPKPEQPapapAPKPEQPapapAPKPEQPapapAPKPEQPapapAPKPEQPapapAPKPEQPapapAPKPEQPTPAPKT (SEQ ID NO: 113) |
| GA47760 | PDGDEEETPAPAPAPKPEQPapapAPKPEQPapapAPKPEQPapapAPKPEQPapapAPKPEQPapapAPKPEQPTPAPKT (SEQ ID NO: 112) |
| GA52612 | PDGDEEETPAPAPAPKPEQPapapAPKPEQPapapAPKPEQPapapAPKPEQPapapAPKPEQPapapAPKPEQPTPAPKT (SEQ ID NO: 112) |
| GA17328 | PDGDEEETPAPAPQPEqpapapAPKPEQPapapAPKPEQPapapAPKPEQPapapAPKPEQPapapAPKPEQPapapKT (SEQ ID NO: 115) |
| GA49447 | PDGDEEETPAPAPQPEqpapapQPEqpapaPKPEQPapaPKPEQPTPAPKT (SEQ ID NO: 116) |
| 2070109 | PDGDEEETPAPAPQPEqpapapQPEqpapaPKPEQPapaPKPEQPTPAPKT (SEQ ID NO: 116) |
| GA14373 | PDGDEEETPAPAPQPEqpapapAPKPEQPapapAPKPEQPapapAPKPEQPapapKT (SEQ ID NO: 117) |
| GA47562 | PDGDEEETPAPAPAPKPEQPapapAPKPEQPapapAPKPEQPapapAPKPEQPapapAPKPEQPTPAPKT (SEQ ID NO: 118) |
| GA13723 | pekpaeEPENPAPA*PKPAPA*PQPEqpapapAPKPEQPapapAPKPEQPapapAPKPEQPapapAPKPEQPapapAPKPEQPTPAPKT (SEQ ID NO: 119) |
| GA47976 | pekpaeEPENPAPA*PKPAPA*PQPEqpapapAPKPEQPapapAPKPEQPapapAPKPEQPapapAPKPEQPapapAPKPEQPTPAPKT (SEQ ID NO: 119) |
| BG8090 | PDGDEEETPAPAPAPKPEQPapapAPKPEQPapapAPKPEQPapapAPKPEQPTPAPKS (SEQ ID NO: 120) |
| AP200 | PDGDEEETPAPAPAPKPEQPapapAPKPEQPapapAPKPEQPapapAPKPEQPTPAPKT (SEQ ID NO: 121) |
| SP-BS293 | PAPAPQPEqpapapQPEqpapapQPEqpapapQPEqpapapQPEqpapapKI (SEQ ID NO: 122) |
| BS397 | PAPAPQPEqpapapQPEqpapapQPEqpapapQPEqpapapQPEqpapapQPEqpapapQPEqpapapQPEqpapapQPEqpapapQPEqpapapQPEqpapapQPEqpapapKI (SEQ ID NO: 123) |
| GA19923 | PDGDEEETPAPAPQPEqpapaPKPEQPapaPKPEQPapaPKPEQPapaPKPEQPAKpekpaeEPTQPEKPATPKT (SEQ ID NO: 124) |

TABLE 1-continued

Example Group 1 PRDs

| Strain | Amino acid sequence |
| --- | --- |
| SPN034183 | PDGDEEETPAPAPQPEqpapa*PKPEQP*papa*PKPEQP*papa*PKPEQP*papa*PKPEQP*AKpekpaeEPTQPEKPATPKT (SEQ ID NO: 124) |
| GA47628 | PDGDEEETPAPAPQPEqpapa*PKPEQP*papa*PKPEQP*papa*PKPEQP*papa*PKPEQP*AKpekpaeEPTQPEKPATPKT (SEQ ID NO: 124) |
| GA18523 | PDGDEEETPAPAPQPEqpapa*PKPEQP*papa*PKPEQP*papa*PKPEQP*papa*PKPEQP*AKpekpaeEPTQPEKPATPKT (SEQ ID NO: 124) |
| GA16833 | PDGDEEETPAPAPQPEqpapa*PKPEQP*papa*PKPEQP*papa*PKPEQP*papa*PKPEQP*AKpekpaeEPTQPEKPATPKT (SEQ ID NO: 124) |
| GA18068 | PDGDEEETPAPAPQPEqpapa*PKPEQP*papa*PKPEQP*papa*PKPEQP*papa*PKPEQP*AKpekpaeEPTQPEKPATPKT (SEQ ID NO: 124) |
| EF3296 | PDGDEEEETPAPAPQPEqpapa*PKPEQP*papa*PKPEqpapa*PKPEQP*papa*PKPEQP*papa***PKPEQP*AKpekpaeEPTQPEKPATPKT (SEQ ID NO: 14) |
| 7533-05 | PDGDEEETPAPAPQPEqpapa*PKPEQP*papa*PKPEQP*AKpekpaeEPTQPEKPATPKT (SEQ ID NO: 126) |
| GA07228 | PDGDEEETPAPAPQPEqpapa*PKPEQP*papa*PKPEQP*AKpekpaeEPTQPEKPATPKT (SEQ ID NO: 126) |
| SP3-BS71 | PDGDEEETPAPAPQPEqpapa*PKPEQP*papa*PKPEQP*AKpekpaeEPTQPEKPATPKT (SEQ ID NO: 126) |
| 3063-00 | PDGDEEETPAPAPQPEqpapa*PKPEQP*papa*PKPEQP*papa*PKPEQP*AKpekpaeEPTQPEKPATPKT (SEQ ID NO: 127) |
| GA43380 | PDGDEEETPAPAPQPEqpapa*PKPEQP*papa*PKPEQP*papa*PKPEQP*AKpekpaeEPTQPEKPATPKT (SEQ ID NO: 127) |
| GA19690 | PDGDEEETPAPAPQPEqpapa*PKPEQP*papa*PKPEQP*papa*PKPEQP*AKpekpaeEPTQPEKPATPKT (SEQ ID NO: 127) |
| OXC141 | PDGDEEETPAPAPQPEqpapa*PKPEQP*papa*PKPEQP*papa*PKPEQP*AKpekpaeEPTQPEKPATPKT (SEQ ID NO: 127) |

*lower case indicates motif PEKPAE (SEQ ID NO: 9) (pekpa);
upper case bold italics indicates motif PKPAPA (SEQ ID NO: 7) (*PKPAPA*);
uppercase italics indicates motif EKPAPAP (SEQ ID NO: 8) (*EKPAPAP*);
lowercase bold indicates motif QPAPAP (SEQ ID NO: 6) (qpapa);
non-motif residues are uppercase, plain font.

As can be seen from Table 1, each of the fifty sequences in Group 1 exhibit characteristic repeats of two motifs: PKPEQP (SEQ ID NO:5) and QPAPAP (SEQ ID NO:6), which are adjacent to each other and usually overlap. See also Table 4.

The twenty-one amino acid sequences in PRD Group 2 polypeptides (Table 2) exhibit characteristic, multiple repeats of PKPAPA (SEQ ID NO:7), except for two sequences characterized instead by multiple repeats of EKPAPAP (SEQ ID NO:8). In the amino acid sequences of the other nineteen Group 2 polypeptides, PKPAPA (SEQ ID NO:7) was generally expressed as a linear tandem repeat, thereby also repeating the motif, KPAPAP (residues 2-7 of SEQ ID NO:8)—tandem repeats characteristic of other Group 2 sequences. This explains how sequences characterized either by EKPAPAP (SEQ ID NO:8) or PKPAPA (SEQ ID NO:7) repeats can be readily considered to belong to a single group. See also Table 4. PRD Group 2 polypeptides and indicated motifs are shown in Table 2:

TABLE 2

Example Group 2 PRDs

| Strain | Amino acid sequence |
| --- | --- |
| GA58981 | PETPAPAPKPAPTPEAPAPA*PKPAPAPKPAPA*PAPTPEAPAPA*PKPAPAPKPAPAPKP APA*PAPTPEAPAPA*PKPAPAPKPAPAPKPAPA*PKPETPKT* (SEQ ID NO: 87) |
| GA56348 | PETPAPA*PKPAPA*PAPTPEAPAPA*PKPAPAPKPAPA*PAPTPEAPAPA*PKPAPAPKPAPKPAPA*PAPTPEAPAPA*PKPAPAPKPAPAPKPAPAPKPAPA*PKPETPKT (SEQ ID NO: 88) |
| 2071004 | PETPAPA*PKPAPA*PAPTPEAPAPA*PKPAPAPKPAPA*PA*PKPAPAPKPAPA*PA*PKPAPA PKPAPAPKPAPAPKPAPA*PKPETPKT (SEQ ID NO: 89) |

TABLE 2-continued

Example Group 2 PRDs

| Strain | Amino acid sequence |
|---|---|
| EF6796 | PETPAPAPAPAPAPAPAPA*PKPAPAPKPAPA*PAPAPA*PKPAPAPKPAPA*PAPAPKpekpa*EKPAPAP*KPETPKT (SEQ ID NO: 90) |
| BG9163 | PETPAPAPAPAPAPAPAPAPAPAPA*PKPAPAPKPAPA*PAPAPA*PKPAPAPKPAPA*PAPAPKpekpa*EKPAPAP*KPETPKT (SEQ ID NO: 91) |
| NP070 | PETPAPAPA*PKPAPA*PAPTPEAPAPA*PKPAPAPKPAPAPKPAPAPKPAPAPKPAPAPKPAPAPKPAPA*PKPETPKT (SEQ ID NO: 92) |
| GA14688 | PETPAPAPA*PKPAPA*PAPTPEAPAPA*PKPAPAPKPAPAPKPAPAPKPAPAPKPAPAPKPAPAPKPAPA*PKPETPKT (SEQ ID NO: 92) |
| GA44128 | PETPAPAPA*PKPAPA*PAPTPEAPAPA*PKPAPAPKPAPAPKPAPAPKPAPAPKPAPAPKPAPAPKPAPA*PKPETPKT (SEQ ID NO: 92) |
| 2080913 | PETPAPAPA*PKPAPA*PAPTPEAPAPA*PKPAPAPKPAPAPKPAPAPKPAPA*PKPAPKpekpa*EKPAPAP*KPETPKT (SEQ ID NO: 93) |
| BG8743 | PETPAPAPA*PKPAPA*PAPTPEAPAPA*PKPAPAPKPAPAPKPAPAPKPAPAPKPAPAPKPAPAPKPAPA*PKP (SEQ ID NO: 94) |
| GA47439 | PETPAPAPAPAPAPAPA*PKPAPAPKPAPAPKPAPAPKPAPAPKPAPAPKPAPA*PAPAPA*PKPAPAPKPAPA*PAPAPAPAPKpekpa*EKPAPAP*KPETPKT (SEQ ID NO: 12) |
| DBL5 | PETPAPAPAPAPAPAPAPTPEAPAPAPA*PKPAPAPKPAPAPKPAPAPKPAPAPKPAPAPKPAPA*PAPAPA*PKPAPA*PAPAPAPKpekpa*EKPAPAP*KPETPKT (SEQ ID NO: 96) |
| GA47502 | PETPAPAPAPAPAPEAPAPAPAPAPA*PKPAPAPKPAPAPKPAPAPKPAPAPKPAPA*PAPAPAPKpekpa*EKPAPAP*KPETPKT (SEQ ID NO: 97) |
| L81905 | PETPAPAPAPAPAPAPTPEAPAPAPAPA*PKPAPAPKPAPAPKPAPAPKPAPAPKPAPA*PAPAPKpekpa*EKPAPAP*KPETPKT (SEQ ID NO: 98) |
| ND6012 | PETPAPAPAPAPAPAPAPAPAPA*PKPAPAPKPAPAPKPAPA*PAPAPAPKpekpa*EKPAPAP*KPETPKT (SEQ ID NO: 13) |
| CGSP14 | PETPAPAPAPAPAPTPEAPAPAPAPAPA*PKPAPAPKPAPAPKPAPAPKPAPAPKPAPA*PAPAPKpekpa*EKPAPAP*KPETPKT (SEQ ID NO: 99) |
| BG9739 | PETPAPAPAPAPAPAPTPEAPAPAPAPA*PKPAPAPKPAPAPKPAPAPKPAPAPKPAPA*PKPAPA*PAPAPKpekpa*EKPAPAP*KPE (SEQ ID NO: 100) |
| 2061376 | PETPAPA*PKPAPA*PAPTPEAPAPA*PKPAPAPKPAPAPKPAPAPKPAPA*PKPETPKT (SEQ ID NO: 101) |
| SP23-BS72 | PETPAPAPA*PKPAPA*PAPTPEAPAPA*PKPAPAPKPAPAPKPAPAPKPAPAPKPAPA*PKPETPKT (SEQ ID NO: 102) |
| SP6-BS73 | PETPAPAPqpapap*EKPAPAP*EKPAPAP*EKPAPAP*EKPAPAP*EKPAPAP*EKPAPAP*EKPAPAP*EKPAPAP*EKPAPAP*EKPAPAP*EKPAPAP*EKPAPAP*EKPAPTPETPKT (SEQ ID NO: 103) |
| E134 | PETPAPAPqpapapekpa*EKPAPAPAPEKPAPA*pekpae*KPAEKPAEEPA*EKPAPAPE*KPAPTPEKPAPTPETPKT (SEQ ID NO: 104) |

*lower case indicates motif PEKPAE (SEQ ID NO: 9) (pekpa);
upper case bold italics indicates motif PKPAPA (SEQ ID NO: 7) (PKPAPA);
uppercase italics indicates motif EKPAPAP (SEQ ID NO: 8) (*EKPAPAP*);
lowercase bold indicates motif QPAPAP (SEQ ID NO: 6) (qpapa);
non-motif residues are uppercase, plain font.

The sixty-five sequences in PRD Group 3 (Table 3) have the greatest diversity of motifs; none of which is repeated in tandem. In addition, each of the group 3 sequences contains a single NPB, and NPBs are found only in Group 3 polypeptides:

TABLE 3

Example Group 3 PRDs

| Strain | Amino acid sequence |
|---|---|
| GA47597 | P*EKPAPAP*ETPAPEAPAEQ***PKPAPAP*qpapap**Kpekpae QPKPE*ktdd*QQAEEDYARRSEEEYNRLTQQQ*ppka*EKPAPAPQPEqpapapKT* (SEQ ID NO: 129) |
| SPN072838 | P*EKPAPAP*ETPAPEAPAEQ***PKPAPAP*qpapap**Kpekpae QPKPE*ktdd*QQAEEDYARRSEEEYNRLTQQQ*ppka*EKPAPAPQPEqpapapKT (SEQ ID NO: 129) |
| GA19101 | P*EKPAPAP*ETPAPEAPAEQ***PKPAPAP*qpapap**Kpekpae QPKPE*ktdd*QQAEEDYARRSEEEYNRLTQQQ*ppka*EKPAPAPQPEqpapapKT (SEQ ID NO: 129) |
| 70585 | P*EKPAPAP*ETPAPEAPAEQ***PKPAPAP*qpapap**Kpekpae QPKPE*ktdd*QQAEEDYARRSEEEYNRLTQQQ*ppka*EKPAPAPQPEqpapapKT (SEQ ID NO: 129) |
| R6 | P*EKPAPAP*ETPAPEAPAEQ***PKPAPAP*qpapap**Kpekpae QPKPE*ktdd*QQAEEDYARRSEEEYNRLTQQQ*ppka*EKPAPAPKT (SEQ ID NO: 130) |
| BG6380 | PAPEAPAEQPKPE*ksae*QQAEEDYARRSEEEYNRLTQQQ*ppka*EKPAEEPTRPAPAPEAPAEQPKPEksaeQQAEEDYARRSEEEYNRLTQQQ*ppka*EKPAEEPTqpapapEQPTEPTQPEKPVAPKT (SEQ ID NO: 133) |
| RX1 | P*EKPAPAP*ETPAPEAPAEQ***PKPAPAP*qpapap**Kpekpae QPKPE*ktdd*QQAEEDYARRSEEEYNRLTQQQ*ppka*EKPAPAPKT (SEQ ID NO: 130) |
| GA16242 | P*EKPAPAP*ETPAPEAPAEQ***PKPAPAP*qpapap**Kpekpae QPKAE*ktdd*QQAEEDYARRSEEEYNRLTQQQ*ppka*EKPAPAPKPEQqpapapKI (SEQ ID NO: 131) |
| GA17545 | P*EKPAPAP*ETPAPEAPAEQ***PKPAPAP*qpapap**Kpekpae QPKAE*ktdd*QQAEEDYARRSEEEYNRLTQQQ*ppka*EKPAPAPKPEQPapap**KI (SEQ ID NO: 131) |
| NP112 | P*EKPAPAP*ETPAPEAPAEQ***PKPAPAP*qpapap**Kpekpae QPKAE*ktdd*QQAEEDYARRSEEEYNRLTQQQ*ppka*EKPAPAPKPEQPapap**KI (SEQ ID NO: 131) |
| GA13856 | P*EKPAPAP*ETPAPEAPAEQ***PKPAPAP*qpapap**Kpekpae QPKAE*ktdd*QQAEEDYARRSEEEYNRLTQQQ*ppka*EKPAPAPKPEQPapap**KI (SEQ ID NO: 131) |
| 2071247 | P*EKPAPAP*ETPAPEAPAEQ***PKPAPAP*qpapap**Kpekpae QPKAE*ktdd*QQAEEDYARRSEEEYNRLTQQQ*ppka*EKPAPAPKPEQPapap**KI (SEQ ID NO: 131) |
| GA17971 | P*EKPAPAP*ETPAPEAPAEQ***PKPAPAP*qpapap**Kpekpae QPKAE*ktdd*QQAEEDYARRSEEEYNRLTQQQ*ppka*EKPAPAPKPEQPVPAPKT (SEQ ID NO: 132) |
| BG6692 | P*EKPAPAP*ETPAPEAPAEQ***PKPAPAP*qpapap**Kpekpae QPKAE*ktdd*QQAEEDYARRSEEEYNRLTQQQ*ppka*EKPAPAPKPEQPAPA (SEQ ID NO: 156) |
| BG8838 | P*EKPAPAP*ETPAPEAPAEQ***PKPAPAP*qpapap**Kpekpae QPKAE*kpad*QQAEEDYDRRSEEEYNRLTQQQ*ppka*EKPAPAPQPEqpapap (SEQ ID NO: 134) |
| SP18-BS74 | P*EKPAPAP*ETPAPEAPAEQ***PKPAPAP*qpapap**Kpekpae QPKAE*kpad*QQAEEDYDRRSEEEYNRLTQQQ*ppka*EKPAPAPQPEqpapapKT (SEQ ID NO: 135) |
| GA13224 | P*EKPAPAP*ETPAPEAPAEQ***PKPAPAP*qpapap**Kpekpae QPKAE*kpad*QQAEEDYARRSEEEYNRLTQQQ*ppka*EKPAPAPQPEqpapapKT (SEQ ID NO: 155) |
| EF10197 | pekpaeEPSQpekpaeEAPAPEQPTEPTQpekpaeQPqpapapQpekpaeETPAPKpekpaeQPKAE*kpad*QQAEEDYARRSEEEYNRLTQQQ*ppka*EKPAPAPKT (SEQ ID NO: 136) |
| A66.1 | PEKSAEEPSQpekpaeEAPAPEQPTEPTQpekpaeETPAPKpekpaeQPKAE*ktdd*QQAEEDYARRSEEEYNRLTQQQ*ppka*EKPAPAPQPEqpapapKT (SEQ ID NO: 137) |
| WU2 | PEKSAEEPSQpekpaeEAPAPEQPTEPTQpekpaeETPAPKpekpaeQPKAE*ktdd*QQAEEDYARRSEEEYNRLTQQQ*ppka*EKPAPAPQPEQ (SEQ ID NO: 138) |
| GA62331 | pekpaeESENPAPA***PKPAPA*PAPKPEQPapapAPKPE*ksad*QQAEEDYARRSEEEYNRLTQQQ*ppka*EKPAPAPAPKPEQPapap**KT (SEQ ID NO: 139) |
| GA54354 | pekpaeESENPAPA***PKPAPA*PAPKPEQPapapAPKPE*ksad*QQAEEDYARRSEEEYNRLTQQQ*ppka*EKPAPAPAPKPEQPapap**KT (SEQ ID NO: 139) |
| 670-6B | pekpaeETPAPAPKPEQPAEQ***PKPAPAP*gpapap**KPE*ktdd*QQAEEDYARRSEEEYNRLPQQQ*ppka*EKPAPAPKPEQPVPAPKPEQPVPAPKT (SEQ ID NO: 17) |

TABLE 3-continued

Example Group 3 PRDs

| Strain | Amino acid sequence |
| --- | --- |
| EU-NP04 | pekpaeETPAPAPKPEQPAEQ*PKPAPA*P*gpapap*KPE*ktdd*QQAEEDYARRSEEEYNRLPQQQp*pka*EKPAPAPKPEQPVPAPKT (SEQ ID NO: 16) |
| gamPNI0373 | pekpaeETPAPAPKPEQPAEQ*PKPAPA*P*gpapap*KPE*ktdd*QQAEEDYARRSEEEYNRLPQQQp*pka*EKPAPAPKPEQPVPAPKT (SEQ ID NO: 16) |
| P1031 | pekpaeETPAPAPKPEQPAEQ*PKPAPA*P*gpapap*KPE*ktdd*QQAEEDYARRSEEEYNRLPQQQp*pka*EKPAPAPKPEQPVPAPKT (SEQ ID NO: 16) |
| PNI0153 | pekpaeETPAPAPKPEQPAEQ*PKPAPA*P*gpapap*KPE*ktdd*QQAEEDYARRSEEEYNRLPQQQp*pka*EKPAPAPKPEQPVPAPKT (SEQ ID NO: 16) |
| GA11304 | pekpaeETPAPAPKPEQPAEQ*PKPAPA*P*gpapap*KPE*ktdd*QQAEEDYARRSEEEYNRLPQQQp*pka*EKPAPAPKPEQPVPAPKT (SEQ ID NO: 16) |
| PCS70012 | pekpaeETPAPAPKPEQPAEQ*PKPAPA*P*gpapap*KPE*ktdd*QQAEEDYARRSEEEYNRLPQQQp*pka*EKPAPAPKPEQPVPAPKT (SEQ ID NO: 16) |
| DBL1 | pekpaeETPAPAPKPEQPAEQ*PKPAPA*P*gpapap*KPE*ktdd*QQAEEDYARRSEEEYNRLPQQQp*pka*EKPAPAPKPEQPVPAPKT (SEQ ID NO: 16) |
| CDC3059-06 | pekpaeEPENPAPA*PKPAPA*PQPEkpekpaeQPKPEk*pdd*QQAEEDYARRSEEEYNRLTQQQ*ppka*EKPAPAPAPKPEQPa*pap*KT (SEQ ID NO: 140) |
| GA04175 | pekpaeEPENPAPA*PKPAPA*PQPEkpekpaeQPKPEk*pdd*QQAEEDYARRSEEEYNRLTQQQ*ppka*EKPAPAPAPKT (SEQ ID NO: 141) |
| 6901-05 | pekpaeEPENPAPA*PKPAPA*PQPEkpekpaeQPKPE*kpdd*QQAEEDYARRSEEEYNRLTQQQ*ppka*EKPAPAPAPKPEQPa*pap*KT (SEQ ID NO: 140) |
| 6963-05 | pekpaeEPENPAPA*PKPAPA*PQPEkpekpaeQPKPE*kpdd*QQAEEDYARRSEEEYNRLTQQQ*ppka*EKPAPAPAPKPEQPa*pap*KT (SEQ ID NO: 140) |
| AC94 | pekpaeEPENPAPA*PKPAPA*PQP*EKPAPAPA*PKPE*ksad*QQAEEDYARRSEEEYNRLTQQQ*ppkaEKPAPAPVPKPEQP**a*pap*KS (SEQ ID NO: 148) |
| SPNA45 | pekpaeEPENPAPA*PKPAPA*PQP*EKPAPAPA*PKPE*ksad*QQAEEDYARRSEEEYNRLTQQQp*pka*EKPAPAPAPKPE*ksad*QQAEEDYARRSEEEYNRLTQQQ*ppka*EKPAPAPKPEQPa*pap*KT (SEQ ID NO: 142) |
| GA60132 | P*EKPAPA*PETPAPEAPAPA*PKPAPA*PQP*EKPAPAP*Kpekpae*QPKPEkpad*QQAEEDYARRSEEEYNRLTQQQ*papa*PKPEQPa*pap*KT (SEQ ID NO: 143) |
| DBL6A | P*EKPAPAPA*PETPAPEAPAEQPKPAPETPAPAPKpekpaeQPKPE*kpad*QQAEEDYARRSEEEYNRLTQQQ*papa*PKPEQPAKpekpaeEPTQPEK (SEQ ID NO: 144) |
| SP14-BS292 | pekpaeEPENPAPA*PKPAPA*PQP*EKPAPAPA*PKPE*ksad*QQAEEDYARRSEEEYNRLTQQQ*ppkaEKPAPAPVPKPEQP**a*pap*KT (SEQ ID NO: 145) |
| INV104 | pekpaeETPAPAPKPEQPAEQ*PKPAPA*PQpekpaeEPENPAPAPQPE*ksad*QQAEEDYARRSEEEYNRLTQQQ*ppka*EKPAPAPQP (SEQ ID NO: 146) |
| GA60080 | PETPAPAPKPETPAPAPEAPAPAPKPEQPa*pap*KPE*ksad*QQAEEDYARRSEEEYNRLTQQQp*pka*EKPAPAPKPEQPa*pap*KT (SEQ ID NO: 147) |
| GA47373 | PDGDEEETPAPAPKPEQPAEQ*PKPAPA*P*gpapap*KPE*ktdd*QQAEEDYARRSEEEYNRLPQQQp*pka*EKPAPAPKPEQPVPAPKT (SEQ ID NO: 18) |
| Hungary19A-6 | PDGDEEETPAPAPKPEQPAEQ*PKPAPA*P*gpapap*KPE*ktdd*QQAEEDYARRSEEEYNRLPQQQp*pka*EKPAPAPKPEQPVPAPKT (SEQ ID NO: 18) |
| GA47210 | PDGDEEETPAPAPKPEQPAEQ*PKPAPA*P*gpapap*KPE*ktdd*QQAEEDYARRSEEEYNRLPQQQp*pka*EKPAPAPKPEQPVPAPKT (SEQ ID NO: 18) |
| GA05245 | PDGDEEETPAPAPKPEQPa*pa**PKPAPA*P*gpapap*KPE*ktdd*QQAEEDYARRSEEEYNRLPQQQp*pka*EKPAPAPKPEQPVPAPKT (SEQ ID NO: 19) |
| GA41301 | PDGDEEETPAPAPKPEQPa*pa**PKPAPA*P*gpapap*KPE*ktdd*QQAEEDYARRSEEEYNRLPQQQp*pka*EKPAPAPKPEQPVPAPKT (SEQ ID NO: 19) |
| SPAR95 | PDGDEEETPAPAPKPEQPAEQ*PKPAPA*P*gpapap*KPE*ktdd*QQAEEDYARRSEEEYNRLPQQQp*pka*EKPAPAPAPKPEQPa*pap*KT (SEQ ID NO: 20) |
| GA49138 | PDGDEEETPAPAPKPEQPAEQ*PKPAPA*P*gpapap*KPE*ktdd*QQAEEDYARRSEEEYNRLPQQQp*pka*EKPAPAPAPKPEQPa*pap*KT (SEQ ID NO: 20) |

TABLE 3-continued

| Example Group 3 PRDs | |
|---|---|
| Strain | Amino acid sequence |
| ATCC63033 | PDGDEEETPAPAPKPEQPAEQ*PKPAPA*PKPE*ktdd*<u>QQAEEDYARRSEEEYNRLPQQQ</u>*ppka*EKP APAPKPEQPVPAP (SEQ ID NO: 21) |
| Netherlands15 B-37 | PDGDEEETPAPEAPAEQPK*pekpae*ETPAPAPKPE*ksad*<u>QQAEEDYARRSEEEYNRLTQQQ</u>*ppk aEKPAPAPA*PKPEQPpapap*KT (SEQ ID NO: 149) |
| GA47522 | PDGDEEETPAPEAPAEQPK*pekpae*ETPAPAPKPE*ksad*<u>QQAEEDYARRSEEEYNRLTQQQ</u>*ppk aEKPAPAPA*PKPEQPpapap*KT (SEQ ID NO: 149) |
| BG7817 | PDGDEEETPAPEAPAEQPK*pekpae*ETPAPAPKPE*ksad*<u>QQAEEDYARRSEEEYNRLTQQQ</u>*ppk aEKPAPAPA*PKPEQPpapap*K (SEQ ID NO: 150) |
| BG11703 | PDGDEEETPPPEAPAEQPK*pekpae*ETPAPAPKPE*ksad*<u>QQAEEDYARRSEEEYNRLTQQQ</u>*ppk aEKPAPAPA*PKPEQPpapap*KS (SEQ ID NO: 151) |
| CDC0288-04 | PDGDEEETPAPEAPAEQPK*pekpae*ETPAPAPKPE*ksad*<u>QQAEEDYARRSEEEYNRLTQQQ</u>*ppk aEKPAPAPA*PKPEQPDPAPKPEQPpapaPKPEQPAK*pekpae*EPTQPEKPATPKT (SEQ ID NO: 152) |
| EF5668 | PDGDEEETPAPAPQ*pekpae*EPENPAPAPKPE*ksad*<u>QQAEEDYARRSEEEYNRLTQQQ</u>*ppka*EK PAPAPQPEqpapapKI (SEQ ID NO: 153) |
| GA40563 | PDGDEEETPAPAPqpapaPKPAPAPQ*pekpae*QPKAE*kpad*<u>QQAEEDYARRSEEEYNRLTQQQ</u>*p pka*EKPAPAPQPEqpapapKT (SEQ ID NO: 154) |
| BG7561 | PDGGEEETPAPAPQPDEPAPAPAPNAEqpapapKPE*ksad*<u>QQAEEDYARRSEGEYNRLTQQQ</u>*pp kaEKPAPAPA*PKPEQPpapap*N (SEQ ID NO: 125) |
| SP14-BS69 | PDGDEEETPAPAPQP*EKPAPAPA*PKPEQPpapap*APKPEQPpapap*APKPE*ktdd*<u>QQAEEDYARRS EEEYNRLPQQQ</u>*ppkaEKPAPA*PKPEQPVPAPKT (SEQ ID NO: 22) |
| G54 | PDGDEEETPAPAPQP*EKPAPAPA*PKPEQPpapap*KPE*ktdd*<u>QQAEEDYARRSEEEYNRLPQQQ</u>*pp kaEKPAPA*PKPEQPVPAPKT (SEQ ID NO: 23) |
| GA17484 | PDGDEEETPAPAPQP*EKPAPAPA*PKPEQPpapap*KPE*ktdd*<u>QQAEEDYARRSEEEYNRLPQQQ</u>*pp kaEKPAPA*PKPEQPVPAPKT (SEQ ID NO: 23) |
| CCRI_1974 | PDGDEEETPAPAPQP*EKPAPAPA*PKPEQPpapap*APKPE*ktdd*<u>QQAEEDYARRSEEEYNRLPQQQ</u> *ppkaEKPAPA*PKPEQPVPAPKT (SEQ ID NO: 24) |
| GA41538 | PDGDEEETPAPAPQP*EKPAPAPA*PKPEQPpapap*APKPE*ktdd*<u>QQAEEDYARRSEEEYNRLPQQQ</u> *ppkaEKPAPA*PKPEQPVPAPKT (SEQ ID NO: 24) |
| GA13430 | PDGDEEETPAPAPQPEqpapapAPKPEQPpapap*KPE*ksad*<u>QQAEEDYARRSEEEYNRLTQQQ</u>*pp kaEKPAPAPA*PKPEQPpapap*KT (SEQ ID NO: 114) |
| 459-5 | PDGDEEETPAPAPQPEqpapapAPKPEQPpapap*KPE*ksad*<u>QQAEEDYARRSEEEYNRLTQQQ</u>*pp kaEKPAPAPA*PKPEQPpapap*KT (SEQ ID NO: 114) |
| SP19-BS75 | PDGDEEETPAPAPQP*EKPAPAPA*PKPEQPpapap*KPE*ksad*<u>QQAEEDYARRSEEEYNRLTQQQ</u>*pp kaEKPAPAPA*PKPEQPpapap*KT (SEQ ID NO: 95) |

*lowercase indicates motif PEKPAE (SEQ ID NO: 9) (*pekpa*);
uppercase bold italics indicates motif PKPAPA (SEQ ID NO: 7) (*PKPAPA*);
uppercase italics indicates motif EKPAPAP (SEQ ID NO: 8) (*EKPAPAP*);
lowercase bold indicates motif QPAPAP (SEQ ID NO: 6) (qpapa);
non-motif residues are uppercase, plain font;
underline indicates NPB,
4 amino acid residues (lowercase italics) on either side of underlined sequence indicate conserved NPB-flanking regions.

Table 4 summarizes common motifs and frequency of their presence (at least once) in each PRD in each of the three PRD Groups; Table 4 table thus shows the likelihood of each motif appearing at least once in each of the polypeptides in each PRD Group:

TABLE 4

Common motifs and frequency of their presence in each PRD group

| Motif | Group 1 | | Group 2 | | Group 3 | |
|---|---|---|---|---|---|---|
| | no. | % | no. | % | no. | % |
| PKPEQP (SEQ ID NO: 5) | 48 | 96 | 0 | 0 | 48 | 74 |
| qpapap (SEQ ID NO: 6) | 50 | 100 | 2 | 10 | 60 | 92 |
| *PKPAPA* (SEQ ID NO: 7) | 2 | 4 | 19 | 90 | 44 | 68 |
| *EKPAPAP* (SEQ ID NO: 8) | 2 | 4 | 12 | 57 | 64 | 99 |
| pekpae (SEQ ID NO: 9) | 16 | 32 | 11 | 52 | 46 | 71 |
| NPB (e.g., QQAEEDYARRSEEEYNRLPQQQ) (SEQ ID NO: 10) | 0 | 0 | 0 | 0 | 65 | 100 |
| Total # sequences analyzed: | 50 | | 21 | | 65 | |

It was reported previously that NPB polypeptides tend to be highly immunogenic, see U.S. Pat. No. 8,808,704. It was also reported that a monoclonal antibody against the PKPEQP (SEQ ID NO:5) motif, found frequently in group 1 PRDs, protected mice against pneumococcal challenge. Daniels et al., 2010. The information presented herein, particularly Examples 4-6, provides evidence of immunogenicity of other portions of partial and complete PRD polypeptides. The present embodiments support additional and ongoing studies to characterize the immunogenicity of various motifs, combinations of motifs, and complete polypeptides.

The clear separation of PRDs into three groups and the frequency of common motifs within each group suggest that a vaccine that incorporates one PRD from each group should be able to generate cross-protective immunity against most pneumococcal strains. This is because a PRD from a particular group should be able to generate cross-protective immunity against pneumococci with other PRDs from the same group—in other words, with PRDs that share many of the same motifs as the vaccine PRD. A vaccine comprising a PRD from each group as defined herein should therefore generate cross-reactive immunity against nearly all PRDs. This underlies the present strategy of creating a vaccine that combines at least one PRD antigen from each of the PRD groups, in particular the strategy of developing a vaccine comprising three aHD-PRD constructs in which the PRDs include one selected from each of the PRD groups.

Another selection strategy for PRD antigens is suggested by the complete or nearly identical homology of some of the PRDs, as shown in Tables 1-3, and indicated by the horizontal lines connecting some strains in FIG. 3. Therefore, choosing as a vaccine antigen a PRD that is shared among several clinically relevant strains increases the likelihood of a protective immune response against all of these strains. For example, DBL1 represents an embodiment of a group 3 PRD antigen (incorporated into PspA03). This PRD is identical to those of six other analyzed strains.

For example, an embodiment of an aHD-PRD construct, PspA01.1 (see SEQ ID NO:1), that includes a group 2 PRD from strain GA47439, stimulated a protective immunogenic response in animal models; and the PRD broadened the cross-reactivity of this response (Examples 4-6). The amino acid sequence of this PRD is:

(SEQ ID NO: 12)
PETPAPAPAPAPAPAPAPAPAPKPAPAPKPAPAPKPAPAPKPAPAPKPAPAP

APAPAPKPAPAPKPAPAPAPAPAPAPKPEKPAEKPAPAPKPETPKT.

Another embodiment of an aHD-PRD construct, PspA01.2 (see SEQ ID NO:2), that includes a group 2 PRD from strain ND6012, stimulated a protective immunogenic response and this PRD broadened its response. The amino acid sequence of this PRD is:

(SEQ ID NO: 13)
PETPAPAPAPAPAPAPAPAPAPAPKPAPAPKPAPAPKPAPAPAPAPAPKP

EKPAEKPAPAPKPETPKT.

Similarly, another embodiment of an aHD-PRD construct, PspA01.3 (see SEQ ID NO:158), that includes a PRD fragment common to the following group 3 PRD strains: GA47597, SPN072838, GA19101, 70585, R6, RX1/D39, GA16242, GA17545, NP112, GA13856, 2071247, GA17971, SP18-BS74, GA13224 and GA60132, stimulated a protective immunogenic response. The amino acid sequence of this PRD is:

(SEQ ID NO: 157)
PEKPAPAPAPETPAPE.

Another embodiment of an aHD-PRD construct, PspA02 (see SEQ ID NO:3), that includes a PRD from the group 1 strain, EF3296, stimulated a protective immunogenic response in animal models(Examples 4-6). The PRD broadened the cross-reactivity of this response. The amino acid sequence of this PDR is:

(SEQ ID NO: 14)
PDGDEEETPAPAPQPEQPAPAPKPEQPAPAPKPEQPAPAPKPEQPAPAPK

PEQPAPAPKPEQPAKPEKPAEEPTQPEKPATPKT.

The PRDs of six other strains, GA19923, SPN034183, GA47628, GA18523, GA16833, and GA18068, are identical with each other and share high homology with the EF3296 PRD (lacking only an APAPKPEQ) (e.g., residues 19-26 of SEQ ID NO:14). Thus, the PRDs from all seven of these Group 1 strains are likely to be antigenic and strong candidates for inclusion in a PspA-based pneumococcal vaccine. The amino acid sequence of the PRD of these six strains is:

(SEQ ID NO: 15)
PDGDEEETPAPAPQPEQPAPAPKPEQPAPAPKPEQPAPAPKPEQPAPAPK

PEQPAKPEKPAEEPTQPEKPATPKT.

Another embodiment of an aHD-PRD construct, PspA03 (see SEQ ID NO:4), comprising a group 3 PRD from strain DBL1, stimulated a protective immunogenic response in animal models. This PRD also broadened the cross-reactivity of the immune response to PspA03. Six pneumococcal strains have exactly the same PRD as DBL1: EU-NP04, gamPNI0373, P1031, PNI0153, GA11304 and PCS70012 (see also Table 3). The amino acid sequence of this PRD is:

(SEQ ID NO: 16)
PEKPAEETPAPAPKPEQPAEQPKPAPAPQPAPAPKPEKTDDQQAEEDYAR

RSEEEYNRLPQQQPPKAEKPAPAPKPEQPVPAPKT

The data provided herein suggest that the immunogenicity of this sequence may be due, in part, to the non-proline block (NPB) in this sequence:

(SEQ ID NO: 10)
QQAEEDYARRSEEEYNRLPQQQ.

Fourteen other pneumococcal strains with analyzed PspAs, as shown in Table 3, also contain this NPB (SEQ ID NO:10). These strains are: 670-6B, GA47373, Hungary19A-6, GA47210, GA05245, GA41301, SPAR95, GA49138, ATCC6303, SP14-BS69, GM, GA17484, CCRI_1974, and GA41538. The PRDs of these strains are strong candidates for inclusion in a PspA-based vaccine comprising at least one aHD-PDR construct. The PRD amino acid sequences for each of these fourteen strains are shown in SEQ ID NO:17 through SEQ ID NO:24.

Another embodiment of an aHD-PRD construct, PspA01.3 (see SEQ ID NO:158), comprising a fragment common to fifteen group 3 PRDs, also stimulated a protective immunogenic response in animal models. Fukuyama et al., 2015. The amino acid sequence of this PRD fragment is: PEKPAPAPETPAPE (SEQ ID NO:157). The fifteen pneumococcal strains with analyzed PspAs that contain this PRD fragment are: GA47597, SPN072838, GA19101, 70585, R6, RX1/D39, GA16242, GA17545, NP112, GA13856, 2071247, GA17971, SP18-BS74, GA13224 and GA60132, as shown in Table 3. Thus, inclusion of this fragment may also enhance cross-reactivity against strains with identical or similar amino acid sequences in their PRDs.

Although there was no clear association between particular PRD groups and particular PspA aHD clades, there was a high degree of non-randomness in the associations (FIG. 2), a point that is relevant (see Example 2).

Example 2: Five Main Groups of aHDs Clade-Defining Regions and aHD Antigen Selection The clade-defining region (CDR), which usually consists of the approximately final 100 amino acids in an aHD, was thought to be the most antigenic domain within the aHD. McDaniel et al., 17 Microb. Pathog. 323 (1994); Roche et al., 2003; Vadesilho et al., 21 Clin. Vaccine Immunol. 940 (2014). Using 124 unique PspA genome sequences identified as described in Example 1, we extracted the aHDs from each sequence. To this information, we added that of 12 aHD sequences analyzed previously (see Hollingshead et al., 2000). We aligned the CDRs of 136 total, unique aHDs in a Geneious software platform (v7.1.7, Biomatters Ltd., New Zealand) using, in part, a Geneious alignment (Global alignment with Blosum62 matrix); then we created dendrograms using the Geneious Tree builder plugin (tree structures, as in FIG. 2). The dendrograms were made using the Neighbor Joining (NJ) method with a Jukes Cantor genetic distance model.

This was not an automated or straightforward process. Although characteristic amino acid sequences often mark the beginning of CDRs (for example, about 70 percent of clade 1 and clade 2 CDRs begin with either LKEID (e.g., residues 1-5 of SEQ ID NO:25) and LKEIG (SEQ ID NO:86), most clade 3 CDRs begin with LAKKQ (e.g., residues 1-5 of SEQ ID NO:32), and most clade 4 CDRs begin with LEK) many CDRs do not begin with characteristic sequences. Instead, the start of CDRs is marked by the beginning of a pattern of amino acid homology that is characteristic for each clade. Homologies often appear between same-clade strains prior to the CDRs. In such cases, however, the inter-strain patterns of homologies usually switch at the beginning of the CDRs. Thus, the transition from pre-CDR to post-CDR regions of aHDs is often marked by a transition in homology patterns. Great skill and judgment were required for determining the beginning of each CDR. The main criterion was to select the beginning of a region that showed high homology with similarly located regions from other strains, and to do so in a way that would be the least arbitrary for the largest percentage of PspAs.

The resulting novel tree diagram (FIG. 2) enables estimation of the relative CDR sequence homology between individual pneumococcal strains, clades, and families. The diagram is constructed so that the sum of the length of the vertical lines connecting any two strains (or the average of any two clades) is proportional to the likelihood of amino acid substitution at any position along a CDR sequence, i.e., proportional to the degree of CDR homology difference. Furthermore, this likelihood can be approximated by comparing this length to that of the vertical key bar shown in FIG. 2, which corresponds to an average of 0.2 single-pair amino acid substitutions per site for this length of vertical separation.

Thus, for example, comparing the length of this key bar to the summed length of the vertical lines connecting an average clade 4 strain and an average clade 5 strain suggests that the likelihood that any amino acid in the CDR of a clade 4 strain differs by one particular amino acid substitution from the similarly positioned amino acid in a clade 5 strain is about 0.35. Values over 1.0 are permitted because probabilities are for single-pair substitutions. If, for example, at the same CDR position some strains in the same clade have leucine (L), some strains have glycine (G), and yet others have tyrosine (Y), this site is considered to have two single-pair substitutions when comparing between average strains in the same clade. The likelihood of multiple single-pair substitutions per site is increased when comparing between strains in different clades and even more so when comparing between strains in different families.

Figure 2A:
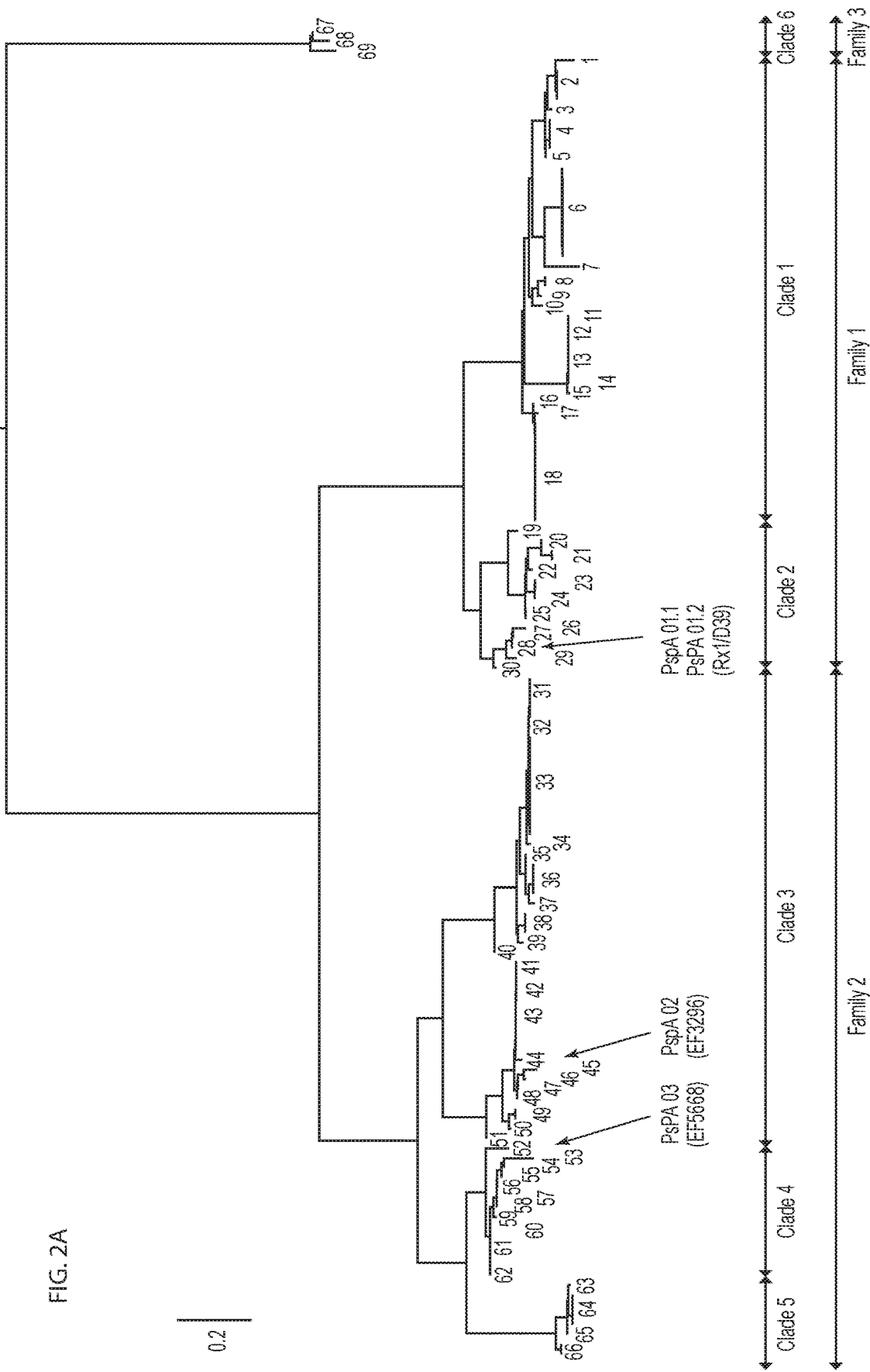
FIG. 2A is an embodiment of a tree structure diagram, mapping 136 pneumococcal strains analyzed and grouped according to amino acid homology of the clade defining regions (CDRs) in the aHDs of their PspA proteins. Family groups are also indicated. The tree diagram was constructed so that the sum of the length of the branch lines connecting any two strains (or the average of any two clades) is proportional to the likelihood of amino acid substitution at any position along a CDR sequence, i.e., proportional to the degree of difference in CDR homology. The length of the key bar corresponds to an average of 0.2 single-pair amino acid substitutions per site for the same branch length of separation between any of the 136 analyzed species. See Example 2. Arrows indicate the strains from which were derived aHD/CDR peptides used in four example embodiments of aHD-PRD constructs. The numerals in FIG. 2A provide a key to bacterial strains, as follows, in which strains followed by "−" are in PRD Group 2; strains followed by "+" are in PRD Group 3; the remainder (no mark) are in PRD Group 1 (see FIG. 2B-FIG. 3D): Clade 1 contains the following bacterial strains indicated by numerals in FIG. 2A: 1, AC94+; 2, CA13723, SPNA45+, GA47976; 3, GA60132+; 4, CDC3059-06+, 69001-05+, GA04175+, 6963-05+; 5, 70585+; 6, BG8743−, NP070−, 2061376−, SP23-BS72−, 208913−, GA58981−, GA56348−, GA14688−, GA44128−, 2071004−; 7, GA60080+; 8, BG9739−, L81905−; 9, DBL6A+; 10, INV104+; 11, 670-6B+; 12, EU-NP04+, gamPNI0373+, P1031+; 13, PNI0153, GA11304+, PCS70012+; 14, DBL1; 15, GA47502−; 16, BG6692+; 17, BG8838+; and 18, SP18-BS74+, GA47597+, SPN072838+, GA19101+, GA13224+, GA16242+, GA17545+, NP112+, GA13856+, GA17971+, 2071247+. Clade 2 contains the following strains indicated by numerals in FIG. 2A: 19, E134−; 20, SP6-BS73−; 21, BG9163−, EF6796−; 22, ND6012; 23, CGSP14−, GA47439−; 24, DBL5−; 25, GA62331+, GA54353+; 26, A66.2+; 27, R6+; 28, Rx1; 29: WU2; and 30, EF10197. Clade 3 includes the following strains indicated by numerals in FIG. 2A: 31, GA18068, GA19923, 3063-00, 7533-05, GA16833; 32, GA43380; 33, SP9-BS68, GA08780, GA17570, SPAR55, GA47751, CDC087-00, NP141, GA16531, GA13637, GA49447, GA40028; 34, GA47794; 35, GA02506; 36, GA47562, GA07914, GA47760, AP200; 37, GA13430+; 38, GA19690, OXC141, GA07228; 39, GA14373; 40, SPN034183; 41, AC122, GA47628; 42, GA17301, GA54644, 2070531; 43, CDC1873-00, GA02270, GA02714, 2070109, GA47283; 44, EF3296; 45, BG8090; 46, GA52612; 47, GA18523; 48, GA17328; 49, GA04216, SPS-BS71; 50, 459-5+; and 51, GA41410. Clade 4 contains the following strains indicated by numerals in FIG. 2A: 52, EF5668+; 53, BG7561+; 54, BG7817+; 55, BG11703+; 56, CDC0288-04+; 57, Netherlands15B-37+; 58, GA7522+; 59, GA40563+; 60, G54+; 61, GA17484+, CCRI 1974+, SP14-BS69+, SP19-BS75+; and 62, GA41538+. Clade 5 contains the following strains indicated by numerals in FIG. 2A: 63, ATCC63033+; 64, GA47373+, GA95245+, GA41301+, GA47210+; 65, Hungary19A-6+; and 66, SPAR95+, GA9128+. Clade 6 contains the following strains indicated by numerals in FIG. 2A: 67, SP-BS293; 68, BS397; and 69, BG6380+.
Figure 2B:
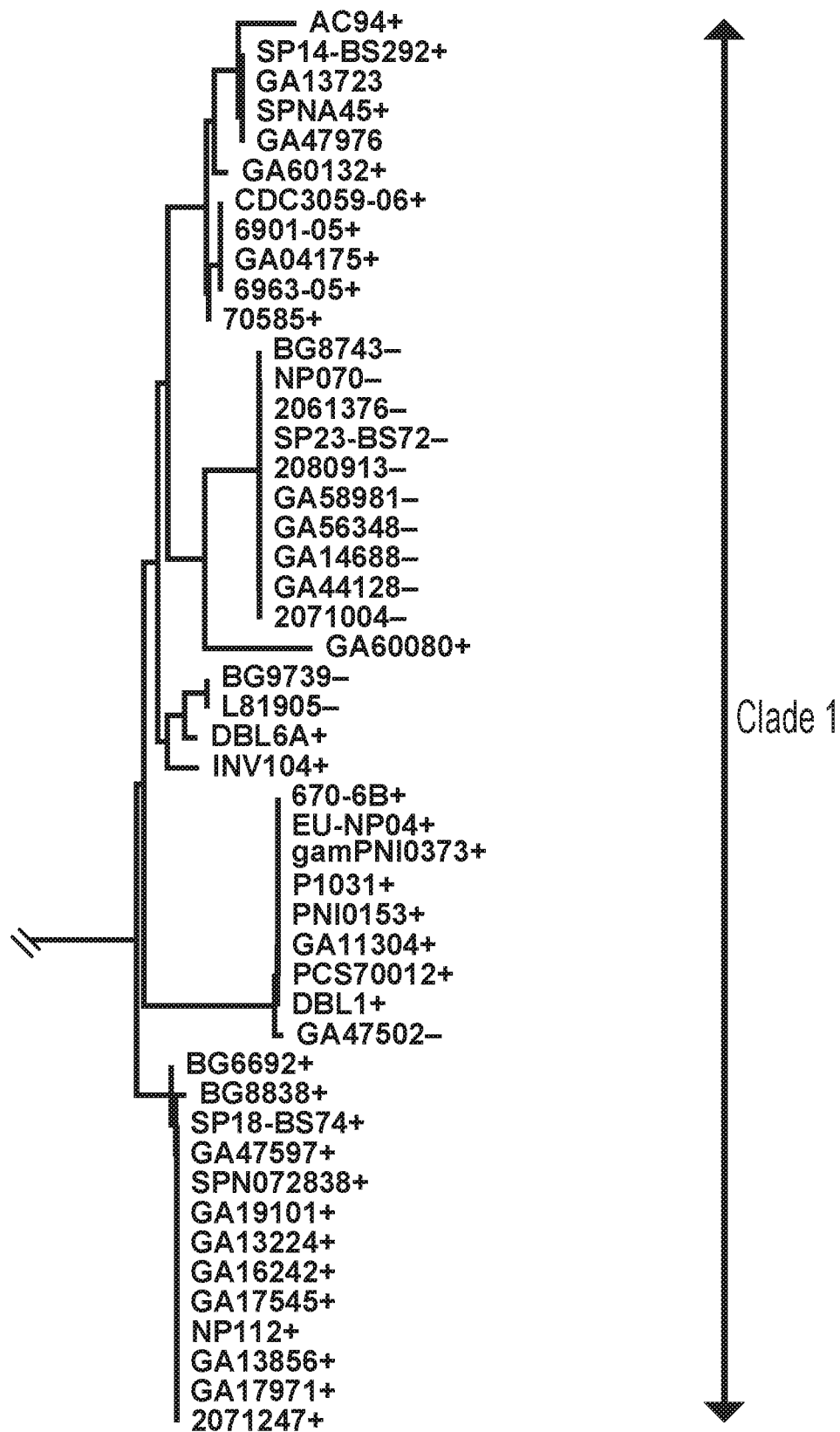
FIG. 2B is an exploded view of FIG. 2A, showing Clade 1 strains.
Figure 2C:
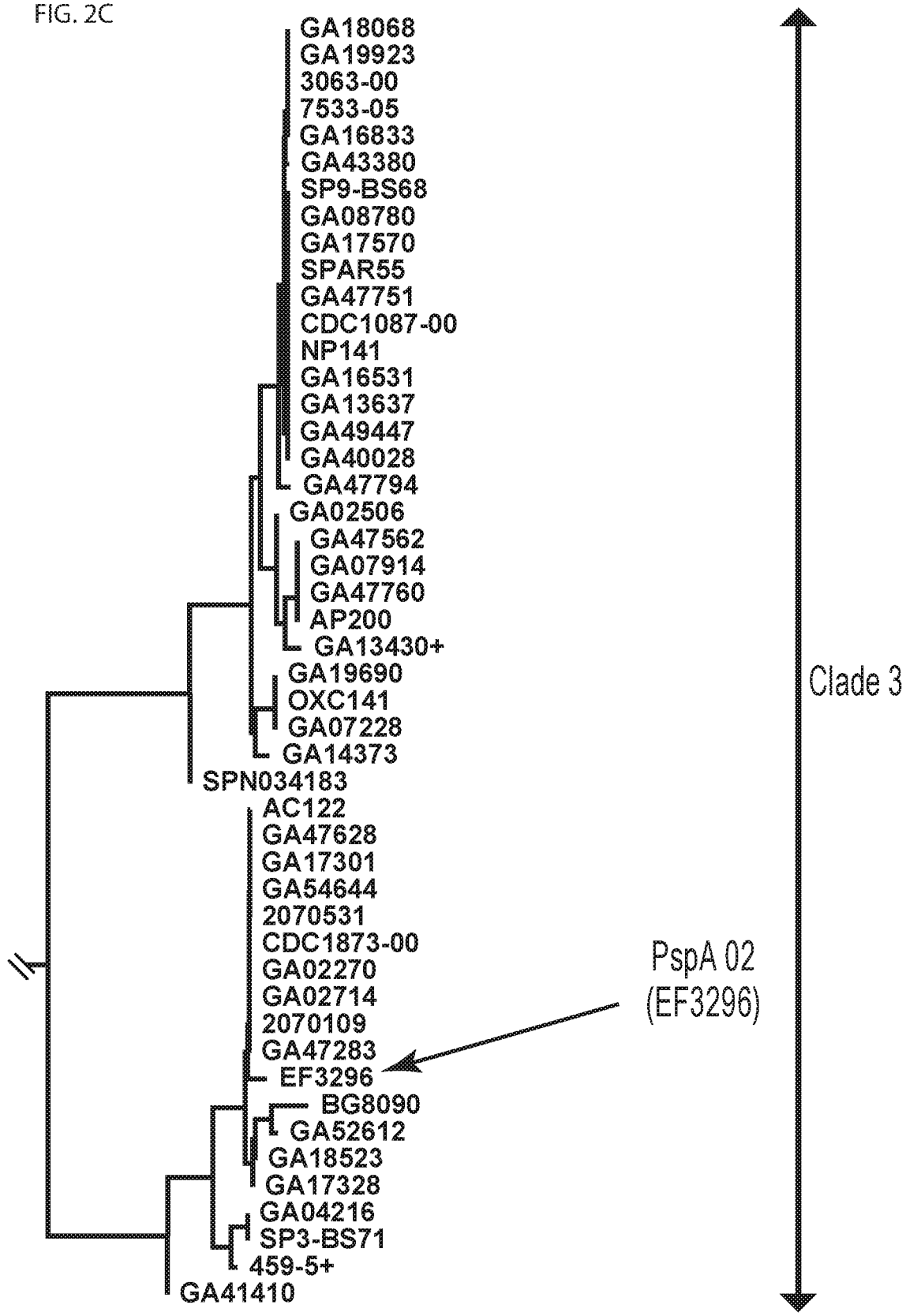
FIG. 2C shows Clade3 strains.
Figure 2D:
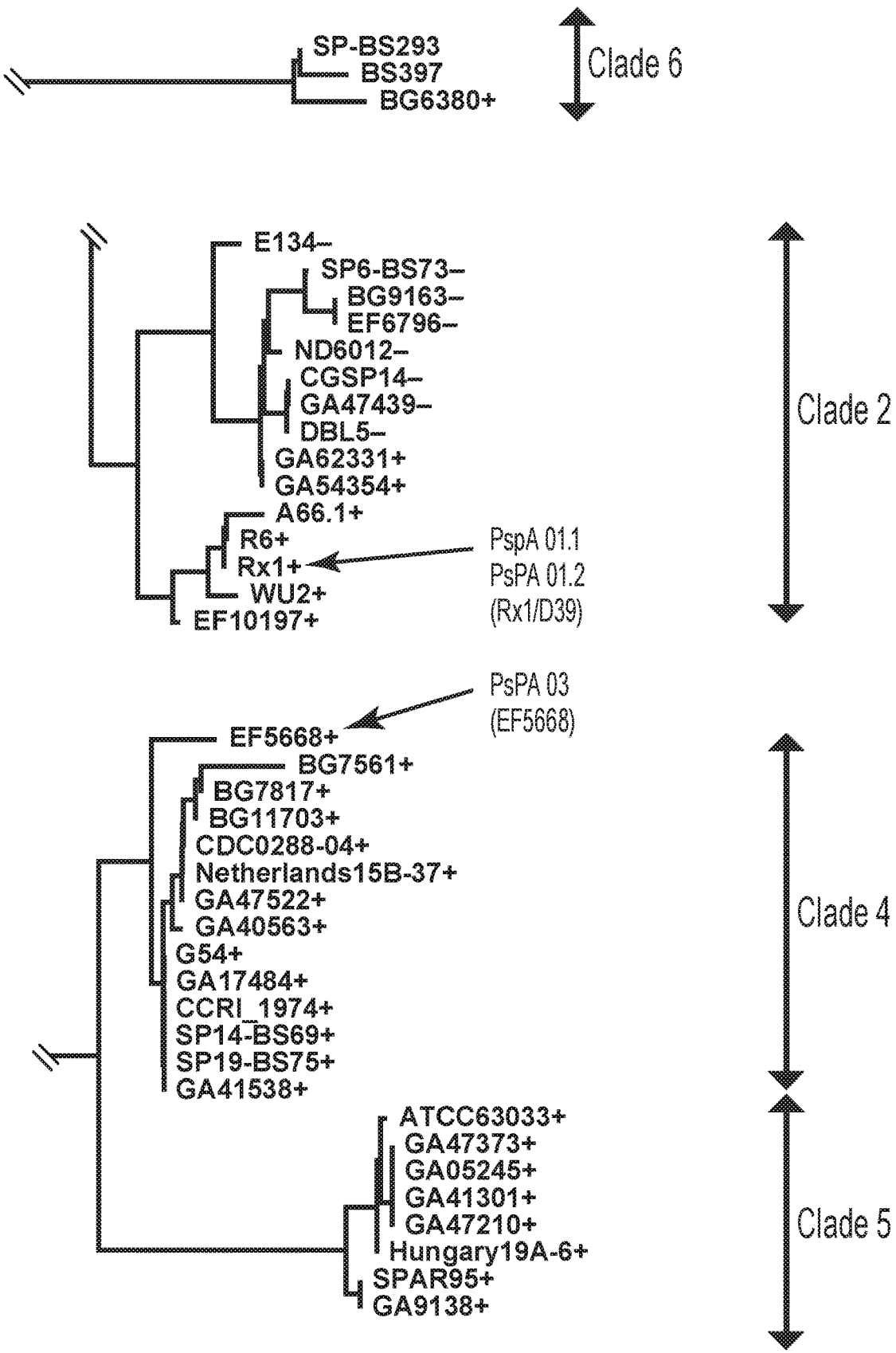
FIG. 2D shows Clades 2, 4, 5, and 6 strains.
Figure 3A:
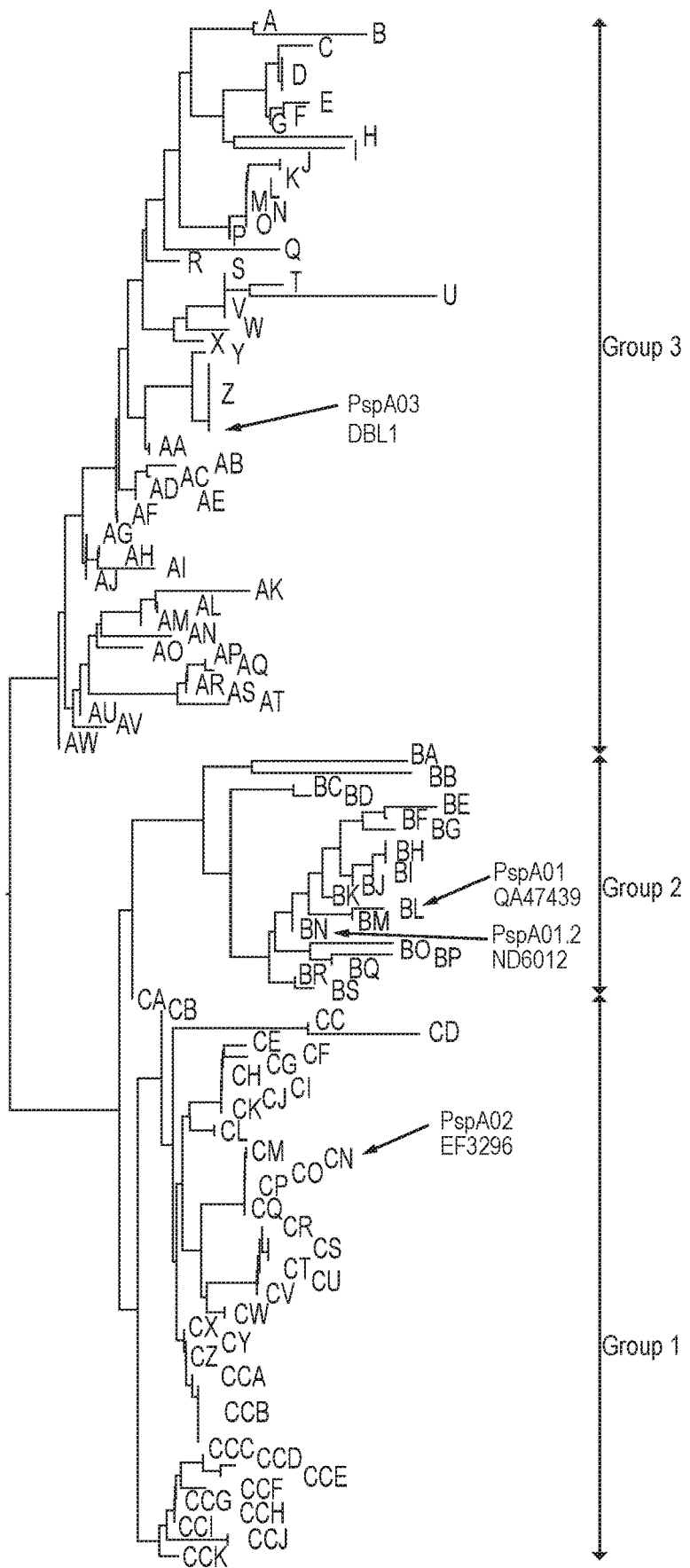
FIG. 3A is an embodiment of a novel tree diagram of 136 pneumococcal strains (same strains as in FIG. 2A), grouped according to amino acid homology among the PRDs of their PspA proteins. This is the first time, to our knowledge, that PRDs have been characterized in this fashion: revealing three PRD Groups. Group 1: plain typeface; Group 2: plain typeface followed by –; Group 3: plain typeface followed by +; arrows indicate the strains that provided PRD components of four embodiments of aHD PRD constructs as indicated; letter code as follows: Group 3, A, A66.1+; B, WU2+; C, BG6692+; D, GA47597+, SPN072838+, GA1901+, 70585+; E, BG8838+; F, SP18-BS74+; G, GA13224+; H, DBL6A+; I, EF10197+; J, R6+, RX1+; K, GA16242+; L, GA17545+; M, NP112+; N, GA17971+; 0, 2071247+; P, GA17971+; Q, INV104+; R, GA60080+; S, CDC3059-06+; T, GA04175+; U, BG6380+; V, 6901-05+, 6963-05+; W, GA60132+; X, SP14-BS292; Y, 670-6B+; Z, EU-NP04+, gamPNI0373+, P1031+, PNI0153+, GA11304+PCS7001+, DBL1+; AA, SPAR95+, GA9138+; AB, ATCC63033+; AC, Hungary19A-6+; AD, GA47373+, AE GA47210+; AF, GA05245+, GA41301+; AG, G54+; AH, CCRI 1974+, GA41538+; AI, SP14-BS69+; AJ, GA17484+; AK, AC94+; AL, GA62331+, GA54354+; AM, SPNA45+; AN, BG7561+; AO, EF5668+; AP, BG7817+; AQ, BG11703+; AR, Netherlands15B-37+; AS, GA47522+; AT, CDC0288-04+; AU, SP19-BHS75+; AV, GA40563+; and AW, GA13430+, 459-5+; Group 2, BA, SP-BS73–; BB, E134–; BC, 2061376–; BD, SP23-BS72–; BE, BG9739–; BF, DBL5–; BG, L81905–; BH, NP070–, GA14688–, GA44128–; BI, BG8743–; BJ, 2080913–; BK, EF6796–; BL, GA47439–; BM, BG9163–; BN, ND6012–; BO, GA58981–, GA56348–; BP, 2071004–; BQ, CGSP14–; and BR, GA47502–; Group 1, CA, GA14373; CB, GA13637; CC, SP-BS293; CD, BS397; CE, AC122; CF, SP9-BS68; CG, GA08780; CH, GA17570; CI, GA17301; CJ, GA54644; CK, 2070531; CL, GA02506, GA04216; CM, GA18068, EF3296; CN, GA19923; CO, SPN034183; CP, GA47628; CQ, GA18523, GA16833; CR, 3063-00; CS, 7533-05, GA07228, SP3-BS71; CT, GA43380; CU, GA19690; CV, OXC141; CW, GA49447, 2070109; CX, GA16531; CY, GA47751; CZ, GA40028, GA47283; CCA, GA02714; CCB, SPAR55, CDC10878-00, NP141, CDC1873-00, GA02270, GA41410; CCC, BG8090; CCD, GA47562; CCE, AP200; GGF, GA47794; CCG, GA07914; CCH, GA47769; CCI, GA52612; CCJ, GA13723, GA47976; and CCK, GA17328.
Figure 3B:
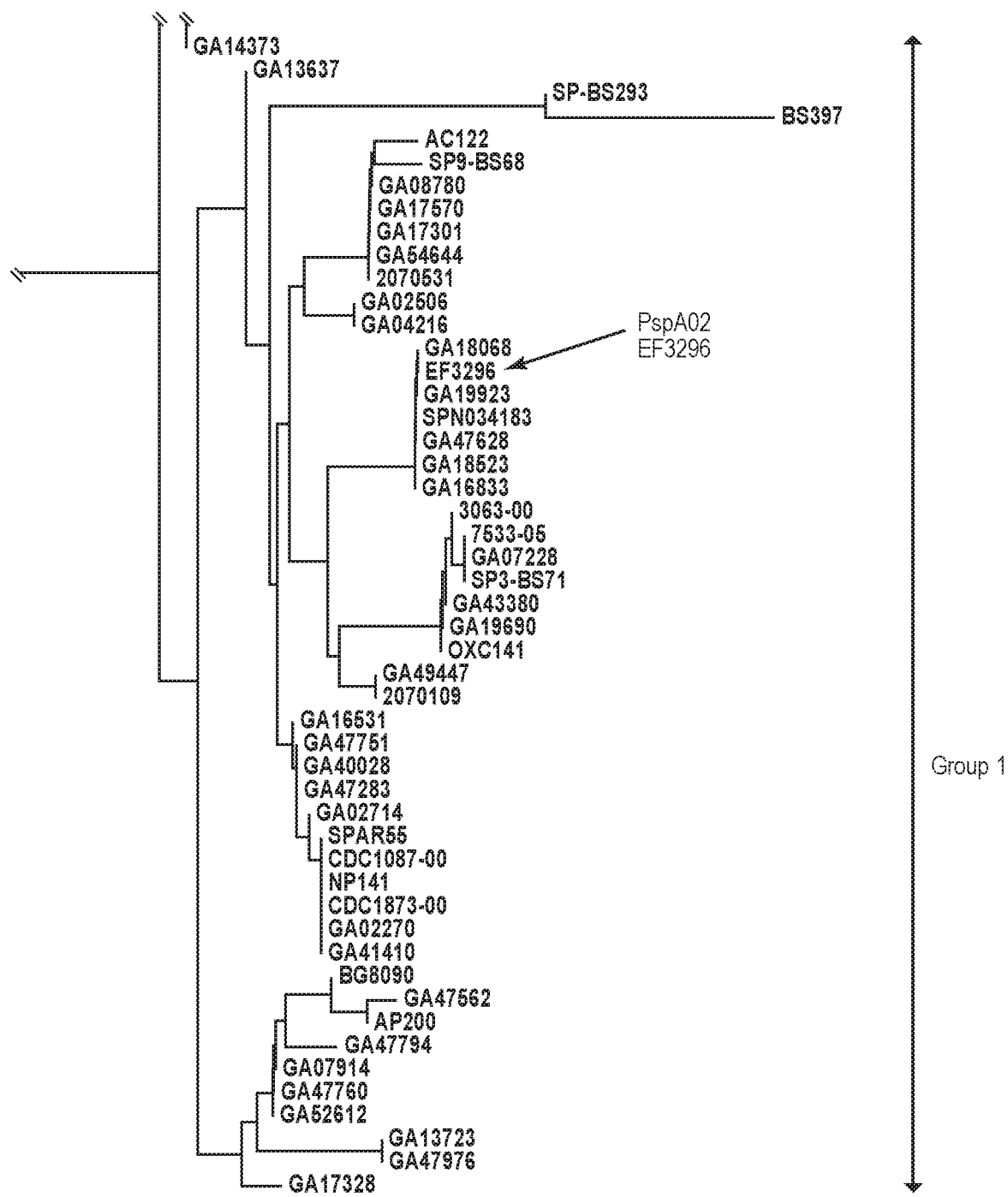
FIG. 3B is an exploded view of FIG. 3A, showing members of PRD Group 1.
Figure 3C:
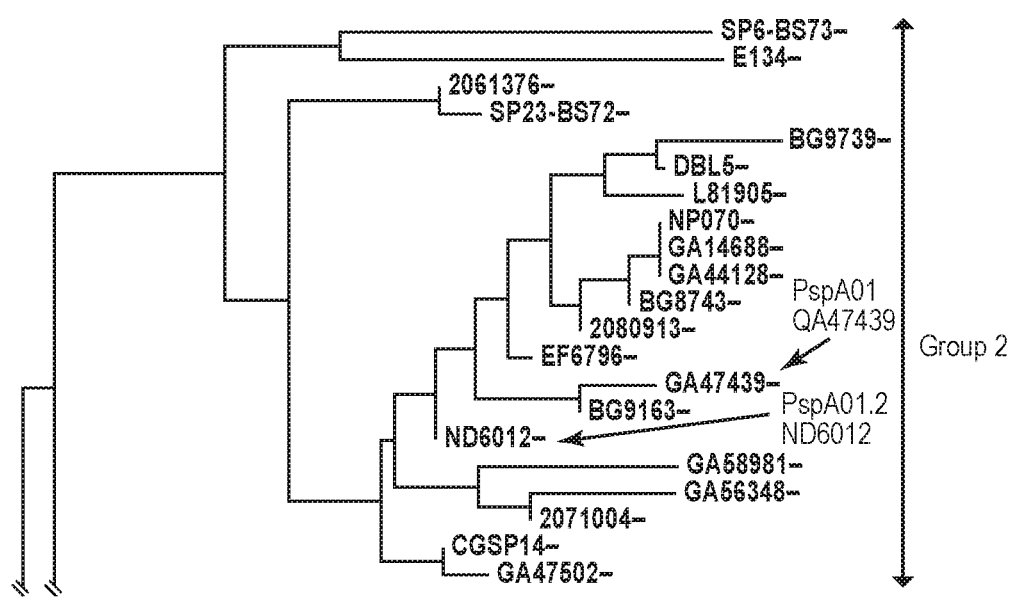
FIG. 3C shows members of PRD Group 2.
Figure 3D:
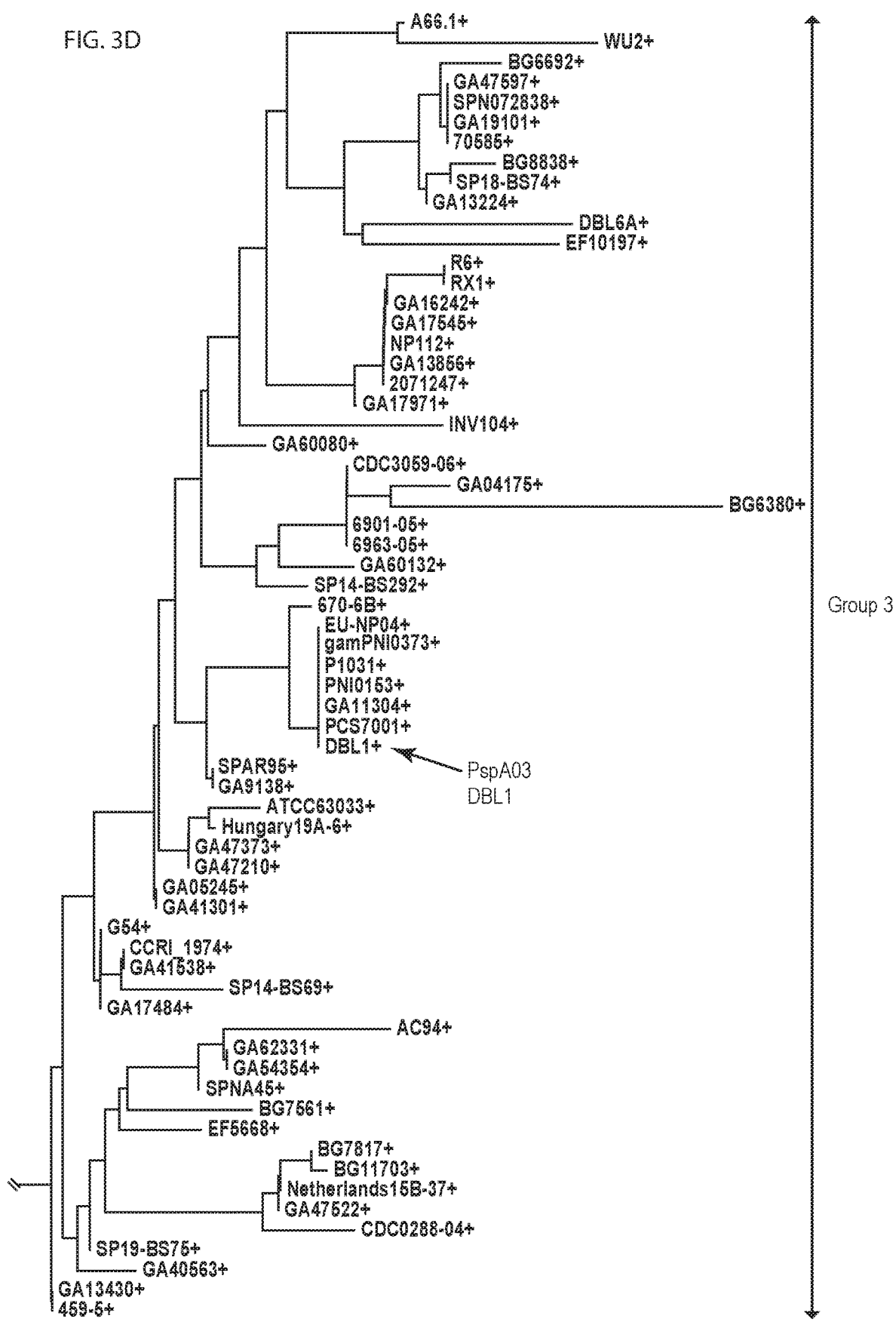
FIG. 3D shows members of PRD Group 3.

FIG. 2A shows a clear separation of CDRs (and consequently of antigenic similarity of the overall aHDs) into three families. The two main families, 1 and 2, consist of two and three clades respectively. Within family 1, clades 1 and 2 share slightly greater homology than clades 3, 4, and 5 in family 2 Family 3 contains only one clade, clade 6, which contains only three of the 136 analyzed sequence strains. To date, research worldwide indicates disease caused by pneumococci with family 3 PspA is rare. Hollingshead et al., 2000; Vela Coral et al., 2001; Hotomi et al., 2013. An unexpected result of this analysis is the high degree of CDR homology between many of the strains assigned in each clade. In FIG. 2A, a straight horizontal line connecting individual strains means complete homology between their CDRs.

Thus, the FIG. 2A-FIG. 2D CDR tree diagram suggests strategies for selecting aHDs to include in the aHD-PRD vaccine antigen constructs. For example, the tree diagram suggests that selecting an aHD from either clade 1 or 2 may likely elicit cross reactivity against most family 1 pneumococcal subtypes of PspA. Furthermore, the somewhat greater diversity in family 2 suggests that at least two aHD antigens may be selected from different family 2 clades, such as one from the large clade 3 and one from clades 4 or 5. These strategies guided selection of aHDs that we joined recombinantly with PRDs to provide three example embodiments of aHD-PRD immunogenic constructs: an aHD from each of clades 2, 3 and 4 (see Example 3).

Animal data indicated that the aHDs of PspA01.1, PspA01.2, PspA02, and PspA03 are immunogenic (see Examples 4-6). There is additional evidence that the cross-reactivity of some aHD antigens is high. Nabors et al., 2000; Darrieux et al., 2007 & 2008; Moreno et al., 2010, Fukuyama et al., 2015.

In the case of PspA01.1 (SEQ ID NO:1), PspA01.2 (SEQ ID NO:2), and PspA01.3 (SEQ ID NO:158), this means the clade 2 CDR sequence derived from strain D39 is immunogenic. A variant this strain, Rx1, lacks a polysaccharide capsule, but has the same PspA. The amino acid sequence of this CDR is:

```
(SEQ ID NO: 25)
LKEIDESESEDYAKEGFRAPLQSKLDARKAKLSKLEELSDKIDELDAEIA

KLEDQLKAAEENNNVEDYFKEGLEKTIAAKKAELEKTEADLKKAVNE.
```

The complete amino acid sequence of the D39/Rx1 aHD is provided in SEQ ID NO:159.

As alternative clade 2 antigens, however, one may select an aHD from one of the following strains: DBL5, CGSP14, GA47439, which share the following CDR sequence:

```
(SEQ ID NO: 26)
LKDINESDSEDYVKEGLRAPLQSELDTKKAKLLKLEELSGKIEELDAEIA

ELEVQLKDAEGNNNVEAYFKEGLEKTTAEKKAELEKAEADLKKAVDE;
``` or from strain ND6012, which has the following, nearly homologous, CDR sequence:

```
(SEQ ID NO: 27)
LKEIDESDSEDYIKEGFRAPLQSELDTKKAKLLKLEELSGKIEELDAEIA

ELEVQLKDAEGNNNVEAYFKEGLEKTTAEKKAELEKAEADLKKAVDE
```

The CDRs of these four strains share close homology with the other analyzed clade 2 CDR sequences (see FIG. 2). Moreover, they all have group 2 PRDs. Eliciting immunity against this CDR provides additional coverage against strains that might not be sufficiently covered by immunization with PRD group 2 antigens. The complete aHD amino acid sequences of DBL5, CGSP14, GA47439 and ND6012 are provided in SEQ ID NO:28 to SEQ ID NO:31.

Our animal data indicate the CDR of the aHD in PspA02 (see SEQ ID NO:3), derived from the clade 3 strain, EF3296, is also immunogenic; the amino acid sequence of this CDR is:

```
(SEQ ID NO: 32)
LAKKQTELEKLLDSLDPEGKTQDELDKEAEEAELDKKADELQNKVADLEK

EISNLEILLGGADSEDDTAALQNKLATKKAELEKTQKELDAALNELG
```

Twenty-six clade 3 pneumococcal strains, GA47628, GA17301, GA54644, 2070531, CDC1873-00, GA02270, GA02714, 2070109, GA47283, EF3296, GA18068, GA19923, 3063-00, 7533-05, GA16833, 5P9-B568, GA08780, GA17570, SPAR55, GA47751, CDC1087-00, NP141, GA16531, GA13637, GA49447, and GA40028 (over half of forty-six clade 3 strains analyzed herein) share substantial identity with this CDR. Thus, aHDs comprising this CDR should provide direct immunity against many pneumococcal strains. The complete aHD amino acid sequences of these twenty-six strains are provided in SEQ ID NO:33 to SEQ ID NO:58.

Animal model data also indicate immunogenicity of the CDR of the aHD in construct PspA03 (see SEQ ID NO:4), derived from clade 4 strain EF5668. The amino acid sequence of this CDR is:

```
(SEQ ID NO: 59)
LEKVLATLDPEGKTQDELDKEAAEAELNEKVEALQNQVAELEEELSKLED

NLKDAETNNVEDYIKEGLEEAIATKKAELEKTQKELDAALNELG;
``` and the amino acid sequence of its complete EF5668 aHD is shown as SEQ ID NO:60.

As an alternative clade 4 aHD antigen, aHDs with CDRs that have even more homology with each other may be selected to increase the likelihood of strong cross-reactivity with as many clinically important strains as possible. Three examples are the strains CDC0288-04, Netherlands15B-37, and GA47522, which all have a CDR with the following amino acid sequence:

```
(SEQ ID NO: 61)
LEKAEAELENLLSTLDPEGKTQDELDKEAAEAELNKKVEALQNQVAELEE

ELSKLEDNLKDAETNNVEDYIKEGLEEAIATKQAELEKTQKELDAALNEL

G.
```

Thus, an alternative strain for aHD proteins may be CDC0288-04, that has the complete aHD amino acid sequence shown in SEQ ID NO:62.

Clade 4 strains GM, GA17484, CCRI_1974, SP14-BS69, SP19-BS75, and GA41538 also have CDRs with the same amino acid sequence:

```
(SEQ ID NO: 63)
LEKAEAELENLLSTLDPEGKTQDELDKEAAEAELNKKVEALQNQVAELEE

ELSKLEDNLKDAETNNVEDYIKEGLEEAIATKKAELEKTQKELDAALNEL

G.
```

Therefore, the aHD of GM, having the complete amino acid sequence shown in SEQ ID NO:64, provides another alternative source for clade 4 aHD antigens.

FIG. 2 provides other guidance selecting additional aHD antigens that may not be conjugated to PRDs. In at least one embodiment, for example, a vaccine composition comprises in addition to three aHD-PRD constructs, at least one, such as one or two, unconjugated aHDs. Considering the aHDs in particular aHD-PRD constructs with homology differences shown in FIG. 2, and in light of particular clinical importance, unconjugated aHDs may be selected from clade 1 and clade 5, such as one unconjugated aHD from clade 1 and one unconjugated aHD from clade 5.

As for a clade 1 strain, another embodiment provides an immunogenic composition comprising at least one unconjugated clade 1 aHD selected from the following pneumococcal strains: BG8743, NP070, 2061376, 5P23-B572, 2080913, GA58981, GA56348, GA14688, GA44128, or 2071004. These strains all have the same CDR sequence:

```
                                                     (SEQ ID NO: 65)
LKEIDESDSEDYIKEGLRAPLQSKLDAKKAKLSKLEELSDKIDELDAEIA

KLEKDVEDFKNSDGEQAEQYLVAAKKDLDAKKAELENTEADLKKAVDE.
```

This region (SEQ ID NO:65) shares close homology to the CDRs of other analyzed clade 1 regions, and thus may elicit strong cross-reactivity against other clade 1 PspAs.

Additionally, the preceding clade 1 strains all have group 2 PRDs. Together, they constitute nearly half of all analyzed strains with group 2 PRDs distributed across all clades. In the event that the group 2 PRD antigens in PspA01.1 and PspA01.2 provide insufficient cross-reactivity against pneumococcal strains having group 2 PRDs, an additional aHD with the above CDR (SEQ ID NO:65) may provide protection against such strains. The complete aHD amino acid sequences of strains BG8743, NP070, 2061376, SP23-BS72, 2080913, GA58981, GA56348, GA14688, GA44128, and 2071004 are shown in SEQ ID NO:66 to SEQ ID NO:75, respectively.

Alternative clade 1 aHD antigens having CDRs with close homology to other clade 1 CDRs include those from strains SP18-BS74, GA47597, SPN072838, GA19101, GA13224, GA16242, GA17545, NP112, GA13856, GA17971, or 2071247; which share substantial identity in the CDR having the following amino acid sequence:

```
                                                     (SEQ ID NO: 76)
LKEIDESDSEDYVKEGLRAPLQSELDAKQAKLSKLEELSDKIDELDAEIA

KLEKNVEDFKNSNGEQAEQYRAAAEEDLAAKQAELEKTEADLKKAVNE.
```

Other alternative clade 1 aHD antigens include those derived from strains 670-6B, EU-NP04, gamPNI0373, P1031, PNI0153, GA11304, or PCS70012, which also share a common CDR having amino acid sequence:

```
                                                     (SEQ ID NO: 77)
LKGIDESDSEDYVKEGLRAPLQSELDAKRTKLSTLEELSDKIDELDAEIA

KLEKNVEYFKKTDAEQTEQYLAAAEKDLADKKAELEKTEADLKKAVNE.
```

Thus, the aHDs of strains NP112 and 670-6B provide two specific alternative embodiments of clade 1 aHD antigens: one from each of the above CDR groups. Their complete amino acid sequences are shown as SEQ ID NO:78 and SEQ ID NO:79, respectively.

Regarding possible clade 5 unconjugated (unlinked) aHDs that may be included in a composition comprising at least one aHD-PRD construct, in at least one embodiment this may be selected from pneumococcal strains GA47373, GA05245, GA41301, GA47210, or Hungary19A-6. These strains constitute most of the analyzed clade 5 strains, and their CDRs are almost completely homologous. For example, the following is the CDR of GA47373 (the complete aHD amino acid sequence of GA47373 is shown in SEQ ID NO:81):

```
                                                     (SEQ ID NO: 80)
LEDAELELEKVLATLDPEGKTQDELDKEAAEDANIEALQNKVADLENKVA

ELDKEVTRLQSDLKDAEENNVEDYVKEGLDKALTDKKVELNNTQKALDTA

QKALDTALNELG.
```

Example 3: Production of Pure, Stable aHD-PRD Constructs Using an *E. coli* Expression System Amino acid sequences of recombinant aHD-PRD constructs were designed according to the embodiment described in Examples 1 and 2. Three particular aHD-PRD constructs were selected for expression: one construct comprising an aHD of family 1 from either clade 1 or 2; two constructs comprising aHDs from family 2, one of which was be from clade 3, and the remaining aHD could be from either clades 4 or 5.

One embodiment included a clade 2 aHD (from strain D39) that was reportedly highly immunogenic. Fukuyama et al., 2015. Another embodiment included a clade 3 aHD (from strain EF3296), reportedly reactive with human antibodies to PspA. Nabors et al., 2000; Roche et al., 2003. An additional embodiment included a clade 4 aHD from strain EF5668 that previous research indicated as highly immunogenic in mice.

To complete the aHD-PRD constructs, sequences of three different complete PRDs, or fragments thereof, were added, one to each of the C-terminal ends of each of the three initially selected aHDs. An added PRD (or fragment thereof) might be the same as found in the naturally occurring pneumococcal strain from which the aHD was derived, or it could be from a different pneumococcal strain, in which case the aHD-PRD construct would be an artificial fusion protein. In one embodiment, each of the PRDs (or fragments thereof) was from a different PRD group (one from each of the three PRD groups). In another embodiment, two or even three of the PRDs (or fragments thereof) were from the same PRD group (see Example 7).

Additional aHD-PRD vaccine antigen constructs can include PRDs selected from groups that show high immunogenicity and cross-reactivity, or contain particular motifs (or combinations thereof) that show high immunogenicity and cross-reactivity.

As indicated in Example 2, an embodiment of a vaccine may include only three aHD-PRD constructs and further include at least one aHD unlinked to any PRD. These aHDs may be selected from among clades not represented in the three main aHD-PRD constructs. Furthermore, another embodiment of a vaccine may comprise only two aHD-PRD constructs and at least one aHD unlinked to any PRD, as these alone may provide sufficient cross-reactivity to protect against most pathogenic pneumococcus strains (see Example 7). Indeed, another embodiment of a vaccine may comprise just one aHD-PRD construct and two or more aHDs unlinked to any PRD.

The amino acid sequences of the initial aHD-PRD constructs are shown herein. These can be expressed in a bacterial expression system using standard genetic engineering techniques known to persons skilled in the art. As an example, the DNA molecules encoding PspA01.1, PspA01.2, PspA01.3, PspA02, and PspA03 can be synthesized separately as viral plasmid DNA molecules using translation codons optimized for an *E. coli* expression system.

An example of a nucleic acid molecule (specifically a DNA) capable of encoding PspA01.1 (SEQ ID NO:1) is shown in SEQ ID NO:82. An example of a DNA molecule encoding PspA01.2 (SEQ ID NO:2) is shown in SEQ ID NO:83. An example of a DNA molecule encoding PspA01.03 (SEQ ID NO:158) is shown in SEQ ID NO:160. An example of a DNA molecule encoding PspA02 (SEQ ID NO:3) is shown in SEQ ID NO:84. Finally, an example of DNA molecule encoding the PspA03 (SEQ ID NO:4) is shown in SEQ ID NO:85.

These plasmid DNAs were cloned separately into pET17b between the HindIII and EcoRI sites. The plasmids were then transfected separately into *E. coli* BL21 (DE3) cells. After culturing the transfected *E. coli*, the sonicated cell supernatant were loaded into both of DEAE- and SP-Sepharose ion exchange chromatography columns. This was followed by gel filtration on a Sephacryl S-200 column, and finally by pooling of the active fractions separately for each of the expressed proteins. FIG. 5 shows the purity of the expression products using lithium dodecyl sulfate polyacrylamide gel electrophoresis. Western blot analysis using polyclonal antibodies against the individual aHD-PRD constructs confirmed their identities, as did monoclonal antibodies that bound to unique epitopes on each of the constructs.

Example 4: Immunogenicity Studies with Single Constructs in IM Formulation

Formulations for intramuscular (IM) administration comprising individual aHD-PRD constructs were prepared with an alum adjuvant. This alum formulation was made by absorbing the individual aHD-PRD constructs described in Example 3 on an aluminum hydroxide ($Al(OH)_3$) gel as described. Lindblad, 82 Immuno. Cell Biol. 497 (2004).

Each of three aHD-PRD constructs (PspA01.1, PspA02, and PPspA03) were tested individually, each construct in two rabbits, to assess direct and cross-reactive immunity. Each rabbit is designated as PspA_R1 or PspA_R2, according to the antigen it received. For example, PspA01.1_R1 and PspA01.1_R2 were the two rabbits immunized with PspA01.1 (FIG. 5). On day 0, each rabbit was immunized IM with 100 μg of the designated antigen with complete Freund's adjuvant. Two weeks later, each rabbit was boosted IM with 100 μg of the designated antigen with incomplete Freund's adjuvant. After an additional two weeks, the sera from individual rabbits were tested using indirect ELISA in wells plated with the individual aHD-PRD constructs (separate wells for each construct). FIG. 5 shows titers of serum IgG (reciprocal $\log_2$ ELISA titers) binding specifically to each of the three antigen constructs. The end-point titers were expressed as reciprocal $\log_2$ of the last dilution that gave an $OD_{450}$ of 0.1 greater than the negative control. The high antibody titers each rabbit generated against the immunizing construct were expected. Notably, however, the titers the rabbits generated against each of the two non-immunizing constructs indicated extent of cross-reactivity against dissimilar antigens. As noted previously, PspA01.1 includes a family 1, clade 2 aHD; while PspA02 and PspA03 include family 2, clades 3 and 4 aHDs, respectively. Thus, it is not surprising that the intra-family but inter-clade cross reactivity is higher than inter-family cross-reactivity.

The following studies with larger numbers of mice confirmed immunogenicity and supported challenge studies.

Using the following procedure, we showed that the IM formulation elicits a strong PspA-specific serum IgG response in mice following a single primary IM immunization and a single booster injection at 7.5 weeks: Thirty 7-week-old BALB/c female mice were divided into three groups of ten and immunized each group with a single aHD-PRD construct formulated with alum as an adjuvant—one of each of the following three constructs, PspA01.1, PspA02 or PspA03, for each of the three groups of mice. Five mice in each group received a 3 μg dose and five received a 10 μg dose. Mice in both groups received an injection volume of 0.02 mL into an upper hind leg muscle. At 7.5 weeks, all mice were boosted with a single injection of the same antigen at the same dose and volume into the same muscle, but this booster dose was not formulated with alum or any other adjuvant.

ELISA assays were used to measure the individual serum titers of IgG antibodies binding to the specific construct with which each mouse was immunized Plates (96-well) were coated with 1 μg/ml of the construct in phosphate-buffered saline (PBS) overnight at 4° C. After blocking with 1% BSA in PBS-Tween, two-fold serial dilutions of samples were added and incubated for 2 hr at room temperature (RT). After washing the samples, we added horseradish peroxidase (HRP)-conjugated goat anti-mouse IgG diluted 1:1000, and incubated the samples for 2 hr at RT. After the incubation, color was developed with the use of 3,3',5,5'-Tetramethyl-benzidine (TMB) Microwell Peroxidase Substrate System (XPL). End-point titers were expressed as the reciprocal log 2 titer of the last dilution that gave an $OD_{450}$ of at least 0.1 greater than the negative control. Elevated serum IgG levels persisted more than eight weeks following the booster injection, indicating a sustained memory response (FIG. 6).

Example 5: Immunogenicity Studies with Single Constructs in IN Formulation

The delivery vehicle for the IN formulation included a cationic cholesteryl-group-bearing pullulan (cCHP or nanogel). Pullulan is a polymer of maltotriose. Production of cCHP are known and provided elsewhere. See e.g., Ayame et al., 19 Bioconj. Chem. 882 (2008); Nochi et al., 2010. Steps include using a yeast expression system to manufacture pullulan, shortening the raw molecule to a weight of 50 kD to 100 kD, covalently attaching cholesteryl groups (~1.1-1.6 per 100 glucose units), and covalently adding cationic amino groups (~20 per 100 glucose units).

One manufacturing method is outlined as follows: A hydroxyl group-containing-hydrocarbon or sterol having 12 to 50 carbon atoms was first allowed to react with a di-isocyanate compound represented by OCN-R1 NCO (wherein R1 represents a hydrocarbon group having 1 to 50 carbon atoms) to produce an isocyanate-group-containing hydrophobic compound containing one molecule of the hydroxyl-group-containing-hydrocarbon (or sterol). The resulting isocyanate-group-containing hydrophobic compound was allowed to react with a polysaccharide to produce a hydrophobic-group-containing polysaccharide that contains a hydrocarbon or steryl group with 12 to 50 carbon atoms. Next, the product was purified with a ketone-based solvent to produce a high-purity hydrophobic-group-containing polysaccharide.

A suitable polysaccharide can be, for example, pullulan, amylopectin, amylose, dextran, hydroxyethyl dextran, mannan, levan, inulin, chitin, chitosan, xyloglucan, or water-soluble cellulose. In at least one embodiment, the polysaccharide is pullulan.

Examples of nanogels suitable for IN vaccine include cholesterol hydrophobic-group-containing polysaccharide (CHP) and a cationic CHP derivative (cCHP). CHP has a structure in which 1 to 10, for example 1 to 2, cholesterol molecules are added by substitution per 100 glucose units of pullulan having a molecular weight of 30,000 to 200,000 kD. An example range of the pullulan molecular weight is 70,000 kD to 100,000 kD.

The degree of cholesterol substitution per 100 glucose units may be chosen based on the size and the degree of hydrophobicity of the antigen. In order to further vary the degree of hydrophobicity of the CHP, one or more alkyl groups having 10 to 30 (e.g., about 12 to 20) carbon atoms each may be added. At least one embodiment provides a nanogel having a particle size of 10 to 40 nm, such as 20 to 30 nm. Such a CHP nanogel has been used in a human clinical trial of a cancer vaccine, where the CHP nanogel serves as a delivery vehicle for cancer antigens.

Another embodiment provides a cCHP nanogel which incorporates a positively charged functional group, for example, a cationic amino group. This enables the nanogel-antigen complex to be retained longer on the negatively charged nasal mucosa surface. The optimal inclusion ratio for the cationic amino group depends on the antigen. An optimal range for most antigens, including PspA, is 18 to 22 (such as 20) per 100 glucose units of the cCHP.

The following describes an example method for combining amino groups with a CHP nanogel: lyophilized CHP (approximately 0.15 g) was dissolved in 15 mL of dimethyl sulfoxide (DMSO) and 1-1'-carbonyldiimidazole (approximately 75 mg) was added thereto under a nitrogen stream. The reaction was allowed to proceed at RT for several hours (e.g., about 1 hr). A cationic amine, for example, ethylenediamine (e.g., about 300 mg) was gradually added to the reaction solution and the mixture stirred for several hr to over a day (e.g., about 24 hr). The resulting reaction solution was dialyzed against distilled water for several days. After dialysis, the reaction solution was freeze-dried to obtain an opalescent solid. The degree of ethylenediamine substitution can be evaluated by elemental analysis using, for example, H-NMR.

After making the nanogel, nanogel formulations of each of three aHD-PRD constructs, PspA01.1, PspA02, and PspA03, were created using reported procedures. See U.S. Pat. No. 8,961,983; Nochi et al., 2010; Kong et al., 2013; Fukuyama et al., 2015. These procedures involved mixing a 2% cCHP solution with a solution containing an aHD-PRD construct at an approximate 1:1 molecular ratio at either 40° C. or 50° C. for 1 hr, then mixing with phosphate-buffered saline (PBS) solution, then passage through a 0.22 μm membrane filter.

Because cCHP dissolves more easily in urea than in PBS, and (unlike dissolving in PBS) does not require ultrasonic equipment, an alternative procedure more suited for larger scale formulation was also employed. This involved mixing with a 6 M urea solution (rather than with PBS) at approximately 4° C.-8° C., followed by dialysis against PBS, and then passage through a 0.22 μm membrane filter. The resulting formulations were composed of a single aHD-PRD construct entrapped in the cross-linked structure of a cCHP (nanogel) molecule. This was confirmed by fluorescence response energy transfer (FRET) using FITC-conjugated aHD-PRD and TRITC-conjugated cCHP nanogel. Furthermore, dynamic light scattering (DLS) confirmed uniform particle size around 40 nm in diameter.

Thirty 7-week-old BALB/c female mice were divided into three groups of ten, and each group immunized with 10 μg of a cCHP-aHD-PRD complex: one of each of the three complexes—cCHP-PspA01.1, cCHP-PspA02, or cCHP-PspA03—for each of the three groups of mice. Five mice in each group received a complex formulated at 40° C. with PBS while five mice in each group received a complex formulated at 50° C. with PBS. In each case, the antigen complexes were contained in 0.006 mL (6 μL) solution, which was dripped into a single nostril.

The same drip administration method can be used for larger animals such as rabbits or dogs. In the case of humans, a solution containing the appropriate amount of a cCHP-aHD-PRD complex (or mixture of complexes) could be delivered by any suitable method, such as being dripped, or sprayed into each nostril in divided doses using a syringe spray device such as Becton Dickinson's AccuSpray®. This device has been used to effectively deliver FluMist® influenza vaccine into primate nasal passages.

The initial (priming) immunization series consisted of three doses, each one week apart. Subsequent experiments indicated that two doses administered a week apart, or even a single dose, also produced a strong antigen-specific IgG response. All mice were boosted with a single nasal dose (same antigen complex, dose, volume, and formulation temperature) at 7.5 weeks.

The same ELISA assays described in Example 4 were used to measure the titers of immunizing-antigen-specific IgG antibodies in the sera of individual mice. These ELISA assays also showed sustained, strong memory responses persisting more than 8 weeks following the booster dose (FIG. 7).

Example 6: Immunogenicity and Challenge Studies with Multiple Constructs

Immunization of mice, with three aHD-PRD constructs, elicited strong serum IgG responses against each of the individual component constructs, and also elicited protective cross-reactive immunity against *S. pneumoniae* strains having aHDs different than those of the immunizing constructs. This was achieved following both IM and IN (nanogel) administration.

The IM immunization procedures were as follows: A mixture comprising 10 μg of each of three aHD-PRD constructs (PspA01.1, PspA02, and PspA03) was formulated with alum, Al(OH)$_3$). Sixty 7-week-old, female, BALB/c mice were immunized with this formulation by successive injections into alternative upper hind leg muscles on day-0. At 7 weeks, the mice were boosted with the same mixture (i.e., 10 μg of each of the three aHD-PRD constructs), but without alum, by successive injections into alternative upper hind leg muscles.

The IN immunization procedures were as follows: Individual cCHP-aHD-PRD complexes were made for each of three example aHD-PRD constructs, PspA01.1, PspA02, and PspA03. Methods for formulating the individual complexes are described at the beginning of Example 5. All complexes were formulated at 40° C. On day-0, sixty 7-week-old female, BALB/c mice were immunized with 10 μg of the cCHP-PspA01.1 complex. This was accomplished by dripping 0.006 mL (6 μL) of a solution containing the cCHP-PspA01.1 complex (comprising 10 μg of PspA01.1) into one nostril of each mouse. On day-1, the same was done with 6 μL of a solution containing the cCHP-PspA02 complex (comprising 10 μg of PspA02). On day-2, the same was done with the cCHP-PspA03 complex (comprising 10 μg of PspA03). This process was repeated five days later (one week after day 0), and again at two weeks following day 0. Thus, by day-16, all sixty mice had been nasally immunized three times with 10 μg of each of three example aHD-PRD constructs PspA01.1, PspA02, and PspA03. At 7 weeks, the mice were boosted with 10 μg of each of the aHD-PRD constructs by dripping 6 μL of a solution containing cCHP-PspA01.1 (10 μg of the respective aHD-PRD construct) into one nostril of each mouse. This process was repeated the next day for cCHP-PspA02 and the next day for cCHP- PspA03. In other words, each mouse received a nasal booster dose of each of the three nanogel-formulated antigens over the course of three days.

Subsequent experiments indicated that two or even only one nasal administration were sufficient for a priming dose. Furthermore, rather than immunizing mice on successive days with different antigens, a mixture of all three cCHP-aHD-PRD constructs can be formulated. If multiple administrations over several days are required, a mixture of all three antigen complexes is administered. When the vaccine is administered to humans, it may also be administered as a mixture of individual antigens complexed with cCHP—although it may be administered by spray rather than liquid drops. The procedures in the brief description of FIG. 8 outline this method of administering a mixture of cCHP-PspA complexes.

Figure 8A:
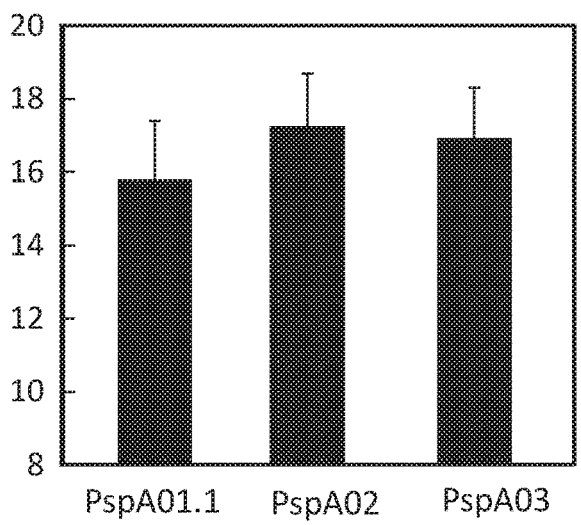
FIG. 8A and FIG. 8B show antigen-specific serum IgG responses in mice following IM (FIG. 8A) or IN (FIG. 8B) immunization (including boosts) with three example aHD-PRD constructs administered together (n=60 per group, IM doses formulated with alum, IN doses formulated with nanogel). y-axis: reciprocal $\log_2$ ELISA titer; bars indicate standard deviations; according to immunizing antigen in IM or IN group. These data show that combined administration of aHD-PRD antigens elicits strong systemic antigen-specific IgG responses, and that the responses produced by IN-nanogel administration are equivalent to those produced by IM administration.
Figure 8B:
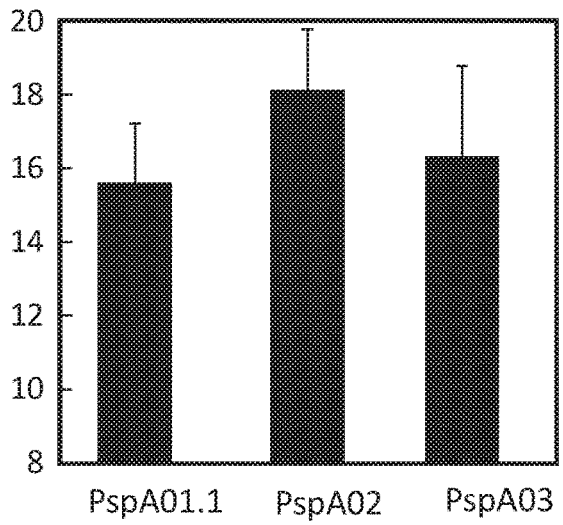

Two weeks following the booster dose, titers of serum IgG against each of the three antigens were determined by ELISA. The serum antigen-specific IgG titers were similar for IM and IN immunized mice. Compare FIG. 6 and FIG. 7; see also FIG. 8. Also, titers against each individual antigen were similar whether the mice were immunized with that antigen only (FIG. 6 and FIG. 7 (booster dose)) or with three antigens together (FIG. 8). The results suggested that: (a) there was little or no antigen competition diminishing the immune response to each antigen, or (b) whatever antigen competition occurred was counter-balanced by cross reactivity, e.g., antibodies raised against one aHD-PRD construct also bound to other constructs.

Five strains of S. pneumoniae were selected as challenge strains: BG8838, A66.1, BG12730, 3JYP2670, and ATCC 6303, which represent a variety of different aHD clades 1 through 5, respectively; as well as polysaccharide capsular serotypes covered well and covered poorly by PPSV23 and PCV13. For example, A66.1, 3JYP2670, and ATCC6303 display polysaccharide capsular antigen 3, which, although it is included in PPSV23 and PCV13, is not covered well by either vaccine. Andrews et al., 2014. BG12730 displays capsular serotype 6A, which is not covered by PPCV23. Thus, these strains allowed us to assess the ability of three embodiments of the aHD-PRD vaccine constructs to protect against pneumococcal strains that are relevant to public health today.

In order to determine appropriate challenge doses of each of these strains, non-immunized mice were challenged in a dose-escalation study to identify the number of colony forming units (CFU, i.e., the number of viable S. pneumoniae bacteria) that would result in 80% mortality within five days. This was done by dripping 0.05 mL of a solution containing $10^5$, $10^6$, $10^7$ or $10^8$ CFU into a single nostril of each mouse. For each strain and each CFU level, five mice were challenged intranasally. On the basis of this study, the following 80% lethal doses were determined initially for the following five challenge strains: BG8838: $1\times10^8$ CFU; A66.1: $1\times10^5$ CFU; BG12730: $1\times10^8$; 3JYP2670: $1\times10^6$; and ATCC 6303: $1\times10^7$ CFU.

The challenge studies proceeded as follows: five weeks after the first boost dose and twelve weeks after first immunization, fifty IM-immunized mice, fifty IN-immunized mice, and fifty naïve controls were challenged intranasally with the five strains at the CFU strengths indicated above. In the case of each strain, 0.05 mL of solution containing the appropriate number of CFU was dripped into one nostril of ten IM immunized mice, ten IN immunized mice, and ten non-immunized control mice. The original protocol called for the mice to be followed for seven days, and this was the procedure followed for mice challenged with A66.1 and 3JYP2670. The studies to determine the appropriate challenge doses (dose ranging studies) were rerun for the other three strains, because for all groups the initial survival rates were either very high or very low. After the new dose-ranging studies, the protocol was changed to follow mice for ten days. Thus, the survival data for BG8838, BG12730 and ATCC6303 follow mice for ten days after challenge.

Figure 9:
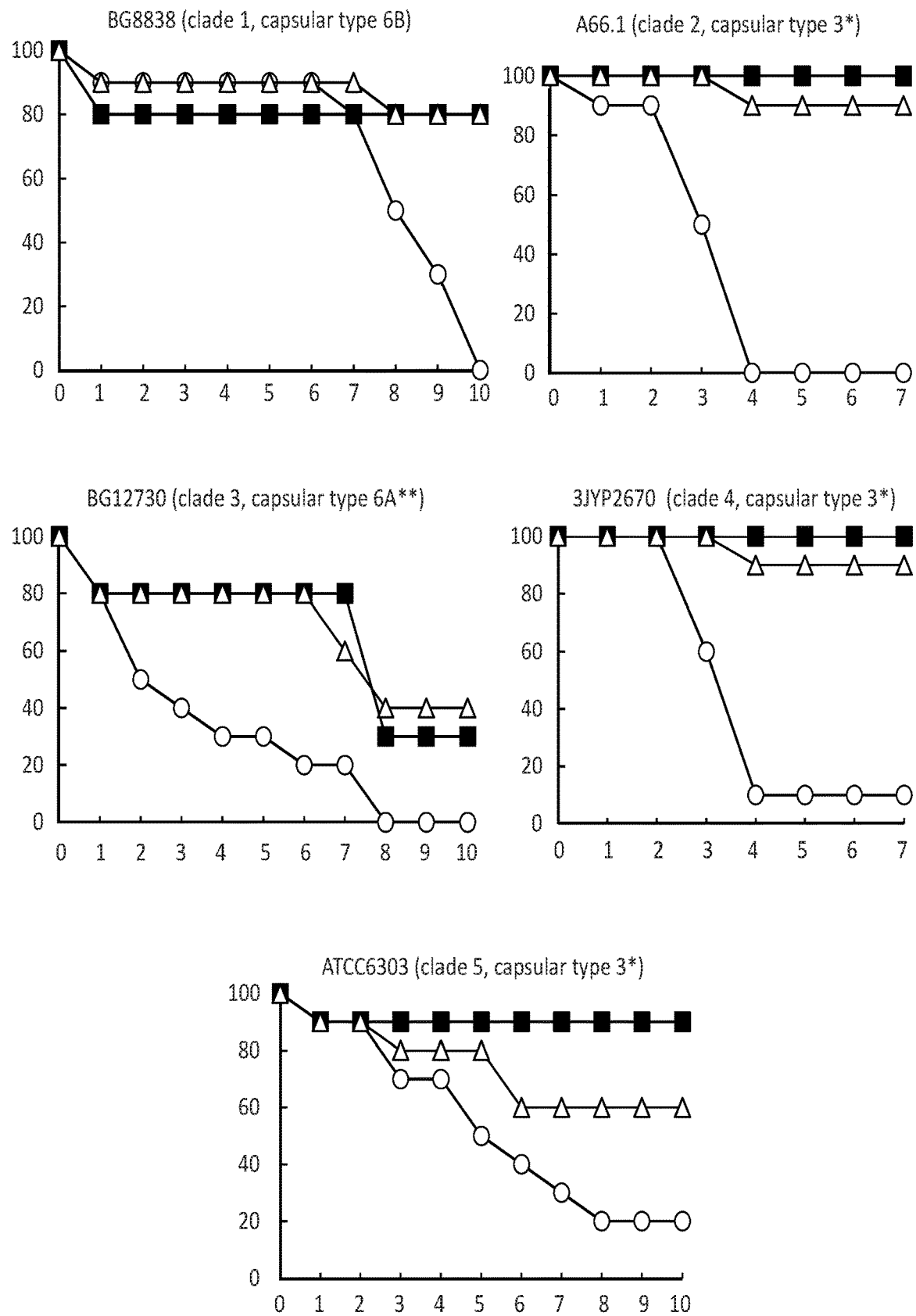
FIG. 9 shows survival curves following intranasal challenge with five pneumococcal strains in control mice (non-immunized) and mice immunized against a mixture of three exemplative aHD-PRD constructs (IM or IN; n=10 per group). y-axis: percent survival; x-axis: days post-intranasal infection with colony forming units (CFU) per mouse of the following strains: Strain BG8838: $1\times10^8$ CFU; A66.1: $1\times10^5$ CFU; BG12730: $1\times10^8$ CFU; 3JYP2670: $1\times10^6$ CFU.

The survival data in FIG. 9 show that both the IM and nanogel-IN formulations protected mice from otherwise lethal challenges. Strains A66.1, 3JYP2670, and ATCC6303 have capsular polysaccharide serotype 3, which is poorly covered by PPSV23 and PCV13 vaccines. The survival curves against challenge with A66.1, 3JYP2670, and ATCC6303 show that the example vaccine composition is advantageous in protecting against strains otherwise poorly covered by PPSV23 and PCV13 vaccines. The results for challenge strains BG8838 (which has a clade 1 PspA) and ATCC6303 (which has a clade 5 PspA) show that the vaccine composition elicited cross-reactivity against both clades. Both of these strains have Group 3 PRDs, so cross protection may have been provided by immunity raised against the PRD Group 3 included in the PspA03 construct. Pneumococcal strain BG12730 has capsular polysaccharide serotype 6A, which is covered by the PCV13 vaccine, but not by PPSV23 vaccine. The survival curves against challenge with strain BG12730 show that the aHD-PDR construct protected against a strain not covered by PPSV23 (see FIG. 9).

Example 7: Immunogenicity of an aHD-PRD Construct with a Short PRD

Additional experimentation suggested that substituting the Group 2 PRD sequence with a short PRD sequence from PRD Groups 1 or 3, or even no PRD sequence at all, may result in an even better immunologic response. In view of the homology between the first 14 amino acid residues—PEKPAPAPETPAPE (SEQ ID NO:157)—of fifteen of the Group 3 PRDs (see discussion in Example 1 and Table 3), an aHD-PRD construct consisting of the aHD of pneumococcus strain D39 was constructed with this PRD fragment. This construct was denoted PspA01.3 (see SEQ ID NO:158). It includes a fragment of the PspA protein in the naturally occurring D39 strain of pneumococcus, which might induce protective immunity in animal models. See Fukuyama et al., 2015.

Cross-reactivity analysis comparing antigen-specific serum IgG generated by PspA01.1, PspA01.2, and PspA01.3 indicated that PspA01.3 is probably more antigenic than either of the other two antigens. When fifteen mice were immunized, five with PspA01.1, five with PspA01.2 and five with PspA01.3, and the titers of their antigen-specific, serum IgG antibodies analyzed, each group reacted best against PspA01.3, even those mice immunized with PspA01.1 and PspA01.2. For example, among the sera of the mice immunized with PspA01.1, the average reciprocal log 2 titer against PspA01.3 was 15.6, while against PspA01.1 and PspA01.2 it was only 15.0. Among the sera of mice immunized with PspA01.2, the average reciprocal log 2 titer against PspA01.3 was 15.8, but it was only 14.4 and 14.8 against PspA01.1 and PspA01.2, respectively.

Additionally, the sera of the mice immunized with PspA01.3 reacted better against PspA01.1 and PspA01.2 than the sera of mice immunized specifically against these antigens. For example, the average reciprocal log 2 IgG titer against PspA01.1 was 16.6 in the sera of mice immunized with PspA01.3, while it was only 15.0 and 14.4 in the sera of mice immunized with PspA01.1 and PspA01.2, respectively. The average reciprocal log 2 titer against PspA01.2 was 17.4 in the sera of the mice immunized with PspA01.3, but it was only 15.0 and 14.8 in the sera of the mice immunized with PspA01.1 and PspA01.2, respectively.

We claim:

1. A composition comprising an immunologically active amount of at least two recombinant aHD-PRD constructs, each construct consisting of a portion of an alpha helical domain (aHD) and a portion of a proline rich domain (PRD) of a *Streptococcus pneumoniae* pneumococcal surface protein A (PspA), wherein each aHD and PRD portion is connected by a peptide bond, a chemical moiety, or a peptide linker, and the composition comprises at least one pharmaceutically acceptable excipient;

wherein the aHD and the PRD are each selected according to the following steps (a) and (b):
(a) selecting a first aHD from clade 1 of PspA family 1, wherein said aHD 1s selected from SEQ ID NO:66 SEQ ID NO:75, SEQ ID NO:78, or SEQ ID NO:79, and selecting a first PRD from a first PRD Group, and
(b) selecting a second aHD from clade 3, clade 4, or clade 5 of PspA family 2, wherein said aHD is selected from SEQ ID NO:33, SEQ ID 42, SEQ ID NO:58, SEQ ID NO:60, SEQ ID NO:62, SEQ ID NO:64, or SEQ ID NO:81, and selecting a second PRD from a second PRD Group, wherein said first and said second PRD Groups are each selected from:
PRD Group 1 consisting of SEQ ID NO:14, SEQ ID NO:15, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:126, SEQ ID NO:127, and SEQ ID NO:128;
PRD Group 2 consisting of SEQ ID NO:12, SEQ ID NO:13, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:96, SEQ ID NO:97, SEQ ID NO:98, SEQ ID NO:99, SEQ ID NO:100, SEQ ID NO:101, SEQ ID NO:102, SEQ ID NO:103, and SEQ ID NO:104; or
PRD Group 3 consisting of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:95, SEQ ID NO:114, SEQ ID NO:125, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO: 142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, and SEQ ID NO:157; wherein said composition is antigenic or immunogenic; and wherein said composition does not occur in nature.

2. The composition of claim 1, wherein each of the at least two recombinant aHD-PRD constructs consists of one aHD linked at its C-terminal end to one PRD or one aHD linked at its N-terminal end to one PRD.

3. The composition of claim 1, further comprising a third recombinant aHD-PRD construct, wherein the aHD and the PRD of the third recombinant aHD-PRD construct are selected according to the following steps:
selecting a third aHD from a clade or family that is different from the clade or family selected in step (a) or (b) of claim 1, and
selecting a third PRD from a third PRD Group.

4. The composition of claim 3, wherein the first aHD of the first recombinant aHD-PRD construct is selected from clade 1 of PspA family 1, the second aHD of the second recombinant aHD PRD construct is selected from clades 3, 4 or 5 of PspA family 2, and the third aHD of the third recombinant aHD-PRD construct is selected from one clade of PspA family 2 that is different from the clade from which the second aHD is selected.

5. The composition of claim 2, wherein the aHD, the PRD, or both, are not identical to any naturally occurring, aHD or PRD proteins or polypeptides, but include amino acid substitutions, deletions, or additions that enhance immunogenicity.

6. The composition of claim 1, wherein one of at least two recombinant aHD-PRD constructs comprises an amino acid sequence encoded by a nucleic acid molecule consisting of a nucleotide sequence shown in SEQ ID NO:84 or SEQ ID NO:85.

7. The composition of claim 1, wherein the composition comprises three, different recombinant aHD-PRD constructs.

* * * * *

SEQUENCE LISTING

<160> NUMBER OF SEQ ID NOS: 160

<210> SEQ ID NO 1
<211> LENGTH: 384
<212> TYPE: PRT
<213> ORGANISM: Artificial Sequence
<220> FEATURE:
<223> OTHER INFORMATION: aHD-PRD construct, a recombinant fusion
      protein, designated PspA01.1

<400> SEQUENCE: 1

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Gln Lys Lys Tyr Asp Glu
                35                  40                  45

Asp Gln Lys Lys Thr Glu Glu Lys Ala Ala Leu Glu Lys Ala Ala Ser
            50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Ala Lys Thr Lys Phe Asn
                100                 105                 110

Thr Val Arg Ala Met Val Val Pro Glu Pro Glu Gln Leu Ala Glu Thr
                115                 120                 125

Lys Lys Lys Ser Glu Glu Ala Lys Gln Lys Ala Pro Glu Leu Thr Lys
            130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Val Ala Pro Gln Ala
                165                 170                 175

Lys Ile Ala Glu Leu Glu Asn Gln Val His Arg Leu Glu Gln Glu Leu
                180                 185                 190

Lys Glu Ile Asp Glu Ser Glu Ser Glu Asp Tyr Ala Lys Glu Gly Phe
                195                 200                 205

Arg Ala Pro Leu Gln Ser Lys Leu Asp Ala Lys Lys Ala Lys Leu Ser
            210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
                245                 250                 255

Glu Asp Tyr Phe Lys Glu Gly Leu Glu Lys Thr Ile Ala Ala Lys Lys
                260                 265                 270

Ala Glu Leu Glu Lys Thr Glu Ala Asp Leu Lys Lys Ala Val Asn Glu
            275                 280                 285

Pro Glu Thr Pro Ala Pro Ala Pro Ala Pro Ala Pro Ala Pro Ala Pro
290                 295                 300

Ala Pro Ala Pro Lys Pro Ala Pro Ala Pro Lys Pro Ala Pro Ala Pro
305                 310                 315                 320

Lys Pro Ala Pro Ala Pro Lys Pro Ala Pro Ala Pro Lys Pro Ala Pro
                325                 330                 335

Ala Pro Ala Pro Ala Pro Lys Pro Ala Pro Ala Pro Lys Pro
                340                 345                 350

Ala Pro Ala Pro Ala Pro Ala Pro Ala Pro Lys Pro Glu Lys
            355                 360                 365

Pro Ala Glu Lys Pro Ala Pro Ala Pro Lys Pro Glu Thr Pro Lys Thr
    370                 375                 380

<210> SEQ ID NO 2
<211> LENGTH: 356
<212> TYPE: PRT
<213> ORGANISM: Artificial Sequence
<220> FEATURE:
<223> OTHER INFORMATION: aHD-PRD construct, a recombinant fusion
      protein, designated PspA01.2

<400> SEQUENCE: 2

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys Tyr Asp Glu
        35                  40                  45

Asp Gln Lys Lys Thr Glu Glu Lys Ala Ala Leu Glu Lys Ala Ala Ser
    50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
            100                 105                 110

Thr Val Arg Ala Met Val Val Pro Glu Pro Glu Gln Leu Ala Glu Thr
        115                 120                 125

Lys Lys Lys Ser Glu Glu Ala Lys Gln Lys Ala Pro Glu Leu Thr Lys
    130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
            180                 185                 190

Lys Glu Ile Asp Glu Ser Glu Ser Glu Asp Tyr Ala Lys Glu Gly Phe
        195                 200                 205

Arg Ala Pro Leu Gln Ser Lys Leu Asp Ala Lys Lys Ala Lys Leu Ser
    210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
        275                 280                 285

Pro Glu Thr Pro Ala Pro Ala Pro Ala Pro Ala Pro Ala Pro Ala Pro
    290                 295                 300

Ala Pro Ala Pro Ala Pro Ala Pro Lys Pro Ala Pro Ala Pro Lys Pro
305                 310                 315                 320

Ala Pro Ala Pro Lys Pro Ala Pro Ala Pro Ala Pro Ala Pro Ala Pro
                325                 330                 335

```
Lys Pro Glu Lys Pro Ala Glu Lys Pro Ala Pro Ala Pro Lys Pro Glu
                340                 345                 350

Thr Pro Lys Thr
        355

<210> SEQ ID NO 3
<211> LENGTH: 495
<212> TYPE: PRT
<213> ORGANISM: Artificial Sequence
<220> FEATURE:
<223> OTHER INFORMATION: aHD-PRD construct, a recombinant fusion
      protein, designated PspA02

<400> SEQUENCE: 3

Glu Glu Ser Pro Gln Val Val Glu Lys Ser Ser Leu Glu Lys Lys Tyr
1               5                   10                  15

Glu Glu Ala Lys Ala Lys Ala Asp Thr Ala Lys Lys Asp Tyr Glu Thr
                20                  25                  30

Ala Lys Lys Lys Ala Glu Asp Ala Gln Lys Lys Tyr Glu Asp Asp Gln
            35                  40                  45

Lys Arg Thr Glu Glu Lys Ala Arg Lys Ala Glu Ala Ser Gln Lys
50                  55                  60

Leu Asn Asp Val Ala Leu Val Gln Asn Ala Tyr Lys Glu Tyr Arg
65                  70                  75                  80

Glu Val Gln Asn Gln Arg Ser Lys Tyr Lys Ser Asp Ala Glu Tyr Gln
                85                  90                  95

Lys Lys Leu Thr Glu Val Asp Ser Lys Ile Glu Lys Ala Arg Lys Glu
            100                 105                 110

Gln Gln Asp Leu Gln Asn Lys Phe Asn Glu Val Arg Ala Val Val Val
        115                 120                 125

Pro Glu Pro Asn Ala Leu Ala Glu Thr Lys Lys Lys Ala Glu Glu Ala
130                 135                 140

Lys Ala Glu Glu Lys Val Ala Lys Arg Lys Tyr Asp Tyr Ala Thr Leu
145                 150                 155                 160

Lys Val Ala Leu Ala Lys Lys Glu Val Glu Ala Lys Glu Leu Glu Ile
                165                 170                 175

Glu Lys Leu Gln Tyr Glu Ile Ser Thr Leu Glu Gln Glu Val Ala Thr
            180                 185                 190

Ala Gln His Gln Val Asp Asn Leu Lys Lys Leu Leu Ala Gly Ala Asp
        195                 200                 205

Pro Asp Asp Gly Thr Glu Val Ile Glu Ala Lys Leu Lys Lys Gly Glu
    210                 215                 220

Ala Glu Leu Asn Ala Lys Gln Ala Glu Leu Ala Lys Lys Gln Thr Glu
225                 230                 235                 240

Leu Glu Lys Leu Leu Asp Ser Leu Asp Pro Glu Gly Lys Thr Gln Asp
                245                 250                 255

Glu Leu Asp Lys Glu Ala Glu Glu Ala Glu Leu Asp Lys Lys Ala Asp
            260                 265                 270

Glu Leu Gln Asn Lys Val Ala Asp Leu Glu Lys Glu Ile Ser Asn Leu
        275                 280                 285

Glu Ile Leu Leu Gly Gly Ala Asp Pro Glu Asp Asp Thr Ala Ala Leu
    290                 295                 300

Gln Asn Lys Leu Ala Ala Lys Lys Ala Glu Leu Ala Lys Lys Gln Thr
305                 310                 315                 320

Glu Leu Glu Lys Leu Leu Asp Ser Leu Asp Pro Glu Gly Lys Thr Gln
```

```
                    325                 330                 335
Asp Glu Leu Asp Lys Glu Ala Glu Ala Glu Leu Asp Lys Lys Ala
                340                 345                 350

Asp Glu Leu Gln Asn Lys Val Ala Asp Leu Glu Lys Glu Ile Ser Asn
                355                 360                 365

Leu Glu Ile Leu Leu Gly Gly Ala Asp Ser Glu Asp Thr Ala Ala
            370                 375                 380

Leu Gln Asn Lys Leu Ala Thr Lys Lys Ala Glu Leu Glu Lys Thr Gln
385                 390                 395                 400

Lys Glu Leu Asp Ala Ala Leu Asn Glu Leu Gly Pro Asp Gly Asp Glu
                405                 410                 415

Glu Glu Thr Pro Ala Pro Ala Pro Gln Pro Glu Gln Pro Ala Pro Ala
                420                 425                 430

Pro Lys Pro Glu Gln Pro Ala Pro Ala Pro Lys Pro Glu Gln Pro Ala
                435                 440                 445

Pro Ala Pro Lys Pro Glu Gln Pro Ala Pro Ala Pro Lys Pro Glu Gln
                450                 455                 460

Pro Ala Pro Ala Pro Lys Pro Glu Gln Pro Ala Lys Pro Glu Lys Pro
465                 470                 475                 480

Ala Glu Glu Pro Thr Gln Pro Glu Lys Pro Ala Thr Pro Lys Thr
                485                 490                 495

<210> SEQ ID NO 4
<211> LENGTH: 430
<212> TYPE: PRT
<213> ORGANISM: Artificial Sequence
<220> FEATURE:
<223> OTHER INFORMATION: aHD-PRD construct, a recombinant fusion
      protein, designated PspA03

<400> SEQUENCE: 4

Glu Glu Ala Pro Val Ala Asn Gln Ser Lys Ala Glu Lys Asp Tyr Asp
1               5                   10                  15

Ala Ala Val Lys Lys Ser Glu Ala Ala Lys Lys Asp Tyr Glu Thr Ala
                20                  25                  30

Lys Lys Lys Ala Glu Asp Ala Gln Lys Lys Tyr Asp Glu Asp Gln Lys
            35                  40                  45

Lys Thr Glu Ala Lys Ala Glu Lys Glu Arg Lys Ala Ser Glu Lys Ile
    50                  55                  60

Ala Glu Ala Thr Lys Glu Val Gln Gln Ala Tyr Leu Ala Tyr Leu Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Glu Ala Ala Phe Ala Thr Ile Arg
                100                 105                 110

Thr Thr Ile Val Val Pro Glu Pro Ser Glu Leu Ala Glu Thr Lys Lys
            115                 120                 125

Lys Ala Glu Glu Ala Thr Lys Glu Ala Glu Val Ala Lys Lys Lys Ser
        130                 135                 140

Glu Glu Ala Ala Lys Glu Val Glu Val Glu Lys Asn Lys Ile Leu Glu
145                 150                 155                 160

Gln Asp Ala Glu Asn Glu Lys Lys Ile Asp Val Leu Gln Asn Lys Val
                165                 170                 175

Ala Asp Leu Glu Lys Gly Ile Ala Pro Tyr Gln Asn Glu Val Ala Glu
                180                 185                 190
```

```
Leu Asn Lys Glu Ile Ala Arg Leu Gln Ser Asp Leu Lys Asp Ala Glu
            195                 200                 205

Glu Asn Asn Val Glu Asp Tyr Ile Lys Glu Gly Leu Glu Gln Ala Ile
        210                 215                 220

Thr Asn Lys Lys Ala Glu Leu Ala Thr Thr Gln Gln Asn Ile Asp Lys
225                 230                 235                 240

Thr Gln Lys Asp Leu Glu Asp Ala Glu Leu Glu Leu Lys Val Leu
            245                 250                 255

Ala Thr Leu Asp Pro Glu Gly Lys Thr Gln Asp Glu Leu Asp Lys Glu
            260                 265                 270

Ala Ala Glu Ala Glu Leu Asn Glu Lys Val Glu Ala Leu Gln Asn Gln
            275                 280                 285

Val Ala Glu Leu Glu Glu Glu Leu Ser Lys Leu Glu Asp Asn Leu Lys
        290                 295                 300

Asp Ala Glu Thr Asn Asn Val Glu Asp Tyr Ile Lys Glu Gly Leu Glu
305                 310                 315                 320

Glu Ala Ile Ala Thr Lys Lys Ala Glu Leu Glu Lys Thr Gln Lys Glu
            325                 330                 335

Leu Asp Ala Ala Leu Asn Glu Leu Gly Pro Glu Lys Pro Ala Glu Glu
            340                 345                 350

Thr Pro Ala Pro Ala Pro Lys Pro Glu Gln Pro Ala Glu Gln Pro Lys
            355                 360                 365

Pro Ala Pro Ala Pro Gln Pro Ala Pro Ala Pro Lys Pro Glu Lys Thr
        370                 375                 380

Asp Asp Gln Gln Ala Glu Glu Asp Tyr Ala Arg Arg Ser Glu Glu Glu
385                 390                 395                 400

Tyr Asn Arg Leu Pro Gln Gln Gln Pro Pro Lys Ala Glu Lys Pro Ala
            405                 410                 415

Pro Ala Pro Lys Pro Glu Gln Pro Val Pro Ala Pro Lys Thr
            420                 425                 430

<210> SEQ ID NO 5
<211> LENGTH: 6
<212> TYPE: PRT
<213> ORGANISM: Streptococcus pneumoniae

<400> SEQUENCE: 5

Pro Lys Pro Glu Gln Pro
1               5

<210> SEQ ID NO 6
<211> LENGTH: 6
<212> TYPE: PRT
<213> ORGANISM: Streptococcus pneumoniae

<400> SEQUENCE: 6

Gln Pro Ala Pro Ala Pro
1               5

<210> SEQ ID NO 7
<211> LENGTH: 6
<212> TYPE: PRT
<213> ORGANISM: Streptococcus pneumoniae

<400> SEQUENCE: 7

Pro Lys Pro Ala Pro Ala
1               5
```

<210> SEQ ID NO 8
<211> LENGTH: 7
<212> TYPE: PRT
<213> ORGANISM: Streptococcus pneumoniae

<400> SEQUENCE: 8

Glu Lys Pro Ala Pro Ala Pro
1               5

<210> SEQ ID NO 9
<211> LENGTH: 6
<212> TYPE: PRT
<213> ORGANISM: Streptococcus pneumoniae

<400> SEQUENCE: 9

Pro Glu Lys Pro Ala Glu
1               5

<210> SEQ ID NO 10
<211> LENGTH: 22
<212> TYPE: PRT
<213> ORGANISM: Streptococcus pneumoniae

<400> SEQUENCE: 10

Gln Gln Ala Glu Glu Asp Tyr Ala Arg Arg Ser Glu Glu Glu Tyr Asn
1               5                   10                  15

Arg Leu Pro Gln Gln Gln
            20

<210> SEQ ID NO 11
<211> LENGTH: 22
<212> TYPE: PRT
<213> ORGANISM: Streptococcus pneumoniae

<400> SEQUENCE: 11

Gln Gln Ala Glu Glu Asp Tyr Ala Arg Arg Ser Glu Glu Glu Tyr Asn
1               5                   10                  15

Arg Leu Thr Gln Gln Gln
            20

<210> SEQ ID NO 12
<211> LENGTH: 96
<212> TYPE: PRT
<213> ORGANISM: Streptococcus pneumoniae

<400> SEQUENCE: 12

Pro Glu Thr Pro Ala Pro Ala Pro Ala Pro Ala Pro Ala Pro Ala Pro
1               5                   10                  15

Ala Pro Ala Pro Lys Pro Ala Pro Ala Pro Lys Pro Ala Pro Ala Pro
            20                  25                  30

Lys Pro Ala Pro Ala Pro Lys Pro Ala Pro Ala Pro Lys Pro Ala Pro
        35                  40                  45

Ala Pro Ala Pro Ala Pro Ala Pro Lys Pro Ala Pro Ala Pro Lys Pro
    50                  55                  60

Ala Pro Ala Pro Ala Pro Ala Pro Ala Pro Lys Pro Glu Lys
65                  70                  75                  80

Pro Ala Glu Lys Pro Ala Pro Ala Pro Lys Pro Glu Thr Pro Lys Thr
                85                  90                  95

<210> SEQ ID NO 13
<211> LENGTH: 68
<212> TYPE: PRT

<213> ORGANISM: Streptococcus pneumoniae

<400> SEQUENCE: 13

Pro Glu Thr Pro Ala Pro Ala Pro Ala Pro Ala Pro Ala Pro Ala Pro
1               5                   10                  15

Ala Pro Ala Pro Ala Pro Ala Pro Lys Pro Ala Pro Ala Pro Lys Pro
            20                  25                  30

Ala Pro Ala Pro Lys Pro Ala Pro Ala Pro Ala Pro Ala Pro Ala Pro
        35                  40                  45

Lys Pro Glu Lys Pro Ala Glu Lys Pro Ala Pro Ala Pro Lys Pro Glu
    50                  55                  60

Thr Pro Lys Thr
65

<210> SEQ ID NO 14
<211> LENGTH: 84
<212> TYPE: PRT
<213> ORGANISM: Artificial Sequence
<220> FEATURE:
<223> OTHER INFORMATION: modified PspA PRD of strain EF3296

<400> SEQUENCE: 14

Pro Asp Gly Asp Glu Glu Glu Thr Pro Ala Pro Ala Pro Gln Pro Glu
1               5                   10                  15

Gln Pro Ala Pro Ala Pro Lys Pro Glu Gln Pro Ala Pro Ala Pro Lys
            20                  25                  30

Pro Glu Gln Pro Ala Pro Ala Pro Lys Pro Glu Gln Pro Ala Pro Ala
        35                  40                  45

Pro Lys Pro Glu Gln Pro Ala Pro Ala Pro Lys Pro Glu Gln Pro Ala
    50                  55                  60

Lys Pro Glu Lys Pro Ala Glu Glu Pro Thr Gln Pro Glu Lys Pro Ala
65                  70                  75                  80

Thr Pro Lys Thr

<210> SEQ ID NO 15
<211> LENGTH: 75
<212> TYPE: PRT
<213> ORGANISM: Streptococcus pneumoniae

<400> SEQUENCE: 15

Pro Asp Gly Asp Glu Glu Glu Thr Pro Ala Pro Ala Pro Gln Pro Glu
1               5                   10                  15

Gln Pro Ala Pro Ala Pro Lys Pro Glu Gln Pro Ala Pro Ala Pro Lys
            20                  25                  30

Pro Glu Gln Pro Ala Pro Ala Pro Lys Pro Glu Gln Pro Ala Pro Ala
        35                  40                  45

Pro Lys Pro Glu Gln Pro Ala Lys Pro Glu Lys Pro Ala Glu Glu Pro
    50                  55                  60

Thr Gln Pro Glu Lys Pro Ala Thr Pro Lys Thr
65                  70                  75

<210> SEQ ID NO 16
<211> LENGTH: 85
<212> TYPE: PRT
<213> ORGANISM: Streptococcus pneumoniae

<400> SEQUENCE: 16

Pro Glu Lys Pro Ala Glu Glu Thr Pro Ala Pro Ala Pro Lys Pro Glu
1               5                   10                  15

```
Gln Pro Ala Glu Gln Pro Lys Pro Ala Pro Ala Pro Gln Pro Ala Pro
            20                  25                  30

Ala Pro Lys Pro Glu Lys Thr Asp Asp Gln Gln Ala Glu Glu Asp Tyr
        35                  40                  45

Ala Arg Arg Ser Glu Glu Glu Tyr Asn Arg Leu Pro Gln Gln Gln Pro
    50                  55                  60

Pro Lys Ala Glu Lys Pro Ala Pro Ala Pro Lys Pro Glu Gln Pro Val
65                  70                  75                  80

Pro Ala Pro Lys Thr
                85

<210> SEQ ID NO 17
<211> LENGTH: 94
<212> TYPE: PRT
<213> ORGANISM: Streptococcus pneumoniae

<400> SEQUENCE: 17

Pro Glu Lys Pro Ala Glu Glu Thr Pro Ala Pro Ala Pro Lys Pro Glu
1               5                   10                  15

Gln Pro Ala Glu Gln Pro Lys Pro Ala Pro Ala Pro Gln Pro Ala Pro
            20                  25                  30

Ala Pro Lys Pro Glu Lys Thr Asp Asp Gln Gln Ala Glu Glu Asp Tyr
        35                  40                  45

Ala Arg Arg Ser Glu Glu Glu Tyr Asn Arg Leu Pro Gln Gln Gln Pro
    50                  55                  60

Pro Lys Ala Glu Lys Pro Ala Pro Ala Pro Lys Pro Glu Gln Pro Val
65                  70                  75                  80

Pro Ala Pro Lys Pro Glu Gln Pro Val Pro Ala Pro Lys Thr
                85                  90

<210> SEQ ID NO 18
<211> LENGTH: 85
<212> TYPE: PRT
<213> ORGANISM: Streptococcus pneumoniae

<400> SEQUENCE: 18

Pro Asp Gly Asp Glu Glu Glu Thr Pro Ala Pro Ala Pro Lys Pro Glu
1               5                   10                  15

Gln Pro Ala Glu Gln Pro Lys Pro Ala Pro Ala Pro Gln Pro Ala Pro
            20                  25                  30

Ala Pro Lys Pro Glu Lys Thr Asp Asp Gln Gln Ala Glu Glu Asp Tyr
        35                  40                  45

Ala Arg Arg Ser Glu Glu Glu Tyr Asn Arg Leu Pro Gln Gln Gln Pro
    50                  55                  60

Pro Lys Ala Glu Lys Pro Ala Pro Ala Pro Lys Pro Glu Gln Pro Val
65                  70                  75                  80

Pro Ala Pro Lys Thr
                85

<210> SEQ ID NO 19
<211> LENGTH: 85
<212> TYPE: PRT
<213> ORGANISM: Streptococcus pneumoniae

<400> SEQUENCE: 19

Pro Asp Gly Asp Glu Glu Glu Thr Pro Ala Pro Ala Pro Lys Pro Glu
1               5                   10                  15
```

Gln Pro Ala Pro Ala Pro Lys Pro Ala Pro Gln Pro Ala Pro
            20                  25                  30

Ala Pro Lys Pro Glu Lys Thr Asp Asp Gln Gln Ala Glu Glu Asp Tyr
        35                  40                  45

Ala Arg Arg Ser Glu Glu Glu Tyr Asn Arg Leu Pro Gln Gln Gln Pro
    50                  55                  60

Pro Lys Ala Glu Lys Pro Ala Pro Ala Pro Lys Pro Gln Pro Val
65                  70                  75                  80

Pro Ala Pro Lys Thr
                85

<210> SEQ ID NO 20
<211> LENGTH: 87
<212> TYPE: PRT
<213> ORGANISM: Streptococcus pneumoniae

<400> SEQUENCE: 20

Pro Asp Gly Asp Glu Glu Glu Thr Pro Ala Pro Ala Pro Lys Pro Glu
1               5                   10                  15

Gln Pro Ala Glu Gln Pro Lys Pro Ala Pro Ala Pro Gln Pro Ala Pro
            20                  25                  30

Ala Pro Lys Pro Glu Lys Thr Asp Asp Gln Gln Ala Glu Glu Asp Tyr
        35                  40                  45

Ala Arg Arg Ser Glu Glu Glu Tyr Asn Arg Leu Pro Gln Gln Gln Pro
    50                  55                  60

Pro Lys Ala Glu Lys Pro Ala Pro Ala Pro Lys Pro Glu Gln
65                  70                  75                  80

Pro Ala Pro Ala Pro Lys Thr
                85

<210> SEQ ID NO 21
<211> LENGTH: 77
<212> TYPE: PRT
<213> ORGANISM: Streptococcus pneumoniae

<400> SEQUENCE: 21

Pro Asp Gly Asp Glu Glu Glu Thr Pro Ala Pro Ala Pro Lys Pro Glu
1               5                   10                  15

Gln Pro Ala Glu Gln Pro Lys Pro Ala Pro Ala Pro Lys Pro Glu Lys
            20                  25                  30

Thr Asp Asp Gln Gln Ala Glu Glu Asp Tyr Ala Arg Arg Ser Glu Glu
        35                  40                  45

Glu Tyr Asn Arg Leu Pro Gln Gln Pro Pro Lys Ala Glu Lys Pro
    50                  55                  60

Ala Pro Ala Pro Lys Pro Glu Gln Pro Val Pro Ala Pro
65                  70                  75

<210> SEQ ID NO 22
<211> LENGTH: 97
<212> TYPE: PRT
<213> ORGANISM: Streptococcus pneumoniae

<400> SEQUENCE: 22

Pro Asp Gly Asp Glu Glu Glu Thr Pro Ala Pro Ala Gln Pro Glu
1               5                   10                  15

Lys Pro Ala Pro Ala Pro Ala Pro Lys Pro Glu Gln Pro Ala Pro Ala
            20                  25                  30

Pro Ala Pro Lys Pro Glu Gln Pro Ala Pro Ala Pro Ala Pro Lys Pro

```
                35                  40                  45
Glu Lys Thr Asp Asp Gln Gln Ala Glu Glu Asp Tyr Ala Arg Arg Ser
     50                  55                  60
Glu Glu Glu Tyr Asn Arg Leu Pro Gln Gln Gln Pro Pro Lys Ala Glu
 65                  70                  75                  80
Lys Pro Ala Pro Ala Pro Lys Pro Glu Gln Pro Val Pro Ala Pro Lys
                 85                  90                  95
Thr

<210> SEQ ID NO 23
<211> LENGTH: 84
<212> TYPE: PRT
<213> ORGANISM: Streptococcus pneumoniae

<400> SEQUENCE: 23

Pro Asp Gly Asp Glu Glu Thr Pro Ala Pro Ala Pro Gln Pro Glu
  1               5                  10                  15

Lys Pro Ala Pro Ala Pro Ala Pro Lys Pro Glu Gln Pro Ala Pro Ala
                 20                  25                  30

Pro Lys Pro Glu Lys Thr Asp Asp Gln Gln Ala Glu Glu Asp Tyr Ala
                 35                  40                  45

Arg Arg Ser Glu Glu Glu Tyr Asn Arg Leu Pro Gln Gln Gln Pro Pro
     50                  55                  60

Lys Ala Glu Lys Pro Ala Pro Ala Pro Lys Pro Glu Gln Pro Val Pro
 65                  70                  75                  80

Ala Pro Lys Thr

<210> SEQ ID NO 24
<211> LENGTH: 86
<212> TYPE: PRT
<213> ORGANISM: Streptococcus pneumoniae

<400> SEQUENCE: 24

Pro Asp Gly Asp Glu Glu Thr Pro Ala Pro Ala Pro Gln Pro Glu
  1               5                  10                  15

Lys Pro Ala Pro Ala Pro Ala Pro Lys Pro Glu Gln Pro Ala Pro Ala
                 20                  25                  30

Pro Ala Pro Lys Pro Glu Lys Thr Asp Asp Gln Gln Ala Glu Glu Asp
                 35                  40                  45

Tyr Ala Arg Arg Ser Glu Glu Glu Tyr Asn Arg Leu Pro Gln Gln Gln
     50                  55                  60

Pro Pro Lys Ala Glu Lys Pro Ala Pro Ala Pro Lys Pro Glu Gln Pro
 65                  70                  75                  80

Val Pro Ala Pro Lys Thr
                 85

<210> SEQ ID NO 25
<211> LENGTH: 97
<212> TYPE: PRT
<213> ORGANISM: Streptococcus pneumoniae

<400> SEQUENCE: 25

Leu Lys Glu Ile Asp Glu Ser Glu Ser Glu Asp Tyr Ala Lys Glu Gly
  1               5                  10                  15

Phe Arg Ala Pro Leu Gln Ser Lys Leu Asp Ala Arg Lys Ala Lys Leu
                 20                  25                  30

Ser Lys Leu Glu Glu Leu Ser Asp Lys Ile Asp Glu Leu Asp Ala Glu
```

```
                    35                  40                  45

Ile Ala Lys Leu Glu Asp Gln Leu Lys Ala Glu Glu Asn Asn Asn
 50                  55                  60

Val Glu Asp Tyr Phe Lys Gly Leu Glu Lys Thr Ile Ala Ala Lys
 65                  70                  75                  80

Lys Ala Glu Leu Glu Lys Thr Glu Ala Asp Leu Lys Lys Ala Val Asn
                 85                  90                  95

Glu

<210> SEQ ID NO 26
<211> LENGTH: 97
<212> TYPE: PRT
<213> ORGANISM: Streptococcus pneumoniae

<400> SEQUENCE: 26

Leu Lys Asp Ile Asn Glu Ser Asp Ser Glu Asp Tyr Val Lys Glu Gly
  1               5                  10                  15

Leu Arg Ala Pro Leu Gln Ser Glu Leu Asp Thr Lys Lys Ala Lys Leu
                 20                  25                  30

Leu Lys Leu Glu Glu Leu Ser Gly Lys Ile Glu Glu Leu Asp Ala Glu
                 35                  40                  45

Ile Ala Glu Leu Glu Val Gln Leu Lys Asp Ala Glu Gly Asn Asn Asn
 50                  55                  60

Val Glu Ala Tyr Phe Lys Gly Leu Glu Lys Thr Thr Ala Glu Lys
 65                  70                  75                  80

Lys Ala Glu Leu Glu Lys Ala Glu Ala Asp Leu Lys Lys Ala Val Asp
                 85                  90                  95

Glu

<210> SEQ ID NO 27
<211> LENGTH: 97
<212> TYPE: PRT
<213> ORGANISM: Streptococcus pneumoniae

<400> SEQUENCE: 27

Leu Lys Glu Ile Asp Glu Ser Asp Ser Glu Asp Tyr Ile Lys Glu Gly
  1               5                  10                  15

Phe Arg Ala Pro Leu Gln Ser Glu Leu Asp Thr Lys Lys Ala Lys Leu
                 20                  25                  30

Leu Lys Leu Glu Glu Leu Ser Gly Lys Ile Glu Glu Leu Asp Ala Glu
                 35                  40                  45

Ile Ala Glu Leu Glu Val Gln Leu Lys Asp Ala Glu Gly Asn Asn Asn
 50                  55                  60

Val Glu Ala Tyr Phe Lys Gly Leu Glu Lys Thr Thr Ala Glu Lys
 65                  70                  75                  80

Lys Ala Glu Leu Glu Lys Ala Glu Ala Asp Leu Lys Lys Ala Val Asp
                 85                  90                  95

Glu

<210> SEQ ID NO 28
<211> LENGTH: 280
<212> TYPE: PRT
<213> ORGANISM: Streptococcus pneumoniae

<400> SEQUENCE: 28

Glu Glu Ala Pro Val Ala Ser Gln Ser Lys Ala Glu Lys Asp Tyr Asp
  1               5                  10                  15
```

Ala Ala Met Glu Lys Tyr Lys Ala Ala Glu Glu Asp Leu Glu Lys Ala
            20                  25                  30

Glu Ala Ala Gln Arg Lys Tyr Asp Glu Asp Gln Lys Lys Ser Glu Glu
        35                  40                  45

Asn Glu Lys Glu Thr Glu Glu Ala Ser Glu Arg Gln Gln Ala Ala Thr
 50                  55                  60

Leu Lys Tyr Gln Leu Lys Leu Arg Glu Tyr Leu Lys Tyr Ile Gln Glu
 65                  70                  75                  80

Lys Asn Lys Glu Lys Ile Ala Lys Ala Glu Lys Glu Met Asn Glu Ala
                85                  90                  95

Lys Gln Glu Glu Asp Lys Glu Lys Ala Asn Leu Asn Lys Val Leu Ala
            100                 105                 110

Lys Val Ile Pro Ser Asp Arg Glu Leu Glu Lys Thr Arg Gln Glu Ala
        115                 120                 125

Glu Lys Ala Lys Lys Asn Ile Pro Glu Leu Lys Lys Val Glu Glu
130                 135                 140

Ala Lys Gln Lys Val Asp Ala Ala Lys Gln Lys Val Asp Ala Glu His
145                 150                 155                 160

Ala Lys Glu Val Ala Pro Gln Ala Lys Ile Ala Glu Leu Glu Asn Gln
                165                 170                 175

Val His Arg Leu Glu Gln Asp Leu Lys Asp Ile Asn Glu Ser Asp Ser
            180                 185                 190

Glu Asp Tyr Val Lys Glu Gly Leu Arg Ala Pro Leu Gln Ser Glu Leu
        195                 200                 205

Asp Thr Lys Lys Ala Lys Leu Lys Leu Glu Leu Ser Gly Lys
 210                 215                 220

Ile Glu Glu Leu Asp Ala Glu Ile Ala Glu Leu Glu Val Gln Leu Lys
225                 230                 235                 240

Asp Ala Glu Gly Asn Asn Asn Val Glu Ala Tyr Phe Lys Glu Gly Leu
                245                 250                 255

Glu Lys Thr Thr Ala Glu Lys Lys Ala Glu Leu Glu Lys Ala Glu Ala
            260                 265                 270

Asp Leu Lys Lys Ala Val Asp Glu
        275                 280

<210> SEQ ID NO 29
<211> LENGTH: 280
<212> TYPE: PRT
<213> ORGANISM: Streptococcus pneumoniae

<400> SEQUENCE: 29

Glu Glu Ala Pro Val Ala Ser Gln Ser Lys Ala Glu Lys Asp Tyr Asp
1               5                   10                  15

Ala Ala Met Glu Lys Tyr Lys Ala Ala Glu Glu Asp Leu Lys Lys Ala
            20                  25                  30

Glu Ala Ala Gln Arg Lys Tyr Asp Glu Asp Gln Lys Lys Thr Glu Glu
        35                  40                  45

Lys Ala Lys Glu Thr Glu Glu Ala Ser Lys Arg Gln Gln Ala Ala Asn
 50                  55                  60

Leu Lys Tyr Gln Leu Lys Leu Arg Glu Tyr Leu Lys Tyr Ile Gln Glu
 65                  70                  75                  80

Lys Asn Lys Glu Lys Ile Ala Lys Ala Glu Lys Glu Met Asn Glu Ala
                85                  90                  95

Lys Gln Glu Glu Asp Lys Glu Lys Ala Asn Leu Asn Lys Val Leu Ala

```
            100                 105                 110
Lys Val Ile Pro Ser Asp Arg Glu Leu Glu Lys Thr Arg Gln Glu Ala
            115                 120                 125

Glu Lys Ala Lys Lys Asn Ile Pro Glu Leu Lys Lys Val Glu Glu
    130                 135                 140

Ala Lys Gln Lys Val Asp Ala Ala Lys Gln Lys Val Asp Ala Glu His
145                 150                 155                 160

Ala Lys Glu Val Ala Pro Gln Ala Lys Ile Ala Glu Leu Glu Asn Gln
                165                 170                 175

Val His Arg Leu Glu Gln Asp Leu Lys Asp Ile Asn Glu Ser Asp Ser
            180                 185                 190

Glu Asp Tyr Val Lys Glu Gly Leu Arg Ala Pro Leu Gln Ser Glu Leu
            195                 200                 205

Asp Thr Lys Lys Ala Lys Leu Leu Lys Leu Glu Leu Ser Gly Lys
            210                 215                 220

Ile Glu Glu Leu Asp Ala Glu Ile Ala Glu Leu Glu Val Gln Leu Lys
225                 230                 235                 240

Asp Ala Glu Gly Asn Asn Asn Val Glu Ala Tyr Phe Lys Glu Gly Leu
                245                 250                 255

Glu Lys Thr Thr Ala Glu Lys Lys Ala Glu Leu Glu Lys Ala Glu Ala
            260                 265                 270

Asp Leu Lys Lys Ala Val Asp Glu
            275                 280

<210> SEQ ID NO 30
<211> LENGTH: 280
<212> TYPE: PRT
<213> ORGANISM: Streptococcus pneumoniae

<400> SEQUENCE: 30

Glu Glu Ala Pro Val Ala Ser Gln Ser Lys Ala Glu Lys Asp Tyr Asp
1               5                   10                  15

Ala Ala Met Glu Lys Tyr Lys Ala Ala Glu Glu Asp Leu Lys Lys Ala
            20                  25                  30

Glu Ala Ala Gln Arg Lys Tyr Asp Glu Asp Gln Lys Lys Thr Glu Glu
        35                  40                  45

Lys Ala Lys Glu Thr Glu Glu Ala Ser Lys Arg Gln Gln Ala Ala Asn
50                  55                  60

Leu Lys Tyr Gln Leu Lys Leu Arg Glu Tyr Leu Lys Tyr Ile Gln Glu
65                  70                  75                  80

Lys Asn Lys Glu Lys Ile Ala Lys Ala Glu Lys Glu Met Asn Glu Ala
                85                  90                  95

Lys Gln Glu Glu Asp Lys Glu Lys Ala Asn Leu Asn Lys Val Leu Ala
            100                 105                 110

Lys Val Ile Pro Ser Asp Arg Glu Leu Glu Lys Thr Arg Gln Glu Ala
            115                 120                 125

Glu Lys Ala Lys Lys Asn Ile Pro Glu Leu Lys Lys Val Glu Glu
    130                 135                 140

Ala Lys Gln Lys Val Asp Ala Ala Lys Gln Lys Val Asp Ala Glu His
145                 150                 155                 160

Ala Lys Glu Val Ala Pro Gln Ala Lys Ile Ala Glu Leu Glu Asn Gln
                165                 170                 175

Val His Arg Leu Glu Gln Asp Leu Lys Asp Ile Asn Glu Ser Asp Ser
            180                 185                 190
```

```
Glu Asp Tyr Val Lys Glu Gly Leu Arg Ala Pro Leu Gln Ser Glu Leu
            195                 200                 205

Asp Thr Lys Lys Ala Lys Leu Leu Lys Leu Glu Glu Leu Ser Gly Lys
210                 215                 220

Ile Glu Glu Leu Asp Ala Glu Ile Ala Glu Leu Glu Val Gln Leu Lys
225                 230                 235                 240

Asp Ala Glu Gly Asn Asn Asn Val Glu Ala Tyr Phe Lys Glu Gly Leu
                245                 250                 255

Glu Lys Thr Thr Ala Glu Lys Lys Ala Glu Leu Glu Lys Ala Glu Ala
            260                 265                 270

Asp Leu Lys Lys Ala Val Asp Glu
            275                 280

<210> SEQ ID NO 31
<211> LENGTH: 302
<212> TYPE: PRT
<213> ORGANISM: Streptococcus pneumoniae

<400> SEQUENCE: 31

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys His Tyr Glu Glu Val
                20                  25                  30

Lys Ala Lys Phe Glu Ala Ala Lys Lys Glu Tyr Glu Asp Gly Lys Ala
            35                  40                  45

Ala Gln Lys Lys Tyr Glu Asp Asp Gln Lys Lys Thr Glu Glu Lys Ala
        50                  55                  60

Glu Glu Glu Arg Lys Ala Ser Glu Glu Glu Gln Ala Ala Asn Leu Lys
65                  70                  75                  80

Tyr Gln Gln Ala Val Leu Lys Tyr Ile Lys Glu Thr Asp Pro Gln Lys
                85                  90                  95

Arg Val Glu Ala Gln Lys Val Met Asp Glu Ala Gln Lys Glu His Thr
            100                 105                 110

Arg Thr Lys Glu Lys Phe Asp Glu Val Arg Ala Lys Val Ile Pro Ser
        115                 120                 125

Glu Glu Glu Leu Lys Lys Thr Arg Gln Lys Ala Glu Glu Ala Lys Leu
130                 135                 140

Lys Glu Ala Glu Val Ala Lys Lys Val Glu Glu Thr Lys Lys Gln Glu
145                 150                 155                 160

Glu Glu Ala Lys Ala Lys Leu Glu Glu Ala Glu Lys Lys Ala Thr Glu
                165                 170                 175

Ala Lys Gln Lys Val Asp Ala Glu Glu Val Ala Pro Gln Ala Lys Ile
            180                 185                 190

Ala Glu Leu Glu Asn Gln Val His Arg Leu Glu Gln Glu Leu Lys Glu
        195                 200                 205

Ile Asp Glu Ser Asp Ser Glu Asp Tyr Ile Lys Glu Gly Phe Arg Ala
210                 215                 220

Pro Leu Gln Ser Glu Leu Asp Thr Lys Lys Ala Lys Leu Leu Lys Leu
225                 230                 235                 240

Glu Glu Leu Ser Gly Lys Ile Glu Glu Leu Asp Ala Glu Ile Ala Glu
                245                 250                 255

Leu Glu Val Gln Leu Lys Asp Ala Glu Gly Asn Asn Asn Val Glu Ala
            260                 265                 270

Tyr Phe Lys Glu Gly Leu Glu Lys Thr Thr Ala Glu Lys Lys Ala Glu
        275                 280                 285
```

```
Leu Glu Lys Ala Glu Ala Asp Leu Lys Lys Ala Val Asp Glu
    290                 295                 300
```

<210> SEQ ID NO 32
<211> LENGTH: 97
<212> TYPE: PRT
<213> ORGANISM: Streptococcus pneumoniae

<400> SEQUENCE: 32

```
Leu Ala Lys Lys Gln Thr Glu Leu Glu Lys Leu Leu Asp Ser Leu Asp
1               5                   10                  15

Pro Glu Gly Lys Thr Gln Asp Glu Leu Asp Lys Glu Ala Glu Glu Ala
                20                  25                  30

Glu Leu Asp Lys Lys Ala Asp Glu Leu Gln Asn Lys Val Ala Asp Leu
            35                  40                  45

Glu Lys Glu Ile Ser Asn Leu Glu Ile Leu Leu Gly Gly Ala Asp Ser
        50                  55                  60

Glu Asp Asp Thr Ala Ala Leu Gln Asn Lys Leu Ala Thr Lys Lys Ala
65                  70                  75                  80

Glu Leu Glu Lys Thr Gln Lys Glu Leu Asp Ala Ala Leu Asn Glu Leu
                85                  90                  95

Gly
```

<210> SEQ ID NO 33
<211> LENGTH: 319
<212> TYPE: PRT
<213> ORGANISM: Streptococcus pneumoniae

<400> SEQUENCE: 33

```
Glu Glu Ser Pro Val Ala Ser Gln Ser Lys Ala Glu Lys Asp Tyr Asp
1               5                   10                  15

Ala Ala Val Lys Lys Ser Glu Ala Ala Lys Lys His Tyr Glu Glu Ala
                20                  25                  30

Lys Lys Lys Ala Glu Asp Ala Gln Lys Lys Tyr Asp Glu Asp Gln Lys
            35                  40                  45

Lys Thr Glu Ala Lys Ala Glu Lys Glu Arg Lys Ala Ser Glu Lys Ile
        50                  55                  60

Ala Glu Ala Thr Lys Glu Val Gln Gln Ala Tyr Leu Ala Tyr Leu Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Glu Ala Ala Phe Ala Thr Ile Arg
                100                 105                 110

Thr Thr Ile Val Val Pro Glu Pro Ser Glu Leu Ala Glu Thr Lys Lys
            115                 120                 125

Lys Ala Glu Glu Ala Lys Ala Glu Glu Lys Val Ala Lys Arg Lys Tyr
        130                 135                 140

Asp Tyr Ala Thr Leu Lys Leu Ala Leu Ala Lys Lys Glu Val Glu Ala
145                 150                 155                 160

Lys Glu Leu Glu Ile Glu Lys Leu Gln Tyr Glu Ile Ser Thr Leu Glu
                165                 170                 175

Gln Glu Val Ala Thr Ala Gln His Gln Val Asp Asn Leu Lys Lys Leu
                180                 185                 190

Leu Ala Gly Ala Asp Pro Asp Asp Gly Thr Glu Val Ile Glu Ala Lys
            195                 200                 205
```

```
Leu Lys Lys Gly Glu Ala Glu Leu Asn Ala Lys Gln Ala Glu Leu Ala
210                 215                 220

Lys Lys Gln Thr Glu Leu Glu Lys Leu Leu Asp Ser Leu Asp Pro Glu
225                 230                 235                 240

Gly Lys Thr Gln Asp Glu Leu Asp Lys Glu Ala Glu Glu Ala Glu Leu
                245                 250                 255

Asp Lys Lys Ala Asp Glu Leu Gln Asn Lys Val Ala Asp Leu Glu Lys
            260                 265                 270

Glu Ile Ser Asn Leu Glu Ile Leu Gly Gly Ala Asp Ser Glu Asp
        275                 280                 285

Asp Thr Ala Ala Leu Gln Asn Lys Leu Ala Thr Lys Lys Ala Glu Leu
    290                 295                 300

Glu Lys Thr Gln Lys Glu Leu Asp Ala Ala Leu Asn Glu Leu Gly
305                 310                 315

<210> SEQ ID NO 34
<211> LENGTH: 319
<212> TYPE: PRT
<213> ORGANISM: Streptococcus pneumoniae

<400> SEQUENCE: 34

Glu Glu Ala Pro Val Ala Ser Gln Ser Lys Ala Glu Lys Asp Tyr Asp
1               5                   10                  15

Ala Ala Val Lys Lys Ser Glu Ala Lys Lys His Tyr Glu Glu Val
            20                  25                  30

Lys Lys Lys Ala Glu Asp Ala Gln Lys Lys Tyr Asp Glu Gly Gln Lys
            35                  40                  45

Lys Thr Val Glu Lys Ala Lys Arg Glu Lys Glu Ala Ser Glu Lys Ile
50                  55                  60

Ala Glu Ala Thr Lys Glu Val Gln Gln Ala Tyr Leu Ala Tyr Gln Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Glu Ala Ala Phe Ala Thr Ile Arg
            100                 105                 110

Thr Thr Ile Val Val Pro Glu Pro Ser Glu Leu Ala Glu Thr Lys Lys
        115                 120                 125

Lys Ala Glu Glu Ala Lys Ala Glu Glu Lys Val Ala Lys Arg Lys Tyr
130                 135                 140

Asp Tyr Ala Thr Leu Lys Val Ala Leu Ala Lys Lys Glu Val Glu Ala
145                 150                 155                 160

Lys Glu Leu Glu Ile Glu Lys Leu Gln Tyr Glu Ile Ser Thr Leu Glu
                165                 170                 175

Gln Glu Val Ala Thr Ala Gln His Gln Val Asp Asn Leu Lys Lys Leu
            180                 185                 190

Leu Ala Gly Ala Asp Pro Asp Asp Gly Thr Glu Val Ile Glu Ala Lys
        195                 200                 205

Leu Asn Lys Gly Glu Ala Glu Leu Asn Ala Lys Gln Ala Glu Leu Ala
210                 215                 220

Lys Lys Gln Thr Glu Leu Glu Lys Leu Leu Asp Ser Leu Asp Pro Glu
225                 230                 235                 240

Gly Lys Thr Gln Asp Glu Leu Asp Lys Glu Ala Glu Glu Ala Glu Leu
                245                 250                 255

Asp Lys Lys Ala Asp Glu Leu Gln Asn Lys Val Ala Asp Leu Glu Lys
            260                 265                 270
```

```
Glu Ile Ser Asn Leu Glu Ile Leu Leu Gly Gly Ala Asp Ser Glu Asp
        275                 280                 285

Asp Thr Ala Ala Leu Gln Asn Lys Leu Ala Thr Lys Lys Ala Glu Leu
    290                 295                 300

Glu Lys Thr Gln Lys Glu Leu Asp Ala Ala Leu Asn Glu Leu Gly
305                 310                 315

<210> SEQ ID NO 35
<211> LENGTH: 319
<212> TYPE: PRT
<213> ORGANISM: Streptococcus pneumoniae

<400> SEQUENCE: 35

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys His Tyr Glu Glu Val
            20                  25                  30

Lys Lys Lys Ala Glu Asp Ala Gln Lys Lys Tyr Asp Glu Gly Gln Lys
        35                  40                  45

Lys Thr Val Glu Lys Ala Lys Arg Glu Lys Glu Ala Ser Glu Lys Ile
    50                  55                  60

Ala Glu Ala Thr Lys Glu Val Gln Gln Ala Tyr Leu Ala Tyr Gln Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Glu Ala Ala Phe Ala Thr Ile Arg
            100                 105                 110

Thr Thr Ile Val Val Pro Glu Pro Ser Glu Leu Ala Glu Thr Lys Lys
        115                 120                 125

Lys Ala Glu Glu Ala Lys Ala Glu Glu Lys Val Ala Lys Arg Lys Tyr
    130                 135                 140

Asp Tyr Ala Thr Leu Lys Val Ala Leu Ala Lys Lys Glu Val Glu Ala
145                 150                 155                 160

Lys Glu Leu Glu Ile Glu Lys Leu Gln Tyr Glu Ile Ser Thr Leu Glu
                165                 170                 175

Gln Glu Val Ala Thr Ala Gln His Gln Val Asp Asn Leu Lys Lys Leu
            180                 185                 190

Leu Ala Gly Ala Asp Pro Asp Asp Gly Thr Glu Val Ile Glu Ala Lys
        195                 200                 205

Leu Asn Lys Gly Glu Ala Glu Leu Asn Ala Lys Gln Ala Glu Leu Ala
    210                 215                 220

Lys Lys Gln Thr Glu Leu Glu Lys Leu Leu Asp Ser Leu Asp Pro Glu
225                 230                 235                 240

Gly Lys Thr Gln Asp Glu Leu Asp Lys Glu Ala Glu Ala Glu Leu
                245                 250                 255

Asp Lys Lys Ala Asp Glu Leu Gln Asn Lys Val Ala Asp Leu Glu Lys
            260                 265                 270

Glu Ile Ser Asn Leu Glu Ile Leu Leu Gly Gly Ala Asp Ser Glu Asp
        275                 280                 285

Asp Thr Ala Ala Leu Gln Asn Lys Leu Ala Thr Lys Lys Ala Glu Leu
    290                 295                 300

Glu Lys Thr Gln Lys Glu Leu Asp Ala Ala Leu Asn Glu Leu Gly
305                 310                 315
```

```
<210> SEQ ID NO 36
<211> LENGTH: 319
<212> TYPE: PRT
<213> ORGANISM: Streptococcus pneumoniae

<400> SEQUENCE: 36
```

| | | | | | | | | | | | | | | |
|---|---|---|---|---|---|---|---|---|---|---|---|---|---|---|
| Glu | Glu | Ala | Pro | Val | Ala | Ser | Gln | Ser | Lys | Ala | Glu | Lys | Asp | Tyr | Asp |
| 1 | | | | 5 | | | | | 10 | | | | | 15 |

Ala Ala Val Lys Lys Ser Glu Ala Ala Lys Lys His Tyr Glu Glu Val
            20                  25                  30

Lys Lys Lys Ala Glu Asp Ala Gln Lys Tyr Asp Glu Gly Gln Lys
        35                  40                  45

Lys Thr Val Glu Lys Ala Lys Arg Glu Lys Glu Ala Ser Glu Lys Ile
 50                  55                  60

Ala Glu Ala Thr Lys Glu Val Gln Gln Ala Tyr Leu Ala Tyr Gln Gln
 65                  70                  75                  80

Ala Ser Asn Glu Ser Gln Arg Lys Glu Ala Asp Lys Ile Lys Glu
            85                  90                  95

Ala Thr Gln Arg Lys Asp Glu Ala Glu Ala Phe Ala Thr Ile Arg
            100                 105                 110

Thr Thr Ile Val Val Pro Glu Pro Ser Glu Leu Ala Glu Thr Lys Lys
            115                 120                 125

Lys Ala Glu Glu Ala Lys Ala Glu Lys Val Ala Lys Arg Lys Tyr
        130                 135                 140

Asp Tyr Ala Thr Leu Lys Val Ala Leu Ala Lys Lys Glu Val Glu Ala
 145                 150                 155                 160

Lys Glu Leu Glu Ile Glu Lys Leu Gln Tyr Glu Ile Ser Thr Leu Glu
                    165                 170                 175

Gln Glu Val Ala Thr Ala Gln His Gln Val Asp Asn Leu Lys Lys Leu
            180                 185                 190

Leu Ala Gly Ala Asp Pro Asp Asp Gly Thr Glu Val Ile Glu Ala Lys
            195                 200                 205

Leu Asn Lys Gly Glu Ala Glu Leu Asn Ala Lys Gln Ala Glu Leu Ala
 210                 215                 220

Lys Lys Gln Thr Glu Leu Glu Lys Leu Leu Asp Ser Leu Asp Pro Glu
 225                 230                 235                 240

Gly Lys Thr Gln Asp Glu Leu Asp Lys Glu Ala Glu Glu Ala Glu Leu
            245                 250                 255

Asp Lys Lys Ala Asp Glu Leu Gln Asn Lys Val Ala Asp Leu Glu Lys
            260                 265                 270

Glu Ile Ser Asn Leu Glu Ile Leu Leu Gly Gly Ala Asp Ser Glu Asp
            275                 280                 285

Asp Thr Ala Ala Leu Gln Asn Lys Leu Ala Thr Lys Lys Ala Glu Leu
            290                 295                 300

Glu Lys Thr Gln Lys Glu Leu Asp Ala Ala Leu Asn Glu Leu Gly
 305                 310                 315

```
<210> SEQ ID NO 37
<211> LENGTH: 218
<212> TYPE: PRT
<213> ORGANISM: Streptococcus pneumoniae

<400> SEQUENCE: 37
```

Glu Glu Ala Pro Val Ala Ser Gln Ser Lys Ala Glu Lys Asp Tyr Asp
 1                   5                  10                  15

Ala Ala Val Lys Lys Ser Glu Ala Ala Lys Lys Asp Tyr Glu Glu Ala

```
            20                  25                  30
Lys Lys Lys Ala Lys Glu Ala Gln Lys Lys Tyr Asp Glu Ala Ala Gln
        35                  40                  45
Glu Val Glu Val Ala Lys Lys Glu Val Glu Ala Lys Glu Leu Glu Ile
    50                  55                  60
Glu Lys Leu Gln Asp Glu Ile Ser Thr Leu Glu Gln Glu Val Ala Thr
65                  70                  75                  80
Ala Gln His Gln Val Asp Asn Leu Lys Lys Leu Leu Ala Gly Ala Asp
                85                  90                  95
Pro Asp Asp Gly Thr Glu Val Ile Glu Ala Lys Leu Lys Lys Gly Glu
            100                 105                 110
Ala Glu Leu Asn Ala Lys Gln Ala Glu Leu Ala Lys Lys Gln Thr Glu
        115                 120                 125
Leu Glu Lys Leu Leu Asp Ser Leu Asp Pro Gly Lys Thr Gln Asp
    130                 135                 140
Glu Leu Asp Lys Glu Ala Glu Glu Ala Glu Leu Asp Lys Lys Ala Asp
145                 150                 155                 160
Glu Leu Gln Asn Lys Val Ala Asp Leu Glu Lys Glu Ile Ser Asn Leu
                165                 170                 175
Glu Ile Leu Leu Gly Gly Ala Asp Ser Glu Asp Asp Thr Ala Ala Leu
            180                 185                 190
Gln Asn Lys Leu Ala Thr Lys Lys Ala Glu Leu Glu Lys Thr Gln Lys
        195                 200                 205
Glu Leu Asp Ala Ala Leu Asn Glu Leu Gly
    210                 215

<210> SEQ ID NO 38
<211> LENGTH: 329
<212> TYPE: PRT
<213> ORGANISM: Streptococcus pneumoniae

<400> SEQUENCE: 38

Glu Glu Ala Pro Val Ala Ser Gln Ser Lys Ala Glu Lys Asp Tyr Asp
1               5                   10                  15
Ala Ala Val Lys Lys Ser Glu Ala Lys Lys Asp Tyr Glu Glu Ala
            20                  25                  30
Lys Lys Lys Ala Lys Glu Ala Gln Lys Lys Tyr Asp Glu Glu Gln Lys
        35                  40                  45
Lys Thr Glu Glu Lys Ala Lys Lys Glu Lys Glu Ala Ala Lys Lys Val
    50                  55                  60
Asp Asp Ala Ser Leu Ala Val Gln Lys Ala His Val Glu Tyr Arg Lys
65                  70                  75                  80
Val Leu Phe Ser Arg Asn Ser Tyr Lys Tyr Lys Ser Asp Tyr Asp Lys
                85                  90                  95
Lys Leu Ala Glu Ala Gln Ala Lys Ile Asp Glu Ala Asn Lys Lys Leu
            100                 105                 110
Thr Ala Ala Asn Asn Glu Phe Gln Thr Val Arg Ala Val Val Pro
        115                 120                 125
Glu Pro Asn Ala Leu Ala Glu Thr Lys Lys Ala Glu Glu Ala Lys
    130                 135                 140
Ala Glu Glu Val Val Ala Lys Lys Tyr Asp Glu Ala Ala Gln Glu
145                 150                 155                 160
Val Glu Val Ala Lys Lys Glu Val Glu Ala Lys Glu Leu Glu Ile Glu
                165                 170                 175
```

```
Lys Leu Gln Asp Glu Ile Ser Thr Leu Glu Gln Glu Val Ala Thr Ala
                180                 185                 190

Gln His Gln Val Asp Asn Leu Lys Lys Leu Leu Ala Gly Ala Asp Pro
            195                 200                 205

Asp Asp Gly Thr Glu Val Ile Glu Ala Lys Leu Lys Lys Gly Glu Ala
        210                 215                 220

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
                245                 250                 255

Leu Asp Lys Glu Ala Glu Ala Glu Leu Asp Lys Lys Ala Asp Glu
            260                 265                 270

Leu Gln Asn Lys Val Ala Asp Leu Glu Lys Glu Ile Ser Asn Leu Glu
        275                 280                 285

Ile Leu Leu Gly Gly Ala Asp Ser Glu Asp Asp Thr Ala Ala Leu Gln
290                 295                 300

Asn Lys Leu Ala Thr Lys Lys Ala Glu Leu Glu Lys Thr Gln Lys Glu
305                 310                 315                 320

Leu Asp Ala Ala Leu Asn Glu Leu Gly
                325
```

<210> SEQ ID NO 39
<211> LENGTH: 329
<212> TYPE: PRT
<213> ORGANISM: Streptococcus pneumoniae

<400> SEQUENCE: 39

```
Glu Glu Ala Pro Val Ala Ser Gln Ser Lys Ala Glu Lys Asp Tyr Asp
1               5                   10                  15

Ala Ala Val Lys Lys Ser Glu Ala Lys Lys Asp Tyr Glu Glu Ala
            20                  25                  30

Lys Lys Lys Ala Lys Glu Ala Gln Lys Lys Tyr Asp Glu Glu Gln Lys
        35                  40                  45

Lys Thr Glu Glu Lys Ala Lys Lys Glu Lys Glu Ala Ala Lys Lys Val
    50                  55                  60

Asp Asp Ala Ser Leu Ala Val Gln Lys Ala His Val Glu Tyr Arg Lys
65                  70                  75                  80

Val Leu Phe Ser Arg Asn Ser Tyr Lys Tyr Lys Ser Asp Tyr Asp Lys
                85                  90                  95

Lys Leu Ala Glu Ala Gln Ala Lys Ile Asp Glu Ala Asn Lys Lys Leu
            100                 105                 110

Thr Ala Ala Asn Asn Glu Phe Gln Thr Val Arg Ala Val Val Val Pro
        115                 120                 125

Glu Pro Asn Ala Leu Ala Glu Thr Lys Lys Lys Ala Glu Glu Ala Lys
    130                 135                 140

Ala Glu Glu Val Val Ala Lys Lys Lys Tyr Asp Glu Ala Ala Gln Glu
145                 150                 155                 160

Val Glu Val Ala Lys Lys Glu Val Glu Ala Lys Glu Leu Glu Ile Glu
                165                 170                 175

Lys Leu Gln Asp Glu Ile Ser Thr Leu Glu Gln Glu Val Ala Thr Ala
            180                 185                 190

Gln His Gln Val Asp Asn Leu Lys Lys Leu Leu Ala Gly Ala Asp Pro
        195                 200                 205

Asp Asp Gly Thr Glu Val Ile Glu Ala Lys Leu Lys Lys Gly Glu Ala
    210                 215                 220
```

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
            245                 250                 255

Leu Asp Lys Glu Ala Glu Glu Ala Glu Leu Asp Lys Lys Ala Asp Glu
            260                 265                 270

Leu Gln Asn Lys Val Ala Asp Leu Glu Lys Glu Ile Ser Asn Leu Glu
            275                 280                 285

Ile Leu Leu Gly Gly Ala Asp Ser Glu Asp Asp Thr Ala Ala Leu Gln
290                 295                 300

Asn Lys Leu Ala Thr Lys Lys Ala Glu Leu Glu Lys Thr Gln Lys Glu
305                 310                 315                 320

Leu Asp Ala Ala Leu Asn Glu Leu Gly
            325

<210> SEQ ID NO 40
<211> LENGTH: 329
<212> TYPE: PRT
<213> ORGANISM: Streptococcus pneumoniae

<400> SEQUENCE: 40

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys Asp Tyr Glu Glu Ala
                20                  25                  30

Lys Lys Lys Ala Lys Glu Ala Gln Lys Lys Tyr Asp Glu Glu Gln Lys
            35                  40                  45

Lys Thr Glu Glu Lys Ala Lys Lys Glu Lys Glu Ala Ala Lys Lys Val
50                  55                  60

Asp Asp Ala Ser Leu Ala Val Gln Lys Ala His Val Glu Tyr Arg Lys
65                  70                  75                  80

Val Leu Phe Ser Arg Asn Ser Tyr Lys Tyr Lys Ser Asp Tyr Asp Lys
                85                  90                  95

Lys Leu Ala Glu Ala Gln Ala Lys Ile Asp Glu Ala Asn Lys Lys Leu
            100                 105                 110

Thr Ala Ala Asn Asn Glu Phe Gln Thr Val Arg Ala Val Val Val Pro
            115                 120                 125

Glu Pro Asn Ala Leu Ala Glu Thr Lys Lys Lys Ala Glu Glu Ala Lys
130                 135                 140

Ala Glu Glu Val Val Ala Lys Lys Lys Ser Asp Glu Ala Ala Gln Glu
145                 150                 155                 160

Val Glu Val Ala Lys Lys Glu Val Glu Ala Lys Glu Leu Glu Ile Glu
                165                 170                 175

Lys Leu Gln Asp Glu Ile Ser Thr Leu Glu Gln Glu Val Ala Thr Ala
            180                 185                 190

Gln His Gln Val Asp Asn Leu Lys Lys Leu Leu Ala Gly Ala Asp Pro
            195                 200                 205

Asp Asp Gly Thr Glu Val Ile Glu Ala Lys Leu Lys Lys Gly Glu Ala
210                 215                 220

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
            245                 250                 255

Leu Asp Lys Glu Ala Glu Glu Ala Glu Leu Asp Lys Lys Ala Asp Glu

```
            260                 265                 270
Leu Gln Asn Lys Val Ala Asp Leu Glu Lys Glu Ile Ser Asn Leu Glu
        275                 280                 285

Ile Leu Leu Gly Gly Ala Asp Ser Glu Asp Asp Thr Ala Ala Leu Gln
    290                 295                 300

Asn Lys Leu Ala Thr Lys Lys Ala Glu Leu Glu Lys Thr Gln Lys Glu
305                 310                 315                 320

Leu Asp Ala Ala Leu Asn Glu Leu Gly
            325

<210> SEQ ID NO 41
<211> LENGTH: 329
<212> TYPE: PRT
<213> ORGANISM: Streptococcus pneumoniae

<400> SEQUENCE: 41

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys Asp Tyr Glu Glu Ala
            20                  25                  30

Lys Lys Lys Ala Lys Glu Ala Gln Lys Lys Tyr Asp Glu Glu Gln Lys
        35                  40                  45

Lys Thr Glu Glu Lys Ala Lys Lys Glu Lys Glu Ala Ala Lys Lys Val
    50                  55                  60

Asp Asp Ala Ser Leu Ala Val Gln Lys Ala His Val Glu Tyr Arg Lys
65                  70                  75                  80

Val Leu Phe Ser Arg Asn Ser Tyr Lys Tyr Lys Ser Asp Tyr Asp Lys
                85                  90                  95

Lys Leu Ala Glu Ala Gln Ala Lys Ile Asp Glu Ala Asn Lys Lys Leu
            100                 105                 110

Thr Ala Ala Asn Asn Glu Phe Gln Thr Val Arg Ala Val Val Val Pro
        115                 120                 125

Glu Pro Asn Ala Leu Ala Glu Thr Lys Lys Lys Ala Glu Glu Ala Lys
    130                 135                 140

Ala Glu Glu Val Val Ala Lys Lys Lys Ser Asp Glu Ala Ala Gln Glu
145                 150                 155                 160

Val Glu Val Ala Lys Lys Glu Val Glu Ala Lys Glu Leu Glu Ile Glu
                165                 170                 175

Lys Leu Gln Asp Glu Ile Ser Thr Leu Glu Gln Glu Val Ala Thr Ala
            180                 185                 190

Gln His Gln Val Asp Asn Leu Lys Leu Leu Ala Gly Ala Asp Pro
        195                 200                 205

Asp Asp Gly Thr Glu Val Ile Glu Ala Lys Leu Lys Lys Gly Glu Ala
    210                 215                 220

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
                245                 250                 255

Leu Asp Lys Glu Ala Glu Glu Ala Glu Leu Asp Lys Lys Ala Asp Glu
            260                 265                 270

Leu Gln Asn Lys Val Ala Asp Leu Glu Lys Glu Ile Ser Asn Leu Glu
        275                 280                 285

Ile Leu Leu Gly Gly Ala Asp Ser Glu Asp Asp Thr Ala Ala Leu Gln
    290                 295                 300
```

```
Asn Lys Leu Ala Thr Lys Lys Ala Glu Leu Glu Lys Thr Gln Lys Glu
305                 310                 315                 320

Leu Asp Ala Ala Leu Asn Glu Leu Gly
                325
```

<210> SEQ ID NO 42
<211> LENGTH: 411
<212> TYPE: PRT
<213> ORGANISM: Streptococcus pneumoniae

<400> SEQUENCE: 42

```
Glu Glu Ser Pro Gln Val Val Glu Lys Ser Leu Glu Lys Lys Tyr
1               5                   10                  15

Glu Glu Ala Lys Ala Lys Ala Asp Thr Ala Lys Lys Asp Tyr Glu Thr
                20                  25                  30

Ala Lys Lys Lys Ala Glu Asp Ala Gln Lys Lys Tyr Glu Asp Asp Gln
                35                  40                  45

Lys Arg Thr Glu Glu Lys Ala Arg Lys Glu Ala Glu Ala Ser Gln Lys
50                  55                  60

Leu Asn Asp Val Ala Leu Val Val Gln Asn Ala Tyr Lys Glu Tyr Arg
65                  70                  75                  80

Glu Val Gln Asn Gln Arg Ser Lys Tyr Lys Ser Asp Ala Glu Tyr Gln
                85                  90                  95

Lys Lys Leu Thr Glu Val Asp Ser Lys Ile Glu Lys Ala Arg Lys Glu
                100                 105                 110

Gln Gln Asp Leu Gln Asn Lys Phe Asn Glu Val Arg Ala Val Val Val
                115                 120                 125

Pro Glu Pro Asn Ala Leu Ala Glu Thr Lys Lys Lys Ala Glu Glu Ala
130                 135                 140

Lys Ala Glu Glu Lys Val Ala Lys Arg Lys Tyr Asp Tyr Ala Thr Leu
145                 150                 155                 160

Lys Val Ala Leu Ala Lys Lys Glu Val Glu Ala Lys Glu Leu Glu Ile
                165                 170                 175

Glu Lys Leu Gln Tyr Glu Ile Ser Thr Leu Glu Gln Glu Val Ala Thr
                180                 185                 190

Ala Gln His Gln Val Asp Asn Leu Lys Lys Leu Leu Ala Gly Ala Asp
                195                 200                 205

Pro Asp Asp Gly Thr Glu Val Ile Glu Ala Lys Leu Lys Lys Gly Glu
210                 215                 220

Ala Glu Leu Asn Ala Lys Gln Ala Glu Leu Ala Lys Lys Gln Thr Glu
225                 230                 235                 240

Leu Glu Lys Leu Leu Asp Ser Leu Asp Pro Glu Gly Lys Thr Gln Asp
                245                 250                 255

Glu Leu Asp Lys Glu Ala Glu Ala Glu Leu Asp Lys Lys Ala Asp
                260                 265                 270

Glu Leu Gln Asn Lys Val Ala Asp Leu Glu Lys Glu Ile Ser Asn Leu
                275                 280                 285

Glu Ile Leu Leu Gly Gly Ala Asp Pro Glu Asp Thr Ala Ala Leu
290                 295                 300

Gln Asn Lys Leu Ala Ala Lys Lys Ala Glu Leu Ala Lys Gln Thr
305                 310                 315                 320

Glu Leu Glu Lys Leu Leu Asp Ser Leu Asp Pro Glu Gly Lys Thr Gln
                325                 330                 335

Asp Glu Leu Asp Lys Glu Ala Glu Ala Glu Leu Asp Lys Lys Ala
                340                 345                 350
```

Asp Glu Leu Gln Asn Lys Val Ala Asp Leu Glu Lys Glu Ile Ser Asn
        355                 360                 365

Leu Glu Ile Leu Leu Gly Gly Ala Asp Ser Glu Asp Thr Ala Ala
        370                 375                 380

Leu Gln Asn Lys Leu Ala Thr Lys Lys Ala Glu Leu Glu Lys Thr Gln
385                 390                 395                 400

Lys Glu Leu Asp Ala Ala Leu Asn Glu Leu Gly
                405                 410

<210> SEQ ID NO 43
<211> LENGTH: 411
<212> TYPE: PRT
<213> ORGANISM: Streptococcus pneumoniae

<400> SEQUENCE: 43

Glu Glu Ser Pro Gln Val Val Glu Lys Ser Leu Glu Lys Lys Tyr
1               5                  10                  15

Glu Glu Ala Lys Ala Lys Ala Asp Thr Ala Lys Lys Asp Tyr Glu Thr
                20                  25                  30

Ala Lys Lys Lys Ala Glu Asp Ala Gln Lys Lys Tyr Glu Asp Asp Gln
            35                  40                  45

Lys Arg Thr Glu Glu Lys Ala Arg Lys Glu Ala Glu Ala Ser Gln Lys
        50                  55                  60

Leu Asn Asp Val Ala Leu Val Val Gln Asn Ala Tyr Lys Glu Tyr Arg
65                  70                  75                  80

Glu Val Gln Asn Gln Arg Ser Lys Tyr Lys Ser Asp Ala Glu Tyr Gln
                85                  90                  95

Lys Lys Leu Thr Glu Val Asp Ser Lys Ile Glu Lys Ala Arg Lys Glu
            100                 105                 110

Gln Gln Asp Leu Gln Asn Lys Phe Asn Glu Val Arg Ala Val Val Val
        115                 120                 125

Pro Glu Pro Asn Ala Leu Ala Glu Thr Lys Lys Ala Glu Glu Ala
    130                 135                 140

Lys Ala Glu Glu Lys Val Ala Lys Arg Lys Tyr Asp Tyr Ala Thr Leu
145                 150                 155                 160

Lys Val Ala Leu Ala Lys Lys Glu Val Glu Ala Lys Glu Leu Glu Ile
                165                 170                 175

Glu Lys Leu Gln Tyr Glu Ile Ser Thr Leu Glu Gln Glu Val Ala Thr
            180                 185                 190

Ala Gln His Gln Val Asp Asn Leu Lys Lys Leu Leu Ala Gly Ala Asp
        195                 200                 205

Pro Asp Asp Gly Thr Glu Val Ile Glu Ala Lys Leu Lys Lys Gly Glu
    210                 215                 220

Ala Glu Leu Asn Ala Lys Gln Ala Glu Leu Ala Lys Lys Gln Thr Glu
225                 230                 235                 240

Leu Glu Lys Leu Leu Asp Ser Leu Asp Pro Glu Gly Lys Thr Gln Asp
                245                 250                 255

Glu Leu Asp Lys Glu Ala Glu Glu Ala Glu Leu Asp Lys Lys Ala Asp
            260                 265                 270

Glu Leu Gln Asn Lys Val Ala Asp Leu Glu Lys Glu Ile Ser Asn Leu
        275                 280                 285

Glu Ile Leu Leu Gly Gly Ala Asp Pro Glu Asp Asp Thr Ala Ala Leu
    290                 295                 300

Gln Asn Lys Leu Ala Ala Lys Lys Ala Glu Leu Ala Lys Lys Gln Thr

```
           305                 310                 315                 320
Glu Leu Glu Lys Leu Leu Asp Ser Leu Asp Pro Gly Lys Thr Gln
                325                 330                 335

Asp Glu Leu Asp Lys Glu Ala Glu Ala Glu Leu Asp Lys Lys Ala
                340                 345                 350

Asp Glu Leu Gln Asn Lys Val Ala Asp Leu Glu Lys Glu Ile Ser Asn
                355                 360                 365

Leu Glu Ile Leu Leu Gly Gly Ala Asp Ser Glu Asp Thr Ala Ala
    370                 375                 380

Leu Gln Asn Lys Leu Ala Thr Lys Lys Ala Glu Leu Glu Lys Thr Gln
    385                 390                 395                 400

Lys Glu Leu Asp Ala Ala Leu Asn Glu Leu Gly
                405                 410

<210> SEQ ID NO 44
<211> LENGTH: 400
<212> TYPE: PRT
<213> ORGANISM: Streptococcus pneumoniae

<400> SEQUENCE: 44

Glu Glu Ser Pro Val Ala Ser Gln Ser Lys Ala Glu Lys Asp Tyr Asp
1               5                   10                  15

Ala Ala Val Lys Lys Ser Glu Ala Ala Lys Lys His Tyr Glu Glu Ala
                20                  25                  30

Lys Lys Lys Ala Glu Asp Ala Gln Lys Lys Tyr Asp Glu Asp Gln Lys
            35                  40                  45

Lys Thr Glu Ala Lys Ala Glu Lys Glu Arg Lys Ala Ser Glu Lys Ile
        50                  55                  60

Ala Glu Ala Thr Lys Glu Val Gln Gln Ala Tyr Leu Ala Tyr Leu Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Glu Ala Phe Ala Thr Ile Arg
                100                 105                 110

Thr Thr Ile Val Val Pro Glu Pro Ser Glu Leu Ala Glu Thr Lys Lys
        115                 120                 125

Lys Ala Glu Glu Ala Lys Ala Glu Glu Lys Val Ala Lys Arg Lys Tyr
    130                 135                 140

Asp Tyr Ala Thr Leu Lys Leu Ala Leu Ala Lys Lys Glu Val Glu Ala
145                 150                 155                 160

Lys Glu Leu Glu Ile Glu Lys Leu Gln Tyr Glu Ile Ser Thr Leu Glu
                165                 170                 175

Gln Glu Val Ala Thr Ala Gln His Gln Val Asp Asn Leu Lys Lys Leu
            180                 185                 190

Leu Ala Gly Ala Asp Pro Asp Asp Gly Thr Glu Val Ile Glu Ala Lys
        195                 200                 205

Leu Lys Lys Gly Glu Ala Glu Leu Asn Ala Lys Gln Ala Glu Leu Ala
    210                 215                 220

Lys Lys Gln Thr Glu Leu Glu Lys Leu Leu Asp Ser Leu Asp Pro Glu
225                 230                 235                 240

Gly Lys Thr Gln Asp Glu Leu Asp Lys Glu Ala Glu Ala Glu Leu
                245                 250                 255

Asp Lys Lys Ala Asp Glu Leu Gln Asn Lys Val Ala Asp Leu Glu Lys
            260                 265                 270
```

```
Glu Ile Ser Asn Leu Glu Ile Leu Gly Gly Ala Asp Pro Glu Asp
            275                 280                 285

Asp Thr Ala Ala Leu Gln Asn Lys Leu Ala Ala Lys Lys Ala Glu Leu
290                 295                 300

Ala Lys Lys Gln Thr Glu Leu Glu Lys Leu Leu Asp Ser Leu Asp Pro
305                 310                 315                 320

Glu Gly Lys Thr Gln Asp Glu Leu Asp Lys Glu Ala Glu Ala Glu
                325                 330                 335

Leu Asp Lys Lys Ala Asp Glu Leu Gln Asn Lys Val Ala Asp Leu Glu
            340                 345                 350

Lys Glu Ile Ser Asn Leu Glu Ile Leu Gly Gly Ala Asp Ser Glu
            355                 360                 365

Asp Asp Thr Ala Ala Leu Gln Asn Lys Leu Ala Thr Lys Lys Ala Glu
370                 375                 380

Leu Glu Lys Thr Gln Lys Glu Leu Asp Ala Ala Leu Asn Glu Leu Gly
385                 390                 395                 400

<210> SEQ ID NO 45
<211> LENGTH: 400
<212> TYPE: PRT
<213> ORGANISM: Streptococcus pneumoniae

<400> SEQUENCE: 45

Glu Glu Ser Pro Val Ala Ser Gln Ser Lys Ala Glu Lys Asp Tyr Asp
1               5                   10                  15

Ala Ala Val Lys Lys Ser Glu Ala Ala Lys Lys His Tyr Glu Glu Ala
            20                  25                  30

Lys Lys Lys Ala Glu Asp Ala Gln Lys Lys Tyr Asp Glu Asp Gln Lys
            35                  40                  45

Lys Thr Glu Ala Lys Ala Glu Lys Glu Arg Lys Ala Ser Glu Lys Ile
50                  55                  60

Ala Glu Ala Thr Lys Glu Val Gln Gln Ala Tyr Leu Ala Tyr Leu Gln
65                  70                  75                  80

Ala Ser Asn Glu Ser Gln Arg Lys Glu Ala Asp Lys Lys Ile Lys Glu
            85                  90                  95

Ala Thr Gln Arg Lys Asp Glu Ala Glu Ala Phe Ala Thr Ile Arg
            100                 105                 110

Thr Thr Ile Val Val Pro Glu Pro Ser Glu Leu Ala Glu Thr Lys Lys
            115                 120                 125

Lys Ala Glu Glu Ala Lys Ala Glu Glu Lys Val Ala Lys Arg Lys Tyr
130                 135                 140

Asp Tyr Ala Thr Leu Lys Leu Ala Leu Ala Lys Lys Glu Val Glu Ala
145                 150                 155                 160

Lys Glu Leu Glu Ile Glu Lys Leu Gln Tyr Glu Ile Ser Thr Leu Glu
                165                 170                 175

Gln Glu Val Ala Thr Ala Gln His Gln Val Asp Asn Leu Lys Lys Leu
            180                 185                 190

Leu Ala Gly Ala Asp Pro Asp Asp Gly Thr Glu Val Ile Glu Ala Lys
            195                 200                 205

Leu Lys Lys Gly Glu Ala Glu Leu Asn Ala Lys Gln Ala Glu Leu Ala
            210                 215                 220

Lys Lys Gln Thr Glu Leu Glu Lys Leu Leu Asp Ser Leu Asp Pro Glu
225                 230                 235                 240

Gly Lys Thr Gln Asp Glu Leu Asp Lys Glu Ala Glu Glu Ala Glu Leu
                245                 250                 255
```

Asp Lys Lys Ala Asp Glu Leu Gln Asn Lys Val Ala Asp Leu Glu Lys
            260                 265                 270

Glu Ile Ser Asn Leu Glu Ile Leu Gly Gly Ala Asp Pro Glu Asp
        275                 280                 285

Asp Thr Ala Ala Leu Gln Asn Lys Leu Ala Ala Lys Ala Glu Leu
    290                 295                 300

Ala Lys Lys Gln Thr Glu Leu Glu Lys Leu Leu Asp Ser Leu Asp Pro
305                 310                 315                 320

Glu Gly Lys Thr Gln Asp Glu Leu Asp Lys Glu Ala Glu Ala Glu
            325                 330                 335

Leu Asp Lys Lys Ala Asp Glu Leu Gln Asn Lys Val Ala Asp Leu Glu
            340                 345                 350

Lys Glu Ile Ser Asn Leu Glu Ile Leu Gly Gly Ala Asp Ser Glu
            355                 360                 365

Asp Asp Thr Ala Ala Leu Gln Asn Lys Leu Ala Thr Lys Lys Ala Glu
    370                 375                 380

Leu Glu Lys Thr Gln Lys Glu Leu Asp Ala Ala Leu Asn Glu Leu Gly
385                 390                 395                 400

<210> SEQ ID NO 46
<211> LENGTH: 400
<212> TYPE: PRT
<213> ORGANISM: Streptococcus pneumoniae

<400> SEQUENCE: 46

Glu Glu Ser Pro Val Ala Ser Gln Ser Lys Ala Glu Lys Asp Tyr Asp
1               5                   10                  15

Ala Ala Val Lys Lys Ser Glu Ala Ala Lys Lys His Tyr Glu Glu Ala
            20                  25                  30

Lys Lys Lys Ala Glu Asp Ala Gln Lys Lys Tyr Asp Glu Asp Gln Lys
        35                  40                  45

Lys Thr Glu Ala Lys Ala Glu Lys Glu Arg Lys Ala Ser Glu Lys Ile
50                  55                  60

Ala Glu Ala Thr Lys Glu Val Gln Gln Ala Tyr Leu Ala Tyr Leu Gln
65                  70                  75                  80

Ala Ser Asn Glu Ser Gln Arg Lys Glu Ala Asp Lys Ile Lys Glu
            85                  90                  95

Ala Thr Gln Arg Lys Asp Glu Ala Glu Ala Phe Ala Thr Ile Arg
            100                 105                 110

Thr Thr Ile Val Val Pro Glu Pro Ser Glu Leu Ala Glu Thr Lys Lys
        115                 120                 125

Lys Ala Glu Glu Ala Lys Ala Glu Glu Lys Val Ala Lys Arg Lys Tyr
130                 135                 140

Asp Tyr Ala Thr Leu Lys Leu Ala Leu Ala Lys Lys Glu Val Glu Ala
145                 150                 155                 160

Lys Glu Leu Glu Ile Glu Lys Leu Gln Tyr Glu Ile Ser Thr Leu Glu
            165                 170                 175

Gln Glu Val Ala Thr Ala Gln His Gln Val Asp Asn Leu Lys Lys Leu
        180                 185                 190

Leu Ala Gly Ala Asp Pro Asp Asp Gly Thr Glu Val Ile Glu Ala Lys
        195                 200                 205

Leu Lys Lys Gly Glu Ala Glu Leu Asn Ala Lys Gln Ala Glu Leu Ala
210                 215                 220

Lys Lys Gln Thr Glu Leu Glu Lys Leu Leu Asp Ser Leu Asp Pro Glu

```
                225                 230                 235                 240
Gly Lys Thr Gln Asp Glu Leu Asp Lys Glu Ala Glu Ala Glu Leu
                    245                 250                 255

Asp Lys Lys Ala Asp Glu Leu Gln Asn Lys Val Ala Asp Leu Glu Lys
                260                 265                 270

Glu Ile Ser Asn Leu Glu Ile Leu Gly Gly Ala Asp Pro Glu Asp
                275                 280                 285

Asp Thr Ala Ala Leu Gln Asn Lys Leu Ala Ala Lys Ala Glu Leu
            290                 295                 300

Ala Lys Lys Gln Thr Glu Leu Glu Lys Leu Leu Asp Ser Leu Asp Pro
305                 310                 315                 320

Glu Gly Lys Thr Gln Asp Glu Leu Asp Lys Glu Ala Glu Ala Glu
                    325                 330                 335

Leu Asp Lys Lys Ala Asp Glu Leu Gln Asn Lys Val Ala Asp Leu Glu
                340                 345                 350

Lys Glu Ile Ser Asn Leu Glu Ile Leu Gly Gly Ala Asp Ser Glu
                355                 360                 365

Asp Asp Thr Ala Ala Leu Gln Asn Lys Leu Ala Thr Lys Lys Ala Glu
        370                 375                 380

Leu Glu Lys Thr Gln Lys Glu Leu Asp Ala Ala Leu Asn Glu Leu Gly
385                 390                 395                 400
```

<210> SEQ ID NO 47
<211> LENGTH: 400
<212> TYPE: PRT
<213> ORGANISM: Streptococcus pneumoniae

<400> SEQUENCE: 47

```
Glu Glu Ser Pro Val Ala Ser Gln Ser Lys Ala Glu Lys Asp Tyr Asp
1               5                   10                  15

Ala Ala Val Lys Lys Ser Glu Ala Ala Lys Lys His Tyr Glu Glu Ala
                20                  25                  30

Lys Lys Lys Ala Glu Asp Ala Gln Lys Lys Tyr Asp Glu Asp Gln Lys
            35                  40                  45

Lys Thr Glu Ala Lys Ala Glu Lys Glu Arg Lys Ala Ser Glu Lys Ile
    50                  55                  60

Ala Glu Ala Thr Lys Glu Val Gln Gln Ala Tyr Leu Ala Tyr Leu Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Glu Ala Ala Phe Ala Thr Ile Arg
                100                 105                 110

Thr Thr Ile Val Val Pro Glu Pro Ser Glu Leu Ala Glu Thr Lys Lys
            115                 120                 125

Lys Ala Glu Glu Ala Lys Ala Glu Glu Lys Val Ala Lys Arg Lys Tyr
    130                 135                 140

Asp Tyr Ala Thr Leu Lys Leu Ala Leu Ala Lys Lys Glu Val Glu Ala
145                 150                 155                 160

Lys Glu Leu Glu Ile Glu Lys Leu Gln Tyr Glu Ile Ser Thr Leu Glu
                165                 170                 175

Gln Glu Val Ala Thr Ala Gln His Gln Val Asp Asn Leu Lys Lys Leu
                180                 185                 190

Leu Ala Gly Ala Asp Pro Asp Asp Gly Thr Glu Val Ile Glu Ala Lys
            195                 200                 205
```

```
Leu Lys Lys Gly Glu Ala Glu Leu Asn Ala Lys Gln Ala Glu Leu Ala
210                 215                 220

Lys Lys Gln Thr Glu Leu Glu Lys Leu Leu Asp Ser Leu Asp Pro Glu
225                 230                 235                 240

Gly Lys Thr Gln Asp Glu Leu Asp Lys Glu Ala Glu Glu Ala Glu Leu
                245                 250                 255

Asp Lys Lys Ala Asp Glu Leu Gln Asn Lys Val Ala Asp Leu Glu Lys
            260                 265                 270

Glu Ile Ser Asn Leu Glu Ile Leu Gly Gly Ala Asp Pro Glu Asp
        275                 280                 285

Asp Thr Ala Ala Leu Gln Asn Lys Leu Ala Ala Lys Ala Glu Leu
290                 295                 300

Ala Lys Lys Gln Thr Glu Leu Glu Lys Leu Leu Asp Ser Leu Asp Pro
305                 310                 315                 320

Glu Gly Lys Thr Gln Asp Glu Leu Asp Lys Glu Ala Glu Glu Ala Glu
                325                 330                 335

Leu Asp Lys Lys Ala Asp Glu Leu Gln Asn Lys Val Ala Asp Leu Glu
            340                 345                 350

Lys Glu Ile Ser Asn Leu Glu Ile Leu Gly Gly Ala Asp Ser Glu
        355                 360                 365

Asp Asp Thr Ala Ala Leu Gln Asn Lys Leu Ala Thr Lys Lys Ala Glu
370                 375                 380

Leu Glu Lys Thr Gln Lys Glu Leu Asp Ala Ala Leu Asn Glu Leu Gly
385                 390                 395                 400

<210> SEQ ID NO 48
<211> LENGTH: 400
<212> TYPE: PRT
<213> ORGANISM: Streptococcus pneumoniae

<400> SEQUENCE: 48

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys His Tyr Glu Glu Val
                20                  25                  30

Lys Lys Lys Ala Glu Asp Ala Gln Lys Lys Tyr Asp Glu Gly Gln Lys
            35                  40                  45

Lys Thr Val Glu Lys Ala Lys Arg Glu Lys Glu Ala Ser Glu Lys Ile
50                  55                  60

Ala Glu Ala Thr Lys Glu Val Gln Gln Ala Tyr Leu Ala Tyr Gln Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Ala Ala Phe Ala Thr Ile Arg
            100                 105                 110

Thr Thr Ile Val Val Pro Glu Pro Ser Glu Leu Ala Glu Thr Lys Lys
        115                 120                 125

Lys Ala Glu Glu Ala Lys Ala Glu Gly Lys Val Ala Lys Arg Lys Tyr
130                 135                 140

Asp Tyr Ala Thr Leu Lys Val Ala Leu Ala Lys Lys Glu Val Glu Ala
145                 150                 155                 160

Lys Glu Leu Glu Ile Glu Lys Leu Gln Tyr Glu Ile Ser Thr Leu Glu
                165                 170                 175

Gln Glu Val Ala Thr Ala Gln His Gln Val Asp Asn Leu Lys Lys Leu
            180                 185                 190
```

```
Leu Ala Gly Ala Asp Pro Asp Gly Thr Glu Val Ile Glu Ala Lys
            195                 200                 205

Leu Asn Lys Gly Glu Ala Glu Leu Asn Ala Lys Gln Ala Glu Leu Ala
210                 215                 220

Lys Lys Gln Thr Glu Leu Glu Lys Leu Leu Asp Ser Leu Asp Pro Glu
225                 230                 235                 240

Gly Lys Thr Gln Asp Glu Leu Asp Lys Glu Ala Glu Ala Glu Leu
                245                 250                 255

Asp Lys Lys Ala Asp Glu Leu Gln Asn Lys Val Ala Asp Leu Glu Lys
            260                 265                 270

Glu Ile Ser Asn Leu Glu Ile Leu Leu Gly Gly Ala Asp Pro Glu Asp
            275                 280                 285

Asp Thr Ala Ala Leu Gln Asn Lys Leu Ala Ala Lys Gln Ala Glu Leu
            290                 295                 300

Ala Lys Lys Gln Thr Glu Leu Glu Lys Leu Leu Asp Ser Leu Asp Pro
305                 310                 315                 320

Glu Gly Lys Thr Gln Asp Glu Leu Asp Lys Glu Ala Glu Ala Glu
                325                 330                 335

Leu Asp Lys Lys Ala Asp Glu Leu Gln Asn Lys Val Ala Asp Leu Glu
            340                 345                 350

Lys Glu Ile Ser Asn Leu Glu Ile Leu Leu Gly Gly Ala Asp Ser Glu
            355                 360                 365

Asp Asp Thr Ala Ala Leu Gln Asn Lys Leu Ala Thr Lys Lys Ala Glu
            370                 375                 380

Leu Glu Lys Thr Gln Lys Glu Leu Asp Ala Ala Leu Asn Glu Leu Gly
385                 390                 395                 400

<210> SEQ ID NO 49
<211> LENGTH: 400
<212> TYPE: PRT
<213> ORGANISM: Streptococcus pneumoniae

<400> SEQUENCE: 49

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys His Tyr Glu Glu Val
                20                  25                  30

Lys Lys Lys Ala Glu Asp Ala Gln Lys Lys Tyr Asp Glu Gly Gln Lys
            35                  40                  45

Lys Thr Val Glu Lys Ala Lys Arg Glu Lys Glu Ala Ser Glu Lys Ile
50                  55                  60

Ala Glu Ala Thr Lys Glu Val Gln Gln Ala Tyr Leu Ala Tyr Gln Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Glu Ala Ala Phe Ala Thr Ile Arg
            100                 105                 110

Thr Thr Ile Val Val Pro Glu Pro Ser Glu Leu Ala Glu Thr Lys Lys
        115                 120                 125

Lys Ala Glu Glu Ala Lys Ala Glu Glu Lys Val Ala Lys Arg Lys Tyr
130                 135                 140

Asp Tyr Ala Thr Leu Lys Val Ala Leu Ala Lys Lys Glu Val Glu Ala
145                 150                 155                 160

Lys Glu Leu Glu Ile Glu Lys Leu Gln Tyr Glu Ile Ser Thr Leu Glu
```

```
                165                 170                 175
Gln Glu Val Ala Thr Ala Gln His Gln Val Asp Asn Leu Lys Lys Leu
            180                 185                 190

Leu Ala Gly Ala Asp Pro Asp Gly Thr Glu Val Ile Glu Ala Lys
        195                 200                 205

Leu Asn Lys Gly Glu Ala Glu Leu Asn Ala Lys Gln Ala Glu Leu Ala
        210                 215                 220

Lys Lys Gln Thr Glu Leu Glu Lys Leu Leu Asp Ser Leu Asp Pro Glu
225                 230                 235                 240

Gly Lys Thr Gln Asp Glu Leu Asp Lys Glu Ala Glu Ala Glu Leu
            245                 250                 255

Asp Lys Lys Ala Asp Glu Leu Gln Asn Lys Val Ala Asp Leu Glu Lys
                260                 265                 270

Glu Ile Ser Asn Leu Glu Ile Leu Leu Gly Gly Ala Asp Pro Glu Asp
            275                 280                 285

Asp Thr Ala Ala Leu Gln Asn Lys Leu Ala Ala Lys Gln Ala Glu Leu
        290                 295                 300

Ala Lys Lys Gln Thr Glu Leu Glu Lys Leu Leu Asp Ser Leu Asp Pro
305                 310                 315                 320

Glu Gly Lys Thr Gln Asp Glu Leu Asp Lys Glu Ala Glu Ala Glu
            325                 330                 335

Leu Asp Lys Lys Ala Asp Glu Leu Gln Asn Lys Val Ala Asp Leu Glu
                340                 345                 350

Lys Glu Ile Ser Asn Leu Glu Ile Leu Leu Gly Gly Ala Asp Ser Glu
            355                 360                 365

Asp Asp Thr Ala Ala Leu Gln Asn Lys Leu Ala Thr Lys Lys Ala Glu
        370                 375                 380

Leu Glu Lys Thr Gln Lys Glu Leu Asp Ala Ala Leu Asn Glu Leu Gly
385                 390                 395                 400

<210> SEQ ID NO 50
<211> LENGTH: 400
<212> TYPE: PRT
<213> ORGANISM: Streptococcus pneumoniae

<400> SEQUENCE: 50

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys His Tyr Glu Glu Val
            20                  25                  30

Lys Lys Lys Ala Glu Asp Ala Gln Lys Lys Tyr Asp Glu Gly Gln Lys
        35                  40                  45

Lys Thr Val Glu Lys Ala Lys Arg Glu Lys Glu Ala Ser Glu Lys Ile
    50                  55                  60

Ala Glu Ala Thr Lys Glu Val Gln Gln Ala Tyr Leu Ala Tyr Gln Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Glu Ala Phe Ala Thr Ile Arg
            100                 105                 110

Thr Thr Ile Val Val Pro Glu Pro Ser Glu Leu Ala Glu Thr Lys Lys
        115                 120                 125

Lys Ala Glu Glu Ala Lys Ala Glu Glu Lys Val Ala Lys Arg Lys Tyr
    130                 135                 140
```

```
Asp Tyr Ala Thr Leu Lys Val Ala Leu Ala Lys Lys Glu Val Glu Ala
145                 150                 155                 160

Lys Glu Leu Glu Ile Glu Lys Leu Gln Tyr Glu Ile Ser Thr Leu Glu
                165                 170                 175

Gln Glu Val Ala Thr Ala Gln His Gln Val Asp Asn Leu Lys Lys Leu
            180                 185                 190

Leu Ala Gly Ala Asp Pro Asp Gly Thr Glu Val Ile Glu Ala Lys
        195                 200                 205

Leu Asn Lys Gly Glu Ala Glu Leu Asn Ala Lys Gln Ala Glu Leu Ala
    210                 215                 220

Lys Lys Gln Thr Glu Leu Glu Lys Leu Leu Asp Ser Leu Asp Pro Glu
225                 230                 235                 240

Gly Lys Thr Gln Asp Glu Leu Asp Lys Glu Ala Glu Glu Ala Glu Leu
                245                 250                 255

Asp Lys Lys Ala Asp Glu Leu Gln Asn Lys Val Ala Asp Leu Glu Lys
            260                 265                 270

Glu Ile Ser Asn Leu Glu Ile Leu Leu Gly Gly Ala Asp Pro Glu Asp
        275                 280                 285

Asp Thr Ala Ala Leu Gln Asn Lys Leu Ala Ala Lys Gln Ala Glu Leu
    290                 295                 300

Ala Lys Lys Gln Thr Glu Leu Glu Lys Leu Leu Asp Ser Leu Asp Pro
305                 310                 315                 320

Glu Gly Lys Thr Gln Asp Glu Leu Asp Lys Glu Ala Glu Glu Ala Glu
                325                 330                 335

Leu Asp Lys Lys Ala Asp Glu Leu Gln Asn Lys Val Ala Asp Leu Glu
            340                 345                 350

Lys Glu Ile Ser Asn Leu Glu Ile Leu Leu Gly Gly Ala Asp Ser Glu
        355                 360                 365

Asp Asp Thr Ala Ala Leu Gln Asn Lys Leu Ala Thr Lys Lys Ala Glu
    370                 375                 380

Leu Glu Lys Thr Gln Lys Glu Leu Asp Ala Ala Leu Asn Glu Leu Gly
385                 390                 395                 400

<210> SEQ ID NO 51
<211> LENGTH: 410
<212> TYPE: PRT
<213> ORGANISM: Streptococcus pneumoniae

<400> SEQUENCE: 51

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys Asp Tyr Glu Glu Ala
                20                  25                  30

Lys Lys Lys Ala Lys Glu Ala Gln Lys Lys Tyr Asp Glu Gln Lys
            35                  40                  45

Lys Thr Glu Glu Lys Ala Lys Lys Glu Lys Ala Ala Lys Lys Val
    50                  55                  60

Asp Asp Ala Ser Leu Ala Val Gln Lys Ala His Val Glu Tyr Arg Lys
65                  70                  75                  80

Val Leu Phe Ser Arg Asn Ser Tyr Lys Tyr Lys Ser Asp Tyr Asp Lys
                85                  90                  95

Lys Leu Ala Glu Ala Gln Ala Lys Ile Asp Glu Ala Asn Lys Lys Leu
            100                 105                 110

Thr Ala Ala Asn Asn Glu Phe Gln Thr Val Arg Ala Val Val Val Pro
    115                 120                 125
```

Glu Pro Asn Ala Leu Ala Glu Thr Lys Lys Ala Glu Ala Lys
            130                 135                 140

Ala Glu Glu Val Val Ala Lys Lys Lys Tyr Asp Glu Ala Ala Gln Glu
145                 150                 155                 160

Val Glu Val Ala Lys Lys Glu Val Glu Ala Lys Glu Leu Glu Ile Glu
                165                 170                 175

Lys Leu Gln Asp Glu Ile Ser Thr Leu Glu Gln Glu Val Ala Thr Ala
            180                 185                 190

Gln His Gln Val Asp Asn Leu Lys Lys Leu Leu Ala Gly Ala Asp Pro
        195                 200                 205

Asp Asp Gly Thr Glu Val Ile Glu Ala Lys Leu Lys Lys Gly Glu Ala
210                 215                 220

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
            245                 250                 255

Leu Asp Lys Glu Ala Glu Ala Glu Leu Asp Lys Lys Ala Asp Glu
            260                 265                 270

Leu Gln Asn Lys Val Ala Asp Leu Glu Lys Glu Ile Ser Asn Leu Glu
            275                 280                 285

Ile Leu Leu Gly Gly Ala Asp Pro Glu Asp Asp Thr Ala Ala Leu Gln
290                 295                 300

Asn Lys Leu Ala Ala Lys Gln Ala Glu Leu Ala Lys Lys Gln Thr Glu
305                 310                 315                 320

Leu Glu Lys Leu Leu Asp Ser Leu Asp Pro Glu Gly Lys Thr Gln Asp
            325                 330                 335

Glu Leu Asp Lys Glu Ala Glu Ala Glu Leu Asp Lys Lys Ala Asp
            340                 345                 350

Glu Leu Gln Asn Lys Val Ala Asp Leu Glu Lys Glu Ile Ser Asn Leu
            355                 360                 365

Glu Ile Leu Leu Gly Gly Ala Asp Ser Glu Asp Asp Thr Ala Ala Leu
            370                 375                 380

Gln Asn Lys Leu Ala Thr Lys Lys Ala Glu Leu Glu Lys Thr Gln Lys
385                 390                 395                 400

Glu Leu Asp Ala Ala Leu Asn Glu Leu Gly
                405                 410

<210> SEQ ID NO 52
<211> LENGTH: 410
<212> TYPE: PRT
<213> ORGANISM: Streptococcus pneumoniae

<400> SEQUENCE: 52

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys Asp Tyr Glu Glu Ala
                20                  25                  30

Lys Lys Lys Ala Lys Glu Ala Gln Lys Lys Tyr Asp Glu Glu Gln Lys
            35                  40                  45

Lys Thr Glu Glu Lys Ala Lys Lys Glu Lys Glu Ala Ala Lys Lys Val
        50                  55                  60

Asp Asp Ala Ser Leu Ala Val Gln Lys Ala His Val Glu Tyr Arg Lys
65                  70                  75                  80

Val Leu Phe Ser Arg Asn Ser Tyr Lys Tyr Lys Ser Asp Tyr Asp Lys

```
                    85                  90                  95
Lys Leu Ala Glu Ala Gln Ala Lys Ile Asp Glu Ala Asn Lys Lys Leu
                100                 105                 110

Thr Ala Ala Asn Asn Glu Phe Gln Thr Val Arg Ala Val Val Val Pro
            115                 120                 125

Glu Pro Asn Ala Leu Ala Glu Thr Lys Lys Lys Ala Glu Glu Ala Lys
        130                 135                 140

Ala Glu Glu Val Val Ala Lys Lys Lys Tyr Asp Glu Ala Ala Gln Glu
145                 150                 155                 160

Val Glu Val Ala Lys Lys Glu Val Glu Ala Lys Glu Leu Glu Ile Glu
                165                 170                 175

Lys Leu Gln Asp Glu Ile Ser Thr Leu Glu Gln Glu Val Ala Thr Ala
            180                 185                 190

Gln His Gln Val Asp Asn Leu Lys Lys Leu Leu Ala Gly Ala Asp Pro
        195                 200                 205

Asp Asp Gly Thr Glu Val Ile Glu Ala Lys Leu Lys Lys Gly Glu Ala
    210                 215                 220

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
                245                 250                 255

Leu Asp Lys Glu Ala Glu Ala Glu Leu Asp Lys Lys Ala Asp Glu
            260                 265                 270

Leu Gln Asn Lys Val Ala Asp Leu Gly Lys Glu Ile Ser Asn Leu Glu
        275                 280                 285

Ile Leu Leu Gly Gly Ala Asp Pro Glu Asp Asp Thr Ala Ala Leu Gln
    290                 295                 300

Asn Lys Leu Ala Ala Lys Gln Ala Glu Leu Ala Lys Lys Gln Thr Glu
305                 310                 315                 320

Leu Glu Lys Leu Leu Asp Ser Leu Asp Pro Glu Gly Lys Thr Gln Asp
                325                 330                 335

Glu Leu Asp Lys Glu Ala Glu Ala Glu Leu Asp Lys Lys Ala Asp
            340                 345                 350

Glu Leu Gln Asn Lys Val Ala Asp Leu Gly Lys Glu Ile Ser Asn Leu
        355                 360                 365

Glu Ile Leu Leu Gly Gly Ala Asp Ser Glu Asp Asp Thr Ala Ala Leu
    370                 375                 380

Gln Asn Lys Leu Ala Thr Lys Ala Glu Leu Glu Lys Thr Gln Lys
385                 390                 395                 400

Glu Leu Asp Ala Ala Leu Asn Glu Leu Gly
                405                 410

<210> SEQ ID NO 53
<211> LENGTH: 410
<212> TYPE: PRT
<213> ORGANISM: Streptococcus pneumoniae

<400> SEQUENCE: 53

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys Asp Tyr Glu Glu Ala
            20                  25                  30

Lys Lys Lys Ala Lys Glu Ala Gln Lys Lys Tyr Asp Glu Glu Gln Lys
        35                  40                  45
```

Lys Thr Glu Glu Lys Ala Lys Glu Lys Glu Ala Lys Lys Val
    50                  55                  60

Asp Asp Ala Ser Leu Ala Val Gln Lys Ala His Val Glu Tyr Arg Lys
65                  70                  75                  80

Val Leu Phe Ser Arg Asn Ser Tyr Lys Tyr Lys Ser Asp Tyr Asp Lys
                85                  90                  95

Lys Leu Ala Glu Ala Gln Ala Lys Ile Asp Glu Ala Asn Lys Lys Leu
            100                 105                 110

Thr Ala Ala Asn Asn Glu Phe Gln Thr Val Arg Ala Val Val Pro
            115                 120                 125

Glu Pro Asn Ala Leu Ala Glu Thr Lys Lys Ala Glu Glu Ala Lys
130                 135                 140

Ala Glu Glu Val Val Ala Lys Lys Ser Asp Glu Ala Ala Gln Glu
145                 150                 155                 160

Val Glu Val Ala Lys Lys Glu Val Ala Lys Glu Leu Glu Ile Glu
                165                 170                 175

Lys Leu Gln Asp Glu Ile Ser Thr Leu Glu Gln Glu Val Ala Thr Ala
            180                 185                 190

Gln His Gln Val Asp Asn Leu Lys Lys Leu Ala Gly Ala Asp Pro
        195                 200                 205

Asp Asp Gly Thr Glu Val Ile Glu Ala Lys Leu Lys Lys Gly Glu Ala
210                 215                 220

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
                245                 250                 255

Leu Asp Lys Glu Ala Glu Ala Glu Leu Asp Lys Lys Ala Asp Glu
            260                 265                 270

Leu Gln Asn Lys Val Ala Asp Leu Glu Lys Glu Ile Ser Asn Leu Glu
            275                 280                 285

Ile Leu Leu Gly Gly Ala Asp Pro Glu Asp Thr Ala Ala Leu Gln
        290                 295                 300

Asn Lys Leu Ala Ala Lys Gln Ala Glu Leu Ala Lys Lys Gln Thr Glu
305                 310                 315                 320

Leu Glu Lys Leu Leu Asp Ser Leu Asp Pro Glu Gly Lys Thr Gln Asp
                325                 330                 335

Glu Leu Asp Lys Glu Ala Glu Ala Glu Leu Asp Lys Lys Ala Asp
            340                 345                 350

Glu Leu Gln Asn Lys Val Ala Asp Leu Glu Lys Glu Ile Ser Asn Leu
            355                 360                 365

Glu Ile Leu Leu Gly Gly Ala Asp Ser Glu Asp Thr Ala Ala Leu
        370                 375                 380

Gln Asn Lys Leu Ala Thr Lys Lys Ala Glu Leu Glu Lys Thr Gln Lys
385                 390                 395                 400

Glu Leu Asp Ala Ala Leu Asn Glu Leu Gly
                405                 410

<210> SEQ ID NO 54
<211> LENGTH: 410
<212> TYPE: PRT
<213> ORGANISM: Streptococcus pneumoniae

<400> SEQUENCE: 54

Glu Glu Ala Pro Val Ala Ser Gln Ser Lys Ala Glu Lys Asp Tyr Asp
1               5                   10                  15

```
Ala Ala Val Lys Lys Ser Glu Ala Ala Lys Lys Asp Tyr Glu Glu Ala
            20                  25                  30
Lys Lys Lys Ala Lys Glu Ala Gln Lys Lys Tyr Asp Glu Gln Lys
        35                  40                  45
Lys Thr Glu Glu Lys Ala Lys Lys Glu Lys Val Ala Lys Lys Val
 50                  55                  60
Asp Asp Ala Ser Leu Ala Val Gln Lys Ala His Val Glu Tyr Arg Lys
 65                  70                  75                  80
Val Leu Phe Ser Arg Asn Ser Tyr Lys Tyr Lys Ser Asp Tyr Asp Lys
                85                  90                  95
Lys Leu Ala Glu Ala Gln Ala Lys Ile Asp Glu Ala Asn Lys Lys Leu
            100                 105                 110
Thr Ala Ala Asn Asn Glu Phe Gln Thr Val Arg Ala Val Val Val Pro
        115                 120                 125
Glu Pro Asn Ala Leu Ala Glu Thr Lys Lys Lys Ala Glu Glu Ala Lys
130                 135                 140
Ala Glu Glu Val Val Ala Lys Lys Ser Asp Glu Ala Ala Gln Glu
145                 150                 155                 160
Val Glu Val Ala Lys Lys Glu Val Glu Ala Lys Glu Leu Glu Ile Glu
                165                 170                 175
Lys Leu Gln Asp Glu Ile Ser Thr Leu Glu Gln Glu Val Ala Thr Ala
            180                 185                 190
Gln His Gln Val Asp Asn Leu Lys Lys Leu Leu Ala Gly Ala Asp Pro
        195                 200                 205
Asp Asp Gly Thr Glu Val Ile Glu Ala Lys Leu Lys Lys Gly Glu Ala
 210                 215                 220
Glu Leu Asn Ala Lys Gln Ala Glu Leu Ala Lys Lys Gln Thr Glu Leu
225                 230                 235                 240
Glu Lys Leu Leu Asp Ser Leu Asp Pro Glu Gly Lys Thr Gln Asp Glu
                245                 250                 255
Leu Asp Lys Glu Ala Glu Glu Ala Glu Leu Asp Lys Lys Ala Asp Glu
            260                 265                 270
Leu Gln Asn Lys Val Ala Asp Leu Glu Lys Glu Ile Ser Asn Leu Glu
        275                 280                 285
Ile Leu Leu Gly Gly Ala Asp Pro Glu Asp Asp Thr Ala Ala Leu Gln
 290                 295                 300
Asn Lys Leu Ala Ala Lys Gln Ala Glu Leu Ala Lys Lys Gln Thr Glu
305                 310                 315                 320
Leu Glu Lys Leu Leu Asp Ser Leu Asp Pro Glu Gly Lys Thr Gln Asp
                325                 330                 335
Glu Leu Asp Lys Glu Ala Glu Glu Ala Glu Leu Asp Lys Lys Ala Asp
            340                 345                 350
Glu Leu Gln Asn Lys Val Ala Asp Leu Glu Lys Glu Ile Ser Asn Leu
        355                 360                 365
Glu Ile Leu Leu Gly Gly Ala Asp Ser Glu Asp Asp Thr Ala Ala Leu
 370                 375                 380
Gln Asn Lys Leu Ala Thr Lys Lys Ala Glu Leu Glu Lys Thr Gln Lys
385                 390                 395                 400
Glu Leu Asp Ala Ala Leu Asn Glu Leu Gly
                405                 410

<210> SEQ ID NO 55
<211> LENGTH: 410
```

<212> TYPE: PRT
<213> ORGANISM: Streptococcus pneumoniae

<400> SEQUENCE: 55

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys Asp Tyr Glu Ala
            20                  25                  30

Lys Lys Lys Ala Lys Glu Ala Gln Lys Lys Tyr Asp Glu Gln Lys
            35                  40                  45

Lys Thr Glu Glu Lys Ala Lys Lys Glu Lys Glu Ala Ala Lys Lys Val
        50                  55                  60

Asp Asp Ala Ser Leu Ala Val Gln Lys Ala His Val Glu Tyr Arg Lys
65                  70                  75                  80

Val Leu Phe Ser Arg Asn Ser Tyr Lys Tyr Lys Ser Asp Tyr Asp Lys
                85                  90                  95

Lys Leu Ala Glu Ala Gln Ala Lys Ile Asp Glu Ala Asn Lys Lys Leu
            100                 105                 110

Thr Ala Ala Asn Asn Glu Phe Gln Thr Val Arg Ala Val Val Val Pro
        115                 120                 125

Glu Pro Asn Ala Leu Ala Glu Thr Lys Lys Lys Ala Glu Glu Ala Lys
130                 135                 140

Ala Glu Glu Val Val Ala Lys Lys Lys Ser Asp Glu Ala Ala Gln Glu
145                 150                 155                 160

Val Glu Val Ala Lys Lys Glu Val Glu Ala Lys Glu Leu Glu Ile Glu
                165                 170                 175

Lys Leu Gln Asp Glu Ile Ser Thr Leu Glu Gln Glu Val Ala Thr Ala
            180                 185                 190

Gln His Gln Val Asp Asn Leu Lys Lys Leu Leu Ala Gly Ala Asp Pro
        195                 200                 205

Asp Asp Gly Thr Glu Val Ile Glu Ala Lys Leu Lys Lys Gly Glu Ala
210                 215                 220

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
                245                 250                 255

Leu Asp Lys Glu Ala Glu Ala Glu Leu Asp Lys Lys Ala Asp Glu
            260                 265                 270

Leu Gln Asn Lys Val Ala Asp Leu Glu Lys Glu Ile Ser Asn Leu Glu
        275                 280                 285

Ile Leu Leu Gly Gly Ala Asp Pro Glu Asp Asp Thr Ala Ala Leu Gln
290                 295                 300

Asn Lys Leu Ala Ala Lys Gln Ala Glu Leu Ala Lys Lys Gln Thr Glu
305                 310                 315                 320

Leu Glu Lys Leu Leu Asp Ser Leu Asp Pro Glu Gly Lys Thr Gln Asp
                325                 330                 335

Glu Leu Asp Lys Glu Ala Glu Ala Glu Leu Asp Lys Lys Ala Asp
            340                 345                 350

Glu Leu Gln Asn Lys Val Ala Asp Leu Glu Lys Glu Ile Ser Asn Leu
        355                 360                 365

Glu Ile Leu Leu Gly Gly Ala Asp Ser Glu Asp Asp Thr Ala Ala Leu
370                 375                 380

Gln Asn Lys Leu Ala Thr Lys Lys Ala Glu Leu Glu Lys Thr Gln Lys
385                 390                 395                 400

-continued

Glu Leu Asp Ala Ala Leu Asn Glu Leu Gly
            405                 410

<210> SEQ ID NO 56
<211> LENGTH: 410
<212> TYPE: PRT
<213> ORGANISM: Streptococcus pneumoniae

<400> SEQUENCE: 56

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys Asp Tyr Glu Glu Ala
                20                  25                  30

Lys Lys Lys Ala Lys Glu Ala Gln Lys Lys Tyr Asp Glu Glu Gln Lys
            35                  40                  45

Lys Thr Glu Glu Lys Ala Lys Lys Glu Lys Glu Ala Ala Lys Lys Val
        50                  55                  60

Asp Asp Ala Ser Leu Ala Val Gln Lys Ala His Val Glu Tyr Arg Lys
65                  70                  75                  80

Val Leu Phe Ser Arg Asn Ser Tyr Lys Tyr Lys Ser Asp Tyr Asp Lys
                85                  90                  95

Lys Leu Ala Glu Ala Gln Ala Lys Ile Asp Glu Ala Asn Lys Lys Leu
            100                 105                 110

Thr Ala Ala Asn Asn Glu Phe Gln Thr Val Arg Ala Val Val Val Pro
        115                 120                 125

Glu Pro Asn Ala Leu Ala Glu Thr Lys Lys Ala Glu Ala Lys
130                 135                 140

Ala Glu Val Val Ala Lys Lys Lys Ser Asp Glu Ala Ala Gln Glu
145                 150                 155                 160

Val Glu Val Ala Lys Lys Glu Val Ala Lys Glu Leu Glu Ile Glu
                165                 170                 175

Lys Leu Gln Asp Glu Ile Ser Thr Leu Glu Gln Glu Val Ala Thr Ala
            180                 185                 190

Gln His Gln Val Asp Asn Leu Lys Lys Leu Leu Ala Gly Ala Asp Pro
        195                 200                 205

Asp Asp Gly Thr Glu Val Ile Glu Ala Lys Leu Lys Lys Gly Glu Ala
210                 215                 220

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
                245                 250                 255

Leu Asp Lys Glu Ala Glu Glu Ala Glu Leu Asp Lys Lys Ala Asp Glu
            260                 265                 270

Leu Gln Asn Lys Val Ala Asp Leu Glu Lys Glu Ile Ser Asn Leu Glu
        275                 280                 285

Ile Leu Leu Gly Gly Ala Asp Pro Glu Asp Thr Ala Ala Leu Gln
290                 295                 300

Asn Lys Leu Ala Ala Lys Gln Ala Glu Leu Ala Lys Lys Gln Thr Glu
305                 310                 315                 320

Leu Glu Lys Leu Leu Asp Ser Leu Asp Pro Glu Gly Lys Thr Gln Asp
                325                 330                 335

Glu Leu Asp Lys Glu Ala Glu Glu Ala Glu Leu Asp Lys Lys Ala Asp
            340                 345                 350

Glu Leu Gln Asn Lys Val Ala Asp Leu Glu Lys Glu Ile Ser Asn Leu

```
                    355                 360                 365
Glu Ile Leu Leu Gly Gly Ala Asp Ser Glu Asp Thr Ala Ala Leu
            370                 375                 380

Gln Asn Lys Leu Ala Thr Lys Lys Ala Glu Leu Glu Lys Thr Gln Lys
385                 390                 395                 400

Glu Leu Asp Ala Ala Leu Asn Glu Leu Gly
                405                 410

<210> SEQ ID NO 57
<211> LENGTH: 410
<212> TYPE: PRT
<213> ORGANISM: Streptococcus pneumoniae

<400> SEQUENCE: 57

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys Asp Tyr Glu Glu Ala
                20                  25                  30

Lys Lys Lys Ala Lys Glu Ala Gln Lys Lys Tyr Asp Glu Glu Gln Lys
            35                  40                  45

Lys Thr Glu Glu Lys Ala Lys Lys Glu Lys Ala Ala Lys Lys Val
50                  55                  60

Asp Asp Ala Ser Leu Ala Val Gln Lys Ala His Val Glu Tyr Arg Lys
65                  70                  75                  80

Val Leu Phe Ser Arg Asn Ser Tyr Lys Tyr Lys Ser Asp Tyr Asp Lys
                85                  90                  95

Lys Leu Ala Glu Ala Gln Ala Lys Ile Asp Glu Ala Asn Lys Lys Leu
            100                 105                 110

Thr Ala Ala Asn Asn Glu Phe Gln Thr Val Arg Ala Val Val Val Pro
        115                 120                 125

Glu Pro Asn Ala Leu Ala Glu Thr Lys Lys Lys Ala Glu Glu Ala Lys
130                 135                 140

Ala Glu Glu Val Val Ala Lys Lys Lys Tyr Asp Glu Ala Ala Gln Glu
145                 150                 155                 160

Val Glu Val Ala Lys Lys Glu Val Glu Ala Lys Glu Leu Glu Ile Glu
                165                 170                 175

Lys Leu Gln Asp Glu Ile Ser Thr Leu Glu Gln Glu Val Ala Thr Ala
            180                 185                 190

Gln His Gln Val Asp Asn Leu Lys Lys Leu Leu Ala Gly Ala Asp Pro
        195                 200                 205

Asp Asp Gly Thr Glu Val Ile Glu Ala Lys Leu Lys Lys Gly Glu Ala
210                 215                 220

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
                245                 250                 255

Leu Asp Lys Glu Ala Glu Ala Glu Leu Asp Lys Lys Ala Asp Glu
            260                 265                 270

Leu Gln Asn Lys Val Ala Asp Leu Glu Lys Glu Ile Ser Asn Leu Glu
        275                 280                 285

Ile Leu Leu Gly Gly Ala Asp Pro Glu Asp Thr Ala Ala Leu Gln
            290                 295                 300

Asn Lys Leu Ala Ala Lys Gln Ala Glu Leu Ala Lys Lys Gln Thr Glu
305                 310                 315                 320
```

```
Leu Glu Lys Leu Leu Asp Ser Leu Asp Pro Glu Gly Lys Thr Gln Asp
            325                 330                 335

Glu Leu Asp Lys Glu Ala Glu Glu Ala Glu Leu Asp Lys Lys Ala Asp
            340                 345                 350

Glu Leu Gln Asn Lys Val Ala Asp Leu Glu Lys Glu Ile Ser Asn Leu
            355                 360                 365

Glu Ile Leu Leu Gly Gly Ala Asp Ser Glu Asp Thr Ala Ala Leu
370                 375                 380

Gln Asn Lys Leu Ala Thr Lys Lys Ala Glu Leu Lys Thr Gln Lys
385                 390                 395                 400

Glu Leu Asp Ala Ala Leu Asn Glu Leu Gly
            405                 410

<210> SEQ ID NO 58
<211> LENGTH: 410
<212> TYPE: PRT
<213> ORGANISM: Streptococcus pneumoniae

<400> SEQUENCE: 58

Glu Glu Ala Pro Val Ala Ser Gln Ser Lys Ala Glu Lys Asp Tyr Asp
1               5                   10                  15

Ala Ala Val Lys Lys Ser Glu Ala Ala Lys Lys Asp Tyr Glu Glu Ala
            20                  25                  30

Lys Lys Lys Ala Lys Glu Ala Gln Lys Lys Tyr Asp Glu Glu Gln Lys
        35                  40                  45

Lys Thr Glu Glu Lys Ala Lys Lys Glu Lys Glu Ala Ala Lys Lys Val
    50                  55                  60

Asp Asp Ala Ser Leu Ala Val Gln Lys Ala His Val Glu Tyr Arg Lys
65                  70                  75                  80

Val Leu Phe Ser Arg Asn Ser Tyr Lys Tyr Lys Ser Asp Tyr Asp Lys
                85                  90                  95

Lys Leu Ala Glu Ala Gln Ala Lys Ile Asp Glu Ala Asn Lys Lys Leu
            100                 105                 110

Thr Ala Ala Asn Asn Glu Phe Gln Thr Val Arg Ala Val Val Val Pro
        115                 120                 125

Glu Pro Asn Ala Leu Ala Glu Thr Lys Lys Lys Ala Glu Glu Ala Lys
    130                 135                 140

Ala Glu Glu Val Val Ala Lys Lys Lys Ser Asp Glu Ala Ala Gln Glu
145                 150                 155                 160

Val Glu Val Ala Lys Lys Glu Val Glu Ala Lys Glu Leu Glu Ile Glu
                165                 170                 175

Lys Leu Gln Asp Glu Ile Ser Thr Leu Glu Gln Glu Val Ala Thr Ala
            180                 185                 190

Gln His Gln Val Asp Asn Leu Lys Lys Leu Leu Ala Gly Ala Asp Pro
        195                 200                 205

Asp Asp Gly Thr Glu Val Ile Glu Ala Lys Leu Lys Lys Gly Glu Ala
    210                 215                 220

Glu Leu Asn Ala Lys Gln Ala Glu Leu Ala Lys Lys Gln Thr Glu Leu
225                 230                 235                 240

Glu Lys Leu Leu Asp Ser Leu Asp Pro Glu Gly Lys Thr Gln Asp Glu
                245                 250                 255

Leu Asp Lys Glu Ala Glu Glu Ala Glu Leu Asp Lys Lys Ala Asp Glu
            260                 265                 270

Leu Gln Asn Lys Val Ala Asp Leu Glu Lys Glu Ile Ser Asn Leu Glu
        275                 280                 285
```

```
Ile Leu Leu Gly Gly Ala Asp Pro Glu Asp Thr Ala Ala Leu Gln
    290                 295                 300

Asn Lys Leu Ala Ala Lys Gln Ala Glu Leu Ala Lys Lys Gln Thr Glu
305                 310                 315                 320

Leu Glu Lys Leu Leu Asp Ser Leu Asp Pro Glu Gly Lys Thr Gln Asp
                325                 330                 335

Glu Leu Asp Lys Glu Ala Glu Ala Glu Leu Asp Lys Lys Ala Asp
            340                 345                 350

Glu Leu Gln Asn Lys Val Ala Asp Leu Glu Lys Glu Ile Ser Asn Leu
                355                 360                 365

Glu Ile Leu Leu Gly Gly Ala Asp Ser Glu Asp Thr Ala Ala Leu
            370                 375                 380

Gln Asn Lys Leu Ala Thr Lys Ala Glu Leu Glu Lys Thr Gln Lys
385                 390                 395                 400

Glu Leu Asp Ala Ala Leu Asn Glu Leu Gly
                405                 410

<210> SEQ ID NO 59
<211> LENGTH: 94
<212> TYPE: PRT
<213> ORGANISM: Streptococcus pneumoniae

<400> SEQUENCE: 59

Leu Glu Lys Val Leu Ala Thr Leu Asp Pro Glu Gly Lys Thr Gln Asp
1               5                   10                  15

Glu Leu Asp Lys Glu Ala Glu Ala Glu Leu Asn Glu Lys Val Glu
            20                  25                  30

Ala Leu Gln Asn Gln Val Ala Glu Leu Glu Glu Glu Leu Ser Lys Leu
                35                  40                  45

Glu Asp Asn Leu Lys Asp Ala Glu Thr Asn Asn Val Glu Asp Tyr Ile
        50                  55                  60

Lys Glu Gly Leu Glu Glu Ala Ile Ala Thr Lys Lys Ala Glu Leu Glu
65                  70                  75                  80

Lys Thr Gln Lys Glu Leu Asp Ala Ala Leu Asn Glu Leu Gly
                85                  90

<210> SEQ ID NO 60
<211> LENGTH: 345
<212> TYPE: PRT
<213> ORGANISM: Streptococcus pneumoniae

<400> SEQUENCE: 60

Glu Glu Ala Pro Val Ala Asn Gln Ser Lys Ala Glu Lys Asp Tyr Asp
1               5                   10                  15

Ala Ala Val Lys Lys Ser Glu Ala Lys Lys Asp Tyr Glu Thr Ala
            20                  25                  30

Lys Lys Lys Ala Glu Asp Ala Gln Lys Lys Tyr Asp Glu Asp Gln Lys
                35                  40                  45

Lys Thr Glu Ala Lys Ala Glu Lys Glu Arg Lys Ala Ser Glu Lys Ile
        50                  55                  60

Ala Glu Ala Thr Lys Glu Val Gln Gln Ala Tyr Leu Ala Tyr Leu Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Glu Ala Ala Phe Ala Thr Ile Arg
                100                 105                 110
```

Thr Thr Ile Val Val Pro Pro Ser Glu Leu Ala Glu Thr Lys Lys
            115                 120                 125

Lys Ala Glu Glu Ala Thr Lys Glu Ala Glu Val Ala Lys Lys Ser
130                 135                 140

Glu Glu Ala Ala Lys Glu Val Glu Val Glu Lys Asn Lys Ile Leu Glu
145                 150                 155                 160

Gln Asp Ala Glu Asn Glu Lys Lys Ile Asp Val Leu Gln Asn Lys Val
                165                 170                 175

Ala Asp Leu Glu Lys Gly Ile Ala Pro Tyr Gln Asn Glu Val Ala Glu
            180                 185                 190

Leu Asn Lys Glu Ile Ala Arg Leu Gln Ser Asp Leu Lys Asp Ala Glu
            195                 200                 205

Glu Asn Asn Val Glu Asp Tyr Ile Lys Glu Gly Leu Glu Gln Ala Ile
        210                 215                 220

Thr Asn Lys Lys Ala Glu Leu Ala Thr Thr Gln Gln Asn Ile Asp Lys
225                 230                 235                 240

Thr Gln Lys Asp Leu Glu Asp Ala Glu Leu Glu Leu Glu Lys Val Leu
                245                 250                 255

Ala Thr Leu Asp Pro Glu Gly Lys Thr Gln Asp Glu Leu Asp Lys Glu
            260                 265                 270

Ala Ala Glu Ala Glu Leu Asn Glu Lys Val Glu Ala Leu Gln Asn Gln
        275                 280                 285

Val Ala Glu Leu Glu Glu Glu Leu Ser Lys Leu Glu Asp Asn Leu Lys
        290                 295                 300

Asp Ala Glu Thr Asn Asn Val Glu Asp Tyr Ile Lys Glu Gly Leu Glu
305                 310                 315                 320

Glu Ala Ile Ala Thr Lys Lys Ala Glu Leu Glu Lys Thr Gln Lys Glu
                325                 330                 335

Leu Asp Ala Ala Leu Asn Glu Leu Gly
            340                 345

<210> SEQ ID NO 61
<211> LENGTH: 101
<212> TYPE: PRT
<213> ORGANISM: Streptococcus pneumoniae

<400> SEQUENCE: 61

Leu Glu Lys Ala Glu Ala Glu Leu Glu Asn Leu Leu Ser Thr Leu Asp
1               5                   10                  15

Pro Glu Gly Lys Thr Gln Asp Glu Leu Asp Lys Glu Ala Ala Glu Ala
                20                  25                  30

Glu Leu Asn Lys Lys Val Glu Ala Leu Gln Asn Gln Val Ala Glu Leu
            35                  40                  45

Glu Glu Glu Leu Ser Lys Leu Glu Asp Asn Leu Lys Asp Ala Glu Thr
        50                  55                  60

Asn Asn Val Glu Asp Tyr Ile Lys Glu Gly Leu Glu Glu Ala Ile Ala
65                  70                  75                  80

Thr Lys Gln Ala Glu Leu Glu Lys Thr Gln Lys Glu Leu Asp Ala Ala
                85                  90                  95

Leu Asn Glu Leu Gly
            100

<210> SEQ ID NO 62
<211> LENGTH: 364
<212> TYPE: PRT

<213> ORGANISM: Streptococcus pneumoniae

<400> SEQUENCE: 62

Glu Glu Ala Pro Val Ala Ser Gln Ser Lys Ala Glu Lys Asp Tyr Asp
1               5                   10                  15

Ala Ala Val Lys Lys Ser Glu Ala Lys Lys Ala Tyr Glu Glu Ala
            20                  25                  30

Lys Lys Lys Ala Glu Asp Ala Gln Lys Lys Tyr Asp Glu Asp Gln Lys
        35                  40                  45

Lys Thr Glu Glu Lys Ala Glu Asn Glu Lys Lys Ala Ala Ala Asp Leu
    50                  55                  60

Asn Glu Ala Thr Glu Val His Gln Lys Ala Tyr Val Arg Tyr Phe Glu
65                  70                  75                  80

Ile Gln Arg Ala Lys Asp Ser Lys Lys Tyr Lys Asn Asn Arg Asp Lys
                85                  90                  95

Tyr Asn Lys Asp Leu Ala Glu Ala Asp Gln Lys Ile Lys Asp Thr Lys
                100                 105                 110

Thr Val Leu Asp Glu Lys Gln Ser Lys Phe Tyr Ala Val Arg Ala Val
            115                 120                 125

Val Val Pro Glu Ala Lys Glu Leu Ala Val Thr Lys Gln Lys Ala Glu
    130                 135                 140

Glu Thr Lys Lys Gly Ala Glu Val Ala Lys Lys Tyr Asp Lys Ala
145                 150                 155                 160

Ala Gln Glu Val Glu Val Ala Lys Lys Glu Val Ala Glu Glu Ala
                165                 170                 175

Glu Leu Asp Lys Lys Val Ala Glu Leu Gln Asn Lys Val Ala Asp Leu
                180                 185                 190

Glu Lys Glu Ile Ala Asp Ala Glu Lys Thr Val Ala Asp Leu Glu Lys
            195                 200                 205

Glu Val Ala Lys Leu Glu Lys Asp Val Glu Gly Phe Lys Glu Ser Asp
    210                 215                 220

Gly Glu Tyr Ala Lys Phe Tyr Leu Glu Ala Ala Glu Lys Asp Leu Ala
225                 230                 235                 240

Thr Lys Lys Ala Lys Leu Ala Glu Ala Lys Ile Lys Ala Ala Thr Lys
                245                 250                 255

Lys Ala Glu Leu Glu Pro Glu Leu Glu Lys Ala Glu Ala Glu Leu Glu
                260                 265                 270

Asn Leu Leu Ser Thr Leu Asp Pro Glu Gly Lys Thr Gln Asp Glu Leu
            275                 280                 285

Asp Lys Glu Ala Ala Glu Ala Glu Leu Asn Lys Lys Val Glu Ala Leu
    290                 295                 300

Gln Asn Gln Val Ala Glu Leu Glu Glu Glu Leu Ser Lys Leu Glu Asp
305                 310                 315                 320

Asn Leu Lys Asp Ala Glu Thr Asn Asn Val Glu Asp Tyr Ile Lys Glu
                325                 330                 335

Gly Leu Glu Glu Ala Ile Ala Thr Lys Gln Ala Glu Leu Glu Lys Thr
                340                 345                 350

Gln Lys Glu Leu Asp Ala Ala Leu Asn Glu Leu Gly
        355                 360

<210> SEQ ID NO 63
<211> LENGTH: 101
<212> TYPE: PRT
<213> ORGANISM: Streptococcus pneumoniae

<400> SEQUENCE: 63

| | | | | | | | | | | | | | | |
|---|---|---|---|---|---|---|---|---|---|---|---|---|---|---|
|Leu|Glu|Lys|Ala|Glu|Ala|Glu|Leu|Glu|Asn|Leu|Leu|Ser|Thr|Leu|Asp|
|1| | | |5| | | | |10| | | | |15| |

Pro Glu Gly Lys Thr Gln Asp Glu Leu Asp Lys Glu Ala Ala Glu Ala
            20                  25                  30

Glu Leu Asn Lys Lys Val Glu Ala Leu Gln Asn Gln Val Ala Glu Leu
            35                  40                  45

Glu Glu Glu Leu Ser Lys Leu Glu Asp Asn Leu Lys Asp Ala Glu Thr
    50                  55                  60

Asn Asn Val Glu Asp Tyr Ile Lys Glu Gly Leu Glu Glu Ala Ile Ala
65                  70                  75                  80

Thr Lys Lys Ala Glu Leu Glu Lys Thr Gln Lys Glu Leu Asp Ala Ala
                85                  90                  95

Leu Asn Glu Leu Gly
            100

<210> SEQ ID NO 64
<211> LENGTH: 357
<212> TYPE: PRT
<213> ORGANISM: Streptococcus pneumoniae

<400> SEQUENCE: 64

Glu Ala Ala Pro Gln Val Val Glu Lys Ser Ser Leu Glu Lys Lys Tyr
1               5                   10                  15

Glu Glu Ala Lys Ala Lys Ala Asp Thr Ala Lys Lys Asp Tyr Glu Thr
            20                  25                  30

Ala Lys Lys Lys Ala Ala Glu Ala Gln Lys Lys Tyr Glu Asp Asp Gln
        35                  40                  45

Lys Arg Thr Glu Glu Lys Gly Ala Leu Glu Glu Thr Ser Arg Lys
    50                  55                  60

Val Asn Asp Ala Thr Leu Glu Val Gln Asn Ala Tyr Val Glu Tyr Gly
65                  70                  75                  80

Glu Ala Asn Lys Lys Gly Lys Asp Arg Glu Lys Lys Leu Ala Asp
                85                  90                  95

Ala Gln Lys Lys Ile Asp Glu Ala Gln Glu Lys Leu Thr Lys Ala Lys
            100                 105                 110

Asn Glu Phe Gln Ser Val Arg Ala Met Val Val Pro Glu Pro Glu Gln
            115                 120                 125

Leu Ala Glu Thr Lys Lys Lys Ala Glu Glu Ala Lys Ala Glu Glu Ala
        130                 135                 140

Val Ala Lys Glu Lys Ser Asp Lys Ala Ala Lys Glu Val Glu Val Ala
145                 150                 155                 160

Lys Lys Arg Val Glu Ala Glu Glu Ala Glu Leu Asp Lys Lys Val Ala
                165                 170                 175

Glu Leu Gln Asn Lys Val Ala Asp Leu Glu Lys Glu Ile Ala Asp Ala
            180                 185                 190

Glu Lys Thr Val Ala Asp Leu Glu Glu Val Ala Lys Leu Glu Lys
        195                 200                 205

Asp Val Glu Asp Phe Lys Asn Ser Asn Gly Glu Gln Ala Glu Gln Tyr
    210                 215                 220

Leu Ala Ala Ala Glu Lys Asp Leu Val Ala Lys Ala Glu Leu Ala
225                 230                 235                 240

Glu Ala Lys Ile Lys Ala Ala Thr Lys Lys Ala Glu Leu Glu Pro Glu
                245                 250                 255

```
Leu Glu Lys Ala Glu Ala Glu Leu Glu Asn Leu Leu Ser Thr Leu Asp
            260                 265                 270

Pro Glu Gly Lys Thr Gln Asp Glu Leu Asp Lys Glu Ala Ala Glu Ala
        275                 280                 285

Glu Leu Asn Lys Lys Val Glu Ala Leu Gln Asn Gln Val Ala Glu Leu
    290                 295                 300

Glu Glu Glu Leu Ser Lys Leu Glu Asp Asn Leu Lys Asp Ala Glu Thr
305                 310                 315                 320

Asn Asn Val Glu Asp Tyr Ile Lys Glu Gly Leu Glu Glu Ala Ile Ala
                325                 330                 335

Thr Lys Lys Ala Glu Leu Glu Lys Thr Gln Lys Glu Leu Asp Ala Ala
            340                 345                 350

Leu Asn Glu Leu Gly
            355

<210> SEQ ID NO 65
<211> LENGTH: 98
<212> TYPE: PRT
<213> ORGANISM: Streptococcus pneumoniae

<400> SEQUENCE: 65

Leu Lys Glu Ile Asp Glu Ser Asp Ser Glu Asp Tyr Ile Lys Glu Gly
1               5                   10                  15

Leu Arg Ala Pro Leu Gln Ser Lys Leu Asp Ala Lys Lys Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Lys Asp Val Glu Asp Phe Lys Asn Ser Asp Gly
    50                  55                  60

Glu Gln Ala Glu Gln Tyr Leu Val Ala Ala Lys Lys Asp Leu Asp Ala
65                  70                  75                  80

Lys Lys Ala Glu Leu Glu Asn Thr Glu Ala Asp Leu Lys Lys Ala Val
            85                  90                  95

Asp Glu

<210> SEQ ID NO 66
<211> LENGTH: 302
<212> TYPE: PRT
<213> ORGANISM: Streptococcus pneumoniae

<400> SEQUENCE: 66

Glu Glu Ala Pro Val Ala Lys Gln Ser Gln Ala Glu Arg Asp Tyr Asp
1               5                   10                  15

Ala Ala Met Lys Lys Ser Glu Ala Ala Lys Lys Glu Tyr Glu Glu Ala
            20                  25                  30

Lys Lys Asp Leu Glu Glu Ala Lys Ala Ala Gln Lys Lys Tyr Glu Asp
        35                  40                  45

Asp Gln Lys Lys Thr Glu Glu Lys Ala Lys Leu Val Gln Lys Ala Asp
    50                  55                  60

Glu Glu Arg Gln Lys Ala Asn Val Ala Val Lys Ala Tyr Leu Lys
65                  70                  75                  80

Leu Arg Glu Ala Gln Glu Gln Leu Asn Lys Ser Pro Asn Asn Lys Lys
            85                  90                  95

Asn Ala Ala Gln Gln Lys Leu Lys Asp Ala Leu Ala His Ile Asp Glu
        100                 105                 110

Val Thr Leu Lys Gln Lys Glu Ala Glu Ala Asn Phe Asn Lys Glu Gln
```

```
            115                 120                 125
Ala Lys Val Val Pro Glu Ala Asp Lys Leu Ala Glu Thr Lys Lys Lys
        130                 135                 140

Ala Glu Gln Ala Glu Lys Lys Glu Pro Glu Leu Ala Lys Lys Val Ala
145                 150                 155                 160

Glu Ala Lys Ala Lys Ala Glu Glu Ala Glu Lys Lys Ala Val Glu Ala
                165                 170                 175

Lys Gln Lys Val Asp Ala Glu Lys Tyr Ala Leu Glu Ala Lys Ile Ala
            180                 185                 190

Glu Leu Glu Tyr Glu Val Gln Gly Leu Glu Lys Glu Leu Lys Glu Ile
        195                 200                 205

Asp Glu Ser Asp Ser Glu Asp Tyr Ile Lys Glu Gly Leu Arg Ala Pro
    210                 215                 220

Leu Gln Ser Lys Leu Asp Ala Lys Lys Ala Lys Leu Ser Lys Leu Glu
225                 230                 235                 240

Glu Leu Ser Asp Lys Ile Asp Glu Leu Asp Ala Glu Ile Ala Lys Leu
                245                 250                 255

Glu Lys Asp Val Glu Asp Phe Lys Asn Ser Asp Gly Glu Gln Ala Glu
            260                 265                 270

Gln Tyr Leu Val Ala Ala Lys Lys Asp Leu Asp Ala Lys Ala Glu
        275                 280                 285

Leu Glu Asn Thr Glu Ala Asp Leu Lys Lys Ala Val Asp Glu
    290                 295                 300

<210> SEQ ID NO 67
<211> LENGTH: 302
<212> TYPE: PRT
<213> ORGANISM: Streptococcus pneumoniae

<400> SEQUENCE: 67

Glu Glu Ala Pro Val Ala Lys Gln Ser Gln Ala Glu Arg Asp Tyr Asp
1               5                   10                  15

Ala Ala Met Lys Lys Ser Glu Ala Ala Lys Lys Glu Tyr Glu Glu Ala
            20                  25                  30

Lys Lys Asp Leu Glu Glu Ala Lys Ala Ala Gln Lys Lys Tyr Glu Asp
        35                  40                  45

Asp Gln Lys Lys Thr Glu Glu Lys Ala Lys Leu Val Gln Lys Ala Asp
    50                  55                  60

Glu Glu Arg Gln Lys Ala Asn Val Ala Val Gln Lys Ala Tyr Leu Lys
65                  70                  75                  80

Leu Arg Glu Ala Gln Glu Gln Leu Asn Lys Ser Pro Asn Asn Lys Lys
                85                  90                  95

Asn Ala Ala Gln Gln Lys Leu Lys Asp Ala Leu Ala His Ile Asp Glu
            100                 105                 110

Val Thr Leu Lys Gln Lys Glu Ala Glu Ala Asn Phe Asn Lys Glu Gln
        115                 120                 125

Ala Lys Val Val Pro Glu Ala Asp Lys Leu Ala Glu Thr Lys Lys Lys
    130                 135                 140

Ala Glu Gln Ala Glu Lys Lys Glu Pro Glu Leu Ala Lys Lys Val Ala
145                 150                 155                 160

Glu Ala Lys Ala Lys Ala Glu Glu Ala Glu Lys Lys Ala Val Glu Ala
                165                 170                 175

Lys Gln Lys Val Asp Ala Glu Lys Tyr Ala Leu Glu Ala Lys Ile Ala
            180                 185                 190
```

Glu Leu Glu Tyr Glu Val Gln Gly Leu Glu Lys Glu Leu Lys Glu Ile
                195                 200                 205

Asp Glu Ser Asp Ser Glu Asp Tyr Ile Lys Glu Gly Leu Arg Ala Pro
            210                 215                 220

Leu Gln Ser Lys Leu Asp Ala Lys Lys Ala Lys Leu Ser Lys Leu Glu
225                 230                 235                 240

Glu Leu Ser Asp Lys Ile Asp Glu Leu Asp Ala Glu Ile Ala Lys Leu
                245                 250                 255

Glu Lys Asp Val Glu Asp Phe Lys Asn Ser Asp Gly Glu Gln Ala Glu
            260                 265                 270

Gln Tyr Leu Val Ala Ala Lys Lys Asp Leu Asp Ala Lys Lys Ala Glu
            275                 280                 285

Leu Glu Asn Thr Glu Ala Asp Leu Lys Lys Ala Val Asp Glu
            290                 295                 300

<210> SEQ ID NO 68
<211> LENGTH: 302
<212> TYPE: PRT
<213> ORGANISM: Streptococcus pneumoniae

<400> SEQUENCE: 68

Glu Glu Ala Pro Val Ala Lys Gln Ser Gln Ala Glu Arg Asp Tyr Asp
1               5                   10                  15

Ala Ala Met Lys Lys Ser Glu Ala Ala Lys Lys Glu Tyr Glu Glu Ala
                20                  25                  30

Lys Lys Asp Leu Glu Glu Ala Lys Ala Ala Gln Lys Lys Tyr Glu Asp
            35                  40                  45

Asp Gln Lys Lys Thr Glu Glu Lys Ala Lys Leu Val Gln Lys Ala Asp
        50                  55                  60

Glu Glu Arg Gln Lys Ala Asn Val Ala Val Gln Lys Ala Tyr Leu Lys
65                  70                  75                  80

Leu Arg Glu Ala Gln Glu Gln Leu Asn Lys Ser Pro Asn Asn Lys Lys
                85                  90                  95

Asn Ala Ala Gln Gln Lys Leu Lys Asp Ala Leu Ala His Ile Asp Glu
            100                 105                 110

Val Thr Leu Lys Gln Lys Glu Ala Glu Ala Asn Phe Asn Lys Glu Gln
        115                 120                 125

Ala Lys Val Val Pro Glu Ala Asp Lys Leu Ala Glu Thr Lys Lys Lys
        130                 135                 140

Ala Glu Gln Ala Glu Lys Lys Glu Pro Glu Leu Ala Lys Lys Val Ala
145                 150                 155                 160

Glu Ala Lys Ala Lys Ala Glu Ala Glu Lys Lys Ala Val Glu Ala
                165                 170                 175

Lys Gln Lys Val Asp Ala Glu Lys Tyr Ala Leu Glu Ala Lys Ile Ala
            180                 185                 190

Glu Leu Glu Tyr Glu Val Gln Gly Leu Glu Lys Glu Leu Lys Glu Ile
                195                 200                 205

Asp Glu Ser Asp Ser Glu Asp Tyr Ile Lys Glu Gly Leu Arg Ala Pro
            210                 215                 220

Leu Gln Ser Lys Leu Asp Ala Lys Lys Ala Lys Leu Ser Lys Leu Glu
225                 230                 235                 240

Glu Leu Ser Asp Lys Ile Asp Glu Leu Asp Ala Glu Ile Ala Lys Leu
                245                 250                 255

Glu Lys Asp Val Glu Asp Phe Lys Asn Ser Asp Gly Glu Gln Ala Glu
            260                 265                 270

Gln Tyr Leu Val Ala Ala Lys Lys Asp Leu Asp Ala Lys Lys Ala Glu
        275                 280                 285

Leu Glu Asn Thr Glu Ala Asp Leu Lys Lys Ala Val Asp Glu
        290                 295                 300

<210> SEQ ID NO 69
<211> LENGTH: 302
<212> TYPE: PRT
<213> ORGANISM: Streptococcus pneumoniae

<400> SEQUENCE: 69

Glu Glu Ala Pro Val Ala Lys Gln Ser Gln Ala Glu Arg Asp Tyr Asp
1               5                   10                  15

Ala Ala Met Lys Lys Ser Glu Ala Ala Lys Lys Glu Tyr Glu Glu Ala
                20                  25                  30

Lys Lys Asp Leu Glu Glu Ala Lys Ala Ala Gln Lys Lys Tyr Glu Asp
            35                  40                  45

Asp Gln Lys Lys Thr Glu Glu Lys Ala Lys Leu Val Gln Lys Ala Asp
        50                  55                  60

Glu Glu Arg Gln Lys Ala Asn Val Ala Val Gln Lys Ala Tyr Leu Lys
65                  70                  75                  80

Leu Arg Glu Ala Gln Glu Gln Leu Asn Lys Ser Pro Asn Asn Lys Lys
                85                  90                  95

Asn Ala Ala Gln Gln Lys Leu Lys Asp Ala Leu Ala His Ile Asp Glu
            100                 105                 110

Val Thr Leu Lys Gln Lys Glu Ala Glu Ala Asn Phe Asn Lys Glu Gln
        115                 120                 125

Ala Lys Val Val Pro Glu Ala Asp Lys Leu Ala Glu Thr Lys Lys Lys
    130                 135                 140

Ala Glu Gln Ala Glu Lys Lys Glu Pro Glu Leu Ala Lys Lys Val Ala
145                 150                 155                 160

Glu Ala Lys Ala Lys Ala Glu Glu Ala Lys Lys Ala Val Glu Ala
                165                 170                 175

Lys Gln Lys Val Asp Ala Glu Lys Tyr Ala Leu Glu Ala Lys Ile Ala
            180                 185                 190

Glu Leu Glu Tyr Glu Val Gln Gly Leu Glu Lys Glu Leu Lys Glu Ile
        195                 200                 205

Asp Glu Ser Asp Ser Glu Asp Tyr Ile Lys Glu Gly Leu Arg Ala Pro
    210                 215                 220

Leu Gln Ser Lys Leu Asp Ala Lys Lys Ala Lys Leu Ser Lys Leu Glu
225                 230                 235                 240

Glu Leu Ser Asp Lys Ile Asp Glu Leu Asp Ala Glu Ile Ala Lys Leu
                245                 250                 255

Glu Lys Asp Val Glu Asp Phe Lys Asn Ser Asp Gly Glu Gln Ala Glu
            260                 265                 270

Gln Tyr Leu Val Ala Ala Lys Lys Asp Leu Asp Ala Lys Lys Ala Glu
        275                 280                 285

Leu Glu Asn Thr Glu Ala Asp Leu Lys Lys Ala Val Asp Glu
        290                 295                 300

<210> SEQ ID NO 70
<211> LENGTH: 302
<212> TYPE: PRT
<213> ORGANISM: Streptococcus pneumoniae

<400> SEQUENCE: 70

Glu Glu Ala Pro Val Ala Lys Gln Ser Gln Ala Glu Arg Asp Tyr Asp
1               5                   10                  15

Ala Ala Met Lys Lys Ser Glu Ala Ala Lys Lys Glu Tyr Glu Ala
            20                  25                  30

Lys Lys Asp Leu Glu Glu Ala Lys Ala Gln Lys Lys Tyr Glu Asp
            35                  40                  45

Asp Gln Lys Lys Thr Glu Glu Lys Ala Lys Leu Val Gln Lys Ala Asp
50                  55                  60

Glu Glu Arg Gln Lys Ala Asn Val Ala Val Gln Lys Ala Tyr Leu Lys
65                  70                  75                  80

Leu Arg Glu Ala Gln Glu Gln Leu Asn Lys Ser Pro Asn Asn Lys Lys
                85                  90                  95

Asn Ala Ala Gln Gln Lys Leu Lys Asp Ala Leu Ala His Ile Asp Glu
            100                 105                 110

Val Thr Leu Lys Gln Lys Glu Ala Glu Ala Asn Phe Asn Lys Glu Gln
            115                 120                 125

Ala Lys Val Val Pro Glu Ala Asp Lys Leu Ala Glu Thr Lys Lys Lys
            130                 135                 140

Ala Glu Gln Ala Glu Lys Lys Glu Pro Glu Leu Ala Lys Lys Val Ala
145                 150                 155                 160

Glu Ala Lys Ala Lys Ala Glu Glu Ala Glu Lys Lys Ala Val Glu Ala
                165                 170                 175

Lys Gln Lys Val Asp Ala Glu Lys Tyr Ala Leu Glu Ala Lys Ile Ala
            180                 185                 190

Glu Leu Glu Tyr Glu Val Gln Gly Leu Glu Lys Glu Leu Lys Glu Ile
            195                 200                 205

Asp Glu Ser Asp Ser Glu Asp Tyr Ile Lys Glu Gly Leu Arg Ala Pro
210                 215                 220

Leu Gln Ser Lys Leu Asp Ala Lys Lys Ala Lys Leu Ser Lys Leu Glu
225                 230                 235                 240

Glu Leu Ser Asp Lys Ile Asp Glu Leu Asp Ala Glu Ile Ala Lys Leu
                245                 250                 255

Glu Lys Asp Val Glu Asp Phe Lys Asn Ser Asp Gly Glu Gln Ala Glu
            260                 265                 270

Gln Tyr Leu Val Ala Ala Lys Lys Asp Leu Asp Ala Lys Lys Ala Glu
            275                 280                 285

Leu Glu Asn Thr Glu Ala Asp Leu Lys Lys Ala Val Asp Glu
290                 295                 300

<210> SEQ ID NO 71
<211> LENGTH: 302
<212> TYPE: PRT
<213> ORGANISM: Streptococcus pneumoniae

<400> SEQUENCE: 71

Glu Glu Ala Pro Val Ala Lys Gln Ser Gln Ala Glu Arg Asp Tyr Asp
1               5                   10                  15

Ala Ala Met Lys Lys Ser Glu Ala Ala Lys Lys Glu Tyr Glu Ala
            20                  25                  30

Lys Lys Asp Leu Glu Glu Ala Lys Ala Gln Lys Lys Tyr Glu Asp
            35                  40                  45

Asp Gln Lys Lys Thr Glu Glu Lys Ala Lys Leu Val Gln Lys Ala Asp
50                  55                  60

Glu Glu Arg Gln Lys Ala Asn Val Ala Val Gln Lys Ala Tyr Leu Lys
65                  70                  75                  80

```
                65                  70                  75                  80
Leu Arg Glu Ala Gln Glu Gln Leu Asn Lys Ser Pro Asn Asn Lys Lys
                    85                  90                  95

Asn Ala Ala Gln Gln Lys Leu Lys Asp Ala Leu Ala His Ile Asp Glu
                100                 105                 110

Val Thr Leu Lys Gln Lys Glu Ala Glu Ala Asn Phe Asn Lys Glu Gln
                115                 120                 125

Ala Lys Val Val Pro Glu Ala Asp Lys Leu Ala Glu Thr Lys Lys Lys
            130                 135                 140

Ala Glu Gln Ala Glu Lys Lys Glu Pro Glu Leu Ala Lys Lys Val Ala
145                 150                 155                 160

Glu Ala Lys Ala Lys Ala Glu Ala Glu Lys Lys Ala Val Glu Ala
                    165                 170                 175

Lys Gln Lys Val Asp Ala Glu Lys Tyr Ala Leu Glu Ala Lys Ile Ala
                180                 185                 190

Glu Leu Glu Tyr Glu Val Gln Gly Leu Glu Lys Glu Leu Lys Glu Ile
                195                 200                 205

Asp Glu Ser Asp Ser Glu Asp Tyr Ile Lys Glu Gly Leu Arg Ala Pro
    210                 215                 220

Leu Gln Ser Lys Leu Asp Ala Lys Ala Lys Leu Ser Lys Leu Glu
225                 230                 235                 240

Glu Leu Ser Asp Lys Ile Asp Glu Leu Asp Ala Glu Ile Ala Lys Leu
                245                 250                 255

Glu Lys Asp Val Glu Asp Phe Lys Asn Ser Asp Gly Glu Gln Ala Glu
                260                 265                 270

Gln Tyr Leu Val Ala Ala Lys Lys Asp Leu Asp Ala Lys Lys Ala Glu
                275                 280                 285

Leu Glu Asn Thr Glu Ala Asp Leu Lys Lys Ala Val Asp Glu
                290                 295                 300

<210> SEQ ID NO 72
<211> LENGTH: 302
<212> TYPE: PRT
<213> ORGANISM: Streptococcus pneumoniae

<400> SEQUENCE: 72

Glu Glu Ala Pro Val Ala Lys Gln Ser Gln Ala Glu Arg Asp Tyr Asp
1               5                   10                  15

Ala Ala Met Lys Lys Ser Glu Ala Ala Lys Lys Glu Tyr Glu Glu Ala
                20                  25                  30

Lys Lys Asp Leu Glu Glu Ala Lys Ala Ala Gln Lys Lys Tyr Glu Asp
            35                  40                  45

Asp Gln Lys Lys Thr Glu Glu Lys Ala Lys Leu Val Gln Lys Ala Asp
    50                  55                  60

Glu Glu Arg Gln Lys Ala Asn Val Ala Val Gln Lys Ala Tyr Leu Lys
65                  70                  75                  80

Leu Arg Glu Ala Gln Glu Gln Leu Asn Lys Ser Pro Asn Asn Lys Lys
                    85                  90                  95

Asn Ala Ala Gln Gln Lys Leu Lys Asp Ala Leu Ala His Ile Asp Glu
                100                 105                 110

Val Thr Leu Lys Gln Lys Glu Ala Glu Ala Asn Phe Asn Lys Glu Gln
                115                 120                 125

Ala Lys Val Val Pro Glu Ala Asp Lys Leu Ala Glu Thr Lys Lys Lys
            130                 135                 140
```

```
Ala Glu Gln Ala Glu Lys Lys Glu Pro Glu Leu Ala Lys Lys Val Ala
145                 150                 155                 160

Glu Ala Lys Ala Lys Ala Glu Glu Ala Glu Lys Lys Ala Val Glu Ala
                165                 170                 175

Lys Gln Lys Val Asp Ala Glu Lys Tyr Ala Leu Glu Ala Lys Ile Ala
            180                 185                 190

Glu Leu Glu Tyr Glu Val Gln Gly Leu Glu Lys Glu Leu Lys Glu Ile
            195                 200                 205

Asp Glu Ser Asp Ser Glu Asp Tyr Ile Lys Glu Gly Leu Arg Ala Pro
        210                 215                 220

Leu Gln Ser Lys Leu Asp Ala Lys Lys Ala Lys Leu Ser Lys Leu Glu
225                 230                 235                 240

Glu Leu Ser Asp Lys Ile Asp Glu Leu Asp Ala Glu Ile Ala Lys Leu
                245                 250                 255

Glu Lys Asp Val Glu Asp Phe Lys Asn Ser Asp Gly Glu Gln Ala Glu
            260                 265                 270

Gln Tyr Leu Val Ala Ala Lys Asp Leu Asp Ala Lys Lys Ala Glu
            275                 280                 285

Leu Glu Asn Thr Glu Ala Asp Leu Lys Lys Ala Val Asp Glu
290                 295                 300

<210> SEQ ID NO 73
<211> LENGTH: 302
<212> TYPE: PRT
<213> ORGANISM: Streptococcus pneumoniae

<400> SEQUENCE: 73

Glu Glu Ala Pro Val Ala Lys Gln Ser Gln Ala Glu Arg Asp Tyr Asp
1               5                   10                  15

Ala Ala Met Lys Lys Ser Glu Ala Lys Lys Glu Tyr Glu Ala
                20                  25                  30

Lys Lys Asp Leu Glu Glu Ala Lys Ala Ala Gln Lys Lys Tyr Glu Asp
            35                  40                  45

Asp Gln Lys Lys Thr Glu Glu Lys Ala Lys Leu Val Gln Lys Ala Asp
        50                  55                  60

Glu Glu Arg Gln Lys Ala Asn Val Ala Val Gln Lys Ala Tyr Leu Lys
65                  70                  75                  80

Leu Arg Glu Ala Gln Glu Gln Leu Asn Lys Ser Pro Asn Asn Lys Lys
                85                  90                  95

Asn Ala Ala Gln Gln Lys Leu Lys Asp Ala Leu Ala His Ile Asp Glu
            100                 105                 110

Val Thr Leu Lys Gln Lys Glu Ala Glu Ala Asn Phe Asn Lys Glu Gln
        115                 120                 125

Ala Lys Val Val Pro Glu Ala Asp Lys Leu Ala Glu Thr Lys Lys Lys
            130                 135                 140

Ala Glu Gln Ala Glu Lys Lys Glu Pro Glu Leu Ala Lys Lys Val Ala
145                 150                 155                 160

Glu Ala Lys Ala Lys Ala Glu Glu Ala Glu Lys Lys Ala Val Glu Ala
                165                 170                 175

Lys Gln Lys Val Asp Ala Glu Lys Tyr Ala Leu Glu Ala Lys Ile Ala
            180                 185                 190

Glu Leu Glu Tyr Glu Val Gln Gly Leu Glu Lys Glu Leu Lys Glu Ile
            195                 200                 205

Asp Glu Ser Asp Ser Glu Asp Tyr Ile Lys Glu Gly Leu Arg Ala Pro
        210                 215                 220
```

Leu Gln Ser Lys Leu Asp Ala Lys Ala Lys Leu Ser Lys Leu Glu
225                 230                 235                 240

Glu Leu Ser Asp Lys Ile Asp Glu Leu Asp Ala Glu Ile Ala Lys Leu
            245                 250                 255

Glu Lys Asp Val Glu Asp Phe Lys Asn Ser Asp Gly Glu Gln Ala Glu
            260                 265                 270

Gln Tyr Leu Val Ala Ala Lys Lys Asp Leu Asp Ala Lys Lys Ala Glu
            275                 280                 285

Leu Glu Asn Thr Glu Ala Asp Leu Lys Lys Ala Val Asp Glu
            290                 295                 300

<210> SEQ ID NO 74
<211> LENGTH: 302
<212> TYPE: PRT
<213> ORGANISM: Streptococcus pneumoniae

<400> SEQUENCE: 74

Glu Glu Ala Pro Val Ala Lys Gln Ser Gln Ala Glu Arg Asp Tyr Asp
1               5                   10                  15

Ala Ala Met Lys Lys Ser Glu Ala Ala Lys Lys Glu Tyr Glu Glu Ala
            20                  25                  30

Lys Lys Asp Leu Glu Glu Ala Lys Ala Ala Gln Lys Lys Tyr Glu Asp
            35                  40                  45

Asp Gln Lys Lys Thr Glu Glu Lys Ala Lys Leu Val Gln Lys Ala Asp
        50                  55                  60

Glu Glu Arg Gln Lys Ala Asn Val Ala Val Gln Lys Ala Tyr Leu Lys
65              70                  75                  80

Leu Arg Glu Ala Gln Glu Gln Leu Asn Lys Ser Pro Asn Asn Lys Lys
                85                  90                  95

Asn Ala Ala Gln Gln Lys Leu Lys Asp Ala Leu Ala His Ile Asp Glu
            100                 105                 110

Val Thr Leu Lys Gln Lys Glu Ala Glu Ala Asn Phe Asn Lys Glu Gln
            115                 120                 125

Ala Lys Val Val Pro Glu Ala Asp Lys Leu Ala Glu Thr Lys Lys Lys
            130                 135                 140

Ala Glu Gln Ala Glu Lys Lys Glu Pro Glu Leu Ala Lys Lys Val Ala
145                 150                 155                 160

Glu Ala Lys Ala Lys Ala Glu Ala Glu Lys Lys Ala Val Glu Ala
            165                 170                 175

Lys Gln Lys Val Asp Ala Glu Lys Tyr Ala Leu Glu Ala Lys Ile Ala
            180                 185                 190

Glu Leu Glu Tyr Glu Val Gln Gly Leu Glu Lys Glu Leu Lys Glu Ile
            195                 200                 205

Asp Glu Ser Asp Ser Glu Asp Tyr Ile Lys Glu Gly Leu Arg Ala Pro
        210                 215                 220

Leu Gln Ser Lys Leu Asp Ala Lys Ala Lys Leu Ser Lys Leu Glu
225                 230                 235                 240

Glu Leu Ser Asp Lys Ile Asp Glu Leu Asp Ala Glu Ile Ala Lys Leu
            245                 250                 255

Glu Lys Asp Val Glu Asp Phe Lys Asn Ser Asp Gly Glu Gln Ala Glu
            260                 265                 270

Gln Tyr Leu Val Ala Ala Lys Lys Asp Leu Asp Ala Lys Lys Ala Glu
            275                 280                 285

Leu Glu Asn Thr Glu Ala Asp Leu Lys Lys Ala Val Asp Glu

```
                   290                 295                 300

<210> SEQ ID NO 75
<211> LENGTH: 302
<212> TYPE: PRT
<213> ORGANISM: Streptococcus pneumoniae

<400> SEQUENCE: 75

Glu Ala Ala Pro Val Ala Asn Gln Ser Gln Ala Glu Lys Asn Tyr Asp
1               5                   10                  15

Val Ala Lys Lys Asp Val Glu Asn Ala Lys Lys Ala Val Glu Asp Ala
            20                  25                  30

Gln Lys Ala Leu Asp Asp Ala Lys Ala Gln Lys Lys Tyr Glu Asp
        35                  40                  45

Asp Gln Lys Lys Thr Glu Glu Lys Ala Lys Leu Val Gln Lys Ala Asp
    50                  55                  60

Glu Glu Arg Gln Lys Ala Asn Val Ala Val Gln Lys Ala Tyr Leu Lys
65                  70                  75                  80

Leu Arg Glu Ala Gln Glu Gln Leu Asn Lys Ser Pro Asn Asn Lys Lys
                85                  90                  95

Asn Ala Ala Gln Gln Lys Leu Lys Asp Ala Leu Ala His Ile Asp Glu
            100                 105                 110

Val Thr Leu Lys Gln Lys Glu Ala Glu Ala Asn Phe Asn Lys Glu Gln
        115                 120                 125

Ala Lys Val Val Pro Glu Ala Asp Lys Leu Ala Glu Thr Lys Lys Lys
    130                 135                 140

Ala Glu Gln Ala Glu Lys Lys Glu Pro Glu Leu Ala Lys Lys Val Ala
145                 150                 155                 160

Glu Ala Lys Ala Lys Ala Glu Glu Ala Glu Lys Lys Ala Val Glu Ala
                165                 170                 175

Lys Gln Lys Val Asp Ala Glu Lys Tyr Ala Leu Glu Ala Lys Ile Ala
            180                 185                 190

Glu Leu Glu Tyr Glu Val Gln Gly Leu Glu Lys Glu Leu Lys Glu Ile
        195                 200                 205

Asp Glu Ser Asp Ser Glu Asp Tyr Ile Lys Glu Gly Leu Arg Ala Pro
    210                 215                 220

Leu Gln Ser Lys Leu Asp Ala Lys Lys Ala Lys Leu Ser Lys Leu Glu
225                 230                 235                 240

Glu Leu Ser Asp Lys Ile Asp Glu Leu Asp Ala Glu Ile Ala Lys Leu
                245                 250                 255

Glu Lys Asp Val Glu Asp Phe Lys Asn Ser Asp Gly Glu Gln Ala Glu
            260                 265                 270

Gln Tyr Leu Val Ala Ala Lys Lys Asp Leu Asp Ala Lys Lys Ala Glu
        275                 280                 285

Leu Glu Asn Thr Glu Ala Asp Leu Lys Lys Ala Val Asp Glu
    290                 295                 300

<210> SEQ ID NO 76
<211> LENGTH: 98
<212> TYPE: PRT
<213> ORGANISM: Streptococcus pneumoniae

<400> SEQUENCE: 76

Leu Lys Glu Ile Asp Glu Ser Asp Ser Glu Asp Tyr Val Lys Glu Gly
1               5                   10                  15

Leu Arg Ala Pro Leu Gln Ser Glu Leu Asp Ala Lys Gln Ala Lys Leu
```

```
                20                  25                  30

Ser Lys Leu Glu Glu Leu Ser Asp Lys Ile Asp Glu Leu Asp Ala Glu
                35                  40                  45

Ile Ala Lys Leu Glu Lys Asn Val Glu Asp Phe Lys Asn Ser Asn Gly
         50                  55                  60

Glu Gln Ala Glu Gln Tyr Arg Ala Ala Ala Glu Asp Leu Ala Ala
 65                  70                  75                  80

Lys Gln Ala Glu Leu Gly Lys Thr Glu Ala Asp Leu Lys Lys Ala Val
                 85                  90                  95

Asn Glu

<210> SEQ ID NO 77
<211> LENGTH: 98
<212> TYPE: PRT
<213> ORGANISM: Streptococcus pneumoniae

<400> SEQUENCE: 77

Leu Lys Gly Ile Asp Glu Ser Asp Ser Glu Asp Tyr Val Lys Glu Gly
 1               5                  10                  15

Leu Arg Ala Pro Leu Gln Ser Glu Leu Asp Ala Lys Arg Thr Lys Leu
                20                  25                  30

Ser Thr Leu Glu Glu Leu Ser Asp Lys Ile Asp Glu Leu Asp Ala Glu
                35                  40                  45

Ile Ala Lys Leu Glu Lys Asn Val Glu Tyr Phe Lys Lys Thr Asp Ala
         50                  55                  60

Glu Gln Thr Glu Gln Tyr Leu Ala Ala Ala Glu Lys Asp Leu Ala Asp
 65                  70                  75                  80

Lys Lys Ala Glu Leu Gly Lys Thr Glu Ala Asp Leu Lys Lys Ala Val
                 85                  90                  95

Asn Glu

<210> SEQ ID NO 78
<211> LENGTH: 294
<212> TYPE: PRT
<213> ORGANISM: Streptococcus pneumoniae

<400> SEQUENCE: 78

Glu Glu Ala Pro Val Ala Ser Gln Ser Lys Ala Glu Lys Asp Tyr Asp
 1               5                  10                  15

Ala Ala Met Glu Lys Tyr Lys Ala Ala Lys Glu Tyr Glu Asp Ala
                20                  25                  30

Lys Lys Val Leu Ala Asp Ala Lys Ala Ala Gln Lys Lys Tyr Asp Glu
                35                  40                  45

Asp Gln Lys Lys Thr Glu Lys Lys Ala Ala Val Lys Lys Ile Asp
         50                  55                  60

Glu Glu His Gln Ala Ala Asn Leu Lys Ser Gln Gln Ala Leu Val Glu
 65                  70                  75                  80

Phe Leu Ala Ala Gln Arg Glu Gly Asn Pro Lys Lys Lys Ala Ala
                 85                  90                  95

Gln Ala Lys Leu Glu Ala Glu Lys Ala Glu Lys Glu Lys Lys Glu
                100                 105                 110

Phe Asp Lys Ala Gln Ala Val Val Pro Glu Ala Thr Glu Leu Ala
                115                 120                 125

Glu Thr Lys Lys Lys Ala Asp Glu Ala Lys Val Lys Glu Pro Glu Leu
                130                 135                 140
```

```
Thr Lys Lys Leu Glu Glu Ala Lys Ala Lys Ser Glu Glu Ala Glu Lys
145                 150                 155                 160

Lys Ala Thr Glu Ala Lys Gln Lys Val Asp Ala Glu His Ala Lys Glu
            165                 170                 175

Val Val Pro Gln Ala Lys Ile Ala Glu Leu Glu Asn Glu Val Gln Lys
            180                 185                 190

Leu Glu Lys Asp Leu Lys Glu Ile Asp Glu Ser Asp Ser Glu Asp Tyr
            195                 200                 205

Val Lys Glu Gly Leu Arg Ala Pro Leu Gln Ser Glu Leu Asp Ala Lys
210                 215                 220

Gln Ala Lys Leu Ser Lys Leu Glu Glu Leu Ser Asp Lys Ile Asp Glu
225                 230                 235                 240

Leu Asp Ala Glu Ile Ala Lys Leu Glu Lys Asn Val Glu Asp Phe Lys
            245                 250                 255

Asn Ser Asn Gly Glu Gln Ala Glu Gln Tyr Arg Ala Ala Ala Glu Glu
            260                 265                 270

Asp Leu Ala Ala Lys Gln Ala Glu Leu Glu Lys Thr Glu Ala Asp Leu
            275                 280                 285

Lys Lys Ala Val Asn Glu
    290

<210> SEQ ID NO 79
<211> LENGTH: 310
<212> TYPE: PRT
<213> ORGANISM: Streptococcus pneumoniae

<400> SEQUENCE: 79

Met Asn Lys Lys Lys Met Ile Leu Thr Ser Leu Ala Ser Val Ala Ile
1               5                   10                  15

Leu Gly Ala Gly Phe Val Ala Ser Gln Pro Thr Val Val Arg Ala Glu
            20                  25                  30

Glu Ala Pro Val Ala Ser Gln Ser Lys Ala Glu Lys Asp Tyr Asp Ala
            35                  40                  45

Ala Lys Arg Asp Ala Glu Asn Ala Lys Lys Ala Leu Glu Glu Ala Lys
    50                  55                  60

Arg Ala Gln Lys Lys Tyr Glu Asp Asp Gln Lys Lys Thr Glu Glu Lys
65                  70                  75                  80

Ala Lys Glu Glu Lys Gln Ala Ser Glu Ala Gln Lys Ala Asn Leu
            85                  90                  95

Lys Tyr Gln Leu Leu Gln Lys Tyr Val Ser Glu Ser Asp Gly Lys
            100                 105                 110

Lys Lys Lys Glu Ile Glu Lys Gln Ala Asp Ala Ala Lys Lys Glu Asn
            115                 120                 125

Glu Ile Lys Lys Ala Glu Leu Asn Lys Ile Arg Gln Glu Ile Val Val
130                 135                 140

Pro Ser Ser Gln Gln Leu Glu Val Thr Arg Arg Lys Ala Glu Val Ala
145                 150                 155                 160

Lys Ala Lys Glu Pro Gly Leu Arg Lys Arg Val Glu Ala Glu Lys
            165                 170                 175

Lys Val Thr Glu Ala Lys Gln Lys Leu Asp Ala Glu Arg Ala Lys Glu
            180                 185                 190

Val Ala Leu Gln Ala Lys Ile Ala Glu Leu Glu Asn Glu Val Tyr Arg
            195                 200                 205

Leu Glu Thr Glu Leu Lys Gly Ile Asp Glu Ser Asp Ser Glu Asp Tyr
210                 215                 220
```

```
Val Lys Glu Gly Leu Arg Ala Pro Leu Gln Ser Glu Leu Asp Ala Lys
225                 230                 235                 240

Arg Thr Lys Leu Ser Thr Leu Glu Glu Leu Ser Asp Lys Ile Asp Glu
                245                 250                 255

Leu Asp Ala Glu Ile Ala Lys Leu Glu Lys Asn Val Glu Tyr Phe Lys
            260                 265                 270

Lys Thr Asp Ala Glu Gln Thr Glu Gln Tyr Leu Ala Ala Ala Glu Lys
        275                 280                 285

Asp Leu Ala Asp Lys Lys Ala Glu Leu Glu Lys Thr Glu Ala Asp Leu
    290                 295                 300

Lys Lys Ala Val Asn Glu
305                 310

<210> SEQ ID NO 80
<211> LENGTH: 112
<212> TYPE: PRT
<213> ORGANISM: Streptococcus pneumoniae

<400> SEQUENCE: 80

Leu Glu Asp Ala Glu Leu Glu Leu Glu Lys Val Leu Ala Thr Leu Asp
1               5                   10                  15

Pro Glu Gly Lys Thr Gln Asp Glu Leu Asp Lys Glu Ala Ala Glu Asp
            20                  25                  30

Ala Asn Ile Glu Ala Leu Gln Asn Lys Val Ala Asp Leu Glu Asn Lys
        35                  40                  45

Val Ala Glu Leu Asp Lys Glu Val Thr Arg Leu Gln Ser Asp Leu Lys
    50                  55                  60

Asp Ala Glu Glu Asn Asn Val Glu Asp Tyr Val Lys Glu Gly Leu Asp
65                  70                  75                  80

Lys Ala Leu Thr Asp Lys Lys Val Glu Leu Asn Asn Thr Gln Lys Ala
                85                  90                  95

Leu Asp Thr Ala Gln Lys Ala Leu Asp Thr Ala Leu Asn Glu Leu Gly
            100                 105                 110

<210> SEQ ID NO 81
<211> LENGTH: 368
<212> TYPE: PRT
<213> ORGANISM: Streptococcus pneumoniae

<400> SEQUENCE: 81

Glu Glu Ala Pro Val Ala Asn Gln Ser Lys Ala Glu Lys Asp Tyr Asp
1               5                   10                  15

Ala Ala Val Lys Lys Ser Glu Ala Ala Lys Lys Asp Tyr Glu Thr Ala
            20                  25                  30

Lys Lys Lys Ala Glu Asp Ala Gln Lys Lys Tyr Asp Glu Asp Gln Lys
        35                  40                  45

Lys Thr Glu Glu Lys Ala Glu Leu Val Arg Lys Ala Asp Glu Lys Arg
    50                  55                  60

Gln Lys Ala Asn Leu Ala Val Gln Glu Ala Tyr Val Lys Phe Gln Glu
65                  70                  75                  80

Ala Gln Arg Glu Phe Asn Glu Ser Pro Ser Arg Lys Lys Ser Asp Ala
                85                  90                  95

Lys Lys Lys Leu Asp Asp Ala Ser Ala His Ile Glu Glu Val Lys Leu
            100                 105                 110

Lys Gln Lys Glu Ala Asp Ala Asn Phe Asn Lys Glu Gln Ala Lys Val
        115                 120                 125
```

```
Ile Pro Glu Ala Ser Asp Leu Ala Val Thr Lys Gln Lys Ala Glu Glu
    130                 135                 140

Ala Lys Lys Glu Ala Glu Val Ala Lys Glu Lys Tyr Asp Lys Ala Val
145                 150                 155                 160

Gln Glu Val Glu Val Glu Lys Asn Lys Ile Leu Glu Gln Asp Ala Glu
                165                 170                 175

Asn Glu Lys Lys Ile Asp Val Leu Gln Asn Lys Val Ala Asp Leu Glu
            180                 185                 190

Lys Gly Ile Ala Pro Tyr Gln Asn Lys Val Ala Glu Leu Asn Lys Glu
        195                 200                 205

Ile Ala Arg Leu Gln Ser Asp Leu Lys Asp Ala Glu Glu Asn Asn Val
    210                 215                 220

Glu Asp Tyr Ile Lys Glu Gly Leu Glu Gln Ala Ile Ala Asp Lys Lys
225                 230                 235                 240

Ala Glu Leu Ala Thr Thr Gln Gln Asn Ile Asp Lys Thr Gln Lys Asp
                245                 250                 255

Leu Glu Asp Ala Glu Leu Glu Leu Glu Lys Val Leu Ala Thr Leu Asp
            260                 265                 270

Pro Glu Gly Lys Thr Gln Asp Glu Leu Asp Lys Glu Ala Ala Glu Asp
        275                 280                 285

Ala Asn Ile Glu Ala Leu Gln Asn Lys Val Ala Asp Leu Glu Asn Lys
    290                 295                 300

Val Ala Glu Leu Asp Lys Glu Val Thr Arg Leu Gln Ser Asp Leu Lys
305                 310                 315                 320

Asp Ala Glu Glu Asn Asn Val Glu Asp Tyr Val Lys Glu Gly Leu Asp
                325                 330                 335

Lys Ala Leu Thr Asp Lys Lys Val Glu Leu Asn Asn Thr Gln Lys Ala
            340                 345                 350

Leu Asp Thr Ala Gln Lys Ala Leu Asp Thr Ala Leu Asn Glu Leu Gly
        355                 360                 365

<210> SEQ ID NO 82
<211> LENGTH: 1074
<212> TYPE: DNA
<213> ORGANISM: Artificial Sequence
<220> FEATURE:
<223> OTHER INFORMATION: DNA coding for PspA01.1 [SEQ ID NO:1]. The ATG
      coding for methionine has been added at the beginning as an
      initiator and TGA has been added at the end as a stop codon

<400> SEQUENCE: 82
atggaagaaa gcccggtggc gagccagagc aaagcggaaa agattatga tgcggcgaaa      60 aaagatgcga aaacgcgaa aaaagcggtg gaagatgcgc agaaagcgct ggatgatgcg     120
aaagcggcgc agaaaaaata cgatgaagac cagaaaaaaa ccgaagaaaa agcggcgctg    180
gaaaaagcgg cgagcgaaga atggataaa gcggtggcgg cggtgcagca ggcgtatctg    240
gcgtatcagc aggcgaccga taaagcggcg aaagatgcgg cggataaaat gattgatgaa    300
gcgaaaaaac gcgaagaaga agcgaaaacc aaatttaaca ccgtgcgcgc gatggtggtt    360
ccggaaccgg aacagctggc ggaaaccaaa agaaaagcg aagaagcgaa acagaaagcg     420
ccggaactga ccaaaaaact ggaagaagcg aaagcgaaac tggaagaagc cgagaaaaaa    480
gcgaccgaag ccaaacaaaa ggttgatgcg gaagaagtgg cgccgcaggc gaaaattgcg    540
gaactggaaa accaggtgca tcgcctggaa caggaactga agaaattga tgaaagcgaa    600 agcgaagatt atgcgaaaga aggctttcgc gcgccgctgc agagcaaact ggatgcgaaa    660
```

```
aaagccaagc tgagcaaact ggaagaactg agcgataaaa ttgatgaact ggatgcggaa      720
attgcgaaac tggaagatca gctgaaagcg gcggaagaaa acaacaacgt ggaagattat      780
tttaaagaag gcctggaaaa aaccattgcg gcgaaaaaag cggaacttga aaaaaccgaa      840
gcggatctga aaaagcggt taatgaaccg gaaaccccgg caccggcgcc ggcaccggcg      900
ccggccccgg ccccggcccc agcgcccgcg ccggccccga agccagcccc ggctcccaaa      960
ccggcaccgg ccccgaaacc ggcccctgcg cccgcccccg cgcccgcgcc gaaaccgaaa     1020
aaaccggcag aaaaaccggc tccggcacct aaaccagaga ccccgaaaac ctga           1074
```

<210> SEQ ID NO 83
<211> LENGTH: 1158
<212> TYPE: DNA
<213> ORGANISM: Artificial Sequence
<220> FEATURE:
<223> OTHER INFORMATION: DNA coding for PspA01.2 [SEQ ID NO:2]. The ATG coding for methionine has been added at the beginning as an initiator and TGA has been added at the end as a stop codon

<400> SEQUENCE: 83

```
atggaagaaa gcccggtggc gagccagagc aaagcggaaa aagattatga tgcggcgaaa       60
aaagatgcga aaacgcgaa aaaagcggtg gaagatgcgc agaaagcgct ggatgatgcg      120
aaagcggcgc agaaaaaata cgatgaagac cagaaaaaaa ccgaagaaaa agcggcgctg      180 gaaaagcgg cgagcgaaga atggataaa gcggtggcgg cggtgcagca ggcgtatctg      240
gcgtatcagc aggcgaccga taagcggcg aaagatgcgg cggataaaat gattgatgaa      300
gcgaaaaaac gcgaagaaga agcgaaaacc aaatttaaca ccgtgcgcgc gatggtggtt      360
ccggaaccgg aacagctggc ggaaaccaaa agaaaagcg aagaagcgaa acagaaagcg      420
ccggaactga ccaaaaaact ggaagaagcg aaagcgaaac tggaagaagc cgagaaaaaa      480
gcgaccgaag ccaaacaaaa ggttgatgcg gaagaagtgg cgccgcaggc gaaaattgcg      540
gaactggaaa accaggtgca tcgcctggaa caggaactga agaaattga tgaaagcgaa      600 agcgaagatt atgcgaaaga aggctttcgc gcgccgctgc agagcaaact ggatgcgaaa      660
aaagccaagc tgagcaaact ggaagaactg agcgataaaa ttgatgaact ggatgcggaa      720
attgcgaaac tggaagatca gctgaaagcg gcggaagaaa acaacaacgt ggaagattat      780
tttaaagaag gcctggaaaa aaccattgcg gcgaaaaaag cggaacttga aaaaaccgaa      840
gcggatctga aaaagcggt taatgaaccg gaaaccccgg caccggcgcc ggcaccggcg      900
ccggccccgg ccccggcccc agcgcccaaa ccggcaccgg ccccgaaacc ggcccctgca      960
ccaaaaccgg cgccggctcc taaacccgcg ccggccccga agccagcccc ggctcccgcc     1020
cccgcgcccg cgccgaaacc ggcgccggcc cctaagccgg caccggctcc agccccggcc     1080 ccggccccctg cgccgaagcc cgaaaaaccg gcagaaaaac cggctccggc acctaaacca     1140
gagaccccga aaacctga                                                   1158
```

<210> SEQ ID NO 84
<211> LENGTH: 1491
<212> TYPE: DNA
<213> ORGANISM: Artificial Sequence
<220> FEATURE:
<223> OTHER INFORMATION: DNA coding for PspA02 [SEQ ID NO:3]. The ATG coding for methionine has been added at the beginning as an initiator and TGA has been added at the end as a stop codon

<400> SEQUENCE: 84

```
atggaagaaa gcccgcaggt ggtggaaaaa agcagcctgg aaaaaaaata tgaagaagcg      60
aaagcgaaag cggataccgc gaaaaaagat tatgaaaccg cgaaaaagaa agcggaagat     120
gcgcagaaaa aatacgaaga cgatcagaaa cgcaccgaag aaaaagcgcg caaagaagcg     180
gaagcgagcc agaaactgaa cgatgtggcg ctggtggtgc agaacgcgta taagaatat      240 cgcgaagtgc agaaccagcg cagcaaatat aaaagcgatg cggaatatca gaaaaaactg     300
accgaagtgg atagcaaaat tgaaaaagcg cgtaaggagc agcaggatct gcagaacaaa     360
tttaacgaag tgcgtgcggt ggtggttccg gaaccgaatg cgctggcgga aaccaaaaaa     420
aaagccgaag aggccaaagc agaggaaaaa gtggcgaaac gcaaatatga ttatgcgacc     480
ctgaaagtgg cgctggcgaa aaaagaagtg gaagcgaaag aactggaaat tgaaaaactg     540
cagtatgaaa ttagcaccct ggaacaggaa gtggcgaccg cgcagcatca ggtggataac     600
ctgaaaaaac tgctggcggg cgcggatccg gatgatggca ccgaagtgat tgaagcgaaa     660
ctgaaaaaag gcgaagcgga actgaacgcg aacaggcgg aactggcgaa aaaacagacc      720
gaactggaaa aactgctgga tagcctggat ccggaaggca aaacccagga tgaactggat     780
aaagaagccg aagaagccga ctggacaaa aaagcagatg aactgcagaa caaagtggcg      840
gatctggaaa agaaattag caatttggag attctgctgg cggtgcaga cccggaagac       900 gataccgcag cgctgcaaaa taaactggcc gcgaaaaaag cggaactggc gaaaaaacaa     960
accgaactgg agaagctgct tgattcgctg gatccgaggg taaaacgca agatgaactg      1020 gataaagaag cggaagaagc ggagctggat aaaaagcgg acgaactgca gaataaggtg     1080
gccgacctgg agaaagaaat cagcaatctc gagatcctgc tgggtggcgc cgacagcgaa     1140
gatgatacgg ccgcgctgca gaataaactc gccaccaaaa aagccgagct cgagaagacc     1200
cagaaagaac tggatgcggc gctgaacgaa ctgggcccgg atggtgatga agaagaaacc     1260
ccggcaccgg caccgcaacc ggaacaaccg cgccggccc caagccggga acagccggca      1320
ccggccccaa agccggagca gccggccccg gcccccaaac cggaacaacc ggcgcctgca     1380
ccgaagccag aacagccggc gccagcgcct aaaccggaac agccagcgaa accggagaag     1440
ccagcggaag aaccgaccca gccggagaaa ccggcaaccc cgaaaacctg a              1491
```

<210> SEQ ID NO 85
<211> LENGTH: 1296
<212> TYPE: DNA
<213> ORGANISM: Artificial Sequence
<220> FEATURE:
<223> OTHER INFORMATION: DNA coding for PspA03 [SEQ ID NO:4]. The ATG
      coding for methionine has been added at the beginning as an
      initiator and TGA has been added at the end as a stop codon

<400> SEQUENCE: 85

```
atggaagaag cgccggtggc gaaccagagc aaagcggaaa agattatga tgcggcggtg       60 aaaaaaagcg aagcggcgaa aaaagattac gagaccgcga aaagaaagc ggaagatgcg      120 cagaaaaaat atgatgaaga tcagaaaaaa accgaagcga agcggaaaa agaacgcaaa      180 gcgagcgaaa aaattgcgga agcgaccaaa gaagtgcagc aggcgtatct ggcgtatctg      240
caggcgagca cgaaagcca gcgcaaagaa gcggataaaa aaattaaaga agcgacccag      300
cgcaaagatg aagcggaagc ggcgtttgcg accattcgca ccaccattgt ggtgccggaa      360
ccgagcgaac tgcggaaac caaaaaaaaa gccgaagaag caacgaaaga ggccgaagtg      420
gcgaaaaaga aagcgaaga agcggcgaaa gaagtggaag tggaaaaaaa caaaattctg      480
gaacaggatg cggaaaacga aaagaaaatt gatgtgctgc agaacaaagt ggcggatctg      540
```

```
gaaaaaggca ttgcgccgta tcagaatgaa gtcgccgagc tcaacaaaga aattgcgcgt    600
ttgcaaagcg atctgaaaga tgcggaagaa acaacgtgg aagattacat taaagaaggc     660
ctggaacagg cgattaccaa caaaaaagcg gaactggcga ccacccagca gaacattgat    720
aaacccagaa agatctggaa gacgcggag ctggaactgg aaaaagtgct ggcgaccctg     780
gatccggaag gcaaaaccca ggatgaactg gataaagaag cggcggaagc ggaactgaac    840
gaaaaagtgg aagcgctgca gaaccaggtg gcggaactgg aagaagaact gagcaaactg    900
gaagataacc tgaaagacgc cgagaccaac aatgttgaag attacattaa agagggtctg    960
gaggaagcga ttgcgaccaa aaaagccgag ctcgaaaaaa cgcaaaaaga gttagatgcg   1020
gcgctgaacg aactgggccc ggaaaaaccg gcagaagaaa ccccggcacc ggcgccgaaa   1080
ccggaacagc cggccgagca gccgaaaccg gcaccggcac cgcaaccggc cccggcgcca   1140
aagccagaga agaccgatga tcagcaggcg gaagaagatt atgcgcgccg cagcgaagaa   1200
gaatataacc gcctgccgca gcagcagccg ccgaaagcag aaaaaccggc gccggccccg   1260
aaaccagaac aaccagttcc ggcaccgaaa acctga                             1296
```

<210> SEQ ID NO 86
<211> LENGTH: 5
<212> TYPE: PRT
<213> ORGANISM: Streptococcus pneumoniae

<400> SEQUENCE: 86

Leu Lys Glu Ile Gly
1               5

<210> SEQ ID NO 87
<211> LENGTH: 98
<212> TYPE: PRT
<213> ORGANISM: Streptococcus pneumoniae

<400> SEQUENCE: 87

Pro Glu Thr Pro Ala Pro Ala Pro Lys Pro Ala Thr Pro Glu Ala
1               5                   10                  15

Pro Ala Pro Ala Pro Lys Pro Ala Pro Ala Pro Lys Pro Ala Pro Ala
            20                  25                  30

Pro Ala Pro Thr Pro Glu Ala Pro Ala Pro Ala Pro Lys Pro Ala Pro
        35                  40                  45

Ala Pro Lys Pro Ala Pro Ala Pro Lys Pro Ala Pro Ala Pro Ala Pro
    50                  55                  60

Thr Pro Glu Ala Pro Ala Pro Ala Pro Lys Pro Ala Pro Ala Pro Lys
65                  70                  75                  80

Pro Ala Pro Ala Pro Lys Pro Ala Pro Ala Pro Lys Pro Glu Thr Pro
                85                  90                  95

Lys Thr

<210> SEQ ID NO 88
<211> LENGTH: 108
<212> TYPE: PRT
<213> ORGANISM: Streptococcus pneumoniae

<400> SEQUENCE: 88

Pro Glu Thr Pro Ala Pro Ala Pro Lys Pro Ala Pro Ala Pro Ala Pro
1               5                   10                  15

Thr Pro Glu Ala Pro Ala Pro Ala Pro Lys Pro Ala Pro Ala Pro Lys
            20                  25                  30

```
Pro Ala Pro Ala Pro Ala Pro Thr Pro Glu Ala Pro Ala Pro Ala Pro
        35                  40                  45

Lys Pro Ala Pro Ala Pro Lys Pro Ala Pro Ala Pro Lys Pro Ala Pro
 50                  55                  60

Ala Pro Ala Pro Thr Pro Glu Ala Pro Ala Pro Ala Pro Lys Pro Ala
 65                  70                  75                  80

Pro Ala Pro Lys Pro Ala Pro Ala Pro Lys Pro Ala Pro Ala Pro Lys
            85                  90                  95

Pro Ala Pro Ala Pro Lys Pro Glu Thr Pro Lys Thr
            100                 105

<210> SEQ ID NO 89
<211> LENGTH: 84
<212> TYPE: PRT
<213> ORGANISM: Streptococcus pneumoniae

<400> SEQUENCE: 89

Pro Glu Thr Pro Ala Pro Ala Pro Lys Pro Ala Pro Ala Pro Ala Pro
 1               5                  10                  15

Thr Pro Glu Ala Pro Ala Pro Ala Pro Lys Pro Ala Pro Ala Pro Lys
            20                  25                  30

Pro Ala Pro Ala Pro Ala Pro Lys Pro Ala Pro Ala Pro Lys Pro Ala
            35                  40                  45

Pro Ala Pro Ala Pro Lys Pro Ala Pro Ala Pro Lys Pro Ala Pro Ala
            50                  55                  60

Pro Lys Pro Ala Pro Ala Pro Lys Pro Ala Pro Ala Pro Lys Pro Glu
 65                  70                  75                  80

Thr Pro Lys Thr

<210> SEQ ID NO 90
<211> LENGTH: 74
<212> TYPE: PRT
<213> ORGANISM: Streptococcus pneumoniae

<400> SEQUENCE: 90

Pro Glu Thr Pro Ala Pro Ala Pro Ala Pro Ala Pro Ala Pro Ala Pro
 1               5                  10                  15

Ala Pro Ala Pro Lys Pro Ala Pro Ala Pro Lys Pro Ala Pro Ala Pro
            20                  25                  30

Ala Pro Ala Pro Ala Pro Lys Pro Ala Pro Ala Pro Lys Pro Ala Pro
            35                  40                  45

Ala Pro Ala Pro Ala Pro Lys Pro Glu Lys Pro Ala Glu Lys Pro Ala
            50                  55                  60

Pro Ala Pro Lys Pro Glu Thr Pro Lys Thr
 65                  70

<210> SEQ ID NO 91
<211> LENGTH: 82
<212> TYPE: PRT
<213> ORGANISM: Streptococcus pneumoniae

<400> SEQUENCE: 91

Pro Glu Thr Pro Ala Pro Ala Pro Ala Pro Ala Pro Ala Pro Ala Pro
 1               5                  10                  15

Ala Pro Ala Pro Ala Pro Ala Pro Ala Pro Ala Pro Lys Pro Ala Pro
            20                  25                  30

Ala Pro Lys Pro Ala Pro Ala Pro Ala Pro Ala Pro Ala Pro Lys Pro
```

```
            35                  40                  45
Ala Pro Ala Pro Lys Pro Ala Pro Ala Pro Ala Pro Lys Pro
     50                  55                  60
Glu Lys Pro Ala Glu Lys Pro Ala Pro Ala Pro Lys Pro Glu Thr Pro
65                  70                  75                  80
Lys Thr

<210> SEQ ID NO 92
<211> LENGTH: 76
<212> TYPE: PRT
<213> ORGANISM: Streptococcus pneumoniae

<400> SEQUENCE: 92

Pro Glu Thr Pro Ala Pro Ala Pro Ala Pro Lys Pro Ala Pro Ala Pro
1               5                   10                  15

Ala Pro Thr Pro Glu Ala Pro Ala Pro Ala Pro Lys Pro Ala Pro Ala
                    20                  25                  30

Pro Lys Pro Ala Pro Ala Pro Lys Pro Ala Pro Ala Pro Lys Pro Ala
                35                  40                  45

Pro Ala Pro Lys Pro Ala Pro Ala Pro Lys Pro Ala Pro Ala Pro Lys
                 50                  55                  60

Pro Ala Pro Ala Pro Lys Pro Glu Thr Pro Lys Thr
65                  70                  75

<210> SEQ ID NO 93
<211> LENGTH: 75
<212> TYPE: PRT
<213> ORGANISM: Streptococcus pneumoniae

<400> SEQUENCE: 93

Pro Glu Thr Pro Ala Pro Ala Pro Ala Pro Lys Pro Ala Pro Ala Pro
1               5                   10                  15

Ala Pro Thr Pro Glu Ala Pro Ala Pro Ala Pro Lys Pro Ala Pro Ala
                    20                  25                  30

Pro Lys Pro Ala Pro Ala Pro Lys Pro Ala Pro Ala Pro Lys Pro Ala
                35                  40                  45

Pro Ala Pro Lys Pro Ala Pro Lys Pro Glu Lys Pro Ala Glu Lys Pro
                50                  55                  60

Ala Pro Ala Pro Lys Pro Glu Thr Pro Lys Thr
65                  70                  75

<210> SEQ ID NO 94
<211> LENGTH: 65
<212> TYPE: PRT
<213> ORGANISM: Streptococcus pneumoniae

<400> SEQUENCE: 94

Pro Glu Thr Pro Ala Pro Ala Pro Ala Pro Lys Pro Ala Pro Ala Pro
1               5                   10                  15

Ala Pro Thr Pro Glu Ala Pro Ala Pro Ala Pro Lys Pro Ala Pro Ala
                    20                  25                  30

Pro Lys Pro Ala Pro Ala Pro Lys Pro Ala Pro Ala Pro Lys Pro Ala
                35                  40                  45

Pro Ala Pro Lys Pro Ala Pro Lys Pro Ala Pro Ala Pro Lys
                50                  55                  60

Pro
65
```

<210> SEQ ID NO 95
<211> LENGTH: 86
<212> TYPE: PRT
<213> ORGANISM: Streptococcus pneumoniae

<400> SEQUENCE: 95

Pro Asp Gly Asp Glu Glu Glu Thr Pro Ala Pro Gln Pro Glu
1               5                   10                  15

Lys Pro Ala Pro Ala Pro Ala Pro Lys Pro Glu Gln Pro Ala Pro Ala
                20                  25                  30

Pro Lys Pro Glu Lys Ser Ala Asp Gln Gln Ala Glu Glu Asp Tyr Ala
            35                  40                  45

Arg Arg Ser Glu Glu Glu Tyr Asn Arg Leu Thr Gln Gln Gln Pro Pro
    50                  55                  60

Lys Ala Glu Lys Pro Ala Pro Ala Pro Ala Pro Lys Pro Glu Gln Pro
65                  70                  75                  80

Ala Pro Ala Pro Lys Thr
                85

<210> SEQ ID NO 96
<211> LENGTH: 101
<212> TYPE: PRT
<213> ORGANISM: Streptococcus pneumoniae

<400> SEQUENCE: 96

Pro Glu Thr Pro Ala Pro Ala Pro Ala Pro Ala Pro Ala Pro Ala Pro
1               5                   10                  15

Thr Pro Glu Ala Pro Ala Pro Ala Pro Lys Pro Ala Pro Ala
                20                  25                  30

Pro Lys Pro Ala Pro Ala Pro Lys Pro Ala Pro Ala Pro Lys Pro Ala
            35                  40                  45

Pro Ala Pro Lys Pro Ala Pro Ala Pro Lys Pro Ala Pro Ala Pro Ala
    50                  55                  60

Pro Ala Pro Ala Pro Lys Pro Ala Pro Ala Pro Ala Pro Ala Pro Ala
65                  70                  75                  80

Pro Lys Pro Glu Lys Pro Ala Glu Lys Pro Ala Pro Ala Pro Lys Pro
                85                  90                  95

Glu Thr Pro Lys Thr
            100

<210> SEQ ID NO 97
<211> LENGTH: 83
<212> TYPE: PRT
<213> ORGANISM: Streptococcus pneumoniae

<400> SEQUENCE: 97

Pro Glu Thr Pro Ala Pro Ala Pro Ala Pro Ala Pro Ala Pro Glu Ala
1               5                   10                  15

Pro Ala Pro Ala Pro Ala Pro Ala Pro Ala Pro Lys Pro Ala Pro Ala
                20                  25                  30

Pro Lys Pro Ala Pro Ala Pro Lys Pro Ala Pro Ala Pro Lys Pro Ala
            35                  40                  45

Pro Ala Pro Lys Pro Ala Pro Ala Pro Ala Pro Ala Pro Ala Pro Lys
    50                  55                  60

Pro Glu Lys Pro Ala Glu Lys Pro Ala Pro Ala Pro Lys Pro Glu Thr
65                  70                  75                  80

Pro Lys Thr

<210> SEQ ID NO 98
<211> LENGTH: 83
<212> TYPE: PRT
<213> ORGANISM: Streptococcus pneumoniae

<400> SEQUENCE: 98

Pro Glu Thr Pro Ala Pro Ala Pro Ala Pro Ala Pro Ala Pro Ala Pro
1               5                   10                  15

Thr Pro Glu Ala Pro Ala Pro Ala Pro Ala Pro Ala Pro Lys Pro Ala
            20                  25                  30

Pro Ala Pro Lys Pro Ala Pro Ala Pro Lys Pro Ala Pro Ala Pro Lys
        35                  40                  45

Pro Ala Pro Ala Pro Lys Pro Ala Pro Ala Pro Ala Pro Ala Pro Lys
    50                  55                  60

Pro Glu Lys Pro Ala Glu Lys Pro Ala Pro Ala Pro Lys Pro Glu Thr
65                  70                  75                  80

Pro Lys Thr

<210> SEQ ID NO 99
<211> LENGTH: 81
<212> TYPE: PRT
<213> ORGANISM: Streptococcus pneumoniae

<400> SEQUENCE: 99

Pro Glu Thr Pro Ala Pro Ala Pro Ala Pro Ala Pro Ala Pro Thr Pro
1               5                   10                  15

Glu Ala Pro Ala Pro Ala Pro Ala Pro Ala Pro Ala Pro Lys Pro Ala
            20                  25                  30

Pro Ala Pro Lys Pro Ala Pro Ala Pro Lys Pro Ala Pro Ala Pro Lys
        35                  40                  45

Pro Ala Pro Ala Pro Lys Pro Ala Pro Ala Pro Ala Pro Lys Pro Glu
    50                  55                  60

Lys Pro Ala Glu Lys Pro Ala Pro Ala Pro Lys Pro Glu Thr Pro Lys
65                  70                  75                  80

Thr

<210> SEQ ID NO 100
<211> LENGTH: 85
<212> TYPE: PRT
<213> ORGANISM: Streptococcus pneumoniae

<400> SEQUENCE: 100

Pro Glu Thr Pro Ala Pro Ala Pro Ala Pro Ala Pro Ala Pro Ala Pro
1               5                   10                  15

Thr Pro Glu Ala Pro Ala Pro Ala Pro Ala Pro Ala Pro Lys Pro Ala
            20                  25                  30

Pro Ala Pro Lys Pro Ala Pro Ala Pro Lys Pro Ala Pro Ala Pro Lys
        35                  40                  45

Pro Ala Pro Ala Pro Lys Pro Ala Pro Ala Pro Lys Pro Ala Pro Ala
    50                  55                  60

Pro Ala Pro Ala Pro Lys Pro Glu Lys Pro Ala Glu Lys Pro Ala Pro
65                  70                  75                  80

Ala Pro Lys Pro Glu
            85

<210> SEQ ID NO 101

```
<211> LENGTH: 56
<212> TYPE: PRT
<213> ORGANISM: Streptococcus pneumoniae

<400> SEQUENCE: 101

Pro Glu Thr Pro Ala Pro Ala Pro Lys Pro Ala Pro Ala Pro Ala Pro
1               5                   10                  15

Thr Pro Glu Ala Pro Ala Pro Ala Pro Lys Pro Ala Pro Ala Pro Lys
            20                  25                  30

Pro Ala Pro Ala Pro Lys Pro Ala Pro Ala Pro Lys Pro Ala Pro Ala
        35                  40                  45

Pro Lys Pro Glu Thr Pro Lys Thr
    50                  55

<210> SEQ ID NO 102
<211> LENGTH: 64
<212> TYPE: PRT
<213> ORGANISM: Streptococcus pneumoniae

<400> SEQUENCE: 102

Pro Glu Thr Pro Ala Pro Ala Pro Ala Pro Lys Pro Ala Pro Ala Pro
1               5                   10                  15

Ala Pro Thr Pro Glu Ala Pro Ala Pro Ala Pro Lys Pro Ala Pro Ala
            20                  25                  30

Pro Lys Pro Ala Pro Ala Pro Lys Pro Ala Pro Ala Pro Lys Pro Ala
        35                  40                  45

Pro Ala Pro Lys Pro Ala Pro Ala Pro Lys Pro Glu Thr Pro Lys Thr
    50                  55                  60

<210> SEQ ID NO 103
<211> LENGTH: 103
<212> TYPE: PRT
<213> ORGANISM: Streptococcus pneumoniae

<400> SEQUENCE: 103

Pro Glu Thr Pro Ala Pro Ala Pro Gln Pro Ala Pro Ala Pro Glu Lys
1               5                   10                  15

Pro Ala Pro Ala Pro Glu Lys Pro Ala Pro Ala Pro Glu Lys Pro Ala
            20                  25                  30

Pro Ala Pro Glu Lys Pro Ala Pro Ala Pro Glu Lys Pro Ala Pro Ala
        35                  40                  45

Pro Glu Lys Pro Ala Pro Ala Pro Glu Lys Pro Ala Pro Ala Pro Glu
    50                  55                  60

Lys Pro Ala Pro Ala Pro Glu Lys Pro Ala Pro Ala Pro Glu Lys Pro
65                  70                  75                  80

Ala Pro Ala Pro Glu Lys Pro Ala Pro Ala Pro Glu Lys Pro Ala Pro
            85                  90                  95

Thr Pro Glu Thr Pro Lys Thr
            100

<210> SEQ ID NO 104
<211> LENGTH: 76
<212> TYPE: PRT
<213> ORGANISM: Streptococcus pneumoniae

<400> SEQUENCE: 104

Pro Glu Thr Pro Ala Pro Ala Pro Gln Pro Ala Pro Ala Pro Glu Lys
1               5                   10                  15

Pro Ala Glu Lys Pro Ala Pro Ala Pro Ala Pro Glu Lys Pro Ala Pro
```

```
                    20                  25                  30

Ala Pro Glu Lys Pro Ala Glu Lys Pro Ala Glu Glu
            35                  40                  45

Pro Ala Glu Lys Pro Ala Pro Ala Pro Glu Lys Pro Ala Pro Thr Pro
        50                  55                  60

Glu Lys Pro Ala Pro Thr Pro Glu Thr Pro Lys Thr
65                  70                  75

<210> SEQ ID NO 105
<211> LENGTH: 78
<212> TYPE: PRT
<213> ORGANISM: Streptococcus pneumoniae

<400> SEQUENCE: 105

Pro Asp Gly Asp Glu Glu Glu Leu Pro Ala Arg Ala Leu Gln Pro Glu
1               5                   10                  15

Gln Pro Ala Pro Ala Pro Lys Pro Glu Gln Pro Thr Pro Ala Pro Lys
            20                  25                  30

Pro Glu Gln Pro Thr Pro Ala Pro Lys Pro Glu Gln Pro Ala Pro Ala
        35                  40                  45

Pro Lys Pro Glu Gln Pro Ala Pro Ala Pro Lys Pro Glu Gln Pro Ala
    50                  55                  60

Pro Ala Pro Lys Pro Glu Gln Pro Thr Pro Ala Pro Lys Thr
65                  70                  75

<210> SEQ ID NO 106
<211> LENGTH: 78
<212> TYPE: PRT
<213> ORGANISM: Streptococcus pneumoniae

<400> SEQUENCE: 106

Pro Asp Gly Asp Glu Glu Glu Thr Pro Ala Pro Ala Gln Pro Glu
1               5                   10                  15

Gln Pro Ala Pro Ala Pro Lys Pro Glu Gln Pro Thr Pro Ala Pro Lys
            20                  25                  30

Pro Glu Gln Pro Thr Pro Ala Pro Lys Pro Glu Gln Pro Ala Pro Ala
        35                  40                  45

Pro Lys Pro Glu Gln Pro Ala Pro Ala Pro Lys Pro Glu Gln Pro Ala
    50                  55                  60

Pro Ala Pro Lys Pro Glu Gln Pro Thr Pro Ala Pro Lys Thr
65                  70                  75

<210> SEQ ID NO 107
<211> LENGTH: 78
<212> TYPE: PRT
<213> ORGANISM: Streptococcus pneumoniae

<400> SEQUENCE: 107

Pro Asp Gly Asp Glu Glu Glu Thr Pro Ala Pro Ala Gln Pro Glu
1               5                   10                  15

Gln Pro Ala Pro Ala Pro Lys Pro Glu Gln Pro Thr Pro Ala Pro Lys
            20                  25                  30

Pro Glu Gln Pro Thr Pro Ala Pro Lys Pro Glu Gln Pro Ala Pro Ala
        35                  40                  45

Pro Lys Pro Glu Gln Pro Ala Pro Ala Pro Lys Pro Glu Gln Pro Ala
    50                  55                  60

Pro Ala Pro Lys Pro Glu Gln Pro Thr Pro Gly Pro Lys Ile
65                  70                  75
```

<210> SEQ ID NO 108
<211> LENGTH: 78
<212> TYPE: PRT
<213> ORGANISM: Streptococcus pneumoniae

<400> SEQUENCE: 108

Pro Asp Gly Asp Glu Glu Glu Thr Pro Ala Pro Ala Pro Gln Pro Glu
1               5                   10                  15

Gln Pro Ala Pro Ala Pro Gln Pro Glu Gln Pro Ala Pro Ala Pro Lys
            20                  25                  30

Pro Glu Gln Pro Ala Pro Ala Pro Lys Pro Glu Gln Pro Thr Pro Ala
        35                  40                  45

Pro Lys Pro Glu Gln Pro Thr Pro Ala Pro Lys Pro Glu Gln Pro Thr
    50                  55                  60

Pro Ala Pro Lys Pro Glu Gln Pro Thr Pro Ala Pro Lys Thr
65                  70                  75

<210> SEQ ID NO 109
<211> LENGTH: 69
<212> TYPE: PRT
<213> ORGANISM: Streptococcus pneumoniae

<400> SEQUENCE: 109

Pro Asp Gly Asp Glu Glu Glu Thr Pro Ala Pro Ala Pro Gln Pro Glu
1               5                   10                  15

Gln Pro Ala Pro Ala Pro Gln Pro Glu Gln Pro Ala Pro Ala Pro Lys
            20                  25                  30

Pro Glu Gln Pro Ala Pro Ala Pro Lys Pro Glu Gln Pro Thr Pro Ala
        35                  40                  45

Pro Lys Pro Glu Gln Pro Thr Pro Ala Pro Lys Pro Glu Gln Pro Thr
    50                  55                  60

Pro Ala Pro Lys Thr
65

<210> SEQ ID NO 110
<211> LENGTH: 60
<212> TYPE: PRT
<213> ORGANISM: Streptococcus pneumoniae

<400> SEQUENCE: 110

Pro Asp Gly Asp Glu Glu Glu Thr Pro Ala Pro Ala Pro Gln Pro Glu
1               5                   10                  15

Gln Pro Ala Pro Ala Pro Gln Pro Glu Gln Pro Ala Pro Ala Pro Lys
            20                  25                  30

Pro Glu Gln Pro Ala Pro Ala Pro Lys Pro Glu Gln Pro Thr Pro Ala
        35                  40                  45

Pro Lys Pro Glu Gln Pro Thr Pro Ala Pro Lys Thr
    50                  55                  60

<210> SEQ ID NO 111
<211> LENGTH: 60
<212> TYPE: PRT
<213> ORGANISM: Streptococcus pneumoniae

<400> SEQUENCE: 111

Pro Asp Gly Asp Glu Glu Glu Thr Pro Ala Pro Ala Pro Gln Pro Glu
1               5                   10                  15

Lys Pro Ala Pro Ala Pro Lys Pro Glu Gln Pro Ala Pro Ala Pro Lys

```
                20                  25                  30

Pro Glu Gln Pro Thr Pro Ala Pro Lys Pro Glu Gln Pro Thr Pro Ala
            35                  40                  45

Pro Lys Pro Glu Gln Pro Thr Pro Ala Pro Lys Pro
        50                  55                  60

<210> SEQ ID NO 112
<211> LENGTH: 81
<212> TYPE: PRT
<213> ORGANISM: Streptococcus pneumoniae

<400> SEQUENCE: 112

Pro Asp Gly Asp Glu Glu Glu Thr Pro Ala Pro Ala Pro Ala Pro Lys
1               5                   10                  15

Pro Glu Gln Pro Ala Pro Ala Pro Ala Pro Lys Pro Glu Gln Pro Ala
            20                  25                  30

Pro Ala Pro Ala Pro Lys Pro Glu Gln Pro Ala Pro Ala Pro Ala Pro
        35                  40                  45

Lys Pro Glu Gln Pro Ala Pro Ala Pro Ala Pro Lys Pro Glu Gln Pro
    50                  55                  60

Ala Pro Ala Pro Ala Pro Lys Pro Glu Gln Pro Thr Pro Ala Pro Lys
65                  70                  75                  80

Thr

<210> SEQ ID NO 113
<211> LENGTH: 92
<212> TYPE: PRT
<213> ORGANISM: Streptococcus pneumoniae

<400> SEQUENCE: 113

Pro Asp Gly Asp Glu Glu Glu Thr Pro Ala Pro Ala Pro Ala Pro Lys
1               5                   10                  15

Pro Glu Gln Pro Ala Pro Ala Pro Ala Pro Lys Pro Glu Gln Pro Ala
            20                  25                  30

Pro Ala Pro Ala Pro Lys Pro Glu Gln Pro Ala Pro Ala Pro Ala Pro
        35                  40                  45

Lys Pro Glu Gln Pro Ala Pro Ala Pro Ala Pro Lys Pro Glu Gln Pro
    50                  55                  60

Ala Pro Ala Pro Ala Pro Lys Pro Glu Gln Pro Ala Pro Ala Pro Ala
65                  70                  75                  80

Pro Lys Pro Glu Gln Pro Thr Pro Ala Pro Lys Thr
            85                  90

<210> SEQ ID NO 114
<211> LENGTH: 86
<212> TYPE: PRT
<213> ORGANISM: Streptococcus pneumoniae

<400> SEQUENCE: 114

Pro Asp Gly Asp Glu Glu Glu Thr Pro Ala Pro Ala Pro Gln Pro Glu
1               5                   10                  15

Gln Pro Ala Pro Ala Pro Ala Pro Lys Pro Glu Gln Pro Ala Pro Ala
            20                  25                  30

Pro Lys Pro Glu Lys Ser Ala Asp Gln Gln Ala Glu Glu Asp Tyr Ala
        35                  40                  45

Arg Arg Ser Glu Glu Glu Tyr Asn Arg Leu Thr Gln Gln Gln Pro Pro
    50                  55                  60
```

```
Lys Ala Glu Lys Pro Ala Pro Ala Pro Lys Pro Glu Gln Pro
 65                  70                  75                  80

Ala Pro Ala Pro Lys Thr
                 85

<210> SEQ ID NO 115
<211> LENGTH: 79
<212> TYPE: PRT
<213> ORGANISM: Streptococcus pneumoniae

<400> SEQUENCE: 115

Pro Asp Gly Asp Glu Glu Glu Thr Pro Ala Pro Ala Pro Gln Pro Glu
  1               5                  10                  15

Gln Pro Ala Pro Ala Pro Ala Pro Lys Pro Glu Gln Pro Ala Pro Ala
             20                  25                  30

Pro Ala Pro Lys Pro Glu Gln Pro Ala Pro Ala Pro Ala Pro Lys Pro
         35                  40                  45

Glu Gln Pro Ala Pro Ala Pro Ala Pro Lys Pro Glu Gln Pro Ala Pro
     50                  55                  60

Ala Pro Ala Pro Lys Pro Glu Gln Pro Ala Pro Ala Pro Lys Thr
 65                  70                  75

<210> SEQ ID NO 116
<211> LENGTH: 51
<212> TYPE: PRT
<213> ORGANISM: Streptococcus pneumoniae

<400> SEQUENCE: 116

Pro Asp Gly Asp Glu Glu Glu Thr Pro Ala Pro Ala Pro Gln Pro Glu
  1               5                  10                  15

Gln Pro Ala Pro Ala Pro Gln Pro Glu Gln Pro Ala Pro Ala Pro Lys
             20                  25                  30

Pro Glu Gln Pro Ala Pro Ala Pro Lys Pro Glu Gln Pro Thr Pro Ala
         35                  40                  45

Pro Lys Thr
     50

<210> SEQ ID NO 117
<211> LENGTH: 57
<212> TYPE: PRT
<213> ORGANISM: Streptococcus pneumoniae

<400> SEQUENCE: 117

Pro Asp Gly Asp Glu Glu Glu Thr Pro Ala Pro Ala Pro Gln Pro Glu
  1               5                  10                  15

Gln Pro Ala Pro Ala Pro Ala Pro Lys Pro Glu Gln Pro Ala Pro Ala
             20                  25                  30

Pro Ala Pro Lys Pro Glu Gln Pro Ala Pro Ala Pro Ala Pro Lys Pro
         35                  40                  45

Glu Gln Pro Ala Pro Ala Pro Lys Thr
     50                  55

<210> SEQ ID NO 118
<211> LENGTH: 70
<212> TYPE: PRT
<213> ORGANISM: Streptococcus pneumoniae

<400> SEQUENCE: 118

Pro Asp Gly Asp Glu Glu Glu Thr Pro Ala Pro Ala Pro Ala Pro Lys
  1               5                  10                  15
```

```
Pro Gln Pro Ala Pro Ala Pro Ala Pro Lys Pro Glu Gln Pro Ala
            20                  25                  30

Pro Ala Pro Ala Pro Lys Pro Glu Gln Pro Ala Pro Ala Pro Ala Pro
        35                  40                  45

Lys Pro Glu Gln Pro Ala Pro Ala Pro Ala Pro Lys Pro Glu Gln Pro
50                  55                  60

Thr Pro Ala Pro Lys Thr
65                  70

<210> SEQ ID NO 119
<211> LENGTH: 87
<212> TYPE: PRT
<213> ORGANISM: Streptococcus pneumoniae

<400> SEQUENCE: 119

Pro Glu Lys Pro Ala Glu Glu Pro Glu Asn Pro Ala Pro Ala Pro Lys
1               5                   10                  15

Pro Ala Pro Ala Pro Gln Pro Glu Gln Pro Ala Pro Ala Pro Ala Pro
            20                  25                  30

Lys Pro Glu Gln Pro Ala Pro Ala Pro Ala Pro Lys Pro Glu Gln Pro
        35                  40                  45

Ala Pro Ala Pro Ala Pro Lys Pro Glu Gln Pro Ala Pro Ala Pro Ala
    50                  55                  60

Pro Lys Pro Glu Gln Pro Ala Pro Ala Pro Ala Pro Lys Pro Glu Gln
65                  70                  75                  80

Pro Thr Pro Ala Pro Lys Thr
                85

<210> SEQ ID NO 120
<211> LENGTH: 59
<212> TYPE: PRT
<213> ORGANISM: Streptococcus pneumoniae

<400> SEQUENCE: 120

Pro Asp Gly Asp Glu Glu Glu Thr Pro Ala Pro Ala Pro Ala Pro Lys
1               5                   10                  15

Pro Glu Gln Pro Ala Pro Ala Pro Ala Pro Lys Pro Glu Gln Pro Ala
            20                  25                  30

Pro Ala Pro Ala Pro Lys Pro Glu Gln Pro Ala Pro Ala Pro Ala Pro
        35                  40                  45

Lys Pro Glu Gln Pro Thr Pro Ala Pro Lys Ser
    50                  55

<210> SEQ ID NO 121
<211> LENGTH: 59
<212> TYPE: PRT
<213> ORGANISM: Streptococcus pneumoniae

<400> SEQUENCE: 121

Pro Asp Gly Asp Glu Glu Glu Thr Pro Ala Pro Ala Pro Ala Pro Lys
1               5                   10                  15

Pro Glu Gln Pro Ala Pro Ala Pro Ala Pro Lys Pro Glu Gln Pro Ala
            20                  25                  30

Pro Ala Pro Ala Pro Lys Pro Glu Gln Pro Ala Pro Ala Pro Ala Pro
        35                  40                  45

Lys Pro Glu Gln Pro Thr Pro Ala Pro Lys Thr
    50                  55
```

<210> SEQ ID NO 122
<211> LENGTH: 61
<212> TYPE: PRT
<213> ORGANISM: Streptococcus pneumoniae

<400> SEQUENCE: 122

Pro Ala Pro Ala Pro Gln Pro Glu Gln Pro Ala Pro Ala Pro Gln Pro
1               5                   10                  15

Glu Gln Pro Ala Pro Ala Pro Gln Pro Glu Gln Pro Ala Pro Ala Pro
            20                  25                  30

Gln Pro Glu Gln Pro Ala Pro Ala Pro Gln Pro Glu Gln Pro Ala Pro
        35                  40                  45

Ala Pro Gln Pro Glu Gln Pro Ala Pro Ala Pro Lys Ile
    50                  55                  60

<210> SEQ ID NO 123
<211> LENGTH: 133
<212> TYPE: PRT
<213> ORGANISM: Streptococcus pneumoniae

<400> SEQUENCE: 123

Pro Ala Pro Ala Pro Gln Pro Glu Gln Pro Ala Pro Ala Pro Gln Pro
1               5                   10                  15

Glu Gln Pro Ala Pro Ala Pro Gln Pro Glu Gln Pro Ala Pro Ala Pro
            20                  25                  30

Gln Pro Glu Gln Pro Ala Pro Ala Pro Gln Pro Glu Gln Pro Ala Pro
        35                  40                  45

Ala Pro Gln Pro Glu Gln Pro Ala Pro Ala Pro Gln Pro Glu Gln Pro
    50                  55                  60

Ala Pro Ala Pro Gln Pro Glu Gln Pro Ala Pro Ala Pro Gln Pro Glu
65                  70                  75                  80

Gln Pro Ala Pro Ala Pro Gln Pro Glu Gln Pro Ala Pro Ala Pro Gln
                85                  90                  95

Pro Glu Gln Pro Ala Pro Ala Pro Gln Pro Glu Gln Pro Ala Pro Ala
            100                 105                 110

Pro Gln Pro Glu Gln Pro Ala Pro Ala Pro Gln Pro Glu Gln Pro Ala
        115                 120                 125

Pro Ala Pro Lys Ile
    130

<210> SEQ ID NO 124
<211> LENGTH: 75
<212> TYPE: PRT
<213> ORGANISM: Streptococcus pneumoniae

<400> SEQUENCE: 124

Pro Asp Gly Asp Glu Glu Thr Pro Ala Pro Gln Pro Glu
1               5                   10                  15

Gln Pro Ala Pro Ala Pro Lys Pro Glu Gln Pro Ala Pro Ala Pro Lys
            20                  25                  30

Pro Glu Gln Pro Ala Pro Ala Pro Lys Pro Glu Gln Pro Ala Pro Ala
        35                  40                  45

Pro Lys Pro Glu Gln Pro Ala Lys Pro Glu Lys Pro Ala Glu Glu Pro
    50                  55                  60

Thr Gln Pro Glu Lys Pro Ala Thr Pro Lys Thr
65                  70                  75

```
<210> SEQ ID NO 125
<211> LENGTH: 85
<212> TYPE: PRT
<213> ORGANISM: Streptococcus pneumoniae

<400> SEQUENCE: 125

Pro Asp Gly Gly Glu Glu Thr Pro Ala Pro Ala Pro Gln Pro Asp
1               5                   10                  15

Glu Pro Ala Pro Ala Pro Asn Ala Glu Gln Pro Ala Pro Ala
            20                  25                  30

Pro Lys Pro Glu Lys Ser Ala Asp Gln Gln Ala Glu Asp Tyr Ala
            35                  40                  45

Arg Arg Ser Glu Gly Glu Tyr Asn Arg Leu Thr Gln Gln Pro Pro
        50                  55                  60

Lys Ala Glu Lys Pro Ala Pro Ala Pro Lys Pro Glu Gln Pro
65                  70                  75                  80

Ala Pro Ala Pro Asn
                85

<210> SEQ ID NO 126
<211> LENGTH: 57
<212> TYPE: PRT
<213> ORGANISM: Streptococcus pneumoniae

<400> SEQUENCE: 126

Pro Asp Gly Asp Glu Glu Thr Pro Ala Pro Ala Pro Gln Pro Glu
1               5                   10                  15

Gln Pro Ala Pro Ala Pro Lys Pro Glu Gln Pro Ala Pro Ala Pro Lys
            20                  25                  30

Pro Glu Gln Pro Ala Lys Pro Glu Lys Pro Ala Glu Glu Pro Thr Gln
        35                  40                  45

Pro Glu Lys Pro Ala Thr Pro Lys Thr
    50                  55

<210> SEQ ID NO 127
<211> LENGTH: 66
<212> TYPE: PRT
<213> ORGANISM: Streptococcus pneumoniae

<400> SEQUENCE: 127

Pro Asp Gly Asp Glu Glu Thr Pro Ala Pro Ala Pro Gln Pro Glu
1               5                   10                  15

Gln Pro Ala Pro Ala Pro Lys Pro Glu Gln Pro Ala Pro Ala Pro Lys
            20                  25                  30

Pro Glu Gln Pro Ala Pro Ala Pro Lys Pro Glu Gln Pro Ala Lys Pro
        35                  40                  45

Glu Lys Pro Ala Glu Glu Pro Thr Gln Pro Glu Lys Pro Ala Thr Pro
    50                  55                  60

Lys Thr
65

<210> SEQ ID NO 128
<211> LENGTH: 69
<212> TYPE: PRT
<213> ORGANISM: Streptococcus pneumoniae

<400> SEQUENCE: 128

Pro Asp Gly Asp Glu Glu Thr Pro Ala Pro Ala Pro Gln Pro Glu
1               5                   10                  15
```

```
Gln Pro Ala Pro Ala Pro Gln Pro Glu Pro Ala Pro Ala Pro Lys
            20                  25                  30

Pro Glu Gln Pro Ala Pro Ala Pro Lys Pro Glu Gln Pro Ala Pro Ala
            35                  40                  45

Pro Lys Pro Glu Gln Pro Thr Pro Ala Pro Lys Pro Glu Gln Pro Thr
    50                  55                  60

Pro Ala Pro Lys Thr
65
```

<210> SEQ ID NO 129
<211> LENGTH: 92
<212> TYPE: PRT
<213> ORGANISM: Streptococcus pneumoniae

<400> SEQUENCE: 129

```
Pro Glu Lys Pro Ala Pro Ala Pro Glu Thr Pro Ala Pro Glu Ala Pro
1               5                   10                  15

Ala Glu Gln Pro Lys Pro Ala Pro Ala Pro Gln Pro Ala Pro Ala Pro
            20                  25                  30

Lys Pro Glu Lys Pro Ala Glu Gln Pro Lys Pro Glu Lys Thr Asp Asp
            35                  40                  45

Gln Gln Ala Glu Glu Asp Tyr Ala Arg Arg Ser Glu Glu Glu Tyr Asn
    50                  55                  60

Arg Leu Thr Gln Gln Gln Pro Pro Lys Ala Glu Lys Pro Ala Pro Ala
65                  70                  75                  80

Pro Gln Pro Glu Gln Pro Ala Pro Ala Pro Lys Thr
                85                  90
```

<210> SEQ ID NO 130
<211> LENGTH: 83
<212> TYPE: PRT
<213> ORGANISM: Streptococcus pneumoniae

<400> SEQUENCE: 130

```
Pro Glu Lys Pro Ala Pro Ala Pro Glu Thr Pro Ala Pro Glu Ala Pro
1               5                   10                  15

Ala Glu Gln Pro Lys Pro Ala Pro Ala Pro Gln Pro Ala Pro Ala Pro
            20                  25                  30

Lys Pro Glu Lys Pro Ala Glu Gln Pro Lys Pro Glu Lys Thr Asp Asp
            35                  40                  45

Gln Gln Ala Glu Glu Asp Tyr Ala Arg Arg Ser Glu Glu Glu Tyr Asn
    50                  55                  60

Arg Leu Thr Gln Gln Gln Pro Pro Lys Ala Glu Lys Pro Ala Pro Ala
65                  70                  75                  80

Pro Lys Thr
```

<210> SEQ ID NO 131
<211> LENGTH: 92
<212> TYPE: PRT
<213> ORGANISM: Streptococcus pneumoniae

<400> SEQUENCE: 131

```
Pro Glu Lys Pro Ala Pro Ala Pro Glu Thr Pro Ala Pro Glu Ala Pro
1               5                   10                  15

Ala Glu Gln Pro Lys Pro Ala Pro Ala Pro Gln Pro Ala Pro Ala Pro
            20                  25                  30

Lys Pro Glu Lys Pro Ala Glu Gln Pro Lys Ala Glu Lys Thr Asp Asp
            35                  40                  45
```

-continued

Gln Gln Ala Glu Glu Asp Tyr Ala Arg Arg Ser Glu Glu Tyr Asn
    50                  55                  60

Arg Leu Thr Gln Gln Gln Pro Pro Lys Ala Glu Lys Pro Ala Pro Ala
65                  70                  75                  80

Pro Lys Pro Glu Gln Pro Ala Pro Ala Pro Lys Ile
                85                  90

<210> SEQ ID NO 132
<211> LENGTH: 92
<212> TYPE: PRT
<213> ORGANISM: Streptococcus pneumoniae

<400> SEQUENCE: 132

Pro Glu Lys Pro Ala Pro Ala Pro Glu Thr Pro Ala Pro Glu Ala Pro
1               5                   10                  15

Ala Glu Gln Pro Lys Pro Ala Pro Ala Pro Gln Pro Ala Pro Ala Pro
                20                  25                  30

Lys Pro Glu Lys Pro Ala Glu Gln Pro Lys Ala Glu Lys Thr Asp Asp
            35                  40                  45

Gln Gln Ala Glu Glu Asp Tyr Ala Arg Arg Ser Glu Glu Tyr Asn
    50                  55                  60

Arg Leu Thr Gln Gln Gln Pro Pro Lys Ala Glu Lys Pro Ala Pro Ala
65                  70                  75                  80

Pro Lys Pro Glu Gln Pro Val Pro Ala Pro Lys Thr
                85                  90

<210> SEQ ID NO 133
<211> LENGTH: 128
<212> TYPE: PRT
<213> ORGANISM: Streptococcus pneumoniae

<400> SEQUENCE: 133

Pro Ala Pro Glu Ala Pro Ala Glu Gln Pro Lys Pro Glu Lys Ser Ala
1               5                   10                  15

Glu Gln Gln Ala Glu Glu Asp Tyr Ala Arg Arg Ser Glu Glu Glu Tyr
                20                  25                  30

Asn Arg Leu Thr Gln Gln Gln Pro Lys Ala Glu Lys Pro Ala Glu
            35                  40                  45

Glu Pro Thr Arg Pro Ala Pro Ala Pro Glu Ala Pro Ala Glu Gln Pro
        50                  55                  60

Lys Pro Glu Lys Ser Ala Glu Gln Gln Ala Glu Glu Asp Tyr Ala Arg
65                  70                  75                  80

Arg Ser Glu Glu Glu Tyr Asn Arg Leu Thr Gln Gln Gln Pro Pro Lys
                85                  90                  95

Ala Glu Lys Pro Ala Glu Glu Pro Thr Gln Pro Ala Pro Ala Pro Glu
                100                 105                 110

Gln Pro Thr Glu Pro Thr Gln Pro Glu Lys Pro Val Ala Pro Lys Thr
            115                 120                 125

<210> SEQ ID NO 134
<211> LENGTH: 90
<212> TYPE: PRT
<213> ORGANISM: Streptococcus pneumoniae

<400> SEQUENCE: 134

Pro Glu Lys Pro Ala Pro Ala Pro Glu Thr Pro Ala Pro Glu Ala Pro
1               5                   10                  15

Ala Glu Gln Pro Lys Pro Ala Pro Gln Pro Ala Pro
            20                  25                  30

Lys Pro Glu Lys Pro Ala Glu Gln Pro Lys Ala Glu Lys Pro Ala Asp
            35                  40                  45

Gln Gln Ala Glu Glu Asp Tyr Asp Arg Arg Ser Glu Glu Tyr Asn
        50                  55                  60

Arg Leu Thr Gln Gln Gln Pro Pro Lys Ala Glu Lys Pro Ala Pro Ala
65                  70                  75                  80

Pro Gln Pro Glu Gln Pro Ala Pro Ala Pro
                85                  90

<210> SEQ ID NO 135
<211> LENGTH: 92
<212> TYPE: PRT
<213> ORGANISM: Streptococcus pneumoniae

<400> SEQUENCE: 135

Pro Glu Lys Pro Ala Pro Ala Pro Glu Thr Pro Ala Pro Glu Ala Pro
1               5                   10                  15

Ala Glu Gln Pro Lys Pro Ala Pro Ala Pro Gln Pro Ala Pro Ala Pro
            20                  25                  30

Lys Pro Glu Lys Pro Ala Glu Gln Pro Lys Ala Glu Lys Pro Ala Asp
            35                  40                  45

Gln Gln Ala Glu Glu Asp Tyr Asp Arg Arg Ser Glu Glu Tyr Asn
        50                  55                  60

Arg Leu Thr Gln Gln Gln Pro Pro Lys Ala Glu Lys Pro Ala Pro Ala
65                  70                  75                  80

Pro Gln Pro Glu Gln Pro Ala Pro Ala Pro Lys Thr
                85                  90

<210> SEQ ID NO 136
<211> LENGTH: 106
<212> TYPE: PRT
<213> ORGANISM: Streptococcus pneumoniae

<400> SEQUENCE: 136

Pro Glu Lys Pro Ala Glu Glu Pro Ser Gln Pro Glu Lys Pro Ala Glu
1               5                   10                  15

Glu Ala Pro Ala Pro Glu Gln Pro Thr Glu Pro Thr Gln Pro Glu Lys
            20                  25                  30

Pro Ala Glu Gln Pro Gln Pro Ala Pro Gln Pro Glu Lys Pro
        35                  40                  45

Ala Glu Glu Thr Pro Ala Pro Lys Pro Glu Lys Pro Ala Glu Gln Pro
    50                  55                  60

Lys Ala Glu Lys Pro Ala Asp Gln Gln Ala Glu Glu Asp Tyr Ala Arg
65                  70                  75                  80

Arg Ser Glu Glu Glu Tyr Asn Arg Leu Thr Gln Gln Gln Pro Pro Lys
                85                  90                  95

Ala Glu Lys Pro Ala Pro Ala Pro Lys Thr
            100                 105

<210> SEQ ID NO 137
<211> LENGTH: 100
<212> TYPE: PRT
<213> ORGANISM: Streptococcus pneumoniae

<400> SEQUENCE: 137

Pro Glu Lys Ser Ala Glu Glu Pro Ser Gln Pro Glu Lys Pro Ala Glu

```
                1               5                   10                  15
            Glu Ala Pro Ala Pro Glu Gln Pro Thr Glu Pro Thr Gln Pro Glu Lys
                            20                  25                  30
            Pro Ala Glu Glu Thr Pro Ala Pro Lys Pro Glu Lys Pro Ala Glu Gln
                            35                  40                  45
            Pro Lys Ala Glu Lys Thr Asp Asp Gln Gln Ala Glu Glu Asp Tyr Ala
                50                  55                  60
            Arg Arg Ser Glu Glu Tyr Asn Arg Leu Thr Gln Gln Gln Pro Pro
            65                  70                  75                  80
            Lys Ala Glu Lys Pro Ala Pro Ala Pro Gln Pro Glu Gln Pro Ala Pro
                            85                  90                  95
            Ala Pro Lys Thr
                        100
```

<210> SEQ ID NO 138
<211> LENGTH: 93
<212> TYPE: PRT
<213> ORGANISM: Streptococcus pneumoniae

<400> SEQUENCE: 138

```
            Pro Glu Lys Ser Ala Glu Glu Pro Ser Gln Pro Glu Lys Pro Ala Glu
            1               5                   10                  15
            Glu Ala Pro Ala Pro Glu Gln Pro Thr Glu Pro Thr Gln Pro Glu Lys
                            20                  25                  30
            Pro Ala Glu Glu Thr Pro Ala Pro Lys Pro Glu Lys Pro Ala Glu Gln
                            35                  40                  45
            Pro Lys Ala Glu Lys Thr Asp Asp Gln Gln Ala Glu Glu Asp Tyr Ala
                50                  55                  60
            Arg Arg Ser Glu Glu Tyr Asn Arg Leu Thr Gln Gln Gln Pro Pro
            65                  70                  75                  80
            Lys Ala Glu Lys Pro Ala Pro Ala Pro Gln Pro Glu Gln
                            85                  90
```

<210> SEQ ID NO 139
<211> LENGTH: 87
<212> TYPE: PRT
<213> ORGANISM: Streptococcus pneumoniae

<400> SEQUENCE: 139

```
            Pro Glu Lys Pro Ala Glu Glu Ser Glu Asn Pro Ala Pro Ala Pro Lys
            1               5                   10                  15
            Pro Ala Pro Ala Pro Ala Pro Lys Pro Glu Gln Pro Ala Pro Ala Pro
                            20                  25                  30
            Ala Pro Lys Pro Glu Lys Ser Ala Asp Gln Gln Ala Glu Glu Asp Tyr
                            35                  40                  45
            Ala Arg Arg Ser Glu Glu Glu Tyr Asn Arg Leu Thr Gln Gln Gln Pro
                50                  55                  60
            Pro Lys Ala Glu Lys Pro Ala Pro Ala Pro Ala Pro Lys Pro Glu Gln
            65                  70                  75                  80
            Pro Ala Pro Ala Pro Lys Thr
                        85
```

<210> SEQ ID NO 140
<211> LENGTH: 86
<212> TYPE: PRT
<213> ORGANISM: Streptococcus pneumoniae

<400> SEQUENCE: 140

```
Pro Glu Lys Pro Ala Glu Glu Pro Glu Asn Pro Ala Pro Ala Pro Lys
1               5                   10                  15

Pro Ala Pro Ala Pro Gln Pro Glu Lys Pro Glu Lys Pro Ala Glu Gln
            20                  25                  30

Pro Lys Pro Glu Lys Pro Asp Asp Gln Gln Ala Glu Glu Asp Tyr Ala
        35                  40                  45

Arg Arg Ser Glu Glu Glu Tyr Asn Arg Leu Thr Gln Gln Gln Pro Pro
    50                  55                  60

Lys Ala Glu Lys Pro Ala Pro Ala Pro Ala Pro Lys Pro Glu Gln Pro
65                  70                  75                  80

Ala Pro Ala Pro Lys Thr
                85
```

<210> SEQ ID NO 141
<211> LENGTH: 77
<212> TYPE: PRT
<213> ORGANISM: Streptococcus pneumoniae

<400> SEQUENCE: 141

```
Pro Glu Lys Pro Ala Glu Glu Pro Glu Asn Pro Ala Pro Ala Pro Lys
1               5                   10                  15

Pro Ala Pro Ala Pro Gln Pro Glu Lys Pro Glu Lys Pro Ala Glu Gln
            20                  25                  30

Pro Lys Pro Glu Lys Pro Asp Asp Gln Gln Ala Glu Glu Asp Tyr Ala
        35                  40                  45

Arg Arg Ser Glu Glu Glu Tyr Asn Arg Leu Thr Gln Gln Gln Pro Pro
    50                  55                  60

Lys Ala Glu Lys Pro Ala Pro Ala Pro Lys Thr
65                  70                  75
```

<210> SEQ ID NO 142
<211> LENGTH: 129
<212> TYPE: PRT
<213> ORGANISM: Streptococcus pneumoniae

<400> SEQUENCE: 142

```
Pro Glu Lys Pro Ala Glu Glu Pro Glu Asn Pro Ala Pro Ala Pro Lys
1               5                   10                  15

Pro Ala Pro Ala Pro Gln Pro Glu Lys Pro Ala Pro Ala Pro Ala Pro
            20                  25                  30

Ala Pro Lys Pro Glu Lys Ser Ala Asp Gln Gln Ala Glu Glu Asp Tyr
        35                  40                  45

Ala Arg Arg Ser Glu Glu Glu Tyr Asn Arg Leu Thr Gln Gln Gln Pro
    50                  55                  60

Pro Lys Ala Glu Lys Pro Ala Pro Ala Pro Lys Pro Glu Lys
65                  70                  75                  80

Ser Ala Asp Gln Gln Ala Glu Glu Asp Tyr Ala Arg Arg Ser Glu Glu
                85                  90                  95

Glu Tyr Asn Arg Leu Thr Gln Gln Gln Pro Pro Lys Ala Glu Lys Pro
                100                 105                 110

Ala Pro Ala Pro Ala Pro Lys Pro Glu Gln Pro Ala Pro Ala Pro Lys
            115                 120                 125

Thr
```

<210> SEQ ID NO 143
<211> LENGTH: 89

<212> TYPE: PRT
<213> ORGANISM: Streptococcus pneumoniae

<400> SEQUENCE: 143

Pro Glu Lys Pro Ala Pro Ala Pro Glu Thr Pro Ala Pro Glu Ala Pro
1               5                   10                  15

Ala Pro Ala Pro Lys Pro Ala Pro Ala Pro Gln Pro Glu Lys Pro Ala
            20                  25                  30

Pro Ala Pro Lys Pro Glu Lys Pro Ala Glu Gln Pro Lys Pro Glu Lys
        35                  40                  45

Pro Ala Asp Gln Gln Ala Glu Glu Asp Tyr Ala Arg Arg Ser Glu Glu
    50                  55                  60

Glu Tyr Asn Arg Leu Thr Gln Gln Gln Pro Ala Pro Ala Pro Lys Pro
65                  70                  75                  80

Glu Gln Pro Ala Pro Ala Pro Lys Thr
                85

<210> SEQ ID NO 144
<211> LENGTH: 96
<212> TYPE: PRT
<213> ORGANISM: Streptococcus pneumoniae

<400> SEQUENCE: 144

Pro Glu Lys Pro Ala Pro Ala Pro Glu Thr Pro Ala Pro Glu Ala Pro
1               5                   10                  15

Ala Pro Ala Glu Gln Pro Lys Pro Ala Pro Glu Thr Pro Ala Pro Ala
            20                  25                  30

Pro Lys Pro Glu Lys Pro Ala Glu Gln Pro Lys Pro Glu Lys Pro Ala
        35                  40                  45

Asp Gln Gln Ala Glu Glu Asp Tyr Ala Arg Arg Ser Glu Glu Glu Tyr
    50                  55                  60

Asn Arg Leu Thr Gln Gln Gln Pro Ala Pro Ala Pro Lys Pro Glu Gln
65                  70                  75                  80

Pro Ala Lys Pro Glu Lys Pro Ala Glu Glu Pro Thr Gln Pro Glu Lys
                85                  90                  95

<210> SEQ ID NO 145
<211> LENGTH: 85
<212> TYPE: PRT
<213> ORGANISM: Streptococcus pneumoniae

<400> SEQUENCE: 145

Pro Glu Lys Pro Ala Glu Glu Pro Asn Pro Ala Pro Ala Pro Lys
1               5                   10                  15

Pro Ala Pro Ala Pro Gln Pro Glu Lys Pro Ala Pro Ala Pro Ala Pro
            20                  25                  30

Lys Pro Glu Lys Ser Ala Asp Gln Gln Ala Glu Glu Asp Tyr Ala Arg
        35                  40                  45

Arg Ser Glu Glu Glu Tyr Asn Arg Leu Thr Gln Gln Pro Pro Lys
    50                  55                  60

Ala Glu Lys Pro Ala Pro Ala Pro Val Pro Lys Pro Glu Gln Pro Ala
65                  70                  75                  80

Pro Ala Pro Lys Thr
                85

<210> SEQ ID NO 146
<211> LENGTH: 86
<212> TYPE: PRT

<213> ORGANISM: Streptococcus pneumoniae

<400> SEQUENCE: 146

Pro Glu Lys Pro Ala Glu Glu Thr Pro Ala Pro Lys Pro Glu
1               5                   10                  15

Gln Pro Ala Glu Gln Pro Lys Pro Ala Pro Ala Pro Gln Pro Glu Lys
            20                  25                  30

Pro Ala Glu Glu Pro Glu Asn Pro Ala Pro Ala Pro Gln Pro Glu Lys
        35                  40                  45

Ser Ala Asp Gln Gln Ala Glu Asp Tyr Ala Arg Arg Ser Glu Glu
    50                  55                  60

Glu Tyr Asn Arg Leu Thr Gln Gln Gln Pro Lys Ala Glu Lys Pro
65                  70                  75                  80

Ala Pro Ala Pro Gln Pro
                85

<210> SEQ ID NO 147
<211> LENGTH: 88
<212> TYPE: PRT
<213> ORGANISM: Streptococcus pneumoniae

<400> SEQUENCE: 147

Pro Glu Thr Pro Ala Pro Ala Pro Lys Pro Glu Thr Pro Ala Pro Ala
1               5                   10                  15

Pro Glu Ala Pro Ala Pro Ala Pro Lys Pro Glu Gln Pro Ala
            20                  25                  30

Pro Ala Pro Lys Pro Glu Lys Ser Ala Asp Gln Gln Ala Glu Glu Asp
        35                  40                  45

Tyr Ala Arg Arg Ser Glu Glu Glu Tyr Asn Arg Leu Thr Gln Gln Gln
    50                  55                  60

Pro Pro Lys Ala Glu Lys Pro Ala Pro Ala Pro Lys Pro Glu
65                  70                  75                  80

Gln Pro Ala Pro Ala Pro Lys Thr
                85

<210> SEQ ID NO 148
<211> LENGTH: 85
<212> TYPE: PRT
<213> ORGANISM: Streptococcus pneumoniae

<400> SEQUENCE: 148

Pro Glu Lys Pro Ala Glu Glu Pro Glu Asn Pro Ala Pro Ala Pro Lys
1               5                   10                  15

Pro Ala Pro Ala Pro Gln Pro Glu Lys Pro Ala Pro Ala Pro Ala Pro
            20                  25                  30

Lys Pro Glu Lys Ser Ala Asp Gln Gln Ala Glu Glu Asp Tyr Ala Arg
        35                  40                  45

Arg Ser Glu Glu Glu Tyr Asn Arg Leu Thr Gln Gln Gln Pro Pro Lys
    50                  55                  60

Ala Glu Lys Pro Ala Pro Ala Pro Val Pro Lys Pro Glu Gln Pro Ala
65                  70                  75                  80

Pro Ala Pro Lys Ser
                85

<210> SEQ ID NO 149
<211> LENGTH: 85
<212> TYPE: PRT
<213> ORGANISM: Streptococcus pneumoniae

<400> SEQUENCE: 149

Pro Asp Gly Asp Glu Glu Thr Pro Ala Pro Glu Ala Pro Ala Glu
1               5                   10                  15

Gln Pro Lys Pro Glu Lys Pro Ala Glu Thr Pro Ala Pro Ala Pro
            20                  25                  30

Lys Pro Glu Lys Ser Ala Asp Gln Gln Ala Glu Glu Asp Tyr Ala Arg
        35                  40                  45

Arg Ser Glu Glu Glu Tyr Asn Arg Leu Thr Gln Gln Pro Pro Lys
    50                  55                  60

Ala Glu Lys Pro Ala Pro Ala Pro Ala Pro Lys Pro Glu Gln Pro Ala
65                  70                  75                  80

Pro Ala Pro Lys Thr
                85

<210> SEQ ID NO 150
<211> LENGTH: 84
<212> TYPE: PRT
<213> ORGANISM: Streptococcus pneumoniae

<400> SEQUENCE: 150

Pro Asp Gly Asp Glu Glu Thr Pro Ala Pro Glu Ala Pro Ala Glu
1               5                   10                  15

Gln Pro Lys Pro Glu Lys Pro Ala Glu Thr Pro Ala Pro Ala Pro
            20                  25                  30

Lys Pro Glu Lys Ser Ala Asp Gln Gln Ala Glu Glu Asp Tyr Ala Arg
        35                  40                  45

Arg Ser Glu Glu Glu Tyr Asn Arg Leu Thr Gln Gln Pro Pro Lys
    50                  55                  60

Ala Glu Lys Pro Ala Pro Ala Pro Ala Pro Lys Pro Glu Gln Pro Ala
65                  70                  75                  80

Pro Ala Pro Lys

<210> SEQ ID NO 151
<211> LENGTH: 85
<212> TYPE: PRT
<213> ORGANISM: Streptococcus pneumoniae

<400> SEQUENCE: 151

Pro Asp Gly Asp Glu Glu Thr Pro Pro Glu Ala Pro Ala Glu
1               5                   10                  15

Gln Pro Lys Pro Glu Lys Pro Ala Glu Thr Pro Ala Pro Ala Pro
            20                  25                  30

Lys Pro Glu Lys Ser Ala Asp Gln Gln Ala Glu Glu Asp Tyr Ala Arg
        35                  40                  45

Arg Ser Glu Glu Glu Tyr Asn Arg Leu Thr Gln Gln Pro Pro Lys
    50                  55                  60

Ala Glu Lys Pro Ala Pro Ala Pro Ala Pro Lys Pro Glu Gln Pro Ala
65                  70                  75                  80

Pro Ala Pro Lys Ser
                85

<210> SEQ ID NO 152
<211> LENGTH: 118
<212> TYPE: PRT
<213> ORGANISM: Streptococcus pneumoniae

<400> SEQUENCE: 152

```
Pro Asp Gly Asp Glu Glu Thr Pro Ala Pro Ala Pro Ala Glu
1               5                   10                  15

Gln Pro Lys Pro Glu Lys Pro Ala Glu Thr Pro Ala Pro Ala Pro
            20                  25                  30

Lys Pro Glu Lys Ser Ala Asp Gln Gln Ala Glu Glu Asp Tyr Ala Arg
        35                  40                  45

Arg Ser Glu Glu Glu Tyr Asn Arg Leu Thr Gln Gln Gln Pro Pro Lys
50                  55                  60

Ala Glu Lys Pro Ala Pro Ala Pro Ala Pro Lys Pro Glu Gln Pro Asp
65                  70                  75                  80

Pro Ala Pro Lys Pro Glu Gln Pro Ala Pro Lys Pro Glu Gln
                85                  90                  95

Pro Ala Lys Pro Glu Lys Pro Ala Glu Glu Pro Thr Gln Pro Glu Lys
                100                 105                 110

Pro Ala Thr Pro Lys Thr
            115
```

<210> SEQ ID NO 153
<211> LENGTH: 80
<212> TYPE: PRT
<213> ORGANISM: Streptococcus pneumoniae

<400> SEQUENCE: 153

```
Pro Asp Gly Asp Glu Glu Glu Thr Pro Ala Pro Ala Pro Gln Pro Glu
1               5                   10                  15

Lys Pro Ala Glu Glu Pro Glu Asn Pro Ala Pro Ala Pro Lys Pro Glu
            20                  25                  30

Lys Ser Ala Asp Gln Gln Ala Glu Glu Asp Tyr Ala Arg Arg Ser Glu
        35                  40                  45

Glu Glu Tyr Asn Arg Leu Thr Gln Gln Gln Pro Pro Lys Ala Glu Lys
50                  55                  60

Pro Ala Pro Ala Pro Gln Pro Glu Gln Pro Ala Pro Ala Pro Lys Ile
65                  70                  75                  80
```

<210> SEQ ID NO 154
<211> LENGTH: 85
<212> TYPE: PRT
<213> ORGANISM: Streptococcus pneumoniae

<400> SEQUENCE: 154

```
Pro Asp Gly Asp Glu Glu Glu Thr Pro Ala Pro Ala Pro Gln Pro Ala
1               5                   10                  15

Pro Ala Pro Lys Pro Ala Pro Ala Pro Gln Pro Glu Lys Pro Ala Glu
            20                  25                  30

Gln Pro Lys Ala Glu Lys Pro Ala Asp Gln Gln Ala Glu Glu Asp Tyr
        35                  40                  45

Ala Arg Arg Ser Glu Glu Glu Tyr Asn Arg Leu Thr Gln Gln Gln Pro
50                  55                  60

Pro Lys Ala Glu Lys Pro Ala Pro Ala Pro Gln Pro Glu Gln Pro Ala
65                  70                  75                  80

Pro Ala Pro Lys Thr
            85
```

<210> SEQ ID NO 155
<211> LENGTH: 92
<212> TYPE: PRT
<213> ORGANISM: Streptococcus pneumoniae

```
<400> SEQUENCE: 155

Pro Glu Lys Pro Ala Pro Ala Pro Glu Thr Pro Ala Pro Glu Ala Pro
1               5                   10                  15

Ala Glu Gln Pro Lys Pro Ala Pro Ala Pro Gln Pro Ala Pro Ala Pro
            20                  25                  30

Lys Pro Glu Lys Pro Ala Glu Gln Pro Lys Ala Glu Lys Pro Ala Asp
        35                  40                  45

Gln Gln Ala Glu Glu Asp Tyr Ala Arg Arg Ser Glu Glu Tyr Asn
50                  55                  60

Arg Leu Thr Gln Gln Pro Pro Lys Ala Glu Lys Pro Ala Pro Ala
65              70                  75                  80

Pro Gln Pro Glu Gln Pro Ala Pro Ala Pro Lys Thr
                85                  90

<210> SEQ ID NO 156
<211> LENGTH: 89
<212> TYPE: PRT
<213> ORGANISM: Streptococcus pneumoniae

<400> SEQUENCE: 156

Pro Glu Lys Pro Ala Pro Ala Pro Glu Thr Pro Ala Pro Glu Ala Pro
1               5                   10                  15

Ala Glu Gln Pro Lys Pro Ala Pro Ala Pro Gln Pro Ala Pro Ala Pro
            20                  25                  30

Lys Pro Glu Lys Pro Ala Glu Gln Pro Lys Ala Glu Lys Thr Asp Asp
        35                  40                  45

Gln Gln Ala Glu Glu Asp Tyr Ala Arg Arg Ser Glu Glu Tyr Asn
50                  55                  60

Arg Leu Thr Gln Gln Pro Pro Lys Ala Glu Lys Pro Ala Pro Ala
65              70                  75                  80

Pro Lys Pro Glu Gln Pro Ala Pro Ala
                85

<210> SEQ ID NO 157
<211> LENGTH: 14
<212> TYPE: PRT
<213> ORGANISM: Streptococcus pneumoniae

<400> SEQUENCE: 157

Pro Glu Lys Pro Ala Pro Ala Pro Glu Thr Pro Ala Pro Glu
1               5                   10

<210> SEQ ID NO 158
<211> LENGTH: 302
<212> TYPE: PRT
<213> ORGANISM: Artificial Sequence
<220> FEATURE:
<223> OTHER INFORMATION: aHD-PRD construct designated PspA01.3

<400> SEQUENCE: 158

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys Tyr Asp Glu
        35                  40                  45

Asp Gln Lys Lys Thr Glu Glu Lys Ala Ala Leu Glu Lys Ala Ala Ser
50                  55                  60
```

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
            85                  90                  95

Ile Asp Glu Ala Lys Lys Arg Glu Glu Ala Lys Thr Lys Phe Asn
                100                 105                 110

Thr Val Arg Ala Met Val Val Pro Glu Pro Glu Gln Leu Ala Glu Thr
                115                 120                 125

Lys Lys Lys Ser Glu Glu Ala Lys Gln Lys Ala Pro Glu Leu Thr Lys
            130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
                180                 185                 190

Lys Glu Ile Asp Glu Ser Glu Ser Glu Asp Tyr Ala Lys Glu Gly Phe
            195                 200                 205

Arg Ala Pro Leu Gln Ser Lys Leu Asp Ala Lys Ala Lys Leu Ser
210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
                275                 280                 285

Pro Glu Lys Pro Ala Pro Ala Pro Glu Thr Pro Ala Pro Glu
            290                 295                 300

<210> SEQ ID NO 159
<211> LENGTH: 288
<212> TYPE: PRT
<213> ORGANISM: Streptococcus pneumoniae

<400> SEQUENCE: 159

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Ala Gln Lys Lys Tyr Asp Glu
            35                  40                  45

Asp Gln Lys Lys Thr Glu Glu Lys Ala Ala Leu Glu Lys Ala Ala Ser
        50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
            85                  90                  95

Ile Asp Glu Ala Lys Lys Arg Glu Glu Ala Lys Thr Lys Phe Asn
                100                 105                 110

Thr Val Arg Ala Met Val Val Pro Glu Pro Glu Gln Leu Ala Glu Thr
                115                 120                 125

Lys Lys Lys Ser Glu Glu Ala Lys Gln Lys Ala Pro Glu Leu Thr Lys

```
                  130                 135                 140
Lys Leu Glu Glu Ala Lys Ala Lys Leu Glu Glu Ala Glu Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
                180                 185                 190

Lys Glu Ile Asp Glu Ser Glu Ser Glu Asp Tyr Ala Lys Glu Gly Phe
            195                 200                 205

Arg Ala Pro Leu Gln Ser Lys Leu Asp Ala Lys Lys Ala Lys Leu Ser
        210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
                245                 250                 255

Glu Asp Tyr Phe Lys Glu Gly Leu Glu Lys Thr Ile Ala Ala Lys Lys
                260                 265                 270

Ala Glu Leu Glu Lys Thr Glu Ala Asp Leu Lys Lys Ala Val Asn Glu
            275                 280                 285

<210> SEQ ID NO 160
<211> LENGTH: 912
<212> TYPE: DNA
<213> ORGANISM: Artificial Sequence
<220> FEATURE:
<223> OTHER INFORMATION: DNA coding for PspA01.3 [SEQ ID NO:158]. The
      ATG coding for methionine has been added at the beginning as an
      initiator and TGA has been added at the end as a stop codon

<400> SEQUENCE: 160
atggaagaaa gcccggtggc gagccagagc aaagcggaaa aagattatga tgcggcgaaa     60
aaagatgcga aaaacgcgaa aaaagcggtg gaagatgcgc agaaagcgct ggatgatgcg    120
aaagcggcgc agaaaaaata tgatgaagat cagaaaaaaa ccgaagaaaa agcggcgctg    180
gaaaaagcgg cgagcgaaga aatggataaa gcggtggcgg cggtgcagca ggcgtatctg    240
gcgtatcagc aggcgaccga taaagcggcg aaagatgcgg cggataaaat gattgatgaa    300
gcgaaaaaac gcgaagaaga agcgaaaacc aaatttaaca ccgtgcgcgc gatggtggtg    360
ccggaaccgg aacagctggc ggaaaccaaa aaaaaagcg aagaagcgaa acagaaagcg     420
ccggaactga ccaaaaaact ggaagaagcg aaagcgaaac tggaagaagc ggaaaaaaaa    480
gcgaccgaag cgaaacagaa agtggatgcg gaagaagtgg cgccgcaggc gaaaattgcg    540
gaactggaaa accaggtgca tcgcctggaa caggaactga agaaattga tgaaagcgaa     600 agcgaagatt atgcgaaaga aggctttcgc gcgccgctgc agagcaaact ggatgcgaaa    660
aaagcgaaac tgagcaaact ggaagaactg agcgataaaa ttgatgaact ggatgcggaa    720
attgcgaaac tggaagatca gctgaaagcg cggaagaaa caacaacgt ggaagattat      780 tttaagaag gcctggaaaa aaccattgcg gcgaaaaaag cggaactgga aaaaaccgaa     840
gcggatctga aaaaagcggt gaacgaaccg gaaaaaccgg cgccggcgcc ggaaaccccg    900
gcgccggaat ga                                                        912
```